US009802941B2

(12) United States Patent
Boesen et al.

(10) Patent No.: US 9,802,941 B2
(45) Date of Patent: Oct. 31, 2017

(54) COMPOUNDS AND METHODS FOR INHIBITING HISTONE DEMETHYLASES

(71) Applicant: Gilead Sciences, Inc., Foster City, CA (US)

(72) Inventors: Thomas Boesen, København Ø (DK); Marc Labelle, Basking Ridge, NJ (US); Ying Yang, Fremont, CA (US); Neerja Saraswat, Winnipeg (CA); Dastagiri Dudekula, Winnipeg (CA); Cyril John Cook, Winnipeg (CA); Ramkrishna Reddy Vakiti, Winnipeg (CA); Rui Zhang, Winnipeg (CA); Farman Ullah, Winnipeg (CA)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/836,397

(22) Filed: Aug. 26, 2015

(65) Prior Publication Data
US 2016/0102096 A1    Apr. 14, 2016

Related U.S. Application Data

(60) Provisional application No. 62/042,717, filed on Aug. 27, 2014.

(51) Int. Cl.

| | | |
|---|---|---|
| *C07D 487/04* | (2006.01) | |
| *A61K 31/5355* | (2006.01) | |
| *C07D 413/12* | (2006.01) | |
| *C07D 409/14* | (2006.01) | |
| *A61K 31/506* | (2006.01) | |
| *C07D 213/79* | (2006.01) | |
| *C07D 413/14* | (2006.01) | |
| *C07D 401/14* | (2006.01) | |
| *A61K 31/501* | (2006.01) | |
| *A61K 31/4985* | (2006.01) | |
| *A61K 31/444* | (2006.01) | |
| *A61K 31/4439* | (2006.01) | |
| *A61K 31/4412* | (2006.01) | |
| *C07D 213/38* | (2006.01) | |
| *C07D 213/48* | (2006.01) | |
| *C07D 213/56* | (2006.01) | |
| *C07D 401/04* | (2006.01) | |
| *C07D 413/04* | (2006.01) | |
| *C07D 401/12* | (2006.01) | |

(52) U.S. Cl.
CPC .......... *C07D 487/04* (2013.01); *A61K 31/444* (2013.01); *A61K 31/4412* (2013.01); *A61K 31/4439* (2013.01); *A61K 31/4985* (2013.01); *A61K 31/501* (2013.01); *A61K 31/506* (2013.01); *A61K 31/5355* (2013.01); *C07D 213/38* (2013.01); *C07D 213/48* (2013.01); *C07D 213/56* (2013.01); *C07D 213/79* (2013.01); *C07D 401/04* (2013.01); *C07D 401/12* (2013.01); *C07D 401/14* (2013.01); *C07D 409/14* (2013.01); *C07D 413/04* (2013.01); *C07D 413/12* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 4,100,274 A | 7/1978 | Dutta et al. | |
| 4,636,505 A | 1/1987 | Tucker | |
| 4,659,516 A | 4/1987 | Bowler | |
| 5,010,099 A | 4/1991 | Gunasekera et al. | |
| 5,843,901 A | 12/1998 | Roeske | |
| 5,874,438 A | 2/1999 | Schohe-Loop et al. | |
| 6,194,181 B1 | 2/2001 | Hofmann et al. | |
| 2008/0177082 A1 | 7/2008 | Wallace et al. | |
| 2009/0246274 A1 | 10/2009 | Bateman et al. | |

(Continued)

FOREIGN PATENT DOCUMENTS

| | | |
|---|---|---|
| CN | 102585150 | 7/2012 |
| EP | 2578569 | 4/2013 |

(Continued)

OTHER PUBLICATIONS

Chang, K. et al. "Inhibition of Histone Demethylases by 4-Carboxy-2.2'-Bipyridyl Compounds" ChemMedChem, (2011) 6(5) p. 759-764.
Cloos et al., "Erasing the Methyl Mark: Histone Demethylases at the Center of Cellular Differentiation and Disease" Genes & Development 22, 1115-1140, 2008.
Lohse, B. et al. "Inhibitors of Histone Demethylases", Bioorganic & Medicinal Chemistry, (2011) 19(12) p. 3625-3636.

(Continued)

*Primary Examiner* — Brian J Davis

(57) ABSTRACT

The present application relates to compounds being of Formula (I), (II), (III), (IV), (V), (VI), (IIIa), (IIIb), (IIIc), (IIId), (IIIe), (IIIf), and (IIIg). Compounds of Formula (I) have the structure:

(I)

wherein Q, $R^1$, $R^{18}$, $R^{19}$, M, A and Y are as defined herein. The compounds of the application can modulate the activity of histone demethylases (HDMEs), and can be useful for the prevention and/or treatment of diseases in which genomic dysregulation is involved in the pathogenesis, e.g., cancer.

47 Claims, No Drawings

(56) References Cited

U.S. PATENT DOCUMENTS

| | | |
|---|---|---|
| 2011/0224190 A1 | 9/2011 | Huang et al. |
| 2012/0282179 A1 | 11/2012 | Aftab et al. |
| 2014/0171432 A1 | 6/2014 | Kanouni et al. |
| 2014/0371195 A1 | 12/2014 | Labelle et al. |
| 2014/0371214 A1 | 12/2014 | Labelle et al. |
| 2015/0065522 A1 | 3/2015 | Albrecht et al. |
| 2015/0203453 A1 | 7/2015 | Labelle et al. |

FOREIGN PATENT DOCUMENTS

| | | |
|---|---|---|
| WO | WO 98/08849 | 3/1998 |
| WO | WO 98/22461 | 5/1998 |
| WO | WO 98/25929 | 6/1998 |
| WO | WO 99/17804 | 4/1999 |
| WO | WO 98/10121 | 9/1999 |
| WO | WO 99/43653 | 9/1999 |
| WO | WO 00/31247 | 6/2000 |
| WO | WO 02/22577 | 3/2002 |
| WO | WO 2008/002671 | 1/2008 |
| WO | WO 2010/056549 | 5/2010 |
| WO | WO 2011/017583 | 2/2011 |
| WO | WO 2012/007007 | 1/2012 |
| WO | WO 2012/042042 | 4/2012 |
| WO | WO 2012/071469 | 5/2012 |
| WO | WO 2012/135113 | 10/2012 |
| WO | WO 2013/025805 | 2/2013 |
| WO | WO 2013/123411 | 8/2013 |
| WO | WO 2014/053491 | 4/2014 |
| WO | WO 2014/089364 | 6/2014 |
| WO | WO 2014/100818 | 6/2014 |
| WO | WO 2014/131777 | 9/2014 |
| WO | WO 2014/151106 | 9/2014 |
| WO | WO 2015/153498 | 10/2015 |

OTHER PUBLICATIONS

Morton, C. and Houghton, P. "Establishment of Human Tumor Xenografts in Immunodeficient Mice", Nature Protocols, 2(2) 247-250, 2007.
Queguiner, G. and Pastour, P. "Reduction Selective des Pyridinedicarboxylates d'Ethyle Dissymetriques" Comptes Rendus des Seances de l'Academie des Sciences, Serie C: Sciences Chimiques (1969), 268(2), 182-185 (with English translation).
Rehse, K. and Mletzko, S. "Antiaggregatorische Und Anticoagulante Eigenschaften Von Oligoaminen. 8. Mitt.: Oligoamine Mit N-Heterocyclischen Teilstrukturen" Arch Pharm. (Weinheim), (1988) 321(9) p. 533-536 (with English translation).
Roy, M. et al. "AlphaLISA JMJD2A Histone H3-Lysine 9 Demethylase Assay", PerkinEimer Technical Note: AlphaLISA #12, Apr. 2011, 2 pages.
International Search Report issued by the International Searching Authority for PCT/EP2013/070457, dated Jan. 14, 2014, 4 pages.
International Search Report issued by the International Searching Authority for PCT/EP2014/053674, dated Mar. 31, 2014, 4 pages.
International Search Report issued by the International Searching Authority for PCT/US2015/023407, dated Jul. 31, 2015, 4 pages.
Written Opinion issued by the International Searching Authority for PCT/EP2013/070457, dated Jan. 14, 2014, 7 pages.
Written Opinion issued by the International Searching Authority for PCT/EP2014/053674, dated Aug. 27, 2015, 7 pages.
Written Opinion issued by the International Searching Authority for PCT/US2015/023407, dated Jul. 31, 2015, 10 pages.
International Search Report and Written Opinion issued by the International Searching Authority for Application No. PCT/US2015/046921, dated Nov. 2, 2015, 13 pages.
Kojima, et al., "Synthesis and Characterization of Mononuclear Ruthenium(III) Pyridylamine Complexes and Mechanistic Insights into Their Catalytic Alkane Functionalization with m-Chloroperbenzoic Acid," Chemistry European Journal, vol. 13, pp. 8212-8222 (2007).

COMPOUNDS AND METHODS FOR INHIBITING HISTONE DEMETHYLASES

CROSS-REFERENCE TO RELATED APPLICATION

This application claims priority to, and the benefit of, U.S. Provisional Application No. 62/042,717, filed Aug. 27, 2014, the contents of which are incorporated herein by reference in their entirety.

INCORPORATION-BY-REFERENCE OF SEQUENCE LISTING

The contents of the file named "GILE-117_01US_ST25.txt", which was created on Oct. 16, 2015 and is 3 KB in size, are hereby incorporated by reference in their entirety.

FIELD OF THE APPLICATION

The present application relates to compounds capable of modulating the activity of histone demethylases (HDMEs), which compounds are useful for the prevention and/or the treatment of diseases in which genomic dysregulation is involved in the pathogenesis, such as cancer.

BACKGROUND

The DNA of eukaryotic cells is packaged into chromatin by winding of the DNA around histone proteins to form nucleosomes, the basic unit of chromatin. One of the important functions of chromatin is to determine regions of active and silenced transcription by changing the ordered chromatin structure. Such changes have profound effects on cellular function since they affect fundamental processes as differentiation, proliferation and apoptosis, and are often referred collectively to as "epigenetic" since they can lead to heritable changes that do not involve changes in gene sequences (Quina, A. S. et al. (2006), Biochem. Pharmacol. 72; 1563-1569)

These highly controlled chromatin changes are mediated by alterations histone proteins associated with DNA in the nucleosome. Most notably, the N-terminal histone tail of Histone H3 and histone H4 are subject to such covalent changes, which include changes in methylation, acetylation, phosphorylation and ubiquitination. The addition or removal of these groups on histones is mediated by specific enzymes, e.g., histone methyl transferases and histone demethylases for methyl groups, histone acetyltransferases and histone deacetylases for acetyl groups. In the event that the activity or expression of these "epigenetic" enzymes is not correctly controlled and regulated it may lead to disease. Cancer, in particular, is an area of high importance in relation to dysregulated epigenetic enzyme activity due to the role of epigenetics in cell differentiation, proliferation and apoptosis, but epigenetics may also play a role in other diseases such as metabolic, inflammatory, neurodegenerative and cardiovascular diseases. Therefore the selective modulation of aberrant action of epigenetic enzymes may hold great promise for the treatment of human disease (Kelly, T. K. et al. (2010), Nat. Biotechnol. 28; 1069-1078, and Cloos, P. et al. (2008), Genes. Dev. 22; 115-1140).

PCT/EP2013/070457 (WO2014/053491) discloses histone demethylase (HDME) inhibitors or activity modulators which are hereby incorporated by reference.

Embodiments of the application provide compounds capable of modulating the activity of histone demethylases and that are useful for the prevention and/or the treatment of diseases in which genomic disregulation is involved in the pathogenesis, e.g., cancer. By way of further example, malnutrition or poor nutrition is thought to have an adverse epigenetic effect and the compounds of the application may therefore have beneficial effect in treating such effects of poor nutrition. Furthermore, epigenetic changes have been found to be linked to behavior. Accordingly, compounds according to the application may be useful in behavior modification. Alternatively or additionally such compounds may be useful for exploring the extent to which different methylases are inhibited by similar compounds as an investigation of the structure, functionality and mechanism of action.

SUMMARY

Compounds of the application may be capable of modulating the activity of histone demethylases. The application features methods of treating or preventing a disease or disorder in which histone demethylation plays a role in a subject in need thereof by administering to said subject a therapeutically effective amount of a compound the application, or a pharmaceutically acceptable salt, or solvate, or prodrug thereof, as defined herein. The methods of the present application can be used in the treatment of HDME-dependent diseases by inhibiting the activity of histone demethylases. Inhibition of histone demethylases provides a novel approach to the prevention and treatment of diseases in which genomic disregulation is involved in the pathogenesis, e.g., cancer, behavior modification.

Accordingly, in a first aspect, the compounds of the application relates to a compound of Formula (I):

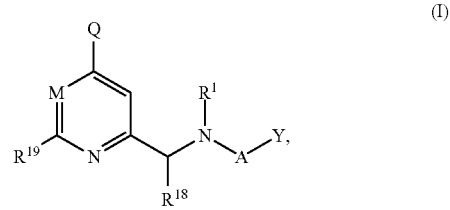

(I)

or a pharmaceutically acceptable salt, or solvate or prodrug thereof wherein each of the variables in Formula (I) is defined and exemplified herein.

In one aspect, a compound of Formula (I) is a compound of any one of formula (II), (III), (IV), (V), (VI) (IIIa), (IIIb), (IIIc), (IIId), (IIIe), (IIIf), (IIIg):

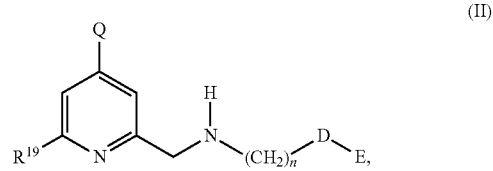

(II)

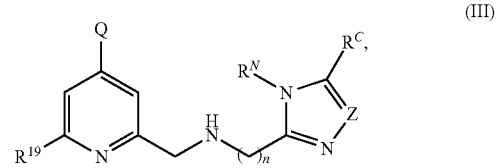

(III)

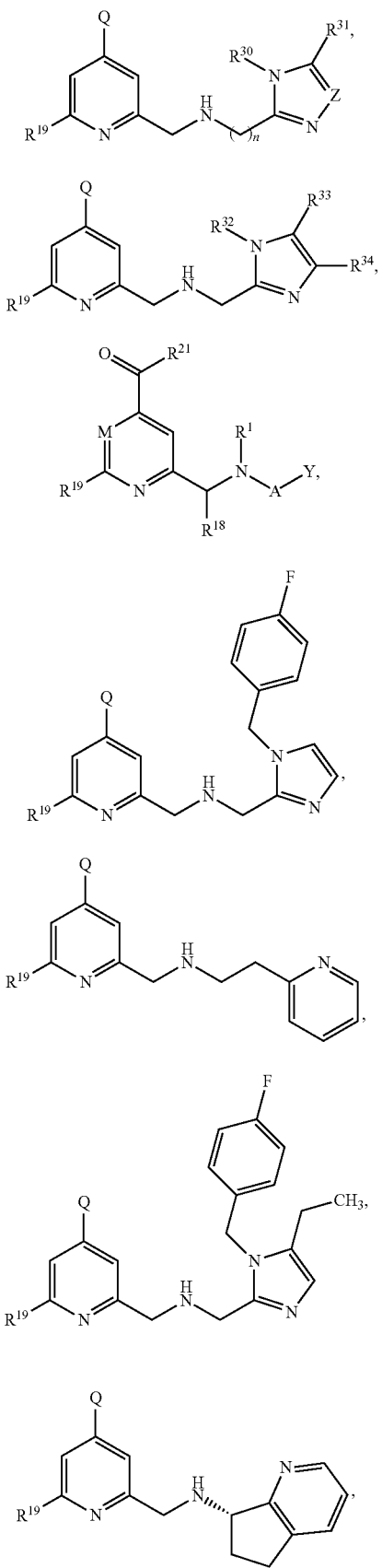
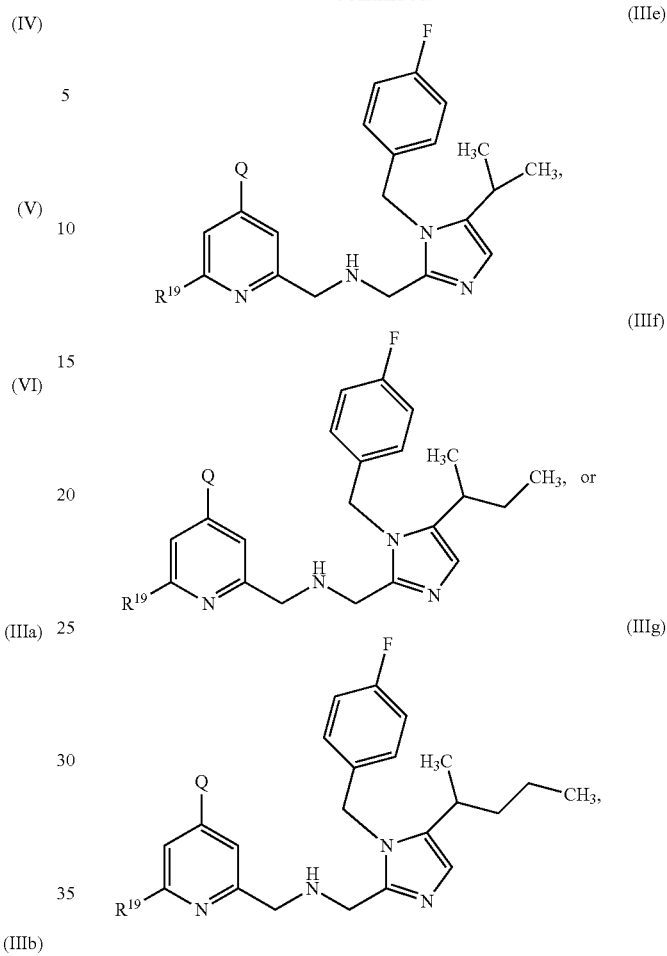

or a pharmaceutically acceptable salt, or solvate or prodrug thereof wherein each of the variables in Formula (II), (III), (IV), (V), (VI), (IIIa), (IIIb), (IIIc), (IIId), (IIIe), (IIIf) and (IIIg), is defined and exemplified herein.

In one aspect, the present application relates to a compound of the application, or a pharmaceutically acceptable salt, or solvate, or prodrug thereof, as defined herein, for use as a medicament useful for the treatment of a HDME-dependent disease, such as for the treatment of cancer In another aspect, the present application relates to a compound of the application, or a pharmaceutically acceptable salt, or solvate, or prodrug thereof, as defined herein, for use in the treatment of a HDME-dependent disease, such as for the treatment of cancer.

In another aspect, the present application relates to the use of a compound of the application, or a pharmaceutically acceptable salt, or solvate, or prodrug thereof, as defined herein, for the preparation of a pharmaceutical composition for the treatment of a HDME-dependent disease, such as for the treatment of cancer.

In another aspect, the present application relates to a method of treating a HDME-dependent disease in a subject in need thereof, wherein said method comprises administering to said subject a therapeutically effective amount of at least one compound of the application, or a pharmaceutically acceptable salt, or solvate or prodrug thereof, as defined herein.

In another aspect, the HDME modulating compounds of the present application may be administered alone or in combination with other compounds, including other HDME modulating compounds, or other therapeutic agents.

In another aspect, the compound of the application, or a pharmaceutically acceptable salt, or solvate or prodrug thereof, as defined herein can be used in the treatment of HDME-dependent diseases by inhibiting HDMEs. Inhibiting HDMEs provides an approach to the prevention and treatment of cancer and other proliferative diseases. Administered alone or optionally in combination with anti-neoplastic compounds, the compound of the application increase the efficacy of the treatment of HDME-dependent diseases.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar to or equivalent to those described herein can be used in the practice and testing of the application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and not intended to be limiting.

Other features and advantages of the application will become apparent from the following detailed description in conjunction with the examples.

DETAILED DESCRIPTION

The above definitions of the compounds of the application are referred to herein by the expressions "a compound of the application," "compounds of the application," "a compound of Formula (I)," and "compounds of Formula (I)." It should be understood, that such references are intended to encompass not only the above general formula in its stated aspects, but also each and every embodiment discussed herein. It should also be understood, that unless stated to the opposite, such references also encompass isomers, mixtures of isomers, isotopic variants, pharmaceutically acceptable salts, solvates and prodrugs of the compounds of the application.

The present application relates to compounds represented by Formula (I)

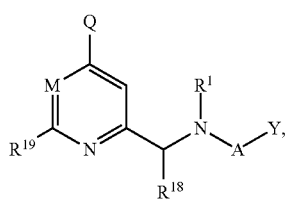

wherein:
Q is selected from $CO_2H$, $CO_2R^{20}$, —CH=$NR^{12}$, —W, —$CH_2NHR^{13}$, —CH=O and —CH$(OR^{17})_2$;
M is CH or N;
A is selected from —C$(R^2)_2$C(O)—, —C$(R^2)_2$C$(R^2)_2$C(O)—, $C_{3-10}$ alkyl, —Z—C$_{3-10}$ cycloalkylene, —Z-heterocyclylene, —Z-heteroarylene and —Z-arylene, wherein the $C_{3-10}$ alkyl, —Z-cycloalkylene, —Z-heterocyclylene, —Z-heteroarylene and —Z-arylene are optionally substituted with one or more $R^3$, or A and Y form a $C_{3-10}$ cycloalkyl or heterocyclic ring;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, wherein the alkyl, alkenyl, alkynyl, cycloalkyl, heterocyclyl, heteroaryl and aryl are optionally substituted with one or more $R^3$;

$R^1$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —$NR^6R^7$, —F and $C_{3-6}$ cycloalkyl; or $R^1$, together with A-Y and the nitrogen atom to which it is attached, forms a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl; or $R^1$ and $R^{18}$, together with the atoms to which they are attached, form a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl;

Each $R^2$ is independently selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; or two $R^2$ substituents on adjacent carbon atoms, together with the carbon atoms to which they are attached, form a $C_{4-10}$ cycloalkyl or heterocyclic ring; or two $R^2$ substituents on the same carbon atom, together with the carbon atom to which they are attached, form a $C_{3-10}$ cycloalkyl or heterocyclic ring; or $R^2$ and Y, together with the carbon atoms to which they are attached, form a $C_{4-10}$ cycloalkyl or heterocyclic ring;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; or two $R^3$ on the same carbon atom may, together with the carbon atom to which they are attached, form a $C_{3-10}$ cycloalkyl or $C_{3-10}$ heterocyclic ring;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—$NR^6R^7$, —Z—C(=O)—$NR^6R^7$, —Z—$NR^6$—C(=O)—$R^7$, —Z—C(=O)—$R^7$, —Z—C (=O)—H, —OR$^7$, halogen, —SR$^7$, —SOR$^7$, —SO$_2$R$^7$, —SO$_2$NR$^6$R$^7$, and —COOR$^7$;

each R$^5$ is independently selected from C$_{1-6}$ alkyl, C$_{1-4}$ fluoroalkyl, C$_{1-4}$ hydroxyalkyl, C$_{1-4}$ alkoxy, C$_{3-6}$ cycloalkyl, —CN, —F, —Cl, —Br, —Z—NR$^6$R$^7$, —Z—C(=O)—NR$^6$R$^7$, —Z—NR$^6$—C(=O)—R$^7$, —Z—C(=O)—R$^7$, —Z—C(=O)—H, —OR$^7$, —SR$^7$, —SOR$^7$, —SO$_2$R$^7$, —SO$_2$NR$^6$R$^7$, and —COOR$^7$;

each R$^6$ and R$^7$ is independently selected from —H, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-heteroaryl and —Z-aryl, wherein the alkyl, alkenyl, alkynyl, cycloalkyl, heterocyclyl, heteroaryl and aryl are optionally substituted with one or more R$^8$; or R$^6$ and R$^7$ may, together with the N-atom to which they are attached, form a heterocyclic ring optionally substituted with one or more R$^8$;

each R$^8$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, wherein the alkyl, alkenyl, alkynyl, cycloalkyl, heterocyclyl, heteroaryl and aryl are optionally substituted with one or more substituents independently selected from C$_{1-4}$ alkyl, C$_{1-4}$ fluoroalkyl, C$_{1-4}$ hydroxyalkyl, C$_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein the heterocyclyl is optionally substituted with one or more R$^4$ and wherein the heteroaryl and aryl are optionally substituted with one or more R$^5$;

each R$^9$ is independently selected from —H, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-aryl, and —Z-heteroaryl, wherein the heterocyclyl is optionally substituted with one or more R$^4$ and wherein the heteroaryl and aryl are optionally substituted with one or more R$^5$;

each of R$^{10}$ and R$^{11}$ is independently selected from —H, C$_{1-6}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, heterocyclyl, heteroaryl, and C$_{6-14}$ aryl, wherein the heterocyclyl is optionally substituted with one or more R$^4$ and wherein the heteroaryl and aryl are optionally substituted with one or more R$^5$; or R$^{10}$ and R$^{11}$ may, together with the N-atom to which they are attached, form a 5- to 7-membered heterocyclic ring optionally substituted with one or more R$^4$;

when Q is —CH=NR$^{12}$, R$^{12}$ is selected from C$_{1-10}$ alkyl, C$_{2-10}$ alkenyl, C$_{2-10}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, —Z—SR$^7$, —Z—SOR$^7$, —Z—SO$_2$R$^7$ and —Z—COOR$^7$, wherein the alkyl, alkenyl, alkynyl, cycloalkyl, heterocyclyl, heteroaryl and aryl are optionally substituted with one or more R$^3$;

when Q is —CH$_2$NHR$^{13}$, R$^{13}$ is selected from —H, —C(O)R$^7$, —C(O)C(O)R$^7$, —C(O)C(O)OR$^7$, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, and —Z-monocyclic-heteroaryl, wherein the alkyl, alkenyl, alkynyl, cycloalkyl, heterocyclyl, and heteroaryl are optionally substituted with one or more R$^8$; or R$^{13}$ is —CR$^{14}$R$^{15}$NR$^6$R$^7$, —CR$^{14}$R$^{15}$CN, or —CR$^{14}$R$^{15}$OR$^7$, wherein each R$^{14}$ and R$^{15}$ is independently selected from —H, C$_{1-8}$ alkyl, C$_{2-8}$ alkenyl, C$_{2-8}$ alkynyl, C$_{3-10}$ cycloalkyl, heterocyclyl, heteroaryl, and C$_{6-14}$ aryl, wherein the alkyl, alkenyl, alkynyl, cycloalkyl, heterocyclyl, heteroaryl and aryl are optionally substituted with one or more R$^3$; or R$^{14}$ and R$^{15}$ together with the intervening carbon atom form a C$_{3-10}$ cycloalkyl or C$_{5-10}$-cycloalkenyl ring optionally substituted with one or more R$^3$;

when Q is W, W is selected from a 1,3-diazacycloalk-2-yl group which is N-substituted with R$^{16}$, optionally further substituted with one or more R$^3$, and optionally containing one or two oxo groups; a 1,3-thiazacycloalk-2-yl group which is N-substituted with R$^{16}$, optionally further substituted with one or more R$^3$ and optionally containing one or two oxo groups; and a 1,3-oxazacycloalk-2-yl group which is N-substituted with R$^{16}$, optionally further substituted with one or more R$^3$, and optionally containing one or two oxo groups, wherein in all three instances two R$^3$ on the same carbon atom may, together with the carbon atom to which they are attached, form a C$_{3-10}$ cycloalkyl or heterocyclic ring;

R$^{16}$ is selected from —H, —C(O)R$^7$, —C(O)C(O)R$^7$ and —C(O)C(O)OR$^7$;

when Q is —CH(OR$^{17}$)$_2$, each R$^{17}$ independently is R$^3$; or wherein two R$^{17}$ together with the intervening —O—CH—O— form a heterocyclic ring optionally substituted with one or more R$^3$ and optionally containing one to two oxo groups;

R$^{18}$ is selected from —H, C$_{1-6}$ alkyl, C$_{1-6}$ fluoroalkyl, C$_{1-6}$ hydroxyalkyl, C$_{2-7}$ alkenyl, C$_{2-7}$ alkynyl, C$_{3-7}$ cycloalkyl, and C$_{3-7}$ oxyalkyl; or R$^{18}$ and A, together with the atoms to which they are attached, form a heterocyclic ring; or R$^{18}$ and Y, together with the atoms to which they are attached, form a heterocyclic ring; or R$^{18}$ and R$^1$, together with the atoms to which they are attached, form a heterocyclic ring;

R$^{19}$ is selected from C$_{1-8}$ alkyl, C$_{2-8}$ alkenyl, C$_{2-8}$ alkynyl, and C$_{3-10}$ cycloalkyl, wherein the alkyl, alkenyl, alkynyl and cycloalkyl are optionally substituted with one or more substituents independently selected from aryl, C$_{1-6}$ alkoxy, heteroaryl, aryloxy, heteroaryloxy, C$_{3-6}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$; and may optionally form a cyclophane structure by attaching to Y or A; and when Q is CO$_2$R$^{20}$, R$^{20}$ is selected from C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-aryl, and —Z-heteroaryl, wherein the C$_{1-8}$ alkyl, C$_{3-10}$ cycloalkyl and heterocyclyl are optionally substituted with one or more R$^4$, and wherein the heteroaryl and aryl are optionally substituted with one or more R$^5$ as defined above;

or a pharmaceutically acceptable salt, or solvate or prodrug thereof.

In one embodiment, the present application relates to compounds represented by Formula (I), wherein:

Q is selected from CO$_2$H, CO$_2$R$^{20}$, —CH=NR$^{12}$, —W, —CH$_2$NHR$^{13}$, —CH=O and —CH(OR$^{17}$)$_2$;

M is CH or N;

A is selected from —C(R$^2$)$_2$C(O)—, —C(R$^2$)$_2$C(R$^2$)$_2$C(O)—, C$_{3-10}$ alkyl, —Z—C$_{3-10}$ cycloalkylene, —Z-heterocyclylene, —Z-heteroarylene and —Z-arylene, wherein the C$_{3-10}$ alkyl, —Z-cycloalkylene, —Z-heterocyclylene, —Z-heteroarylene and —Z-arylene are optionally substituted with one or more R$^3$, or A and Y form a C$_{3-10}$ cycloalkyl or C$_{5-10}$ heterocyclic ring;

Y is selected from —H, —NR$^6$R$^7$, —OR$^7$, C$_{1-8}$ alkyl, C$_{2-8}$ alkenyl, C$_{2-8}$ alkynyl, C$_{3-10}$ cycloalkyl, C$_{5-10}$ heterocyclyl, C$_{5-14}$ heteroaryl and C$_{6-14}$ aryl, wherein the alkyl, alkenyl, alkynyl, cycloalkyl, heterocyclyl, heteroaryl and aryl are optionally substituted with one or more R$^3$;

$R^1$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —NR$^6$R$^7$, —F and $C_{3-6}$ cycloalkyl; or $R^1$, together with A-Y forms a nitrogen-containing $C_{5-10}$ heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —NR$^6$R$^7$, —F and $C_{3-6}$ cycloalkyl; or $R^1$ and $R^{18}$ together form a nitrogen-containing $C_{5-10}$ heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —NR$^6$R$^7$, —F and $C_{3-6}$ cycloalkyl;

$R^2$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$; or two $R^2$ substituents form a $C_{3-10}$ cycloalkyl or $C_{5-10}$ heterocyclic ring; or $R^2$ and Y form a $C_{3-10}$ cycloalkyl or $C_{5-10}$ heterocyclic ring;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein the heterocyclyl is optionally substituted with one or more R$^4$, and wherein the heteroaryl and aryl are optionally substituted with one or more R$^5$; or two $R^3$ on the same carbon atom may together form a spiro group;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—NR$^6$R$^7$, —Z—C(=O)—NR$^6$R$^7$, —Z—NR$^6$—C(=O)—R$^7$, —Z—C(=O)—R$^7$, —Z—C(=O)—H, —OR$^7$, halogen, —SR$^7$, —SOR$^7$, —SO$_2$R$^7$, —SO$_2$NR$^6$R$^7$, and —COOR$^7$;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, —Z—NR$^6$R$^7$, —Z—C(=O)—NR$^6$R$^7$, —Z—NR$^6$—C(=O)—R$^7$, —Z—C(=O)—R$^7$, —Z—C(=O)—H, —OR$^7$, —SR$^7$, —SOR$^7$, —SO$_2$R$^7$, —SO$_2$NR$^6$R$^7$, and —COOR$^7$;

each $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, wherein the alkyl, alkenyl, alkynyl, cycloalkyl, heterocyclyl, heteroaryl and aryl are optionally substituted with one or more R$^8$; or $R^6$ and $R^7$ may, together with the N-atom to which they are attached, form a $C_{5-10}$ heterocyclic ring optionally substituted with one or more R$^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, wherein the alkyl, alkenyl, alkynyl, cycloalkyl, heterocyclyl, heteroaryl and aryl are optionally substituted with one or more substituents independently selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein the heterocyclyl is optionally substituted with one or more R$^4$ and wherein the heteroaryl and aryl are optionally substituted with one or more R$^5$;

each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the heterocyclyl is optionally substituted with one or more R$^4$ and wherein the heteroaryl and aryl are optionally substituted with one or more R$^5$;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, $C_{5-10}$ heterocyclyl, $C_{5-10}$ heteroaryl, and $C_{6-14}$ aryl, wherein the heterocyclyl is optionally substituted with one or more R$^4$ and wherein the heteroaryl and aryl are optionally substituted with one or more R$^5$; or $R^{10}$ and $R^{11}$ may, together with the N-atom to which they are attached, form a 5- to 7-membered heterocyclic ring optionally substituted with one or more R$^4$;

when Q is —CH=NR$^{12}$, $R^{12}$ is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, —Z—SR$^7$, —Z—SOR$^7$, —Z—SO$_2$R$^7$ and —Z—COOR$^7$, wherein the alkyl, alkenyl, alkynyl, cycloalkyl, heterocyclyl, heteroaryl and aryl are optionally substituted with one or more R$^3$;

when Q is —CH$_2$NHR$^{13}$, $R^{13}$ is selected from —H, —C(O)R$^7$, —C(O)C(O)R$^7$, —C(O)C(O)OR$^7$, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, and —Z-monocyclic-heteroaryl, wherein the alkyl, alkenyl, alkynyl, cycloalkyl, heterocyclyl, and heteroaryl are optionally substituted with one or more R$^8$; or $R^{13}$ is —CR$^{14}$R$^{15}$NR$^6$R$^7$, —CR$^{14}$R$^{15}$CN, or —CR$^{14}$R$^{15}$OR$^7$, wherein each $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, $C_{5-10}$ heterocyclyl, $C_{5-10}$ heteroaryl, and $C_{6-14}$ aryl, wherein the alkyl, alkenyl, alkynyl, cycloalkyl, heterocyclyl, heteroaryl and aryl are optionally substituted with one or more R$^3$; or wherein $R^{14}$ and $R^{15}$ together with the intervening carbon atom form a $C_{3-10}$ cycloalkyl or $C_{5-10}$-cycloalkenyl ring optionally substituted with one or more R$^3$;

when Q is W, W is selected from a 1,3-diaza-$C_{5-7}$-cycloalk-2-yl group which is N-substituted with R$^{16}$, optionally further substituted with one or more R$^3$, and optionally containing one or two oxo groups; a 1,3-thiaza-$C_{5-7}$-cycloalk-2-yl group which is N-substituted with R$^{16}$, optionally further substituted with one or more R$^3$ and optionally containing one or two oxo groups; and a 1,3-oxaza-$C_{5-7}$-cycloalk-2-yl group which is N-substituted with R$^{16}$, optionally further substituted with one or more R$^3$, and optionally containing one or two oxo groups, wherein in all three instances two R$^3$ on the same carbon atom may together form a spiro group;

$R^{16}$ is selected from —H, —C(O)$R^7$, —C(O)C(O)$R^7$ and —C(O)C(O)O$R^7$;

when Q is —CH(O$R^{17}$)$_2$, each $R^{17}$ independently is $R^3$; or wherein two $R^{17}$ together with the intervening —O—CH—O— form a $C_{5-10}$ heterocyclic ring optionally substituted with one or more $R^3$ and optionally containing one to two oxo groups;

$R^{18}$ is selected from —H, $C_{1-6}$ alkyl, $C_{1-6}$ fluoroalkyl, $C_{1-6}$ hydroxyalkyl, $C_{2-7}$ alkenyl, $C_{2-7}$ alkynyl, $C_{3-7}$ cycloalkyl, and $C_{3-7}$ oxyalkyl; or $R^{18}$ and A form a $C_{3-10}$ cycloalkyl or $C_{5-10}$ heterocyclic ring; or $R^{18}$ and Y form a $C_{3-10}$ cycloalkyl or $C_{5-10}$ heterocyclic ring; or $R^{18}$ and $R^1$ form a $C_{3-10}$ cycloalkyl or $C_{5-10}$ heterocyclic ring;

$R^{19}$ is selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from aryl, $C_{1-6}$ alkoxy, heteroaryl, aryloxy, heteroaryloxy, $C_{3-6}$ cycloalkyl, —Z-heterocyclyl, —Z-aryl, —Z-heteroaryl, —Z—N$R^6R^7$, —Z—C(=O)—N$R^6R^7$, —Z—N$R^6$—C(=O)—$R^7$, —Z—C(=O)—$R^7$, —Z—O$R^7$, halogen, —Z—S$R^7$, —Z—SO$R^7$, —Z—SO$_2R^7$, —Z—SO$_2$N$R^6R^7$ and —Z—COO$R^7$; and may optionally form a cyclophane structure by attaching to Y or A; and when Q is CO$_2R^{20}$, $R^{20}$ is selected from $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the $C_{1-8}$ alkyl, $C_{3-10}$ cycloalkyl and heterocyclyl are optionally substituted with one or more $R^4$, and wherein the heteroaryl and aryl are optionally substituted with one or more $R^5$ as defined above;

or a pharmaceutically acceptable salt or solvate thereof.

In one embodiment, in any compound being of Formula (I), M is CH.

In one embodiment, in any compound being of Formula (I), M is N.

In one embodiment, in any compound being of Formula (I), A is selected from —Z-heterocyclylene, —Z-arylene, and —Z-heteroarylene. In one embodiment, A is selected from —Z-heterocyclylene, —C($R^2$)$_2$C(O)—, and —Z-heteroarylene. In one embodiment, A is —Z-heteroarylene. In one embodiment, A is —Z-arylene.

In one embodiment, in any compound being of Formula (I), Y is selected from —H, —O$R^7$, —N$R^6R^7$, $C_{1-8}$ alkyl, $C_{2-8}$ alkenyl, and $C_{2-8}$ alkynyl. In one embodiment, Y is selected from —H and $C_{1-8}$ alkyl. In one embodiment, Y is selected from —H and $C_{1-4}$ alkyl. In one embodiment, Y is selected from —H, methyl, ethyl, propyl, iso-propyl, butyl, sec-butyl and tert-butyl. In one embodiment, Y is —H. In one embodiment, Y is ethyl.

In one embodiment, in any compound being of Formula (I), each $R^3$ is independently selected from —Z-heterocyclyl, —Z-aryl, and —Z-heteroaryl wherein the heterocyclyl is optionally substituted with one or more $R^4$, and the aryl, and heteroaryl are optionally substituted with one or more $R^5$. In one embodiment, $R^3$ is —Z-aryl optionally substituted with one or more $R^5$. In one embodiment, $R^3$ is phenyl optionally substituted with one or more $R^5$.

In one embodiment, in any compound being of Formula (I), Z is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, in any compound being of Formula (I), $R^1$ is selected from —H, $C_{1-8}$ alkyl, $C_{2-8}$ alkenyl, and $C_{2-8}$ alkynyl. In one embodiment, $R^1$ is selected from —H and $C_{1-8}$ alkyl. In one embodiment, $R^1$ is selected from —H and $C_{1-4}$ alkyl. In one embodiment, $R^1$ is —H.

In one embodiment, in any compound being of Formula (I), $R^{18}$ is selected from —H, $C_{1-6}$ alkyl, $C_{1-6}$ fluoroalkyl, $C_{1-6}$ hydroxyalkyl, $C_{2-7}$ alkenyl, and $C_{2-7}$ alkynyl. In one embodiment, $R^{18}$ is selected from —H and $C_{1-6}$ alkyl. In one embodiment, $R^{18}$ is —H.

In one embodiment, in any compound being of Formula (I), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—N$R^6R^7$ or —Z—O$R^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—O$R^7$. In one embodiment, $R^{19}$ is selected from methyl, ethyl, propyl, iso-propyl, butyl, sec-butyl, and tert-butyl, optionally substituted with one —Z—O$R^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —CH$_2$OH. In one embodiment, $R^{19}$ is methyl. In one embodiment, $R^{19}$ is —CH$_2$OH.

In one embodiment, in any compound being of Formula (I), Q is selected from CO$_2$H, W, and CO$_2R^{20}$. In one embodiment, Q is CO$_2$H. In one embodiment, Q is W. In one embodiment, Q is CO$_2R^{20}$.

In one embodiment, in any compound being of Formula (I), $R^{19}$ is selected from methyl, ethyl, propyl, iso-propyl, butyl, sec-butyl, and tert-butyl, optionally substituted with one —Z—O$R^7$, and Q is selected from CO$_2$H, W, and CO$_2R^{20}$.

In one embodiment, in any compound being of Formula (I), $R^{19}$ is selected from methyl, ethyl, propyl, iso-propyl, butyl, sec-butyl, and tert-butyl and Q is selected from CO$_2$H, W, and CO$_2R^{20}$.

In one embodiment, in any compound being of Formula (I), $R^{19}$ is methyl, and Q is selected from CO$_2$H, W, and CO$_2R^{20}$.

In one embodiment, in any compound being of Formula (I), $R^{19}$ is —CH$_2$OH, and Q is selected from CO$_2$H, W, and CO$_2R^{20}$.

In one embodiment, in any compound being of Formula (I), $R^{19}$ is selected from methyl, ethyl, propyl, iso-propyl, butyl, sec-butyl, and tert-butyl, optionally substituted with one —Z—O$R^7$, and Q is CO$_2$H.

In one embodiment, in any compound being of Formula (I), $R^{19}$ is selected from methyl, ethyl, propyl, iso-propyl, butyl, sec-butyl, and tert-butyl and Q is CO$_2$H.

In one embodiment, in any compound being of Formula (I), $R^{19}$ is methyl, and Q is CO$_2$H.

In one embodiment, in any compound being of Formula (I), $R^{19}$ is —CH$_2$OH, and Q is CO$_2$H.

In one embodiment, in any compound being of Formula (I), $R^{19}$ is selected from methyl, ethyl, propyl, iso-propyl, butyl, sec-butyl, and tert-butyl, optionally substituted with one —Z—O$R^7$, and Q is W.

In one embodiment, in any compound being of Formula (I), $R^{19}$ is selected from methyl, ethyl, propyl, iso-propyl, butyl, sec-butyl, and tert-butyl and Q is W.

In one embodiment, in any compound being of Formula (I), $R^{19}$ is methyl, and Q is W.

In one embodiment, in any compound being of Formula (I), $R^{19}$ is —$CH_2OH$, and Q is W.

In one embodiment, in any compound being of Formula (I), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (I), $R^{19}$ is selected from methyl, ethyl, propyl, iso-propyl, butyl, sec-butyl, and tert-butyl and Q is $CO_2R^{20}$.

In one embodiment, in any compound being of Formula (I), $R^{19}$ is methyl, and Q is $CO_2R^{20}$.

In one embodiment, in any compound being of Formula (I), $R^{19}$ is —$CH_2OH$, and Q is $CO_2R^{20}$.

In one embodiment, in any compound being of Formula (I), Q is $CO_2H$, $R^1$ is —H and $R^{18}$ is —H.

In one embodiment, in any compound being of Formula (I), Q is $CO_2H$, $R^1$ is —H, $R^{18}$ is —H, A is —Z-heteroarylene and Z is a single bond. In one embodiment, Q is $CO_2H$, $R^1$ is —H, $R^{18}$ is —H, A is —Z-heteroarylene and Z is $C_{1-4}$ alkylene.

In one embodiment, in any compound being of Formula (I), Q is $CO_2H$, $R^1$ is —H, $R^{18}$ is —H and A is —Z-heteroarylene. In one embodiment, Q is $CO_2H$, $R^1$ is —H, $R^{18}$ is —H, A is —Z-heteroarylene, and $R^3$ is —Z-aryl.

In one embodiment, in any compound being of Formula (I), Q is $CO_2H$, $R^1$ is —H, $R^{18}$ is —H, A is —Z-heteroarylene, $R^3$ is —Z-aryl and Y is —H. In one embodiment, Q is $CO_2H$, $R^1$ is —H, $R^{18}$ is —H, A is —Z-heteroarylene, $R^3$ is —Z-aryl and Y is $C_{1-8}$ alkyl.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, and $R^{18}$ is —H.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, and Z is selected from a single bond and $C_{1-4}$ alkylene.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, and Q is $CO_2H$.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, and Q is W.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, and Q is $CO_2R^{20}$.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is $CO_2H$, and $R^{19}$ is methyl.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is $CO_2H$, and $R^{19}$ is —$CH_2OH$.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is W, and $R^{19}$ is methyl.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is W, and $R^{19}$ is —$CH_2OH$.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is $CO_2R^{20}$, and $R^{19}$ is methyl.

In one embodiment, in any compound being of Formula (I), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, Q is $CO_2R^{20}$, and $R^{19}$ is —$CH_2OH$.

In one embodiment, the present application relates to a compound being of Formula (I), further being of Formula (II):

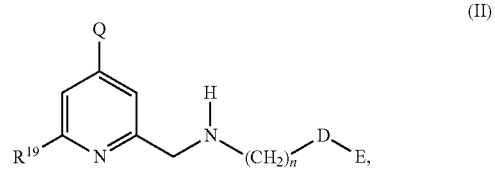

or a pharmaceutically acceptable salt, or solvate or prodrug thereof, wherein:

D is Z-heteroarylene optionally substituted with one to three $R^{23}$;

E is Z-aryl or Z-heteroaryl optionally substituted with one to three $R^{24}$;

each $R^{23}$ is independently selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, $C_{5-10}$ heterocyclyl, $C_{5-14}$ heteroaryl and $C_{6-14}$ aryl;

each $R^{24}$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

n is 0 to 3; and

Q, $R^6$, $R^7$, $R^{19}$, and Z are as defined above.

In one embodiment, n is 0. In one embodiment, n is 1. In one embodiment, n is 2. In one embodiment, n is 3.

In one embodiment, D is imidazolyl optionally substituted with one to three $R^{23}$. In one embodiment, D is pyridinyl optionally substituted with one to three $R^{23}$. In one embodiment, D is triazolyl optionally substituted with one to three $R^{23}$. In one embodiment, D is

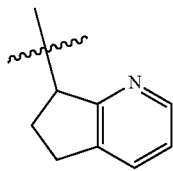 [SMILES: *C1CCc2cccnc21]

optionally substituted with one to three $R^{23}$.

In one embodiment, each $R^{23}$ is —H, $OR^7$, or $C_{1-8}$ alkyl.
In one embodiment, $R^{23}$ is —H or $C_{1-8}$ alkyl.
In one embodiment, $R^{23}$ is —H.
In one embodiment, $R^{23}$ is $OR^7$. In one embodiment, $R^{23}$ is $OCH_3$. In one embodiment, $R^{23}$ is O—Z-aryl. In one embodiment, $R^{23}$ is O—Z-phenyl. In one embodiment, $R^{23}$ is O—$CH_2$-phenyl.

In one embodiment, $R^{23}$ is $C_{1-8}$ alkyl. In one embodiment, $R^{23}$ is $C_{1-6}$-alkyl. In one embodiment, $R^{23}$ is $C_{1-4}$ alkyl. In one embodiment, $R^{23}$ is methyl, ethyl, propyl, iso-propyl, butyl, sec-butyl, or tert-butyl. In one embodiment, $R^{23}$ is methyl, ethyl, propyl, iso-propyl, or butyl. In one embodiment, $R^{23}$ is methyl. In one embodiment, $R^{23}$ is ethyl. In one embodiment, $R^{23}$ is propyl. In one embodiment, $R^{23}$ is iso-propyl. In one embodiment, $R^{23}$ is butyl.

In one embodiment, E is Z-aryl optionally substituted with one to three $R^{24}$. In one embodiment, E is Z-phenyl optionally substituted with one to three $R^{24}$. In one embodiment, E is Z-phenyl optionally substituted with one $R^{24}$.

In one embodiment, E is Z-heteroaryl optionally substituted with one to three $R^{24}$. In one embodiment, E is Z-thiophenyl optionally substituted with one to three $R^{24}$.

In one embodiment, each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br. In one embodiment, each $R^{24}$ is independently selected from $C_{1-6}$ alkyl, —F, —Cl, and —Br. In one embodiment, each $R^{24}$ is independently selected from —F, —Cl, and —Br. In one embodiment, each $R^{24}$ is independently selected from —F and —Cl. In one embodiment, each $R^{24}$ is —F. In one embodiment, each $R^{24}$ is —Cl.

In one embodiment, D is Z-heteroarylene optionally substituted with one to three $R^{23}$, and E is Z-aryl optionally substituted with one to three $R^{24}$.

In one embodiment, D is Z-heteroarylene optionally substituted with one to three $R^{23}$, and E is Z-heteroaryl optionally substituted with one to three $R^{24}$.

In one embodiment, D is Z-heteroarylene optionally substituted with one to three $R^{23}$, wherein each $R^{23}$ is —H, $OR^7$, or $C_{1-8}$ alkyl, and E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br.

In one embodiment, D is Z-heteroarylene optionally substituted with one to three $R^{23}$, wherein each $R^{23}$ is —H, $OR^7$, or $C_{1-8}$ alkyl, and E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, and n is 1.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, and n is 2.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, and n is 1.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, and n is 2.

In one embodiment, Z, in any compound being of Formula (II), is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 1, and Z is a single bond or $C_{1-4}$ alkylene.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 2, and Z is a single bond or $C_{1-4}$ alkylene.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 1, and Z is a single bond or $C_{1-4}$ alkylene.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 2, and Z is a single bond or $C_{1-4}$ alkylene.

In one embodiment, in any compound being of Formula (II), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is methyl. In one embodiment, $R^{19}$ is —$CH_2OH$.

In one embodiment, in any compound being of Formula (II), Q is selected from $CO_2H$, W, and $CO_2R^{20}$. In one embodiment, Q is $CO_2H$. In one embodiment, Q is W. In one embodiment, Q is $CO_2R^{20}$.

In one embodiment, in any compound being of Formula (II), $R^{19}$ is selected from methyl, ethyl, propyl, iso-propyl, butyl, sec-butyl, and tert-butyl, optionally substituted with one —Z—$OR^7$, and Q is selected from $CO_2H$, W, and $CO_2R^{20}$.

In one embodiment, in any compound being of Formula (II), $R^{19}$ is selected from methyl, ethyl, propyl, iso-propyl, butyl, sec-butyl, and tert-butyl and Q is selected from $CO_2H$, W, and $CO_2R^{20}$.

In one embodiment, in any compound being of Formula (II), $R^{19}$ is methyl, and Q is selected from $CO_2H$, W, and $CO_2R^{20}$.

In one embodiment, in any compound being of Formula (II), $R^{19}$ is —$CH_2OH$, and Q is selected from $CO_2H$, W, and $CO_2R^{20}$.

In one embodiment, in any compound being of Formula (II), $R^{19}$ is selected from methyl, ethyl, propyl, iso-propyl, butyl, sec-butyl, and tert-butyl, optionally substituted with one —Z—$OR^7$, and Q is $CO_2H$.

In one embodiment, in any compound being of Formula (II), $R^{19}$ is selected from methyl, ethyl, propyl, iso-propyl, butyl, sec-butyl, and tert-butyl and Q is $CO_2H$.

In one embodiment, in any compound being of Formula (II), $R^{19}$ is methyl, and Q is $CO_2H$.

In one embodiment, in any compound being of Formula (II), $R^{19}$ is —$CH_2OH$, and Q is $CO_2H$.

In one embodiment, in any compound being of Formula (II), $R^{19}$ is selected from methyl, ethyl, propyl, iso-propyl, butyl, sec-butyl, and tert-butyl, optionally substituted with one —Z—$OR^7$, and Q is W.

In one embodiment, in any compound being of Formula (II), $R^{19}$ is selected from methyl, ethyl, propyl, iso-propyl, butyl, sec-butyl, and tert-butyl and Q is W.

In one embodiment, in any compound being of Formula (II), $R^{19}$ is methyl, and Q is W.

In one embodiment, in any compound being of Formula (II), $R^{19}$ is —$CH_2OH$, and Q is W.

In one embodiment, in any compound being of Formula (II), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (II), $R^{19}$ is selected from methyl, ethyl, propyl, iso-propyl, butyl, sec-butyl, and tert-butyl and Q is $CO_2R^{20}$.

In one embodiment, in any compound being of Formula (II), $R^{19}$ is methyl, and Q is $CO_2R^{20}$.

In one embodiment, in any compound being of Formula (II), $R^{19}$ is —$CH_2OH$, and Q is $CO_2R^{20}$.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, D is Z-heteroarylene optionally substituted with one to three $R^{23}$, wherein each $R^{23}$ is —H, $OR^7$, or $C_{1-8}$ alkyl, E is Z-aryl optionally substituted with one to three $R^{24}$, wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, D is Z-heteroarylene optionally substituted with one to three $R^{23}$, wherein each $R^{23}$ is —H, $OR^7$, or $C_{1-8}$ alkyl, E is Z-heteroaryl optionally substituted with one to three $R^{24}$ wherein each $R^{24}$ is independently selected from $C_{1-6}$ alkyl, $C_{1-4}$ fluoroalkyl, $C_{1-4}$ hydroxyalkyl, $C_{1-4}$ alkoxy, —F, —Cl, and —Br, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, the present application relates to a compound being of Formula (I), further being of Formula (III):

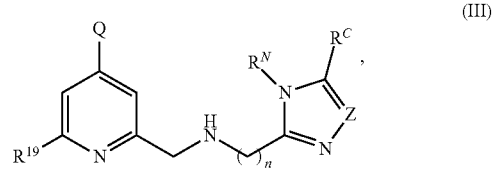

or a pharmaceutically acceptable salt, or solvate or prodrug thereof, wherein:

Z is N or $CR^Z$;

$R^N$, $R^C$, and $R^Z$ are each independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$;

n is 1 or 2; and

Q, $R^{19}$, $R^4$, $R^5$, $R^6$, $R^7$, and Z are as defined above.

In one embodiment, Z is N. In one embodiment, Z is $CR^Z$.

In one embodiment, $R^N$ is selected from $C_{1-6}$ alkyl, $C_{1-4}$ fluoroalkyl, $C_{2-6}$ alkenyl, —Z-aryl, and —Z-heteroaryl.

In one embodiment, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$.

In one embodiment, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$.

In one embodiment, n is 1. In one embodiment, n is 2.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, and n is 1.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, and n is 2.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, and n is 1.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, and n is 2.

In one embodiment, Z, in any compound being of Formula (III), is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, n is 1, and Z is a single bond or $C_{1-4}$ alkylene.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, n is 2, and Z is a single bond or $C_{1-4}$ alkylene.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, n is 1, and Z is a single bond or $C_{1-4}$ alkylene.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, n is 2, and Z is a single bond or $C_{1-4}$ alkylene.

In one embodiment, in any compound being of Formula (III), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is methyl. In one embodiment, $R^{19}$ is —$CH_2OH$.

In one embodiment, in any compound being of Formula (III), Q is selected from $CO_2H$, W, and $CO_2R^{20}$. In one embodiment, Q is $CO_2H$. In one embodiment, Q is W. In one embodiment, Q is $CO_2R^{20}$.

In one embodiment, in any compound being of Formula (III), $R^{19}$ is selected from methyl, ethyl, propyl, iso-propyl, butyl, sec-butyl, and tert-butyl, optionally substituted with one —Z—$OR^7$, and Q is selected from $CO_2H$, W, and $CO_2R^{20}$.

In one embodiment, in any compound being of Formula (III), $R^{19}$ is selected from methyl, ethyl, propyl, iso-propyl, butyl, sec-butyl, and tert-butyl and Q is selected from $CO_2H$, W, and $CO_2R^{20}$.

In one embodiment, in any compound being of Formula (III), $R^{19}$ is methyl, and Q is selected from $CO_2H$, W, and $CO_2R^{20}$.

In one embodiment, in any compound being of Formula (III), $R^{19}$ is —$CH_2OH$, and Q is selected from $CO_2H$, W, and $CO_2R^{20}$.

In one embodiment, in any compound being of Formula (III), $R^{19}$ is selected from methyl, ethyl, propyl, iso-propyl, butyl, sec-butyl, and tert-butyl, optionally substituted with one —Z—$OR^7$, and Q is $CO_2H$.

In one embodiment, in any compound being of Formula (III), $R^{19}$ is selected from methyl, ethyl, propyl, iso-propyl, butyl, sec-butyl, and tert-butyl and Q is $CO_2H$.

In one embodiment, in any compound being of Formula (III), $R^{19}$ is methyl, and Q is $CO_2H$.

In one embodiment, in any compound being of Formula (III), $R^{19}$ is —$CH_2OH$, and Q is $CO_2H$.

In one embodiment, in any compound being of Formula (III), $R^{19}$ is selected from methyl, ethyl, propyl, iso-propyl, butyl, sec-butyl, and tert-butyl, optionally substituted with one —Z—$OR^7$, and Q is W.

In one embodiment, in any compound being of Formula (III), $R^{19}$ is selected from methyl, ethyl, propyl, iso-propyl, butyl, sec-butyl, and tert-butyl and Q is W.

In one embodiment, in any compound being of Formula (III), $R^{19}$ is methyl, and Q is W.

In one embodiment, in any compound being of Formula (III), $R^{19}$ is —$CH_2OH$, and Q is W.

In one embodiment, in any compound being of Formula (III), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (III), $R^{19}$ is selected from methyl, ethyl, propyl, iso-propyl, butyl, sec-butyl, and tert-butyl and Q is $CO_2R^{20}$.

In one embodiment, in any compound being of Formula (III), $R^{19}$ is methyl, and Q is $CO_2R^{20}$.

In one embodiment, in any compound being of Formula (III), $R^{19}$ is —$CH_2OH$, and Q is $CO_2R^{20}$.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, Z is N, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, Z is $CR^Z$, $R^N$ is selected from $C_{1-6}$ alkyl, $C_{1-4}$ fluoroalkyl, $C_{2-6}$ alkenyl, —Z-aryl, and, —Z-heteroaryl, $R^C$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, and —Z—$SR^7$, $R^Z$ is selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, and —Z—$COOR^7$, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, the present application relates to a compound being of Formula (I), further being of Formula (IV):

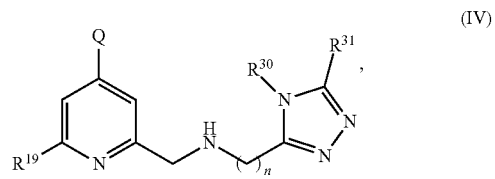

(IV)

or a pharmaceutically acceptable salt, or solvate or prodrug thereof, wherein:

$R^{30}$ and $R^{31}$ are independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; and n is 1 or 2; and Q, $R^{19}$, $R^4$, $R^5$, $R^6$, $R^7$, and Z are as defined above.

In one embodiment, $R^{30}$ is —H, $C_{1-6}$ alkyl, $C_{1-4}$ fluoroalkyl, $C_{1-4}$ hydroxyalkyl, $C_{3-10}$ cycloalkyl, —Z-heterocyclyl, —Z-aryl, or —Z-heteroaryl, wherein the heterocyclyl is optionally substituted with one or more $R^4$, and wherein the heteroaryl and aryl are optionally substituted with one or more $R^5$.

In one embodiment, $R^{30}$ is $C_{1-6}$ alkyl, —Z-aryl, or —Z-heteroaryl, wherein the heteroaryl and aryl are optionally substituted with one or more $R^5$.

In one embodiment, $R^{30}$ is $C_{1-6}$ alkyl.

In one embodiment, $R^{30}$ is —Z-aryl or —Z-heteroaryl, each optionally substituted with one or more $R^5$.

In one embodiment, $R^{30}$ is —Z-aryl optionally substituted with one or more $R^5$. In one embodiment, $R^{30}$ is —Z-phenyl optionally substituted with one or more $R^5$. In one embodiment, $R^{30}$ is —Z-phenyl optionally substituted with one or more —F or —Cl. In one embodiment, $R^{30}$ is —Z-phenyl optionally substituted with one or more —F. In one embodiment, $R^{30}$ is —Z-phenyl optionally substituted with one —F. In one embodiment, $R^{30}$ is —Z-phenyl optionally substituted with one or more —Cl. In one embodiment, $R^{30}$ is —Z-phenyl optionally substituted with one —Cl. In one embodiment, $R^{30}$ is —Z-phenyl optionally substituted with two —Cl.

In one embodiment, $R^{30}$ is —Z-heteroaryl, optionally substituted with one or more $R^5$.

In one embodiment, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$.

In one embodiment, $R^{31}$ is —H, $C_{1-6}$ alkyl, $C_{1-4}$ hydroxyalkyl, $C_{3-10}$ cycloalkyl, —Z-aryl, —Z-heteroaryl, —Z—$NR^6R^7$, —Z—$OR^7$, or —Z—$SR^7$.

In one embodiment, $R^{31}$ is —H.

In one embodiment, $R^{31}$ is $C_{1-6}$ alkyl. In one embodiment, $R^{31}$ is methyl. In one embodiment, $R^{31}$ is ethyl. In one embodiment, $R^{31}$ is propyl.

In one embodiment, $R^{31}$ is $C_{2-6}$ alkenyl.

In one embodiment, $R^{31}$ is $C_{1-4}$ hydroxyalkyl.

In one embodiment, $R^{31}$ is $C_{3-10}$ cycloalkyl. In one embodiment, $R^{31}$ is $C_{3-6}$ cycloalkyl. In one embodiment, $R^{31}$ is cyclopropyl. In one embodiment, $R^{31}$ is cyclobutyl.

In one embodiment, $R^{31}$ is —Z-aryl, —Z-heteroaryl, —Z—$NR^6R^7$, —Z—$OR^7$, or —Z—$SR^7$.

In one embodiment, $R^{31}$ is —Z-aryl.

In one embodiment, $R^{31}$ is —Z-heteroaryl.

In one embodiment, $R^{31}$ is —Z—$NR^6R^7$.

In one embodiment, $R^{31}$ is —Z—$OR^7$.

In one embodiment, $R^{31}$ is —Z—$SR^7$.

In one embodiment, n is 1. In one embodiment, n is 2.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, and n is 1.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, and n is 2.

In one embodiment, Z, in any compound being of Formula (IV), is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 1, and Z is a single bond or $C_{1-4}$ alkylene.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 2, and Z is a single bond or $C_{1-4}$ alkylene.

In one embodiment, $R^{30}$ is —Z-aryl, wherein aryl is optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 1, and Z is a single bond or $C_{1-4}$ alkylene.

In one embodiment, $R^{30}$ is —Z-aryl, wherein aryl is optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 2, and Z is a single bond or $C_{1-4}$ alkylene.

In one embodiment, in any compound being of Formula (IV), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is methyl. In one embodiment, $R^{19}$ is —$CH_2OH$.

In one embodiment, in any compound being of Formula (IV), Q is selected from $CO_2H$, W, and $CO_2R^{20}$. In one embodiment, Q is $CO_2H$. In one embodiment, Q is W. In one embodiment, Q is $CO_2R^{20}$.

In one embodiment, in any compound being of Formula (IV), $R^{19}$ is selected from methyl, ethyl, propyl, iso-propyl, butyl, sec-butyl, and tert-butyl, optionally substituted with one —Z—$OR^7$, and Q is selected from $CO_2H$, W, and $CO_2R^{20}$.

In one embodiment, in any compound being of Formula (IV), $R^{19}$ is selected from methyl, ethyl, propyl, iso-propyl, butyl, sec-butyl, and tert-butyl and Q is selected from $CO_2H$, W, and $CO_2R^{20}$.

In one embodiment, in any compound being of Formula (IV), $R^{19}$ is methyl, and Q is selected from $CO_2H$, W, and $CO_2R^{20}$.

In one embodiment, in any compound being of Formula (IV), $R^{19}$ is —$CH_2OH$, and Q is selected from $CO_2H$, W, and $CO_2R^{20}$.

In one embodiment, in any compound being of Formula (IV), $R^{19}$ is selected from methyl, ethyl, propyl, iso-propyl, butyl, sec-butyl, and tert-butyl, optionally substituted with one —Z—$OR^7$, and Q is $CO_2H$.

In one embodiment, in any compound being of Formula (IV), $R^{19}$ is selected from methyl, ethyl, propyl, iso-propyl, butyl, sec-butyl, and tert-butyl and Q is $CO_2H$.

In one embodiment, in any compound being of Formula (IV), $R^{19}$ is methyl, and Q is $CO_2H$.

In one embodiment, in any compound being of Formula (IV), $R^{19}$ is —$CH_2OH$, and Q is $CO_2H$.

In one embodiment, in any compound being of Formula (IV), $R^{19}$ is selected from methyl, ethyl, propyl, iso-propyl, butyl, sec-butyl, and tert-butyl, optionally substituted with one —Z—$OR^7$, and Q is W.

In one embodiment, in any compound being of Formula (IV), $R^{19}$ is selected from methyl, ethyl, propyl, iso-propyl, butyl, sec-butyl, and tert-butyl and Q is W.

In one embodiment, in any compound being of Formula (IV), $R^{19}$ is methyl, and Q is W.

In one embodiment, in any compound being of Formula (IV), $R^{19}$ is —$CH_2OH$, and Q is W.

In one embodiment, in any compound being of Formula (IV), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (IV), $R^{19}$ is selected from methyl, ethyl, propyl, iso-propyl, butyl, sec-butyl, and tert-butyl and Q is $CO_2R^{20}$.

In one embodiment, in any compound being of Formula (IV), $R^{19}$ is methyl, and Q is $CO_2R^{20}$.

In one embodiment, in any compound being of Formula (IV), $R^{19}$ is —$CH_2OH$, and Q is $CO_2R^{20}$.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, $R^{30}$ is $C_{1-6}$ alkyl, —Z-aryl, or —Z-heteroaryl, wherein the heteroaryl and aryl are optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, $R^{30}$ is —Z-aryl, wherein aryl is optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 1, Z is a single bond or $C_{1-4}$ alkylene, Q is selected from $CO_2H$, W, and $CO_2R^{20}$, and $R^{19}$ is selected from methyl and —$CH_2OH$.

In one embodiment, $R^{30}$ is —Z-aryl, wherein aryl is optionally substituted with one or more $R^5$, $R^{31}$ is independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$OR^7$, halogen, and —Z—$SR^7$, wherein the heterocyclyl is optionally substituted with one or more $R^4$, and wherein the heteroaryl and aryl are optionally substituted with one or more $R^5$, n is 2, Z is a single bond or $C_{1-4}$ alkylene, Q is selected from $CO_2H$, W, and $CO_2R^{20}$, and $R^{19}$ is selected from methyl and —$CH_2OH$.

In one embodiment, the present application relates to a compound being of Formula (I), further being of Formula (V):

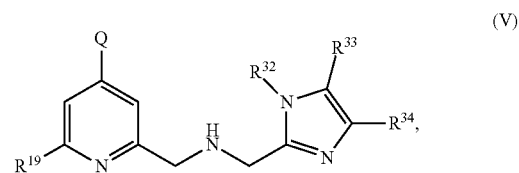

or a pharmaceutically acceptable salt, or solvate or prodrug thereof, wherein:

$R^{32}$, $R^{33}$, and $R^{34}$ are independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; and Q, $R^{19}$, $R^4$, $R^5$, $R^6$, $R^7$, and Z are as defined above.

In one embodiment, $R^{32}$ is $C_{1-6}$ alkyl, $C_{1-4}$ fluoroalkyl, $C_{2-6}$ alkenyl, —Z-aryl, or —Z-heteroaryl.

In one embodiment, $R^{33}$ is —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z—$NR^6R^7$, —Z—C(=O)—$NR^6R^7$, —Z—$NR^6$—C(=O)—$R^7$, or —Z—$SR^7$.

In one embodiment, $R^{34}$ is —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z—C(=O)—$R^7$, or —Z—$COOR^7$.

In one embodiment, $R^{32}$ is $C_{1-6}$ alkyl and $R^{33}$ and $R^{34}$ are both —H.

In one embodiment, $R^{32}$ is $C_{2-6}$ alkenyl and $R^{33}$ and $R^{34}$ are both —H.

In one embodiment, $R^{32}$ is —Z-aryl and $R^{33}$ and $R^{34}$ are both —H.

In one embodiment, $R^{32}$ is —Z-heteroaryl and $R^{33}$ and $R^{34}$ are both —H.

In one embodiment, $R^{32}$ is —Z-aryl, $R^{33}$ is $C_{1-6}$ alkyl, $C_{2-6}$ alkenyl, or $C_{1-4}$ hydroxyalkyl, and $R^{34}$ is —H.

In one embodiment, $R^{32}$ is —Z-aryl, and $R^{33}$ and $R^{34}$ are each $C_{1-6}$ alkyl.

In one embodiment, Z, in any compound being of Formula (V), is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, $R^{32}$ is $C_{1-6}$ alkyl, $R^{33}$ and $R^{34}$ are both —H, and Z is $C_{1-4}$ alkylene.

In one embodiment, $R^{32}$ is $C_{1-6}$ alkyl, $R^{33}$ and $R^{34}$ are both —H, and Z is a single bond.

In one embodiment, $R^{32}$ is $C_{2-6}$ alkenyl, $R^{33}$ and $R^{34}$ are both —H, and Z is $C_{1-4}$ alkylene.

In one embodiment, $R^{32}$ is $C_{2-6}$ alkenyl, $R^{33}$ and $R^{34}$ are both —H, and Z is a single bond.

In one embodiment, $R^{32}$ is —Z-aryl, $R^{33}$ and $R^{34}$ are both —H, and Z is $C_{1-4}$ alkylene.

In one embodiment, $R^{32}$ is —Z-aryl, $R^{33}$ and $R^{34}$ are both —H, and Z is a single bond.

In one embodiment, $R^{32}$ is —Z-heteroaryl, $R^{33}$ and $R^{34}$ are both —H, and Z is $C_{1-4}$ alkylene.

In one embodiment, $R^{32}$ is —Z-heteroaryl, $R^{33}$ and $R^{34}$ are both —H, and Z is a single bond.

In one embodiment, $R^{32}$ is —Z-aryl, $R^{33}$ is $C_{1-6}$ alkyl, $C_{2-6}$ alkenyl, or $C_{1-4}$ hydroxyalkyl, $R^{34}$ is —H, and Z is $C_{1-4}$ alkylene.

In one embodiment, $R^{32}$ is —Z-aryl, $R^{33}$ is $C_{1-6}$ alkyl, $C_{2-6}$ alkenyl, or $C_{1-4}$ hydroxyalkyl, $R^{34}$ is —H, and Z is a single bond.

In one embodiment, $R^{32}$ is —Z-aryl, $R^{33}$ and $R^{34}$ are each $C_{1-6}$ alkyl, and Z is $C_{1-4}$ alkylene.

In one embodiment, $R^{32}$ is —Z-aryl, $R^{33}$ and $R^{34}$ are each $C_{1-6}$ alkyl, and Z is a single bond.

In one embodiment, in any compound being of Formula (V), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is methyl. In one embodiment, $R^{19}$ is —$CH_2OH$.

In one embodiment, in any compound being of Formula (V), Q is selected from $CO_2H$, W, and $CO_2R^{20}$. In one embodiment, Q is $CO_2H$. In one embodiment, Q is W. In one embodiment, Q is $CO_2R^{20}$.

In one embodiment, in any compound being of Formula (V), $R^{19}$ is selected from methyl, ethyl, propyl, iso-propyl, butyl, sec-butyl, and tert-butyl, optionally substituted with one —Z—$OR^7$, and Q is selected from $CO_2H$, W, and $CO_2R^{20}$.

In one embodiment, in any compound being of Formula (V), $R^{19}$ is selected from methyl, ethyl, propyl, iso-propyl, butyl, sec-butyl, and tert-butyl and Q is selected from $CO_2H$, W, and $CO_2R^{20}$.

In one embodiment, in any compound being of Formula (V), $R^{19}$ is methyl, and Q is selected from $CO_2H$, W, and $CO_2R^{20}$.

In one embodiment, in any compound being of Formula (V), $R^{19}$ is —$CH_2OH$, and Q is selected from $CO_2H$, W, and $CO_2R^{20}$.

In one embodiment, in any compound being of Formula (V), $R^{19}$ is selected from methyl, ethyl, propyl, iso-propyl, butyl, sec-butyl, and tert-butyl, optionally substituted with one —Z—$OR^7$, and Q is $CO_2H$.

In one embodiment, in any compound being of Formula (V), $R^{19}$ is selected from methyl, ethyl, propyl, iso-propyl, butyl, sec-butyl, and tert-butyl and Q is $CO_2H$.

In one embodiment, in any compound being of Formula (V), $R^{19}$ is methyl, and Q is $CO_2H$.

In one embodiment, in any compound being of Formula (V), $R^{19}$ is —$CH_2OH$, and Q is $CO_2H$.

In one embodiment, in any compound being of Formula (V), $R^{19}$ is selected from methyl, ethyl, propyl, iso-propyl, butyl, sec-butyl, and tert-butyl, optionally substituted with one —Z—$OR^7$, and Q is W.

In one embodiment, in any compound being of Formula (V), $R^{19}$ is selected from methyl, ethyl, propyl, iso-propyl, butyl, sec-butyl, and tert-butyl and Q is W.

In one embodiment, in any compound being of Formula (V), $R^{19}$ is methyl, and Q is W.

In one embodiment, in any compound being of Formula (V), $R^{19}$ is —$CH_2OH$, and Q is W.

In one embodiment, in any compound being of Formula (V), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (V), $R^{19}$ is selected from methyl, ethyl, propyl, iso-propyl, butyl, sec-butyl, and tert-butyl and Q is $CO_2R^{20}$.

In one embodiment, in any compound being of Formula (V), $R^{19}$ is methyl, and Q is $CO_2R^{20}$.

In one embodiment, in any compound being of Formula (V), $R^{19}$ is —$CH_2OH$, and Q is $CO_2R^{20}$.

In one embodiment, $R^{32}$ is $C_{1-6}$ alkyl, $R^{33}$ and $R^{34}$ are both —H, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is $C_{1-6}$ alkyl, $R^{33}$ and $R^{34}$ are both —H, Z is a single bond, Q is selected from $CO_2H$, W, and $CO_2R^{20}$, and $R^{19}$ is selected from methyl and —$CH_2OH$.

In one embodiment, $R^{32}$ is $C_{2-6}$ alkenyl, $R^{33}$ and $R^{34}$ are both —H, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is $C_{2-6}$ alkenyl, $R^{33}$ and $R^{34}$ are both —H, Z is a single bond, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ and $R^{34}$ are both —H, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ and $R^{34}$ are both —H, Z is a single bond, Q is selected from $CO_2H$, W, and $CO_2R^{20}$, and $R^{19}$ is selected from methyl and —$CH_2OH$.

In one embodiment, $R^{32}$ is —Z-heteroaryl, $R^{33}$ and $R^{34}$ are both —H, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is —Z-heteroaryl, $R^{33}$ and $R^{34}$ are both —H, Z is a single bond, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ is $C_{1-6}$ alkyl, $C_{2-6}$ alkenyl, or $C_{1-4}$ hydroxyalkyl, $R^{34}$ is —H, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ is $C_{1-6}$ alkyl, $C_{2-6}$ alkenyl, or $C_{1-4}$ hydroxyalkyl, $R^{34}$ is —H, Z is a single bond, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ and $R^{34}$ are each $C_{1-6}$ alkyl, Z is $C_{1-4}$ alkylene, Q is selected from $CO_2H$, W, and $CO_2R^{20}$, and $R^{19}$ is selected from methyl and —$CH_2OH$.

In one embodiment, $R^{32}$ is —Z-aryl, $R^{33}$ and $R^{34}$ are each $C_{1-6}$ alkyl, Z is a single bond, Q is selected from $CO_2H$, W, and $CO_2R^{20}$, and $R^{19}$ is selected from methyl and —$CH_2OH$.

In one embodiment, a compound of the application may be of Formula (VI):

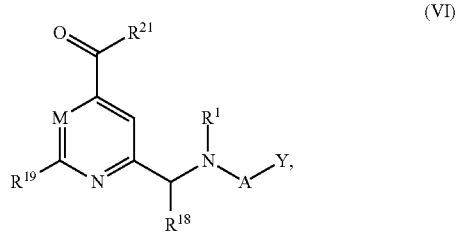

(VI)

or a pharmaceutically acceptable salt or solvate thereof,
wherein:
M is CH or N;
A is selected from —$C(R^2)_2C(O)$—, —$C(R^2)_2C(R^2)_2C(O)$—, $C_{3-10}$ alkyl, —Z—$C_{3-10}$ cycloalkylene, —Z-heterocyclylene, —Z-heteroarylene and —Z-arylene, wherein the $C_{3-10}$ alkyl, —Z-cycloalkylene, —Z-heterocyclylene, —Z-heteroarylene and —Z-arylene are optionally substituted with one or more $R^3$, or A and Y form a $C_{3-10}$ cycloalkyl or heterocyclic ring;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, wherein the alkyl, alkenyl, alkynyl, cycloalkyl, heterocyclyl, heteroaryl and aryl are optionally substituted with one or more $R^3$;

$R^1$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —$NR^6R^7$, —F and $C_{3-6}$ cycloalkyl; or $R^1$, together with A-Y and the nitrogen atom to which it is attached, forms a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl; or $R^1$ and $R^{18}$, together with the atoms to which they are attached, form a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl;

Each $R^2$ is independently selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—$NR^6R^7$, —Z—$C(=O)$—$NR^6R^7$, —Z—$NR^6$—$C(=O)$—$R^7$, —Z—$C(=O)$—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; or two $R^2$ substituents on adjacent carbon atoms, together with the carbon atoms to which they are attached, form a $C_{4-10}$ cycloalkyl or heterocyclic ring; or two $R^2$ substituents on the same carbon atom, together with the carbon atom to which they are attached, form a $C_{3-10}$ cycloalkyl or heterocyclic ring; or $R^2$ and Y, together with the carbon atoms to which they are attached, form a $C_{4-10}$ cycloalkyl or heterocyclic ring;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—$C(=O)$—$NR^6R^7$, —Z—$NR^6$—$C(=O)$—$R^7$, —Z—$C(=O)$—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; or two $R^3$ on the same carbon atom may, together with the carbon atom to which they are attached, form a $C_{3-10}$ cycloalkyl or heterocyclic ring;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—$NR^6R^7$, —Z—$C(=O)$—$NR^6R^7$, —Z—$NR^6$—$C(=O)$—$R^7$, —Z—$C(=O)$—$R^7$, —Z—$C(=O)$—H, —$OR^7$, halogen, —$SR^7$, —$SOR^7$, —$SO_2R^7$, —$SO_2NR^6R^7$, and —$COOR^7$;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, —Z—$NR^6R^7$, —Z—$C(=O)$—$NR^6R^7$, —Z—$NR^6$—$C(=O)$—$R^7$, —Z—$C(=O)$—$R^7$, —Z—$C(=O)$—H, —$OR^7$, —$SR^7$, —$SOR^7$, —$SO_2R^7$, —$SO_2NR^6R^7$, and —$COOR^7$;

each $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, wherein the alkyl, alkenyl, alkynyl, cycloalkyl, heterocyclyl, heteroaryl and aryl are optionally substituted with one or more $R^8$; or $R^6$ and $R^7$ may, together with the N-atom to which they are attached, form a heterocyclic ring optionally substituted with one or more $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—$C(O)$—$NR^{10}R^{11}$, —Z—$OR^9$, halogen, —CN, —Z—$SR^9$, —Z—$SOR^9$, —Z—$SO_2R^9$ and —Z—$COOR^9$, wherein the alkyl, alkenyl, alkynyl, cycloalkyl, heterocyclyl, heteroaryl and aryl are optionally substituted with one or more substituents independently selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—$C(=O)$—$NR^{10}R^{11}$, —Z—$OR^9$, halogen, —CN, —Z—$SR^9$, —Z—$SOR^9$, —Z—$SO_2R^9$ and —Z—$COOR^9$; wherein the heterocyclyl is optionally substituted with one or more $R^4$ and wherein the heteroaryl and aryl are optionally substituted with one or more $R^5$;

each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the heterocyclyl is optionally substituted with one or more $R^4$ and wherein the heteroaryl and aryl are optionally substituted with one or more $R^5$;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and $C_{6-14}$ aryl, wherein the heterocyclyl is optionally substituted with one or more $R^4$ and wherein the heteroaryl and aryl are optionally substituted with one or more $R^5$; or $R^{10}$ and $R^{11}$ may, together with the N-atom to which they are attached, form a 5- to 7-membered heterocyclic ring optionally substituted with one or more $R^4$;

$R^{18}$ is selected from —H, $C_{1-6}$ alkyl, $C_{1-6}$ fluoroalkyl, $C_{1-6}$ hydroxyalkyl, $C_{2-7}$ alkenyl, $C_{2-7}$ alkynyl, $C_{3-7}$ cycloalkyl, and $C_{3-7}$ oxyalkyl; or $R^{18}$ and A, together with the atoms to which they are attached, form a heterocyclic ring; or $R^{18}$ and Y, together with the atoms to which they are attached, form a heterocyclic ring; or $R^{18}$ and $R^1$, together with the atoms to which they are attached, form a heterocyclic ring;

$R^{19}$ is selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from aryl, $C_{1-6}$ alkoxy, heteroaryl, aryloxy, heteroaryloxy, $C_{3-6}$ cycloalkyl, —Z—heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, halogen, —Z—$SR^7$, —Z—$SOR^7$, —Z—$SO_2R^7$, —Z—$SO_2NR^6R^7$ and —Z—$COOR^7$; and may optionally form a cyclophane structure by attaching to Y or A; and wherein:

$R^{21}$ is $(R^{22})_2N$— or $R^{22}O$, wherein $R^{22}$ is $C_{1-8}$ alkyl, $C_{2-8}$ alkenyl, $C_{2-8}$ alkynyl, $C_{3-10}$ cycloalkyl, and aryloxy optionally substituted with one or more substituents independently selected from —OH, aryl, $C_{1-6}$ alkoxy, heteroaryl, aryloxy, heteroaryloxy, —F, a sulfonamide moiety, and $C_{3-6}$ cycloalkyl; wherein one $R^{22}$ in $(R^{22})_2N$— is optionally —H.

In one embodiment, a compound of the application may be of Formula (VI), wherein:

M is CH or N;

A is selected from —$C(R^2)_2C(O)$—, —$C(R^2)_2C(R^2)_2C(O)$—, $C_{3-10}$ alkyl, —Z—$C_{3-10}$ cycloalkylene, —Z-heterocyclylene, —Z-heteroarylene and —Z-arylene, wherein the $C_{3-10}$ alkyl, —Z-cycloalkylene, —Z-heterocyclylene, —Z-heteroarylene and —Z-arylene are optionally substituted with one or more $R^3$, or A and Y form a $C_{3-10}$ cycloalkyl or $C_{5-10}$ heterocyclic ring;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, $C_{5-10}$ heterocyclyl, $C_{5-14}$ heteroaryl and $C_{6-14}$ aryl, wherein the alkyl, alkenyl, alkynyl, cycloalkyl, heterocyclyl, heteroaryl and aryl are optionally substituted with one or more $R^3$;

$R^1$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —$NR^6R^7$, —F and $C_{3-6}$ cycloalkyl; or $R^1$, together with A-Y forms a nitrogen-containing $C_{5-10}$ heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl; or $R^1$ and $R^{18}$ together form a nitrogen-containing $C_{5-10}$ heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl;

$R^2$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; or two $R^2$ substituents form a $C_{3-10}$ cycloalkyl or $C_{5-10}$ heterocyclic ring; or $R^2$ and Y form a $C_{3-10}$ cycloalkyl or $C_{5-10}$ heterocyclic ring;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; or two $R^3$ on the same carbon atom may together form a spiro group;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—$NR^6R^7$, —Z—C(=O)—$NR^6R^7$, —Z—$NR^6$—C(=O)—$R^7$, —Z—C(=O)—$R^7$, —Z—C(=O)—H, —$OR^7$, halogen, —$SR^7$, —$SOR^7$, —$SO_2R^7$, —$SO_2NR^6R^7$, and —$COOR^7$;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, —Z—$NR^6R^7$, —Z—C(=O)—$NR^6R^7$, —Z—$NR^6$—C(=O)—$R^7$, —Z—C(=O)—$R^7$, —Z—C(=O)—H, —$OR^7$, —$SR^7$, —$SOR^7$, —$SO_2R^7$, —$SO_2NR^6R^7$, and —$COOR^7$;

each $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, wherein the alkyl, alkenyl, alkynyl, cycloalkyl, heterocyclyl, heteroaryl and aryl are optionally substituted with one or more $R^8$; or $R^6$ and $R^7$ may, together with the N-atom to which they are attached, form a $C_{5-10}$ heterocyclic ring optionally substituted with one or more $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(O)—$NR^{10}R^{11}$, —Z—$OR^9$, halogen, —CN, —Z—$SR^9$, —Z—$SOR^9$, —Z—$SO_2R^9$ and —Z—$COOR^9$, wherein the alkyl, alkenyl, alkynyl, cycloalkyl, heterocyclyl, heteroaryl and aryl are optionally substituted with one or more substituents independently selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein the heterocyclyl is optionally substituted with one or more $R^4$ and wherein the heteroaryl and aryl are optionally substituted with one or more $R^5$;

each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z- heteroaryl, wherein the heterocyclyl is optionally substituted with one or more $R^4$ and wherein the heteroaryl and aryl are optionally substituted with one or more $R^5$;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, $C_{5-10}$ heterocyclyl, $C_{5-10}$ heteroaryl, and $C_{6-14}$ aryl, wherein the heterocyclyl is optionally substituted with one or more $R^4$ and wherein the heteroaryl and aryl are optionally substituted with one or more $R^5$; or $R^{10}$ and $R^{11}$ may, together with the N-atom to which they are attached, form a 5- to 7-membered heterocyclic ring optionally substituted with one or more $R^4$;

$R^{18}$ is selected from —H, $C_{1-6}$ alkyl, $C_{1-6}$ fluoroalkyl, $C_{1-6}$ hydroxyalkyl, $C_{2-7}$ alkenyl, $C_{2-7}$ alkynyl, $C_{3-7}$ cycloalkyl, and $C_{3-7}$ oxyalkyl; or $R^{18}$ and A form a $C_{3-10}$ cycloalkyl or $C_{5-10}$ heterocyclic ring; or $R^{18}$ and Y form a $C_{3-10}$ cycloalkyl or $C_{5-10}$ heterocyclic ring; or $R^{18}$ and $R^1$ form a $C_{3-10}$ cycloalkyl or $C_{5-10}$ heterocyclic ring;

$R^{19}$ is selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from aryl, $C_{1-6}$ alkoxy, heteroaryl, aryloxy, heteroaryloxy, $C_{3-6}$ cycloalkyl, —Z—heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; and may optionally form a cyclophane structure by attaching to Y or A; and wherein $R^{21}$ is $(R^{22})_2N$— or $R^{22}O$, where each $R^{22}$ independently may be consistent with any of the examples of prodrugs provided herein. In particular, each $R^{22}$ independently may be selected from $C_{1-8}$ alkyl, $C_{2-8}$ alkenyl, $C_{2-8}$ alkynyl, $C_{3-10}$ cycloalkyl, and aryloxy wherein the alkyl, alkenyl, alkynyl, cycloalkyl and aryloxy may be optionally substituted with one or more substituents independently selected from —OH, aryl, $C_{1-6}$ alkoxy, heteroaryl, aryloxy, heteroaryloxy, —F, a sulfonamide moiety, and $C_{3-6}$ cycloalkyl; and one $R^{22}$ in $(R^{22})_2N$— may be, and preferably is, —H.

In one embodiment, in any compound being of Formula (VI), M is CH.

In one embodiment, in any compound being of Formula (VI), M is N.

In one embodiment, in any compound being of Formula (VI), A is selected from —Z-heterocyclylene, —Z-arylene, and —Z-heteroarylene. In one embodiment, A is selected from —Z-heterocyclylene, —C(R²)₂C(O)—, and —Z-heteroarylene. In one embodiment, A is —Z-heteroarylene. In one embodiment, A is —Z-arylene.

In one embodiment, in any compound being of Formula (VI), Y is selected from —H, —$OR^7$, —$NR^6R^7$, $C_{1-8}$ alkyl, $C_{2-8}$ alkenyl, and $C_{2-8}$ alkynyl. In one embodiment, Y is selected from —H and $C_{1-8}$ alkyl. In one embodiment, Y is selected from —H and $C_{1-4}$ alkyl. In one embodiment, Y is selected from —H, methyl, ethyl, propyl, iso-propyl, butyl, sec-butyl and tert-butyl. In one embodiment, Y is —H. In one embodiment, Y is ethyl.

In one embodiment, in any compound being of Formula (VI), each $R^3$ is independently selected from —Z-heterocyclyl, —Z-aryl, and —Z-heteroaryl wherein the heterocyclyl is optionally substituted with one or more $R^4$, and the aryl, and heteroaryl are optionally substituted with one or more $R^5$. In one embodiment, $R^3$ is —Z-aryl optionally substituted with one or more $R^5$. In one embodiment, $R^3$ is phenyl optionally substituted with one or more $R^5$.

In one embodiment, in any compound being of Formula (VI), Z is selected from a single bond, $C_{1-4}$ alkylene, heterocyclylene and $C_{3-6}$ cycloalkylene. In one embodiment, Z is selected from a single bond and $C_{1-4}$ alkylene. In one embodiment, Z is selected from a single bond, methylene, ethylene, propylene and butylene. In one embodiment, Z is a single bond. In one embodiment, Z is methylene. In one embodiment, Z is ethylene. In one embodiment, Z is propylene. In one embodiment, Z is butylene.

In one embodiment, in any compound being of Formula (VI), $R^1$ is selected from —H, $C_{1-8}$ alkyl, $C_{2-8}$ alkenyl, and $C_{2-8}$ alkynyl. In one embodiment, $R^1$ is selected from —H and $C_{1-8}$ alkyl. In one embodiment, $R^1$ is selected from —H and $C_{1-4}$ alkyl. In one embodiment, $R^1$ is —H.

In one embodiment, in any compound being of Formula (VI), $R^{18}$ is selected from —H, $C_{1-6}$ alkyl, $C_{1-6}$ fluoroalkyl, $C_{1-6}$ hydroxyalkyl, $C_{2-7}$ alkenyl, and $C_{2-7}$ alkynyl. In one embodiment, $R^{18}$ is selected from —H and $C_{1-6}$ alkyl. In one embodiment, $R^{18}$ is —H.

In one embodiment, in any compound being of Formula (VI), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is methyl. In one embodiment, $R^{19}$ is —$CH_2OH$.

In one embodiment, $R^{21}$ is $(R^{22})_2N$—.

In one embodiment, $R^{21}$ is $(R^{22})_2N$—, and one $R^{22}$ is —H.

In one embodiment, $R^{21}$ is $(R^{22})_2N$—, one $R^{22}$ is —H, and the other $R^{22}$ is $C_{1-8}$ alkyl, $C_{2-8}$ alkenyl, $C_{2-8}$ alkynyl, or $C_{3-10}$ cycloalkyl.

In one embodiment, $R^{21}$ is $(R^{22})_2N$—, one $R^{22}$ is —H, and the other $R^{22}$ is $C_{1-8}$ alkyl or $C_{3-10}$ cycloalkyl. In one embodiment, $R^{21}$ is $(R^{22})_2N$—, one $R^{22}$ is —H, and the other $R^{22}$ is $C_{1-8}$ alkyl. In one embodiment, $R^{21}$ is $(R^{22})_2N$—, one $R^{22}$ is —H, and the other $R^{22}$ is $C_{3-10}$ cycloalkyl.

In one embodiment, $R^{21}$ is $R^{22}O$.

In one embodiment, $R^{22}$ is $C_{1-8}$ alkyl optionally substituted with one or more of —OH, aryl, $C_{1-6}$ alkoxy, heteroaryl, aryloxy, heteroaryloxy, —F, a sulfonamide moiety, and $C_{3-6}$ cycloalkyl.

In one embodiment, $R^{22}$ is $C_{1-8}$ alkyl optionally substituted with one or more —F.

In one embodiment, $R^{22}$ is methyl.
In one embodiment, $R^{22}$ is ethyl.
In one embodiment, $R^{22}$ is propyl.
In one embodiment, $R^{22}$ is 2-propyl.
In one embodiment, $R^{22}$ is butyl.
In one embodiment, $R^{22}$ is 2-butyl.
In one embodiment, $R^{22}$ is iso-butyl.
In one embodiment, $R^{22}$ is tert-butyl.
In one embodiment, $R^{22}$ is methyl, substituted with one or more —F.

In one embodiment, $R^{22}$ is ethyl, substituted with one or more —F.

In one embodiment, $R^{22}$ is propyl, substituted with one or more —F.

In one embodiment, $R^{22}$ is 2-propyl, substituted with one or more —F.

In one embodiment, $R^{22}$ is butyl, substituted with one or more —F.

In one embodiment, $R^{22}$ is 2-butyl, substituted with one or more —F.

In one embodiment, $R^{22}$ is iso-butyl, substituted with one or more —F.

In one embodiment, $R^{22}$ is tert-butyl, substituted with one or more —F.

In one embodiment, in any compound being of Formula (VI), $R^{19}$ is selected from methyl, ethyl, propyl, iso-propyl, butyl, sec-butyl, and tert-butyl, optionally substituted with one —Z—$OR^7$, and $R^{21}$ is $(R^{22})_2N$—.

In one embodiment, in any compound being of Formula (VI), $R^{19}$ is selected from methyl, ethyl, propyl, iso-propyl, butyl, sec-butyl, and tert-butyl and $R^{21}$ is $(R^{22})_2N$—.

In one embodiment, in any compound being of Formula (VI), $R^{19}$ is methyl, and $R^{21}$ is $(R^{22})_2N$—.

In one embodiment, in any compound being of Formula (VI), $R^{19}$ is —$CH_2OH$, and $R^{21}$ is $(R^{22})_2N$—.

In one embodiment, in any compound being of Formula (VI), $R^{19}$ is selected from methyl, ethyl, propyl, iso-propyl, butyl, sec-butyl, and tert-butyl, optionally substituted with one —Z—$OR^7$, and $R^{21}$ is $R^{22}O$.

In one embodiment, in any compound being of Formula (VI), $R^{19}$ is selected from methyl, ethyl, propyl, iso-propyl, butyl, sec-butyl, and tert-butyl and $R^{21}$ is $R^{22}O$.

In one embodiment, in any compound being of Formula (VI), $R^{19}$ is methyl, and $R^{21}$ is $R^{22}O$.

In one embodiment, in any compound being of Formula (VI), $R^{19}$ is —$CH_2OH$, and $R^{21}$ is $R^{22}O$.

In one embodiment, in any compound being of Formula (VI), $R^1$ is —H and $R^{18}$ is —H.

In one embodiment, in any compound being of Formula (VI), $R^1$ is —H, $R^{18}$ is —H, A is —Z-heteroarylene and Z is a single bond. In one embodiment, $R^1$ is —H, $R^{18}$ is —H, A is —Z-heteroarylene and Z is $C_{1-4}$ alkylene.

In one embodiment, in any compound being of Formula (VI), $R^1$ is —H, $R^{18}$ is —H and A is —Z-heteroarylene. In one embodiment, $R^1$ is —H, $R^{18}$ is —H, A is —Z-heteroarylene, and $R^3$ is —Z-aryl.

In one embodiment, in any compound being of Formula (VI), $R^1$ is —H, $R^{18}$ is —H, A is —Z-heteroarylene, $R^3$ is —Z-aryl and Y is —H. In one embodiment, $R^1$ is —H, $R^{18}$ is —H, A is —Z-heteroarylene, $R^3$ is —Z-aryl and Y is $C_{1-8}$ alkyl.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, and $R^{18}$ is —H.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, and Z is selected from a single bond and $C_{1-4}$ alkylene.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, and $R^{19}$ is methyl.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, and $R^{19}$ is —$CH_2OH$.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is methyl, and $R^{21}$ is $(R^{22})_2N$—.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is —$CH_2OH$, and $R^{21}$ is $(R^{22})_2N$—.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is methyl, and $R^{21}$ is $R^{22}O$.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is —$CH_2OH$, and $R^{21}$ is $R^{22}O$.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is methyl, and $R^{21}$ is $(R^{22})_2N$—, wherein one $R^{22}$ is —H, and the other $R^{22}$ is $C_{1-8}$ alkyl or $C_{3-10}$ cycloalkyl.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is —$CH_2OH$, and $R^{21}$ is $(R^{22})_2N$—, wherein one $R^{22}$ is —H, and the other $R^{22}$ is $C_{1-8}$ alkyl or $C_{3-10}$ cycloalkyl.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is methyl, and $R^{21}$ is $R^{22}O$, wherein $R^{22}$ is $C_{1-8}$ alkyl optionally substituted with one or more —F.

In one embodiment, in any compound being of Formula (VI), M is CH, A is selected from —Z-heterocyclylene, —Z-arylene, and —Z-heteroarylene, Y is selected from —H and $C_{1-8}$ alkyl, $R^1$ is —H, each $R^3$ is independently selected from —Z-heterocyclyl, —Z-aryl, and —Z-heteroaryl, $R^{18}$ is —H, Z is selected from a single bond and $C_{1-4}$ alkylene, $R^{19}$ is —$CH_2OH$, and $R^{21}$ is $R^{22}O$, wherein $R^{22}$ is $C_{1-8}$ alkyl optionally substituted with one or more —F.

In one embodiment, the present application relates to a compound being of Formula (I), further being of Formula (IIIa), (IIIb), (IIIc), (IIId), (IIIe), (IIIf), or (IIIg):

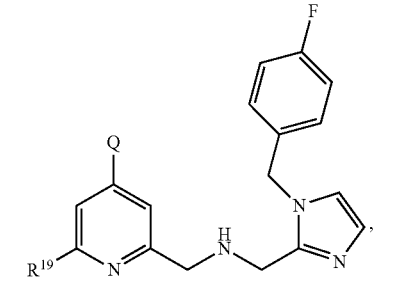

IIIa

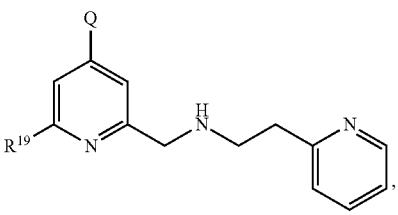

IIIb

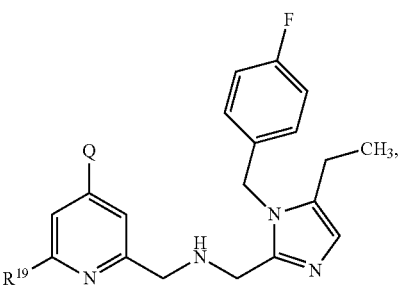

IIIc

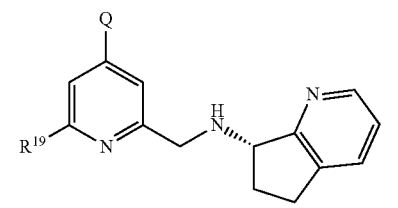

IIId

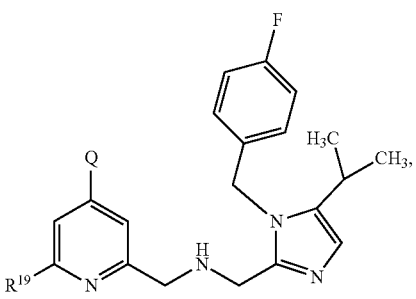

IIIe

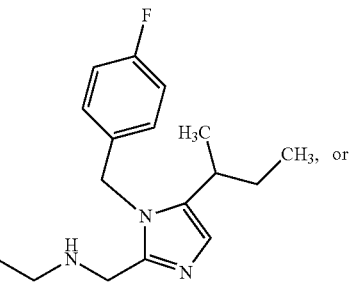

IIIf

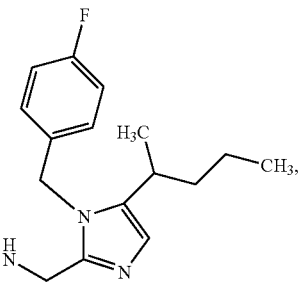

IIIg or a pharmaceutically acceptable salt, or solvate or prodrug thereof, and

Q and $R^{19}$ are as defined above.

In one embodiment, in any compound being of Formula (IIIa), (IIIb), (IIIc), (IIId), (IIIe), (IIIf), or (IIIg), $R^{19}$ is selected from $C_{1-8}$ alkyl, $C_{2-8}$ alkenyl, $C_{2-8}$ alkynyl, and $C_{3-10}$ cycloalkyl. In one embodiment, $R^{19}$ is selected from $C_{1-8}$ alkyl, $C_{2-8}$ alkenyl, and $C_{2-8}$ alkynyl. In one embodiment, $R^{19}$ is selected from $C_{1-8}$ alkyl, $C_{2-8}$ alkenyl, and $C_{2-8}$ alkynyl, optionally substituted with one or more —Z—$NR^6R^7$ or —Z—$OR^7$. In one embodiment, $R^{19}$ is selected from methyl, ethyl, propyl, iso-propyl, butyl, sec-butyl, tert-butyl, ethenyl, propenyl, butenyl, ethynyl, propynyl, and butynyl. In one embodiment, $R^{19}$ is $C_{1-8}$ alkyl optionally substituted with one or more —Z—$OR^7$. In one embodiment, $R^{19}$ is selected from methyl, ethyl, propyl, iso-propyl, butyl, sec-butyl, and tert-butyl, optionally substituted with one —Z—$OR^7$. In one embodiment, $R^{19}$ is selected from methyl, ethyl, propyl, iso-propyl, butyl, sec-butyl, and tert-butyl, optionally substituted with one —OH. In one embodiment, $R^{19}$ is selected from methyl, ethyl, propyl, iso-propyl, butyl, sec-butyl, and tert-butyl. In one embodiment, $R^{19}$ is selected from methyl and —$CH_2OH$. In one embodiment, $R^{19}$ is selected from methyl and —$CH_2OH$. In one embodiment, $R^{19}$ is methyl. In one embodiment, $R^{19}$ is —$CH_2OH$.

In one embodiment, in any compound being of Formula (IIIa), (IIIb), (IIIc), (IIId), (IIIe), (IIIf), or (IIIg), Q is selected from $CO_2H$, W, and $CO_2R^{20}$. In one embodiment, Q is $CO_2H$. In one embodiment, Q is W. In one embodiment, Q is $CO_2R^{20}$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl, optionally substituted with one —Z—$OR^7$, and Q is selected from $CO_2H$, W, and $CO_2R^{20}$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl and Q is selected from $CO_2H$, W, and $CO_2R^{20}$.

In one embodiment, in any compound being of Formula (IIIa), (IIIb), (IIIc), (IIId), (IIIe), (IIIf), or (IIIg), $R^{19}$ is methyl, and Q is selected from $CO_2H$, W, and $CO_2R^{20}$.

In one embodiment, in any compound being of Formula (IIIa), (IIIb), (IIIc), (IIId), (IIIe), (IIIf), or (IIIg), $R^{19}$ is —$CH_2OH$, and Q is selected from $CO_2H$, W, and $CO_2R^{20}$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl, optionally substituted with one —Z—$OR^7$, and Q is $CO_2H$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl and Q is $CO_2H$.

In one embodiment, in any compound being of Formula (IIIa), (IIIb), (IIIc), (IIId), (IIIe), (IIIf), or (IIIg), $R^{19}$ is methyl, and Q is $CO_2H$.

In one embodiment, in any compound being of Formula (IIIa), (IIIb), (IIIc), (IIId), (IIIe), (IIIf), or (IIIg), $R^{19}$ is —$CH_2OH$, and Q is $CO_2H$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl, optionally substituted with one —Z—$OR^7$, and Q is W.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl and Q is W.

In one embodiment, in any compound being of Formula (IIIa), (IIIb), (IIIc), (IIId), (IIIe), (IIIf), or (IIIg), $R^{19}$ is methyl, and Q is W.

In one embodiment, in any compound being of Formula (IIIa), (IIIb), (IIIc), (IIId), (IIIe), (IIIf), or (IIIg), $R^{19}$ is —$CH_2OH$, and Q is W.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl, optionally substituted with one —Z—$OR^7$, and Q is $CO_2R^{20}$.

In one embodiment, in any compound being of Formula (IIIa), (IIIb), (IIIc), (IIId), (IIIe), (IIIf), or (IIIg), $R^{19}$ is selected from methyl, ethyl, propyl, iso-propyl, butyl, sec-butyl, and tert-butyl and Q is $CO_2R^{20}$.

In one embodiment, in any compound being of Formula (IIIa), (IIIb), (IIIc), (IIId), (IIIe), (IIIf), or (IIIg), $R^{19}$ is methyl, and Q is $CO_2R^{20}$.

In one embodiment, in any compound being of Formula (IIIa), (IIIb), (IIIc), (IIId), (IIIe), (IIIf), or (IIIg), $R^{19}$ is —$CH_2OH$, and Q is $CO_2R^{20}$.

In one embodiment, Y, in any compound or formula of the application, is

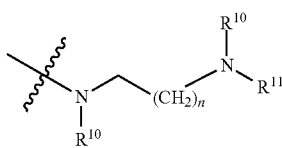

wherein n is from 1 to 3.

In one embodiment, Y, in any compound or formula of the application, is

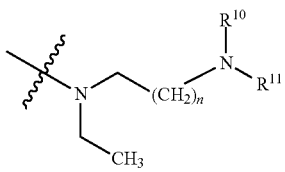

wherein n is from 1 to 3.

In one embodiment, Y, in any compound or formula of the application, is

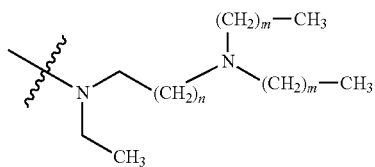

wherein n is from 1 to 3 and each m independently is from 0 to 2.

In one embodiment, Y, in any compound or formula of the application, is heterocyclyl, heteroaryl or aryl, any of which may be optionally substituted with one or more $R^3$.

In one embodiment, Y, in any compound or formula of the application, is —H.

In one embodiment, Y, in any compound or formula of the application, is $C_{1-8}$ alkyl.

In one embodiment, Q, for any compound or formula of the application, is:

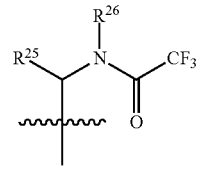

wherein $R^{25}$ and $R^{26}$ are —H, or together form a 1,3-diaza-$C_{5-7}$-cycloalk-2-yl group which is N-substituted with $R^{16}$ and optionally further substituted with one or more $R^3$, and optionally containing one or two oxo groups; a 1,3-thiaza-$C_{5-7}$-cycloalk-2-yl group which is N-substituted with $R^{16}$ and optionally further substituted with one or more $R^3$ and optionally containing one or two oxo groups; an 1,3-oxaza-$C_{5-7}$-cycloalk-2-yl group which is N-substituted with $R^{16}$ and optionally further substituted with one or more $R^3$, and optionally containing one or two oxo groups, wherein in all three instances two $R^3$ on the same carbon atom may, together with the carbon atom to which they are attached, form a $C_{3-10}$ cycloalkyl or $C_{3-10}$ heterocyclic ring.

In one embodiment, Q, for any compound or formula of the application, is selected from:

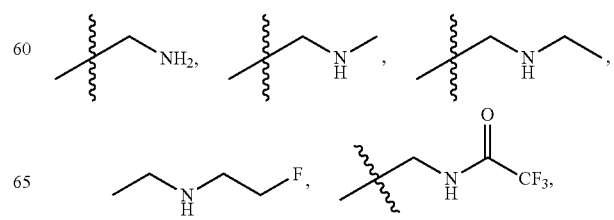

-continued

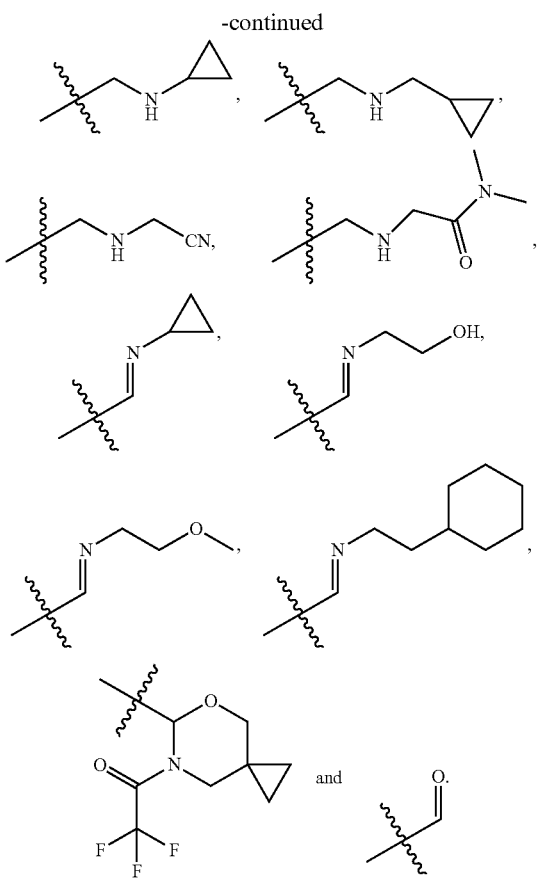

In one embodiment, Q, for any compound or formula of the application, is selected from:

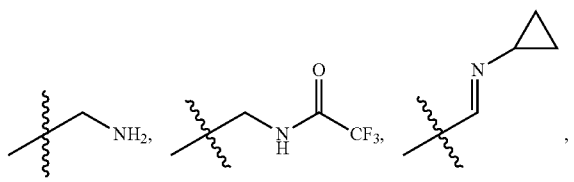

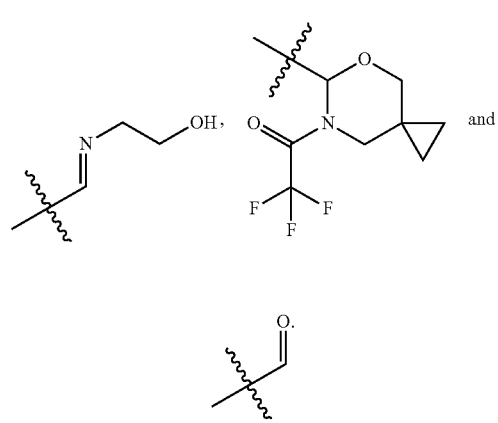

In one embodiment, Q, for any compound or formula of the application, is

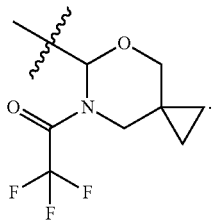 [SMILES: *C1OCC2(CC2)CN1C(=O)C(F)(F)F]

In one embodiment, Q, for any compound or formula of the application, is —CH=NR$^{12}$, wherein:

R$^{12}$ is selected from C$_{1-10}$ alkyl, C$_{2-10}$ alkenyl, C$_{2-10}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$ and —Z—COOR$^7$. In one embodiment, R$^{12}$ is selected from —Z—OR$^7$, C$_{3-10}$ cycloalkyl, —Z-heterocyclyl, —Z-aryl, and —Z-heteroaryl.

In one embodiment, Q, for any compound or formula of the application, is CH$_2$NHR$^{13}$, wherein:

R$^{13}$ is selected from —H, —C(O)R$^7$, —C(O)C(O)R$^7$, —C(O)C(O)OR$^7$, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-monocyclic-heteroaryl, —CR$^{14}$R$^{15}$NR$^6$R$^7$, and —CR$^{14}$R$^{15}$CN. In one embodiment, R$^{13}$ is selected from —H, —C(O)R$^7$, C$_{1-8}$ alkyl, C$_{3-10}$ cycloalkyl, —CR$^{14}$R$^{15}$NR$^6$R$^7$, and —CR$^{14}$R$^{15}$CN.

In one embodiment, each R$^7$, for any compound or formula of the application, is independently selected from —H, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-heteroaryl and —Z-aryl. In one embodiment, each R$^7$ is independently selected from —H, C$_{1-8}$ alkyl, C$_{1-4}$ fluoroalkyl, and C$_{1-4}$ hydroxyalkyl.

In one embodiment, -A-Y, in any compound or formula of the application, is a moiety that includes 1-3 cyclic moieties selected from monocyclic cycloalkyl, monocyclic heterocyclyl, monocyclic heteroaryl, bicyclic heteroaryl and monocyclic aryl.

In one embodiment, the compound of the application is a compound having any one of the following structures:

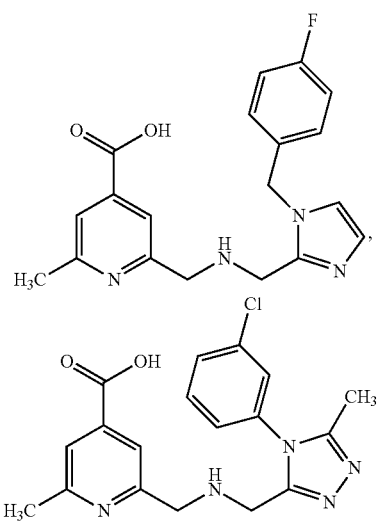

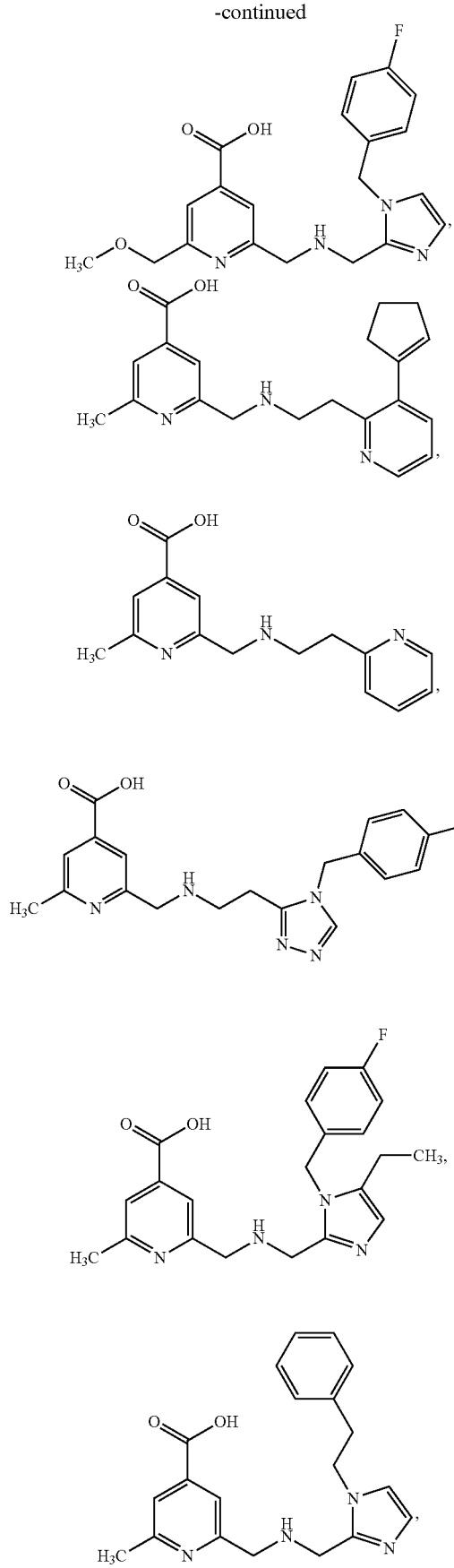
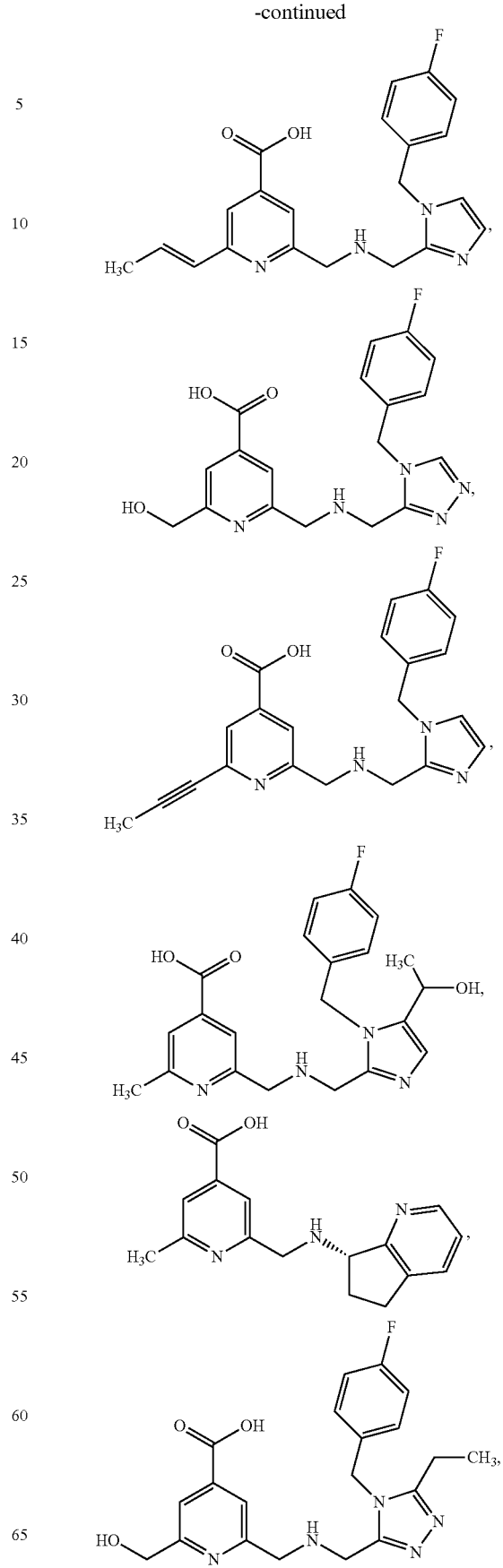

-continued
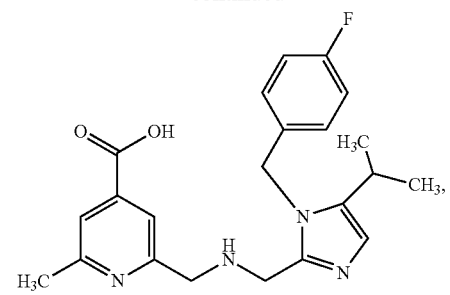
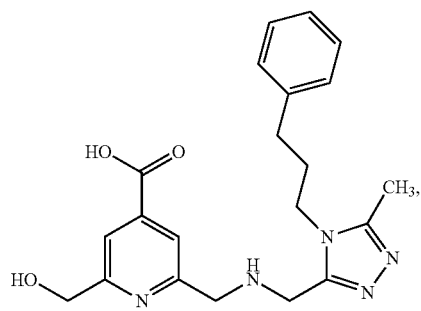
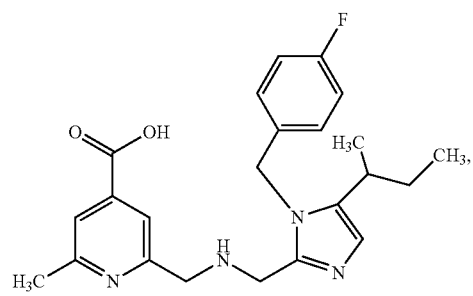
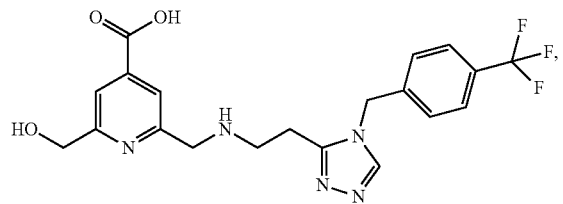
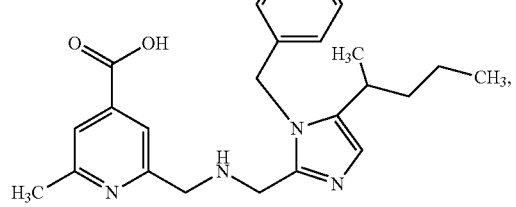
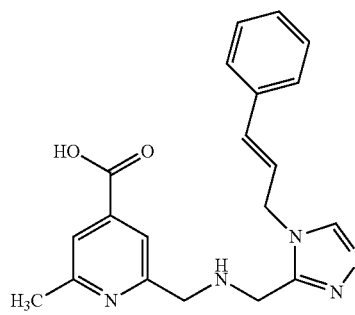
-continued
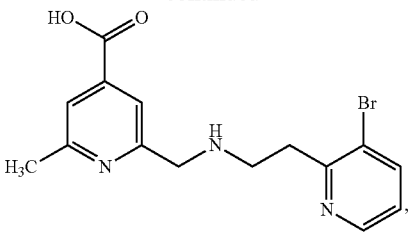
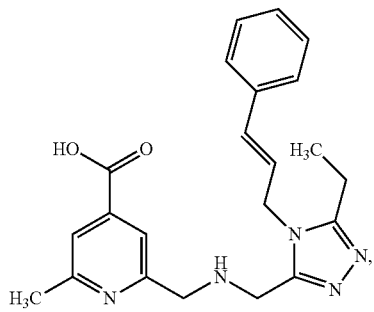
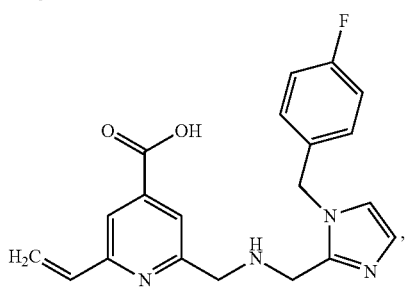
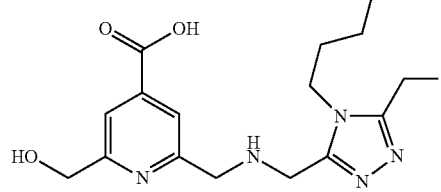
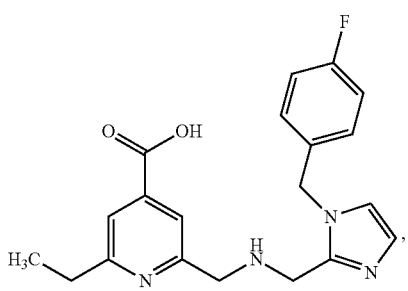
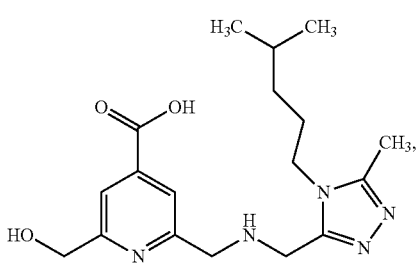

47
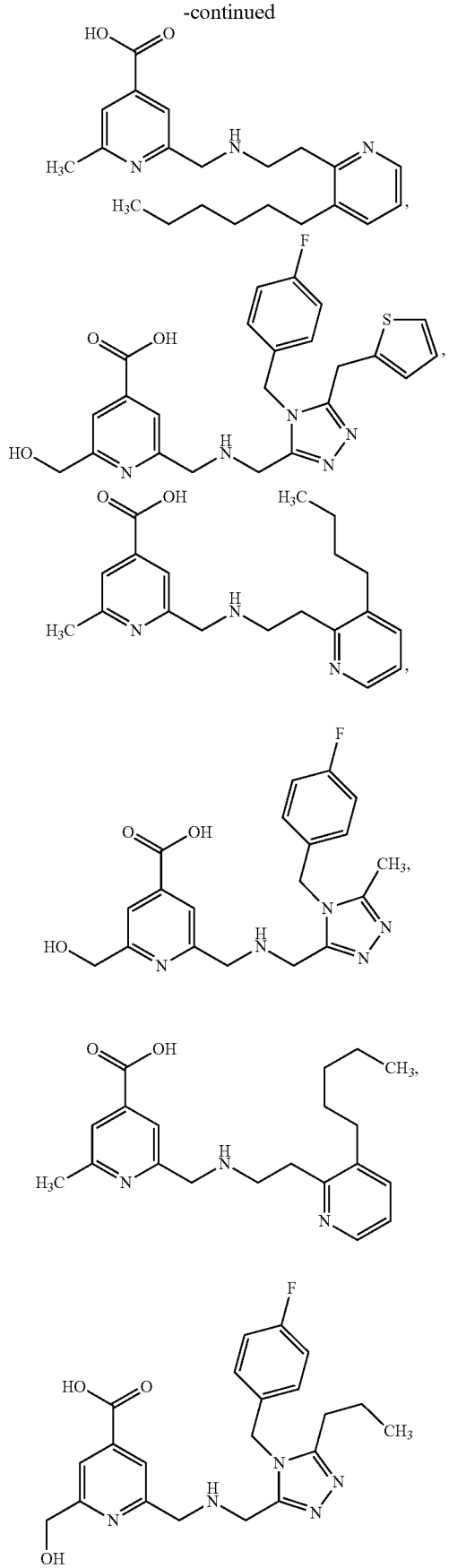
48
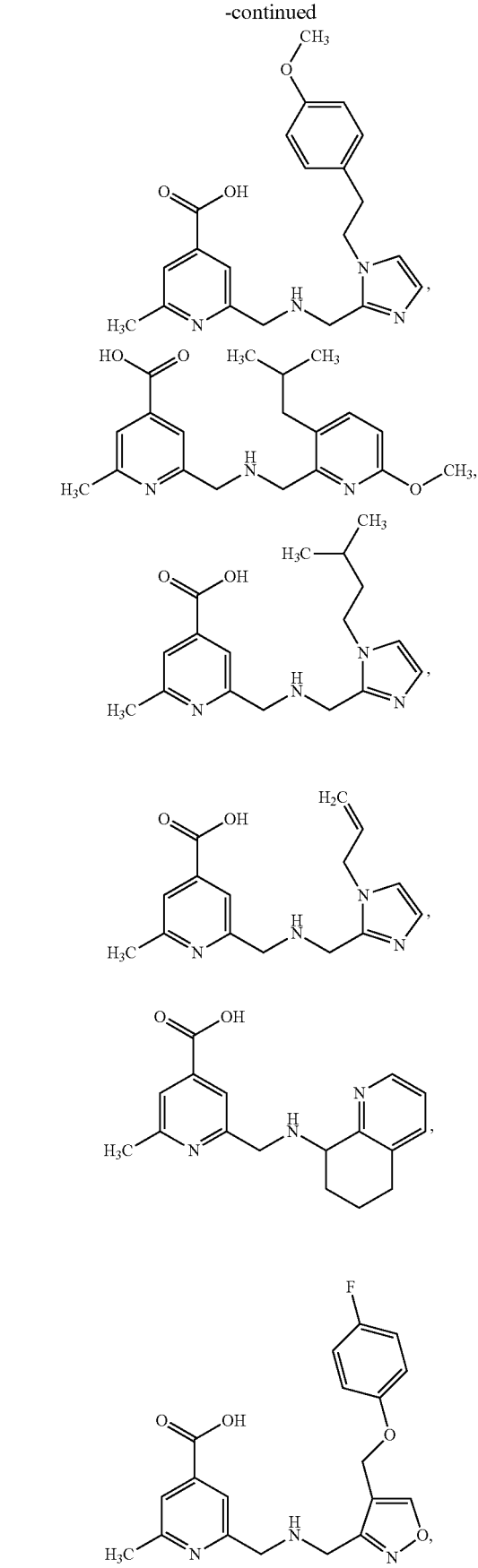

-continued
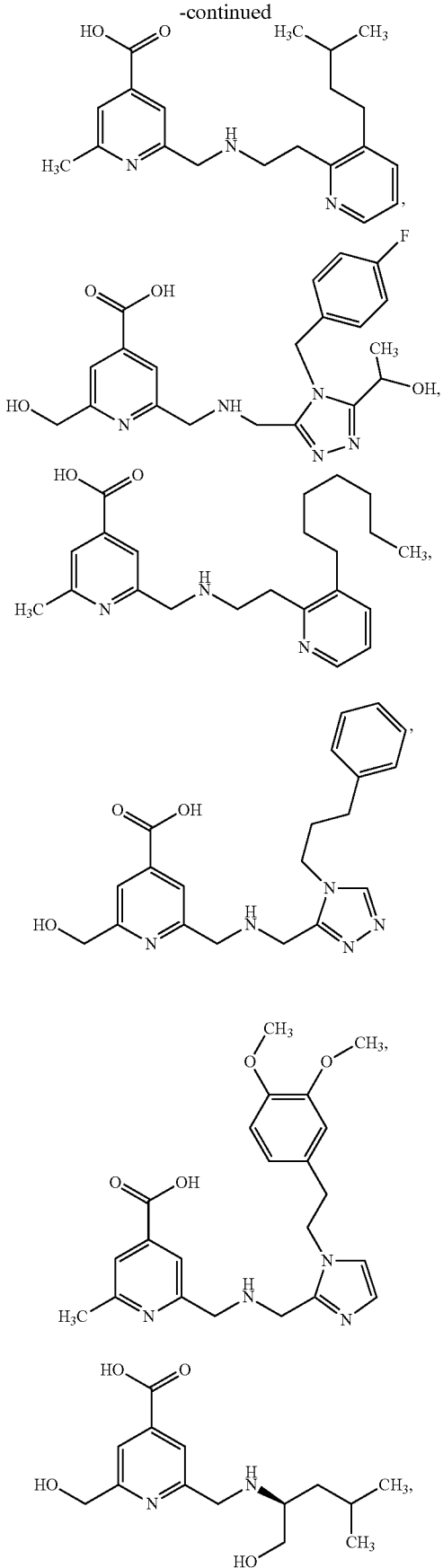
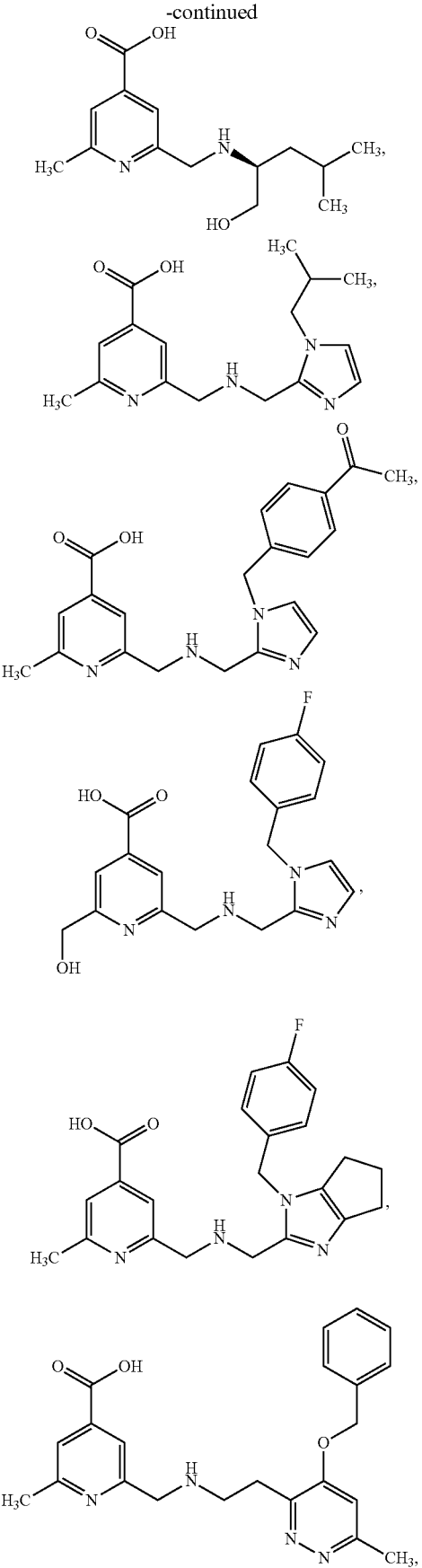

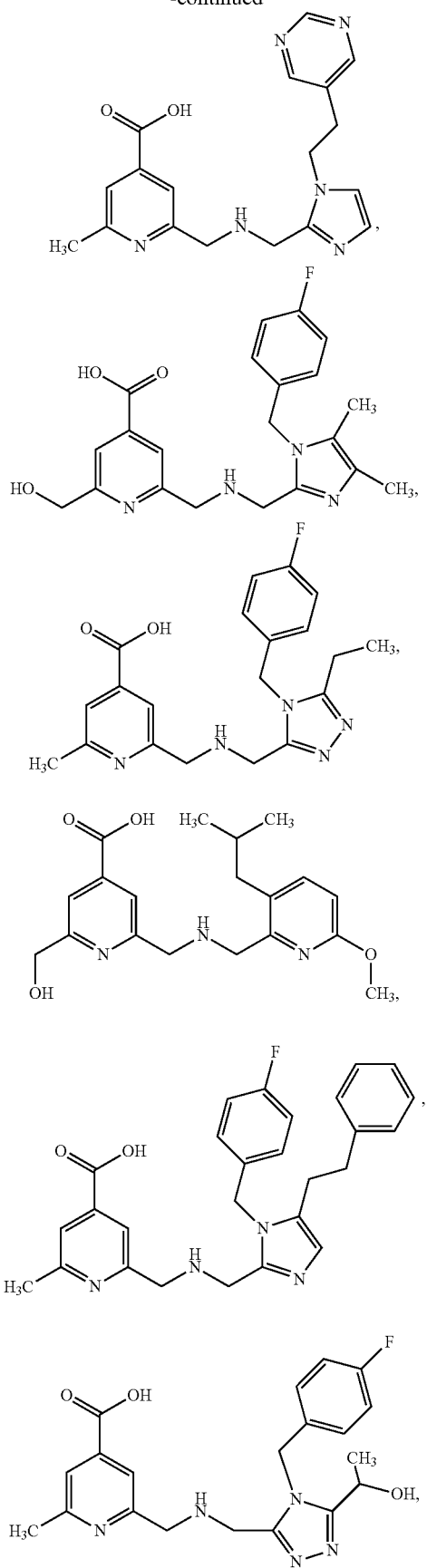
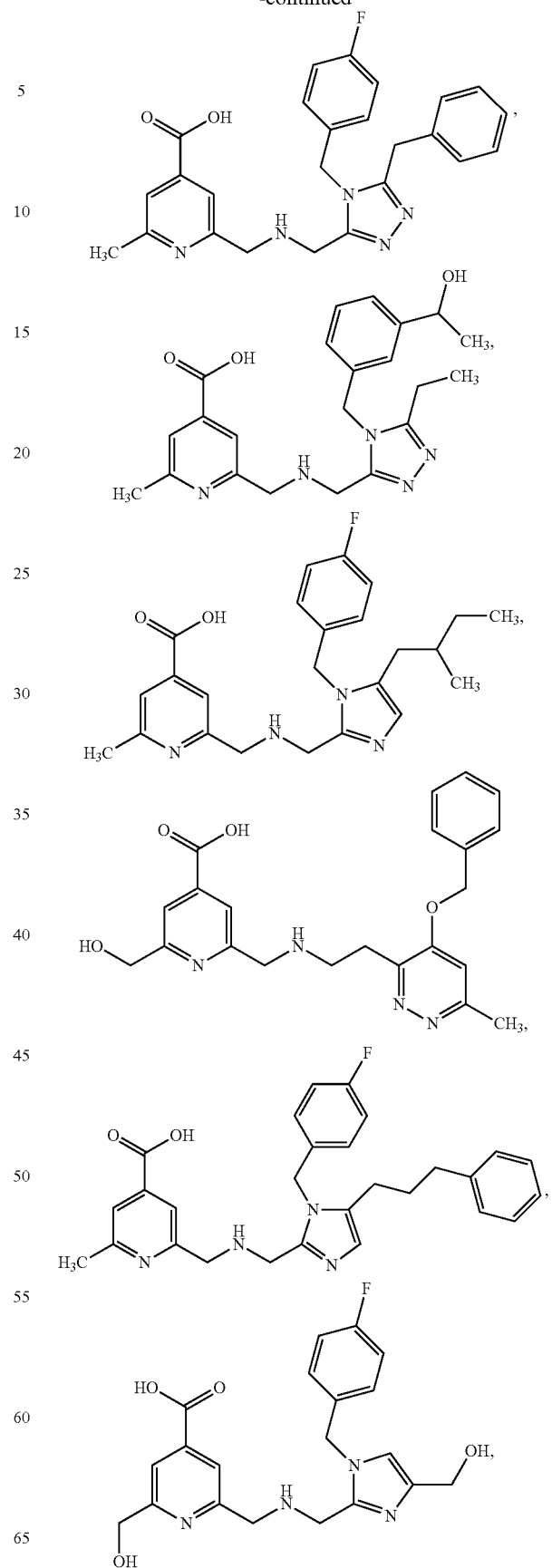

53
-continued
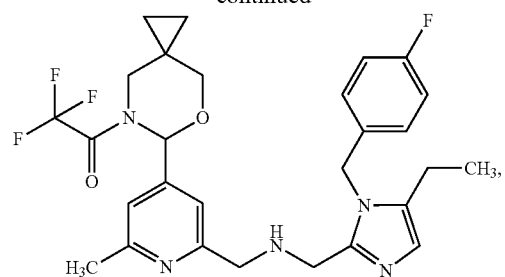
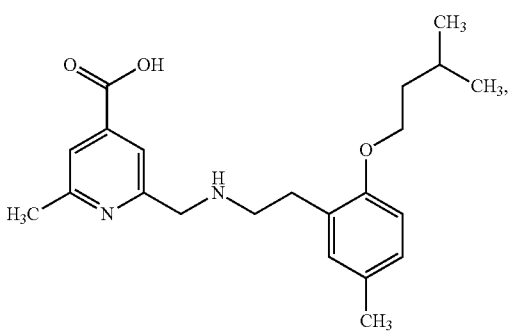
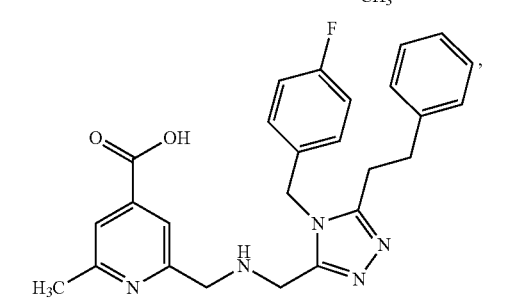
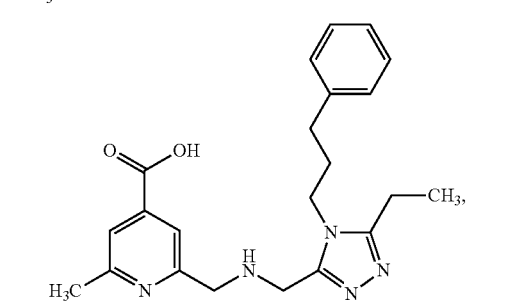
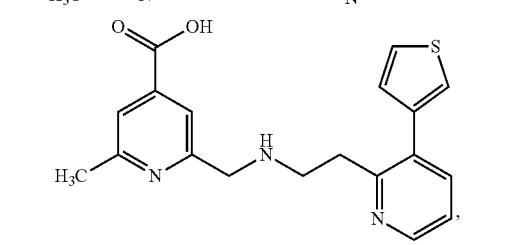
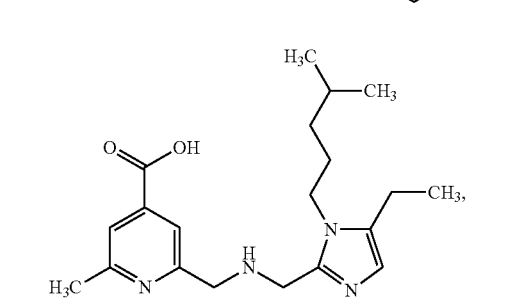
54
-continued
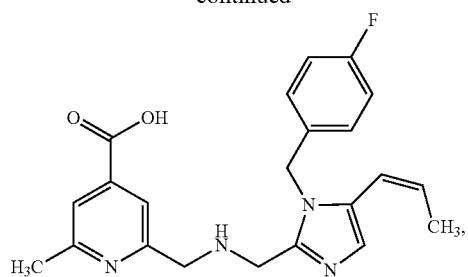
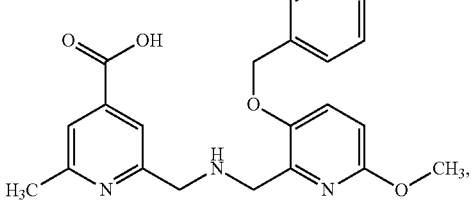
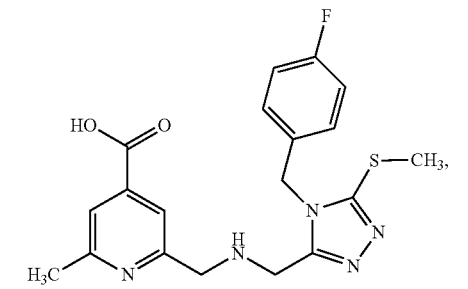
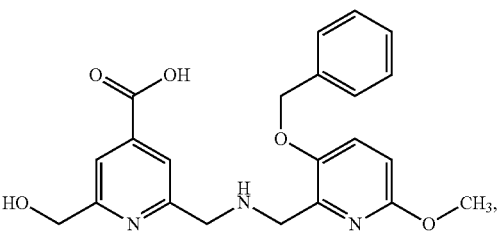
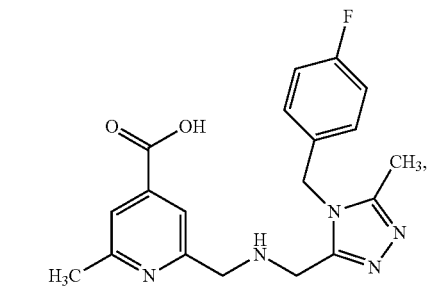
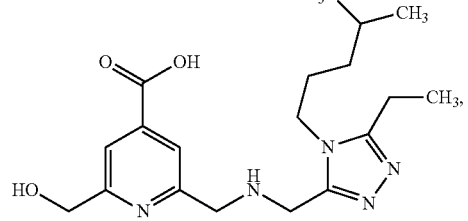

55
-continued
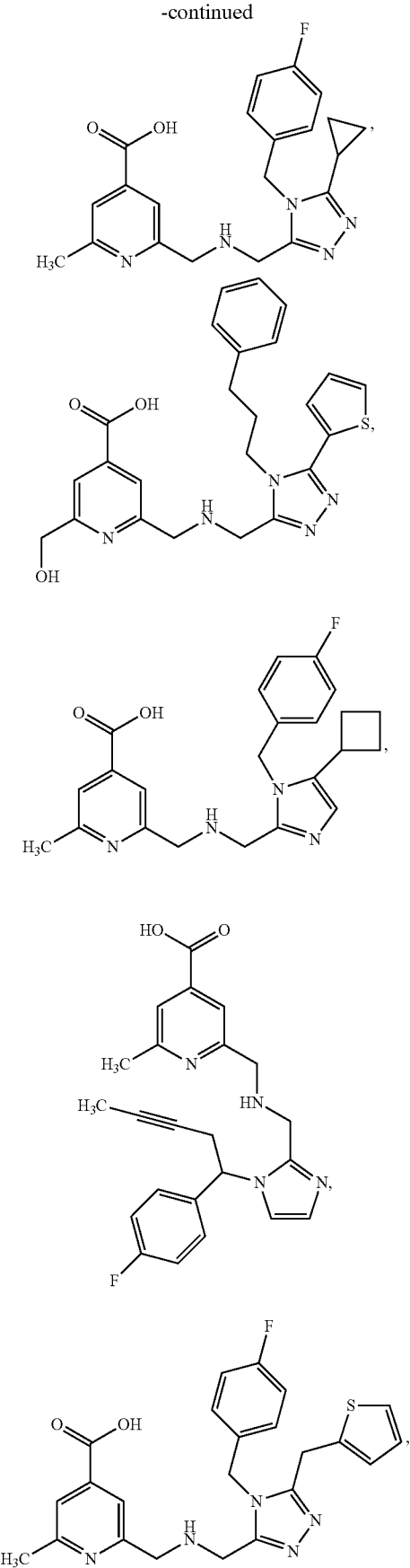
56
-continued
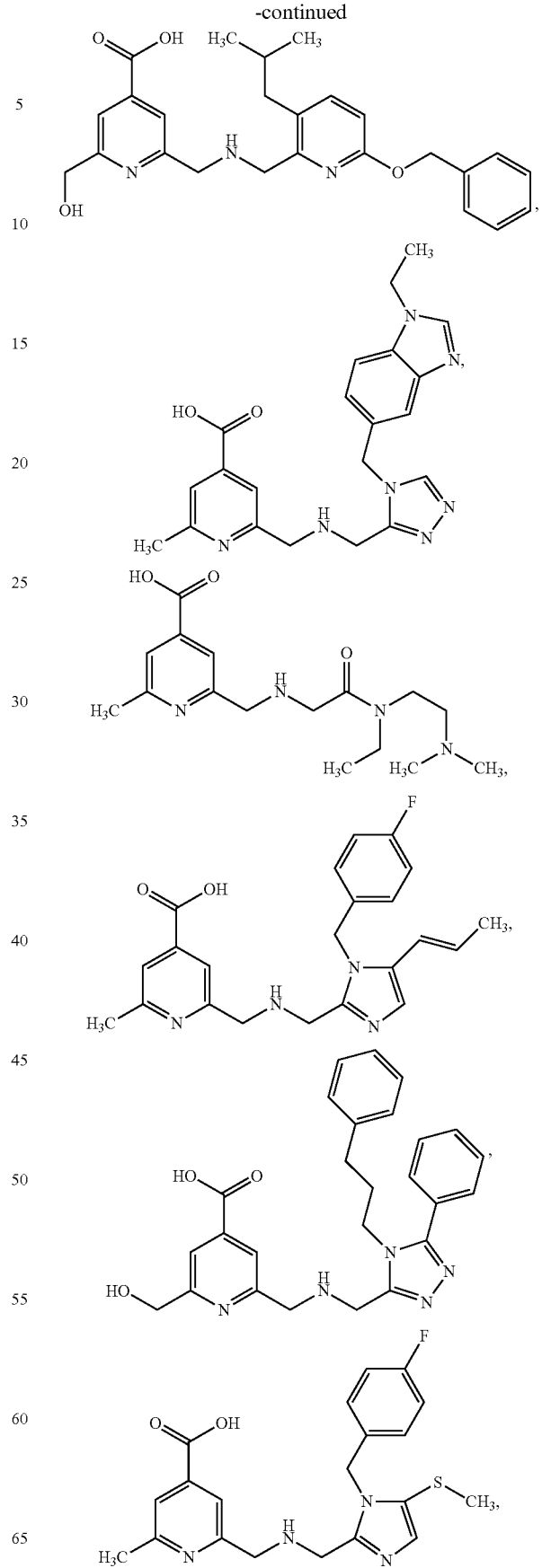

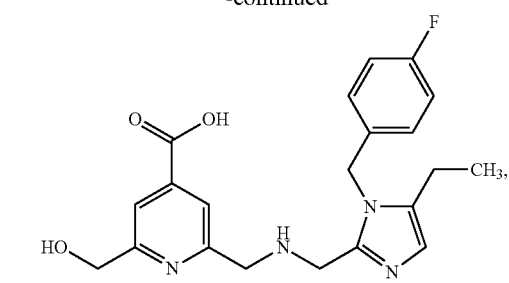
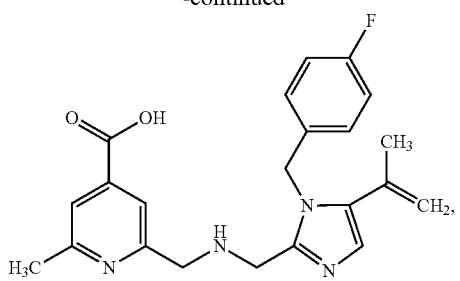
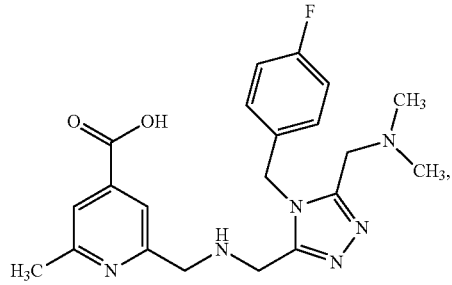
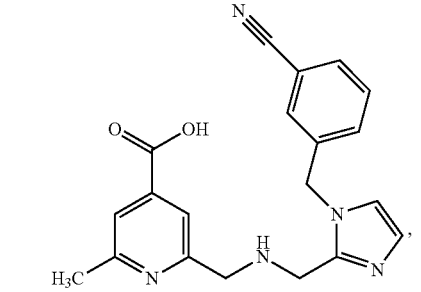
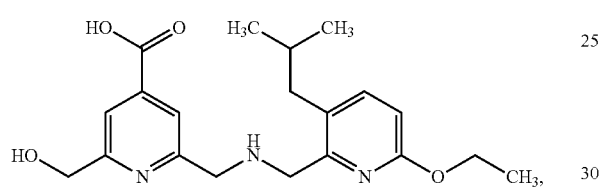
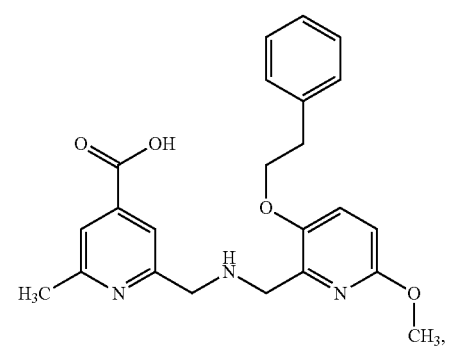
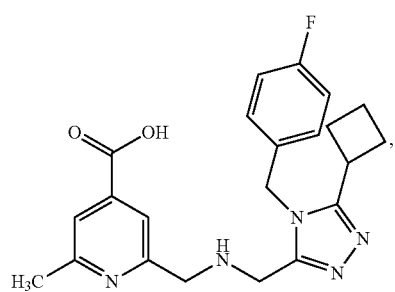
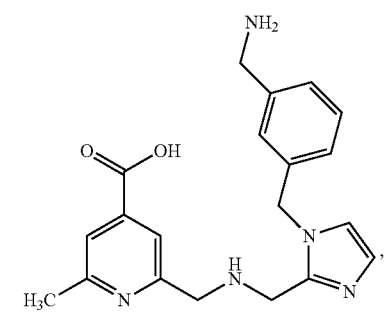
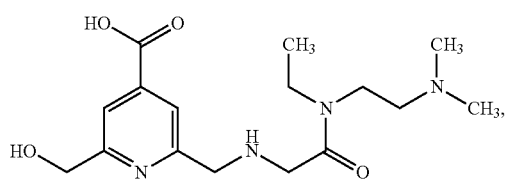
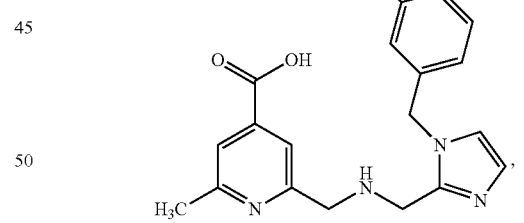
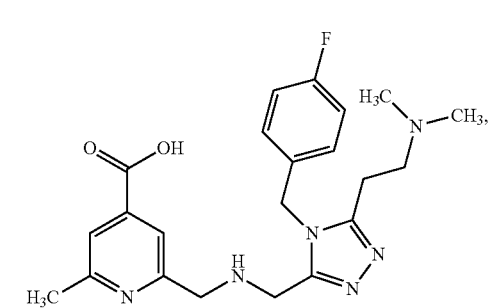
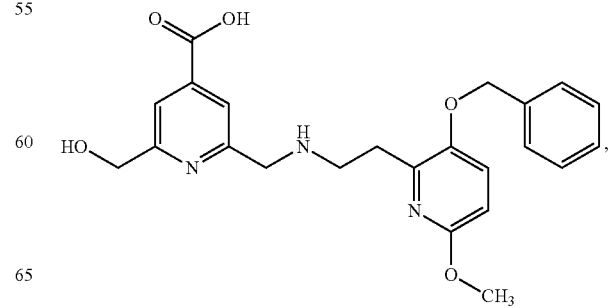
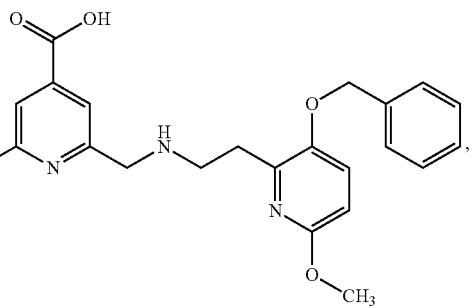

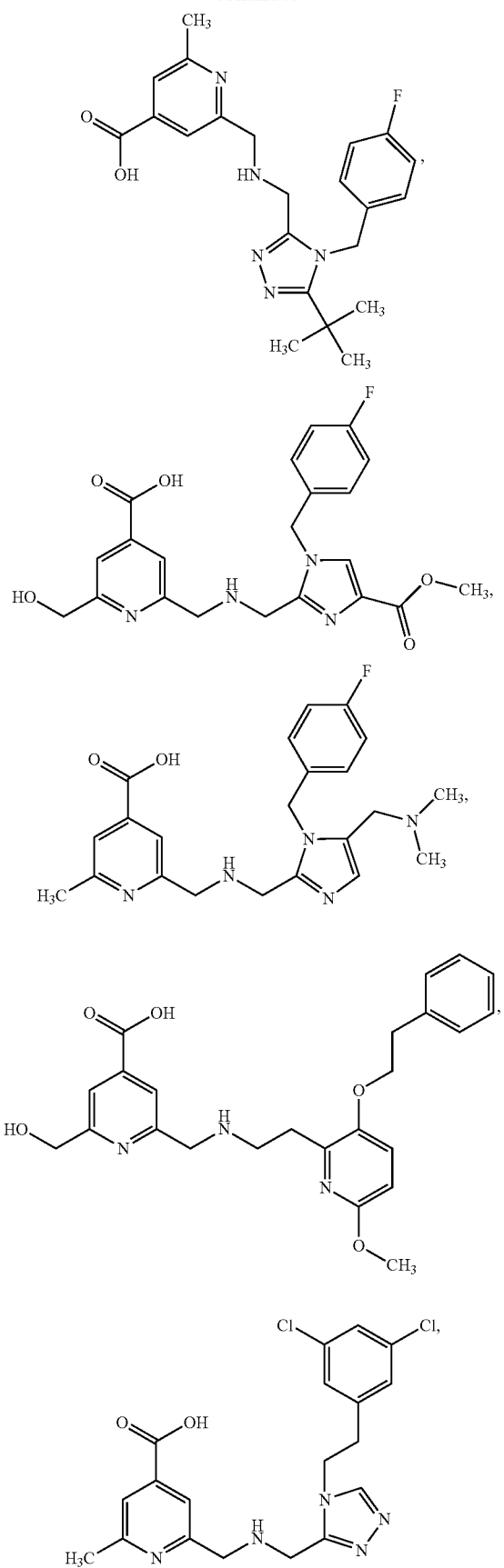
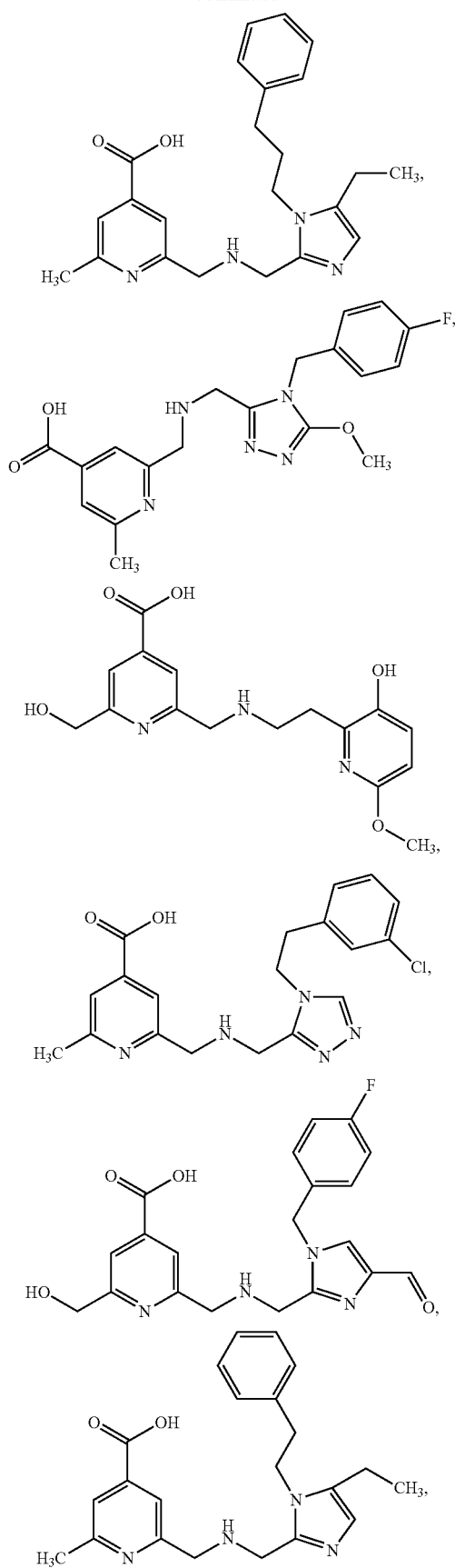

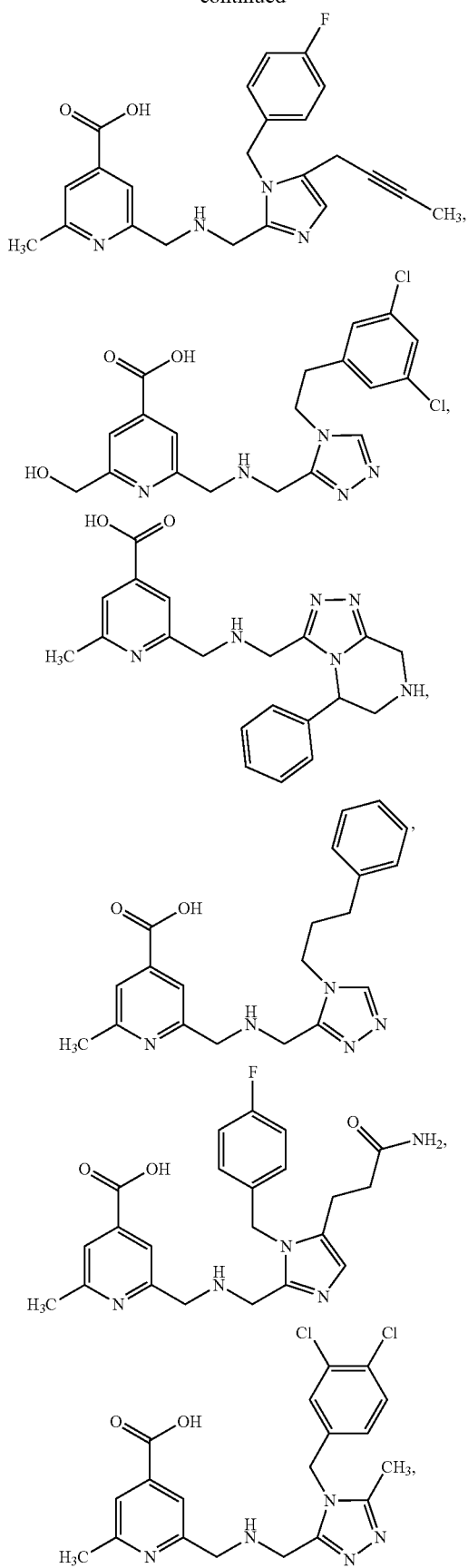

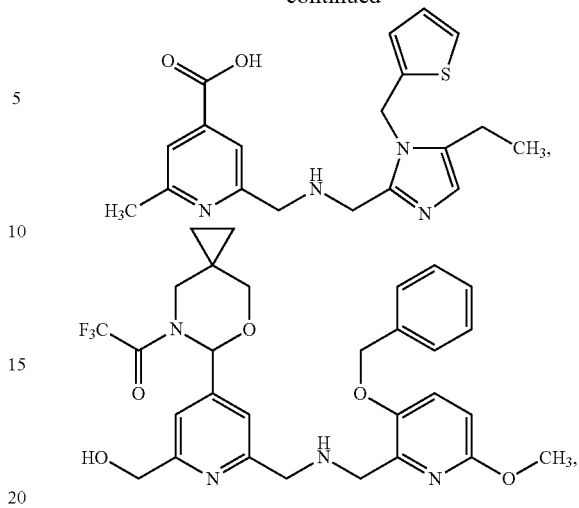

or a pharmaceutically acceptable salt, or solvate or prodrug thereof.

In another aspect, the present application relates to a pharmaceutical composition comprising at least one compound of the application, or a pharmaceutically acceptable salt thereof, or solvate, or prodrug thereof, as defined herein, and optionally one or more pharmaceutically acceptable excipients, diluents and/or carriers. In one embodiment, the pharmaceutical composition comprises one or more further active substances.

Prodrugs

The compound of the application may be provided as a prodrug. The term "prodrug" used herein is intended to mean a compound which—upon exposure to certain physiological conditions—will liberate the compound of the application which then will be able to exhibit the desired biological action. A typical example is a labile ester of a carboxylic acid, in particular the pyridine carboxylic acid group of the compound of the application which, e.g., is capable of liberating the latent carboxylic acid group. Another example is a carbamic acid of an amine, in particular the pyridine amine group of the compound of the application, which is capable of liberating the latent amine.

Illustrative examples of esters of a carboxylic acid group (in particular the pyridine carboxylic acid) are $C_{1-6}$ alkyl esters, e.g., methyl esters, ethyl esters, 2-propyl esters, phenyl esters, 2-aminoethyl esters, including (5-methyl-2-oxo-2H-1,3-dioxol-4-yl)methyl esters, 4-methoxyphenyl esters, 2-(ethoxycarbonyl)phenyl esters, {4-[(ethoxycarbonyl)(methyl)amino]phenyl}methyl esters, 2-(dimethylamino)ethyl esters, 3-(dimethylamino)propyl esters, [(ethoxycarbonyl)amino]phenylmethyl esters, 2,6-dimethoxyphenyl esters, 2,6-dimethylphenyl esters, 4-tert-butylphenyl esters, 4-oxopentan-2-yl esters, 4-(trifluoroacetamido)butan-2-yl esters, 4-(2,2,2-trifluoro-N-methylacetamido)butan-2-yl esters, 5-(trifluoroacetamido pent-1-en-3-yl esters, 5-(2,2,2-trifluoro-N-methylacetamido)pent-1-en-3-yl esters, 1,3-bis(hexadecanoyloxy) propan-2-yl esters, 2,3-bis(hexadecanoyloxy)propyl esters, 4-oxo-4-(propan-2-yloxy)-1-(trifluoroacetamido)butan-2-yl esters, 1-oxo-1-(propan-2-yloxy)-5-(trifluoroacetamido) pentan-3-yl esters, 2,2,2-trifluoethyl esters, 2,6-bis(propan-2-yloxy)phenyl esters, 2-fluoroethyl esters, 2,2-difluoroethyl esters, and the like.

Definitions

The term "alkyl" as used herein refers to a saturated, straight or branched hydrocarbon chain. In one embodiment, the hydrocarbon chain contains from one to 8 carbon atoms ($C_{1-8}$-alkyl). In one embodiment, from one to six carbon atoms ($C_{1-6}$-alkyl). In one embodiment, from one to four carbon atoms ($C_{1-4}$-alkyl). In one embodiment, "alkyl" includes methyl, ethyl, propyl, isopropyl, butyl, isobutyl, secondary butyl, tertiary butyl, pentyl, 2-methylbutyl, isopentyl, neopentyl, tertiary pentyl, pentan-2-yl, pentan-3-yl, hexyl, isohexyl, 4-methyl-pentan-2-yl, heptyl and octyl. In one embodiment, "alkyl" represents a $C_{1-4}$-alkyl group, which includes methyl, ethyl, propyl, isopropyl, butyl, isobutyl, secondary butyl, and tertiary butyl. Correspondingly, the term "alkylene" means the corresponding biradical (-alkyl-).

The term "cycloalkyl" as used herein refers to a cyclic alkyl group. In one embodiment, "cycloalkyl" contains from three to ten carbon atoms ($C_{3-10}$-cycloalkyl). In one embodiment, from three to eight carbon atoms ($C_{3-8}$-cycloalkyl). In one embodiment, from three to six carbon atoms ($C_{3-6}$-cycloalkyl), which includes cyclopropyl, cyclobutyl, cyclopentyl, cyclohexyl, cycloheptyl and cyclooctyl. Furthermore, the term "cycloalkyl" as used herein may also include polycyclic groups, including fused, bridged, spiro, and mixed cycloalkyl groups, such as, for example, bicyclo[2.2.2]octyl, bicyclo[2.2.1]heptanyl, decalinyl and adamantyl. Correspondingly, the term "cycloalkylene" means the corresponding biradical (-cycloalkyl-).

The term "cycloalkyl" as used herein refers to a cyclic alkyl group. In one embodiment, "cycloalkyl" contains from three to ten carbon atoms ($C_{3-10}$-cycloalkyl). In one embodiment, from three to eight carbon atoms ($C_{3-8}$-cycloalkyl). In one embodiment, from three to six carbon atoms ($C_{3-6}$-cycloalkyl), which includes cyclopropyl, cyclobutyl, cyclopentyl, cyclohexyl, cycloheptyl and cyclooctyl. Furthermore, the term "cycloalkyl" as used herein may also include polycyclic groups, such as, for example, bicyclo[2.2.2]octyl, bicyclo[2.2.1]heptanyl, decalinyl and adamantyl. Correspondingly, the term "cycloalkylene" means the corresponding biradical (-cycloalkyl-).

The term "alkenyl" as used herein refers to a straight or branched hydrocarbon chain or cyclic hydrocarbons containing one or more double bonds, including di-enes, tri-enes and poly-enes. In one embodiment, the alkenyl group comprises from two to eight carbon atoms ($C_{2-8}$-alkenyl). In one embodiment, from two to six carbon atoms ($C_{2-6}$-alkenyl). In one embodiment, from two to four carbon atoms ($C_{2-4}$-alkenyl). In one embodiment, examples of alkenyl groups include ethenyl; 1- or 2-propenyl; 1-, 2- or 3-butenyl, or 1,3-but-dienyl; 1-, 2-, 3-, 4- or 5-hexenyl, or 1,3-hex-dienyl, or 1,3,5-hex-trienyl; 1-, 2-, 3-, 4-, 5-, 6-, or 7-octenyl, or 1,3-octadienyl, or 1,3,5-octatrienyl, or 1,3,5,7-octatetraenyl, or cyclopentenyl or cyclohexenyl. Correspondingly, the term "alkenylene" means the corresponding biradical (-alkenyl-).

The term "alkynyl" as used herein refers to a straight or branched hydrocarbon chain containing one or more triple bonds, including di-ynes, tri-ynes and poly-ynes. In one embodiment, the alkynyl group comprises of from two to eight carbon atoms ($C_{2-8}$-alkynyl). In one embodiment, from two to six carbon atoms ($C_{2-6}$-alkynyl). In one embodiment, from two to four carbon atoms ($C_{2-4}$-alkynyl). In one embodiment, examples of alkynyl groups include ethynyl; 1- or 2-propynyl; 1-, 2- or 3-butynyl, or 1,3-but-diynyl; 1-, 2-, 3-, 4- or 5-hexynyl, or 1,3-hex-diynyl, or 1,3,5-hex-triynyl; 1-, 2-, 3-, 4-, 5-, 6-, or 7-octynyl, or 1,3-oct-diynyl, or 1,3,5-oct-triynyl, or 1,3,5,7-oct-tetraynyl. Correspondingly, the term "alkynylene" means the corresponding biradical (-alkynyl-).

The terms "halo" and "halogen" as used herein refer to fluoro (—F), chloro (—Cl), bromo (—Br), and iodo (—I). Thus a trihalomethyl group represents, e.g., a trifluoromethyl group, or a trichloromethyl group. In one embodiment, the terms "halo" and "halogen" designate fluoro or chloro.

The term "fluoroalkyl" as used herein refers to an alkyl group as defined herein which is substituted one or more times with one or more fluoro. In one embodiment, a fluoroalkyl group is substituted with one fluoro. In one embodiment, a fluoroalkyl group is substituted with two fluoros. In one embodiment, a fluoroalkyl group is substituted with three or more fluoros. In one embodiment, the term "fluoroalkyl" is perfluorinated, which, as used herein, refers to an alkyl group as defined herein wherein all hydrogen atoms are replaced by fluoro atoms. In one embodiment, a fluoroalkyl group is trifluoromethyl. In one embodiment, a fluoroalkyl group is pentafluoroethyl. In one embodiment, a fluoroalkyl group is heptafluoropropyl.

The term "alkoxy" as used herein refers to an "alkyl-O—" group, wherein alkyl is as defined herein.

The term "hydroxyalkyl" as used herein refers to an alkyl group (as defined herein), which alkyl group is substituted one or more times with hydroxy. In one embodiment, hydroxyalkyl includes HO—$CH_2$—, HO—$CH_2$—$CH_2$— and $CH_3$—CH(OH)—.

The term "oxy" as used herein refers to an "—O—" group.

The term "oxo" as used herein refers to an "=O" group.

The term "amine" as used herein refers to primary (R—$NH_2$, R≠H), secondary ($R_2$—NH, $R_2$≠H) and tertiary ($R_3$—N, $R_3$≠H) amines. A substituted amine is intended to mean an amine where at least one of the hydrogen atoms has been replaced by the substituent.

The term "carbamoyl" as used herein refers to a "$H_2$N(C=O)—" group.

The term "aryl", as used herein, unless otherwise indicated, includes carbocyclic aromatic ring systems derived from an aromatic hydrocarbon by removal of a hydrogen atom. Aryl furthermore includes bi-, tri- and polycyclic ring systems. In one embodiment, aryl groups include phenyl, naphthyl, indenyl, indanyl, fluorenyl, biphenyl, indenyl, naphthyl, anthracenyl, phenanthrenyl, pentalenyl, azulenyl, and biphenylenyl. In one embodiment, aryl group is phenyl, naphthyl or indanyl. In one embodiment, aryl group is phenyl. Any aryl used may be optionally substituted. Correspondingly, the term "arylene" means the corresponding biradical (-aryl-).

The term "heteroaryl", as used herein, refers to aromatic groups containing one or more heteroatoms selected from O, S, and N. In one embodiment, the heteroaryl group has one to four heteroatoms. In one embodiment, from one to three heteroatoms. In one embodiment, the heteroaryl group contains from five to fourteen total atoms, wherein one or more atom is selected from O, S, and N. In one embodiment, the heteroaryl group contains from five to ten total atoms, wherein one or more atom is selected from O, S, and N. In one embodiment, the heteroaryl group contains from five to seven total atoms, wherein one or more atom is selected from O, S, and N. In one embodiment, the heteroaryl group contains five total atoms, wherein one or more atom is selected from O, S, and N. In one embodiment, the heteroaryl group contains six total atoms, wherein one or more atom is selected from O, S, and N. Heteroaryl furthermore includes bi-, tri- and polycyclic groups, wherein at least one ring of the group is aromatic, and at least one of the rings contains a heteroatom selected from 0, S, and N. Heteroaryl also include ring systems substituted with one or more oxo moieties. In one embodiment, heteroaryl groups include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, pteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, 5,6,7,8-tetrahydro-[1,2,4]triazolo[4,3,a]pyrazinyl, dihydroquinolyl, tetrahydroquinolyl, dihydroisoquinolyl, tetrahydroisoquinolyl, cyclopentapyridinyl, cyclopenta-imidazolyl, benzofuryl, furopyridinyl, pyrolopyrimidinyl, azaindolyl, pyrazolinyl, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-).

The term "heteroaryl", as used herein, refers to aromatic groups containing one or more heteroatoms selected from O, S, and N. In one embodiment, the heteroaryl group has one to four heteroatoms. In one embodiment, from one to three heteroatoms. Heteroaryl furthermore includes bi-, tri- and polycyclic groups, wherein at least one ring of the group is aromatic, and at least one of the rings contains a heteroatom selected from O, S, and N. Heteroaryl also include ring systems substituted with one or more oxo moieties. In one embodiment, heteroaryl groups include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, pteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, 5,6,7,8-tetrahydro-[1,2,4]triazolo[4,3,a]pyrazinyl, dihydroquinolyl, tetrahydroquinolyl, dihydroisoquinolyl, tetrahydroisoquinolyl, cyclopentapyridinyl, cyclopenta-imidazolyl, benzofuryl, furopyridinyl, pyrolopyrimidinyl, azaindolyl, pyrazolinyl, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-).

The term "heterocyclyl" as used herein, refers to cyclic non-aromatic groups containing one or more heteroatoms selected from O, S, and N. In one embodiment, the heterocyclyl group has from one to four heteroatoms. In one embodiment, one to three heteroatoms. In one embodiment, the heterocyclyl group contains from three to fourteen total atoms, wherein one or more atom is selected from O, S, and N. In one embodiment, the heterocyclyl group contains from three to ten total atoms, wherein one or more atom is selected from O, S, and N. In one embodiment, the heterocyclyl group contains from five to seven total atoms, wherein one or more atom is selected from O, S, and N. In one embodiment, the heterocyclyl group contains five total atoms, wherein one or more atom is selected from O, S, and N. In one embodiment, the heterocyclyl group contains six total atoms, wherein one or more atom is selected from O, S, and N. Heterocyclyl furthermore includes bi-, tri- and polycyclic non-aromatic groups, including fused, bridged, spiro, and mixed heterocyclyl groups, and at least one of the rings contains a heteroatom selected from O, S, and N. Heterocyclyl also include ring systems substituted with one or more oxo moieties. In one embodiment, examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholinyl, thiomorpholinyl, 1,4-oxathianyl, benzofuranyl, isobenzofuranyl, indazolyl, benzimidazolyl, tetrahydroisoquinolyl, cyclopentapyridinyl, quinolinyl, isoquinolinyl, chromanyl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocyclylene" means the corresponding biradical (-heterocyclyl-).

The term "heterocyclyl" as used herein, refers to cyclic non-aromatic groups containing one or more heteroatoms selected from O, S, and N. In one embodiment, the heterocyclyl group has from one to four heteroatoms. In one embodiment, one to three heteroatoms. Heterocyclyl furthermore includes bi-, tri- and polycyclic non-aromatic groups, and at least one of the rings contains a heteroatom selected from O, S, and N. Heterocyclyl also include ring systems substituted with one or more oxo moieties. In one embodiment, examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholinyl, thiomorpholinyl, 1,4-oxathianyl, benzofuranyl, isobenzofuranyl, indazolyl, benzimidazolyl, tetrahydroisoquinolyl, cyclopentapyridinyl, quinolinyl, isoquinolinyl, chromanyl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocyclylene" means the corresponding biradical (-heterocyclyl-).

The term "N-heterocyclic ring" as used herein, refers to a heterocyclyl or a heteroaryl as defined herein having at least one nitrogen atom, and being bound via a nitrogen atom. In one embodiment, examples of N-heterocyclic rings include pyrrolidinyl, pyrrolyl, 3H-pyrrolyl, pyrazolyl, pyrazolidinyl, imidazolyl, imidazolidinyl, 3H-pyrazolyl, 1,2-oxazolyl, 1,2-thiazolyl, 1,3-thiazolyl, piperidinyl, pyridinyl, pyridazinyl, pyrazinyl, piperazinyl, morpholinyl, pyridinyl, pyridazinyl, pyrimidinyl, pyrazolyl, pyrazinyl, tetrazolyl, and the like.

Isomers

The compounds of the application, or a pharmaceutically acceptable salt, or solvate, or prodrug thereof, may exist as geometric isomers (i.e., cis-trans isomers), optical isomers or stereoisomers, such as diastereomers, as well as tautomers. Accordingly, it should be understood that the definition of the compounds of the application, or a pharmaceutically acceptable salt, or solvate, or prodrug thereof, includes each and every individual isomer corresponding to the structural formula of the compound of the application, or a pharmaceutically acceptable salt, or solvate, or prodrug thereof, including cis-trans isomers, stereoisomers and tautomers, as well as racemic mixtures of these. Hence, the definition of the compounds of the application, or a pharmaceutically acceptable salt, or solvate, or prodrug thereof, is also intended to encompass all R- and S-isomers of a chemical structure in any ratio, e.g., with enrichment (i.e. enantiomeric excess or diastereomeric excess) of one of the possible isomers and corresponding smaller ratios of other isomers.

Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the application, or a pharmaceutically acceptable salt, or solvate, or prodrug thereof, with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. Optically active compounds of the application, or a pharmaceutically acceptable salt, or solvate, or prodrug thereof, can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

Pharmaceutically Acceptable Salts

The compounds of the application may be provided in any form suitable for the intended administration, in particular including pharmaceutically acceptable salts, solvates and prodrugs of the compound of the application.

Pharmaceutically acceptable salts refer to salts of the compounds of the application, which are considered to be acceptable for clinical and/or veterinary use. Typical pharmaceutically acceptable salts include those salts prepared by reaction of the compounds of The application a mineral or organic acid or an organic or inorganic base. Such salts are known as acid addition salts and base addition salts, respectively. It will be recognized that the particular counter-ion or multiple counter-ions forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology.

Examples of pharmaceutically acceptable addition salts include acid addition salts formed with inorganic acids e.g., hydrochloric, hydrobromic, sulfuric, nitric, hydroiodic, metaphosphoric, or phosphoric acid; and organic acids e.g., succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, oxalic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts.

Solvates

The compound of The application may be provided in dissoluble or indissoluble forms together with a pharmaceutically acceptable solvent such as water, ethanol, and the like. Dissoluble forms may also include hydrated forms such as the mono-hydrate, the dihydrate, the hemihydrate, the trihydrate, the tetrahydrate, and the like.

Isotopic Variations

Elemental symbols and element names are used herein to include isotopes of the named elements. In particular one, some, or all hydrogens may be deuterium. Radioactive isotopes may be used, for instance to facilitate tracing the fate of the compounds or their metabolic products after administration.

Methods for Preparing Compounds of the Application

The compounds of the application, or a pharmaceutically acceptable salt, or solvate, or prodrug thereof, as defined herein may be prepared by conventional methods of chemical synthesis, e.g., those described in the working examples, and starting from readily available starting materials. The starting materials for the processes described in the present application are known or may readily be prepared by conventional methods from commercially available chemicals. The final products of the reactions described herein may be isolated by conventional techniques, e.g., by extraction, crystallization, distillation, or chromatography.

Generally, the compounds of the application may be prepared according to synthetic routes A, B, C, or D. These synthetic routes are given as non-limiting examples on how the compounds of the application may be prepared.

Synthetic Routes

Synthetic Route A

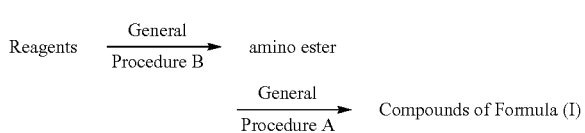

Synthetic Route B

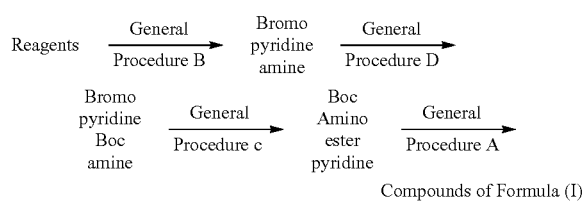

Synthetic Route C

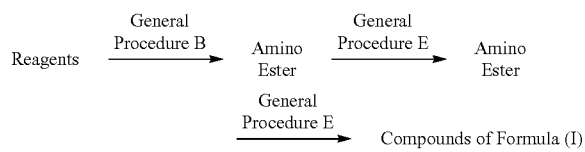

Synthetic Route D

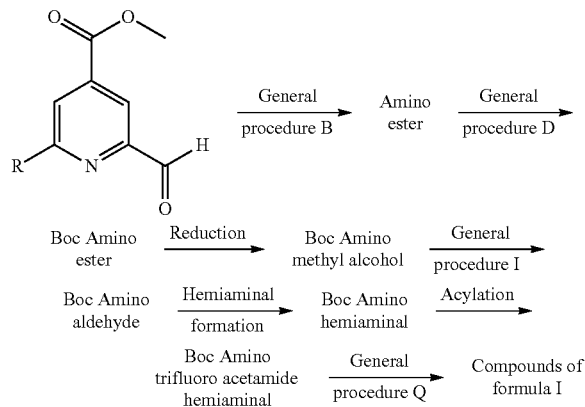

Useful general procedures to prepare the compounds of the application include general procedures A-U. These procedures are given as non-limiting examples on how the compounds of the application may be prepared.

General Procedures

General Procedure A (Ester Hydrolysis)

The ester was dissolved in a solvent such as MeOH-THF-$H_2O$ (1:1:1) and an alkali hydroxide such as KOH (1.0 equivalent (eq)) was added. The reaction mixture was stirred at room temperature. Solvents were removed in vacuo to give the alkali salt of the product. The product was optionally deprotected and purified by chromatography if needed.

General Procedure B (Reductive Amination)

A solution of aldehyde and amine with optionally protected functional groups (1.3 equiv.) in a solvent such as 1,2-dichloroethane was stirred for 1-24 hours at room temperature, before $NaBH(AcO)_3$ (2 equivalents) was added. The mixture was stirred at room temperature. The product was optionally deprotected and purified by chromatography if needed.

General Procedure C (Suzuki-Miyaura Cross Coupling)

[1,1'-Bis(diphenylphosphino)ferrocene]dichloropalladium(II) ($Pd(dppf)_2Cl_2$) (0.03 eq), potassium alkynyl trifluoroborate (2.0 eq) and triethylamine ($Et_3N$) (1.5 eq) were added to a solution of a bromide in a solvent such as THF. The reaction mixture was refluxed. Solvents were removed in vacuo and the product was purified by chromatography if needed.

General Procedure D (Boc Protection of Amines)

Di-tert-butylcarbonate ($Boc_2O$) (1.2 eq) and $NaHCO_3$ (4.0 eq) were added to a solution of amine in $THF/H_2O$. The reaction mixture was stirred at room temperature. Evaporation gave the title compound which was purified by chromatography if needed.

General Procedure E (Reduction of Nitriles, Azides, and Oximes)

A slurry of a nitrile, azide, or oxime and Pd/C in a solvent such as MeOH was stirred in the presence of $H_2$. The product was isolated by filtration and purified chromatography if needed.

General Procedure F (Nucleophilic Substitution of Sulfonate)

A nucleophile, such as an azide (2.0 eq), was added to a solution of a sulfonate ester in a solvent such as dimethylformamide and the product was isolated by concentration of the reaction mixture. Trituration with a solvent such as dichloromethane and purification by chromatography if needed.

General Procedure G (Formation of Sulfonate Ester)

An alcohol dissolved in a solvent such as dichloromethane was treated with sulfonyl chloride (2 eq) and triethylamine (2 eq). The product was isolated by aqueous workup and chromatography if needed.

General Procedure H (Formation of Oxime)

Hydroxylamine hydrochloride (1.3 eq) and $Na_2CO_3$ (0.5 eq) was added to a suspension of aldehyde in a solvent such as $H_2O$ at 0° C. The reaction mixture was stirred at room temperature. Filtration at 0° C. afforded the title compound or the product was isolated after workup and chromatography if needed.

General Procedure I (Oxidation of Benzylic Alcohol)

A mixture of the benzylic alcohol can be oxidized by $MnO_2$, Dess-Martin periodinane, or by Swern Oxidation in a solvent such as toluene or dichloromethane. Filtration, aqueous work-up, and purification by chromatography, if necessary, can afford the title compound.

General Procedure J (Phthalimide to Primary Amine)

Hydrazine monohydrate (1.5 eq) was added to a solution of alkyl phthalimide in a solvent such as EtOH (ethanol). The reaction mixture was refluxed for 3 hours. The mixture was filtered at 0° C. and evaporation of the filtrate gave the title compound, which was purified by chromatography if needed.

General Procedure K (Mitsunobu Reaction)

An azodicarbonyl compound (1.3 eq), such as 1,1'-(azodicarbonyl)dipiperidine, $PPh_3$ (1.3 eq) and a suitable nucleophile such as phthalimide (1.3 eq), were added to a solution of the alcohol in a solvent such as THF. The reaction mixture was stirred at room temperature. The mixture was filtered at 0° C. and workup afforded the title compound which was purified by chromatography if needed.

General Procedure L (2 (or 6)-hydroxymethyl pyridine from 2 (or 6)-methyl pyridine)

m-CPBA (meta-chloroperoxybenzoic acid) (1.2 eq) was added to a solution of 2-methyl pyridine in DCM (dichloromethane) at 0° C. and the resulting mixture was then stirred at room temperature. The resulting residue from an aqueous workup was dissolved in DCM and TFAA (trifluoroacetic anhydride) (10 eq). The mixture was then stirred at room temperature. Aqueous work up afforded the title compound which was purified by chromatography if needed.

General Procedure M (Alkyl Ethers from Alcohols)

NaH (60% in mineral oil, 1.5 eq) and an alkyl halide such as methyl iodide (3.0 eq) were added to a solution of a primary alcohol in DMF (dimethylformamide). The mixture was stirred at room temperature overnight. Aqueous work up gave the title compound which was purified by chromatography if needed.

General Procedure N (Substitution of Aromatic Compounds)

To a solution of the aromatic compound in a solvent such as THF at −78° C. was added n-butyllithium (1 eq) followed by freshly distilled DMF (1 eq) and the resulting mixture was stirred at 0° C. Aqueous work up provided the title compound which was purified by chromatography if needed.

General Procedure O (Synthesis of 1,5-substituted imidazoles)

A mixture of alkyl aldehyde, alkylamine, and tosyl methylisocyanide in an anhydrous solvent such as DMF were stirred at room temperature. Aqueous work up provided the title compound, which was purified by chromatography if needed.

General Procedure P (Synthesis of Triazole)

Prepared from literature procedure (Ref: Journal of Medicinal Chemistry, 2007, 50, 1939-1957) from [(t-butoxycarbonyl)amino]acetic acid, amine and other suitable reagents.

General Procedure Q (Removal of Protecting Group)

Acid such as hydrochloric acid, trifluoroacetic acid, or acetic acid was added at room temperature to a solution of the methyl 2-{[(tert-butyldimethylsilyl)oxy]methyl}-6-{[({4-[(4-fluorophenyl)methyl]-4H-1,2,4-triazol-3-yl}methyl)amino]methyl}pyridine-4-carboxylate in solvent such as water, THF, or DCM. The reaction mixture was stirred 1 hour to overnight. The product was isolated by concentration and column chromatography if needed.

General Procedure R (Cyano Insertion)

A compound such as 2-methoxy-5-phenethoxypyridine 1-oxide in a solvent such as DCM was treated with reagents such as dimethylcarbamoyl chloride and trimethylsilyl chloride for 12 h. The product was isolated by aqueous workup and chromatography if needed.

General Procedure S (Formation of N-Oxide)

Oxidizing agent such as m-CPBA (meta-chloroperoxybenzoic acid) was added to a solution of 2-methoxy-5-(2-phenylethoxy)pyridine in solvent such as dichloromethane at 0° C. and the resulting mixture was then stirred at room temperature. The product was isolated by aqueous workup and chromatography if needed.

General Procedure T (N or O-Alkylation)

6-Methoxypyridin-3-ol in a solution such as DMF or THF was added base such as $K_2CO_3$ and (2-bromoethyl)benzene. The mixture can be heated or at room temperature overnight. The product was isolated by aqueous workup and chromatography if needed.

General Procedure U (Formation of Silyl Ether)

Tert-butyldimethylsilyl chloride was added to a solution of alcohol (methyl 2,6-bis(hydroxymethyl)pyridine-4-carboxylate), triethylamine and 4-dimethylaminopyridine in solvent such as dichloromethane at 0° C., stirred at room temperature overnight. The product was isolated by aqueous workup and chromatography if needed.

Other methods that may be useful to prepare the compounds of the application include methods A through Q, AA through EE, VV through ZZ, and AB through AS. These methods are given as non-limiting examples on how the compounds of the application may be prepared.

Useful methods for the generation of intermediates in route to compounds of the application are described in Example 1.

Preparation of Compounds of Formula (I): Q is $C(O)R^{21}$

Scheme 1

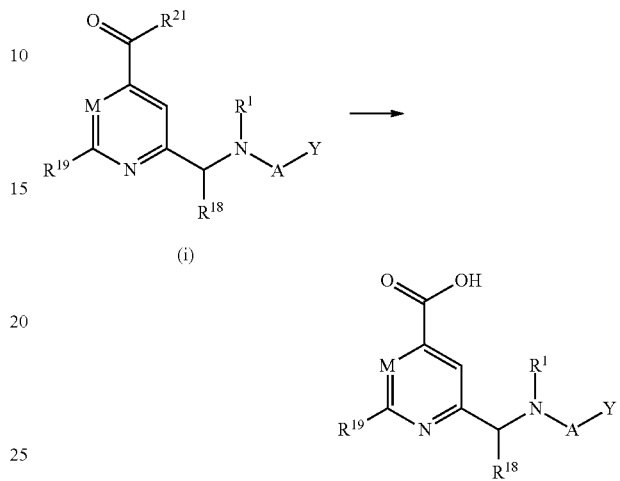

(i)

Method A

The compound of Formula (I) may be prepared according to scheme 1 at room temperature, or by heating for up to several hours by use of a solvent such as DMSO, an alcohol, or tetrahydrofuran, and a base such as LiOH, KOH, or NaOH. A purification method such as silica gel chromatography is employed if needed.

Method B

The compound of Formula (I) may be prepared according to scheme 1 at room temperature, or by heating for up to several hours by use of a solvent such as water, DMSO, an alcohol, or tetrahydrofuran, and an aqueous acid. A purification method such as silica gel chromatography is employed if needed.

Scheme 2

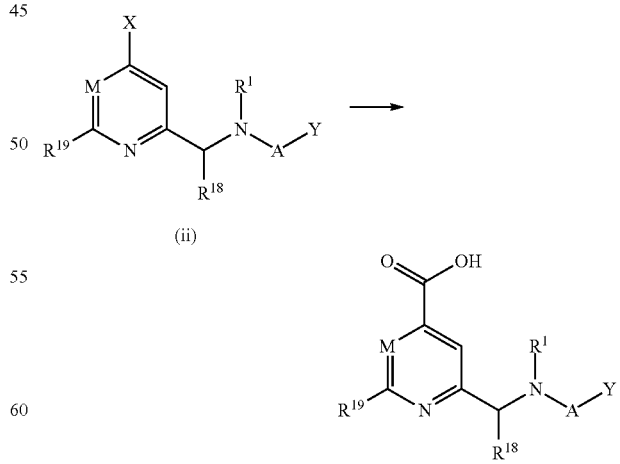

(ii)

Method C

The compound of Formula (I), where $R^1$ is a suitable amine protecting group (i.e., tert-butoxy carbonyl (Boc)) or as defined above, may be prepared from halides or triflates (ii) (X=halogen, OTf) according to scheme 2 either at room temperature or by heating for several hours in a solvent such as toluene or tetrahydrofuran in the presence of a base such as cesium carbonate or potassium tert-butoxide, a catalyst such as Pd complex and optionally a salt such as lithium chloride and carbon monoxide. A purification method such as silica gel chromatography is employed if needed.

Preparation of Compounds of Formula (I): Q is CH$_2$NHR$^{13}$

Scheme 3

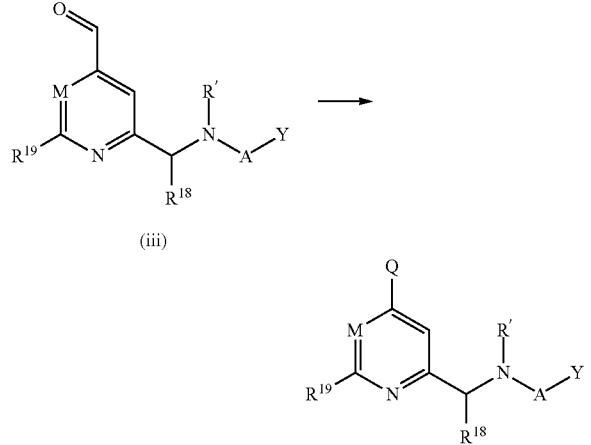

(iii)

Method D

Compounds of Formula (I) may be prepared from intermediate (iii) according to scheme 3, where R' is a suitable protecting group or R$^1$, in one-pot or by a stepwise procedure by mixing with an amine, optionally containing orthogonal protected reactive sites, and a reducing agent such as NaBH$_4$, NaBH(OAc)$_3$, NaCNBH$_3$, or Et$_3$SiH, either at room temperature or by heating for up to several hours in a solvent such as an alcohol, DCE, DCM, water, or toluene, and by optionally adding a catalyst such as an acid or a Lewis acid. Optionally, protecting groups may be removed and a purification method such as silica gel chromatography is employed if needed.

Scheme 4

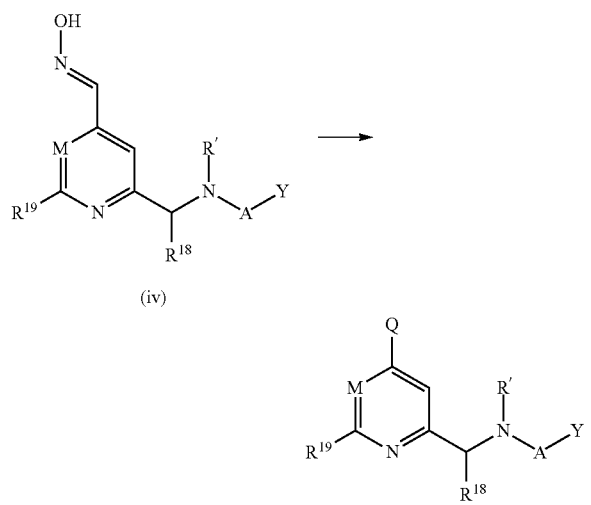

(iv)

Method E

Compounds of Formula (I) may be prepared from oximes (iv), optionally containing orthogonally protected reactive sites, according to scheme 4, where R' is a suitable protecting group or R$^1$, by use of reducing agents, such as a hydrogen atmosphere over a suitable catalyst, such as palladium on charcoal, in a suitable solvent, such as an alcohol. Optionally, protecting groups may be removed and a purification method such as silica gel chromatography is employed if needed.

Scheme 5

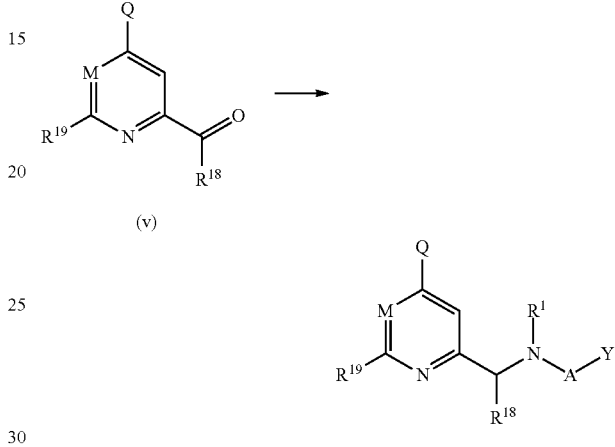

(v)

Method F

Compounds of Formula (I) may be prepared from intermediate (v) according to scheme 5 analogously to Method D.

Scheme 6

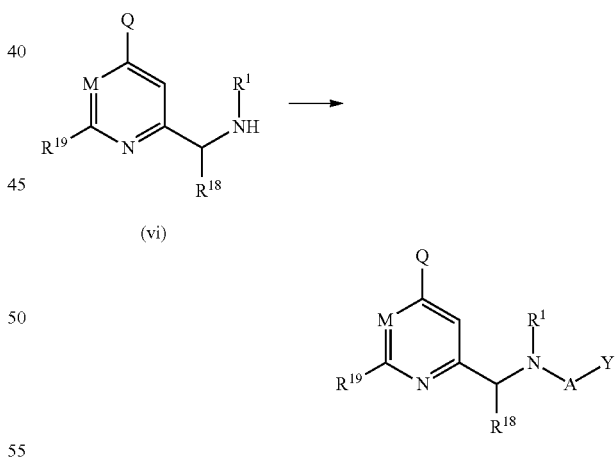

(vi)

Method G

Compounds of Formula (I) may be prepared according to scheme 6 using a suitable solvent such as toluene or tetrahydrofuran, a base such as cesium carbonate or potassium t-butoxide, a suitable catalyst such as Pd$_2$(dba)$_3$, optionally a suitable salt such as lithium chloride and the desired electrophile such as aryl bromide or heteroaryl bromide. The compounds of Formula (I) are generated at room temperature or by heating for several hours, such as for 2 to 5 hours. Optionally, protecting groups may be removed and a purification method such as silica gel chromatography is employed if needed.

Method H

Compounds of Formula (I) may be prepared from amines according to scheme 6 according to Method D.

Method I

The compounds of Formula (I) may be prepared according to scheme 6 by use of a solvent such as DMF or THF, a base such as sodium hydride or cesium carbonate and a suitable electrophilic species such as an epoxide, a heteroaromatic chloride, an aliphatic, allylic or benzylic bromide, chloride or sulfonate, or a carbonyl chloride. Optionally, protecting groups may be removed and a purification method such as silica gel chromatography is employed if needed.

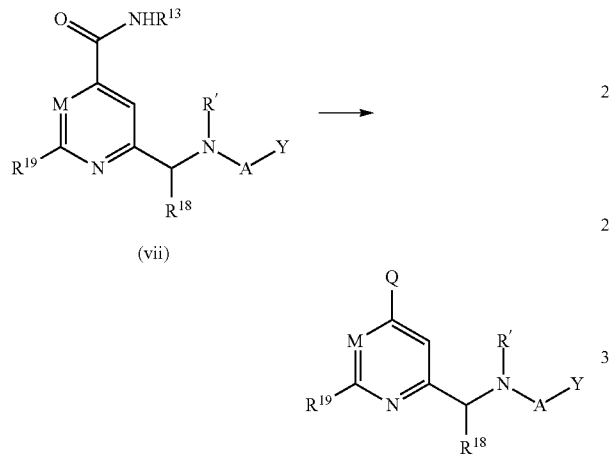

(vii)

(Scheme 7)

Method J

Compounds of Formula (I) may be prepared from amides (vii), optionally containing orthogonal protected reactive sites, according to scheme 7, where R' is a suitable protecting group or $R^1$, by use of reducing agents, such as lithium aluminium hydride or borane-complexes, in a suitable solvent, such as an ether or tetrahydrofuran. Optionally, protecting groups may be removed and a purification method such as silica gel chromatography is employed if needed.

Preparation of Compounds of Formula (I): Q is CH=$NR^{12}$

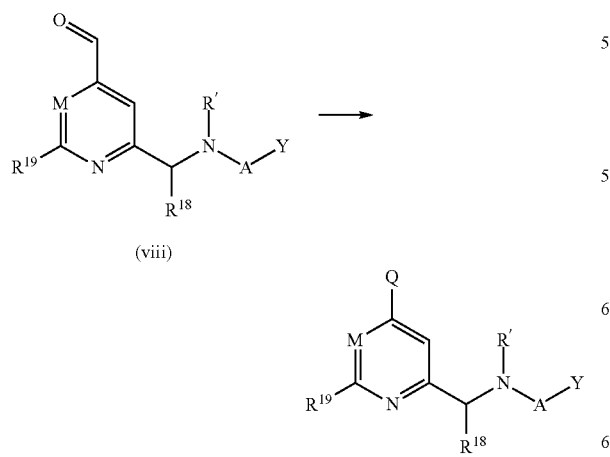

(viii)

(Scheme 8)

Method K

Compounds of Formula (I) may be prepared from intermediate (viii) according to scheme 8, where R' is a suitable protecting group or $R^1$, by mixing with an amine, optionally containing orthogonally protected reactive sites, either at room temperature or by heating for up to several hours in a solvent such as an alcohol, DCE, DCM, water, or toluene, and by optionally adding a catalyst such as a Lewis acid. Optionally, protecting groups may be removed and a purification method such as silica gel chromatography is employed if needed.

Preparation of Compounds of Formula (I): Q is CH=O

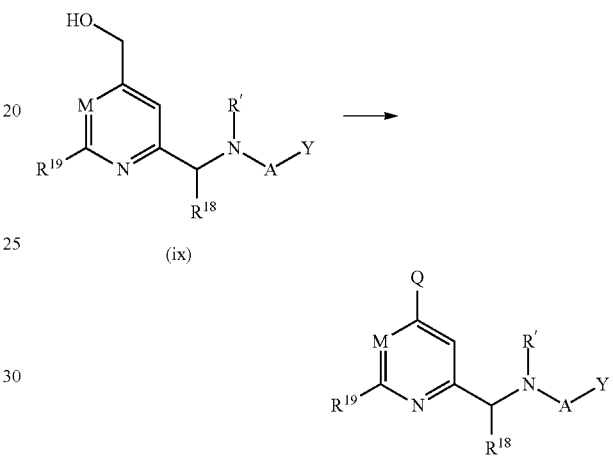

(ix)

(Scheme 9)

Method L

Compounds of Formula (I) may be prepared according to scheme 9, where R' is a suitable protecting group or $R^1$, by a Swern or alternatively a Dess-Martin oxidation of the alcohol to aldehyde. Optionally, protecting groups may be removed and a purification method such as silica gel chromatography is employed if needed.

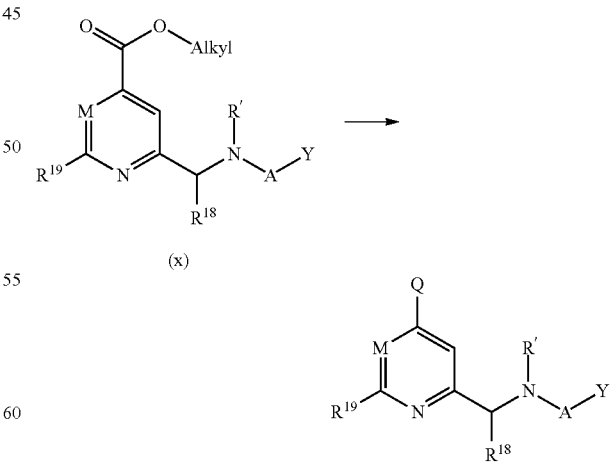

(x)

(Scheme 10)

Method M

Compounds of Formula (I) may be prepared from esters (x), where R' is a suitable protecting group or $R^1$, optionally containing orthogonal protected reactive sites, according to scheme 10, by use of reducing agents, such as DIBAL-H, in a suitable solvent, such as toluene. Optionally, protecting groups may be removed and a purification method such as silica gel chromatography is employed if needed.

Scheme 11

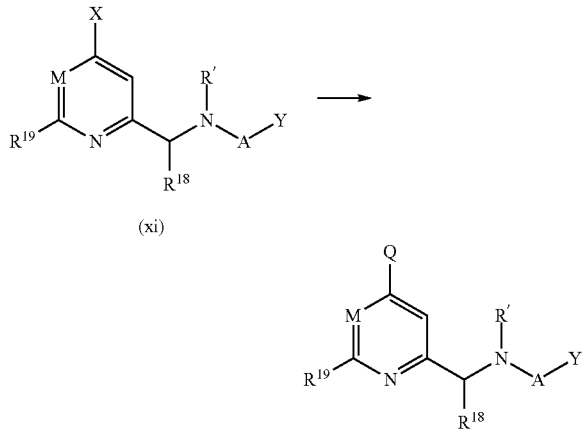

(xi)

Method N

Compounds of (I) may prepared at low temperature, e.g., at −78° C., from halides (xi), where R' is a suitable protecting group or $R^1$, optionally containing orthogonal protected reactive sites according to scheme 11 (X designates a halogen atom) by halogen metal exchange, e.g., by treatment with an alkyl lithium reagent, followed by addition of DMF in a solvent, such as dichloromethane. Optionally, protecting groups may be removed and a purification method such as silica gel chromatography is employed if needed.

Preparation of Compounds of Formula (I): Q is $CH(OR^{17})_2$

Scheme 12

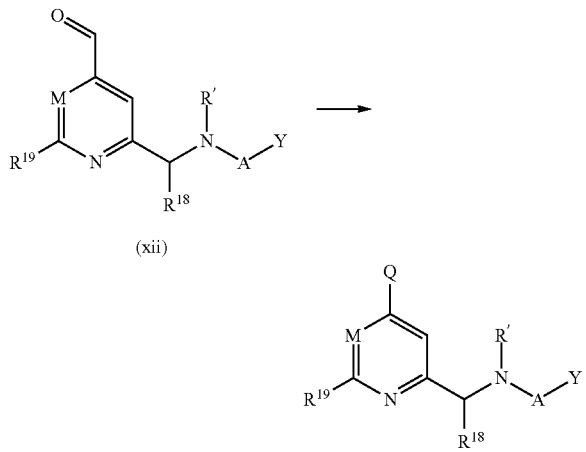

(xii)

Method O

Compounds of Formula (I) may prepared from intermediates (xii) according to scheme 12 by stirring in an alcohol in the presence of a Lewis acid or an acid, such as HCl or pyridinium toluene-4-sulfonate, optionally by reacting with trialkyl orthoformate or in the presence of a drying agent such as an inorganic dry salt, or with azeotropic removal of water, at room temperature or by heating for several hours depending on the method. Optionally, protecting groups may be removed and a purification method such as silica gel chromatography is employed if needed.

Preparation of Compounds of Formula (I): Q is W and $R^{16}$ is H

Method P

Compounds of Formula (I) may prepared from intermediates (xii) according to scheme 12 by stirring in a diamine, an amino alcohol or an amino thiol, optionally in the presence of an acid such as HCl or pyridinium toluene-4-sulfonate, optionally in the presence of a drying agent such as an inorganic dry salt, molecular sieves, or with azeotropic removal of water, at room temperature or by heating for several hours depending on the method. Optionally, protecting groups may be removed and a purification method such as silica gel chromatography is employed if needed.

Preparation of Compounds of Formula (I): Q is W and $R^3$ is not H

Method Q

Compounds of Formula (I) may prepared from the aforementioned compound where Q is W and $R^{16}$ is —H, by reacting with a suitably activated acyl group such as an acyl halide or acyl anhydride at room temperature or by heating for several hours in a solvent such as dichloroethane or THF. Optionally, protecting groups may be removed and a purification method such as silica gel chromatography is employed if needed.

Preparation of Reagents and Intermediates in Route to Compounds of Formula (I)

Scheme 13

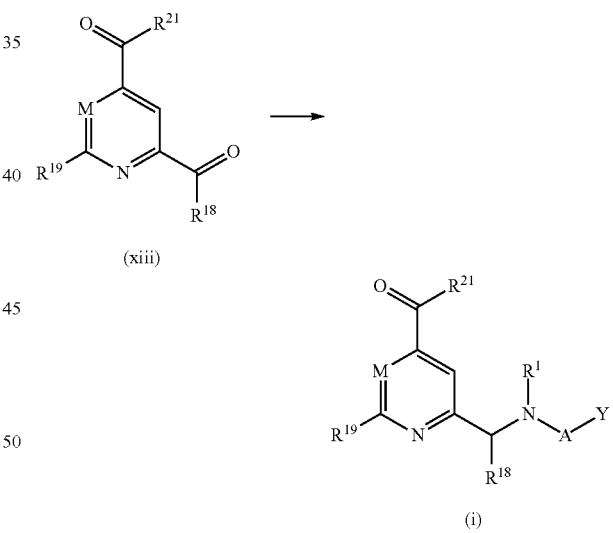

Method AA

Intermediates (i) may be prepared from intermediates (xiii) according to scheme 13 in one-pot or by a stepwise procedure by mixing with an amine, optionally containing orthogonal protected reactive sites, and a reducing agent such as $NaBH_4$, $NaBH(OAc)_3$, $NaCNBH_3$, or $Et_3SiH$, either at room temperature or by heating for up to several hours in a solvent such as an alcohol, DCE, DCM, water, or toluene, and by optionally adding a catalyst such as an acid or a Lewis acid. Optionally, protecting groups may be removed and a purification method such as silica gel chromatography is employed if needed.

Scheme 14

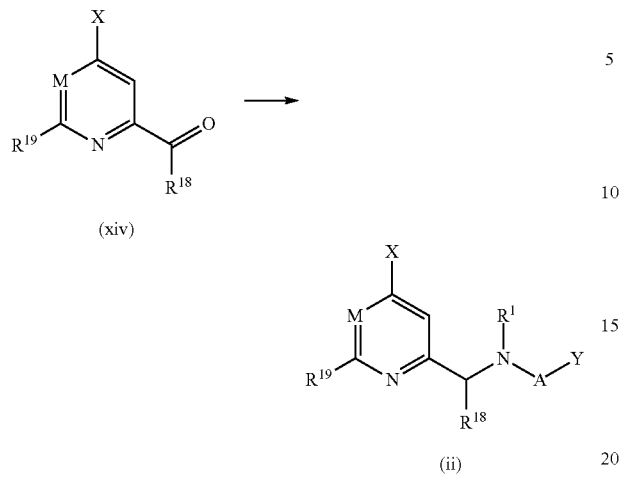

(xiv)

(ii)

Scheme 16

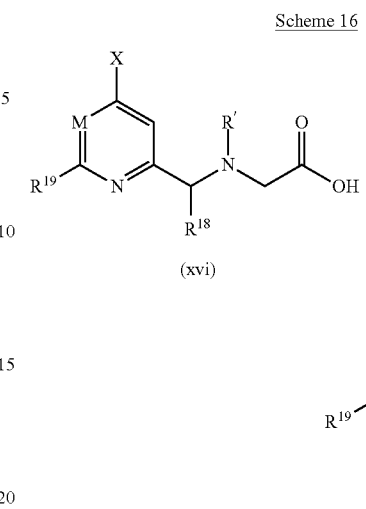

(xvi)

(iia)

Method BB

Intermediates (ii) may be prepared from intermediates (xiv) according to Scheme 14 analogously to Method AA.

Method DD

Intermediates (iia) may be prepared from (xvi) according to scheme 16 analogously to Method CC.

Scheme 15

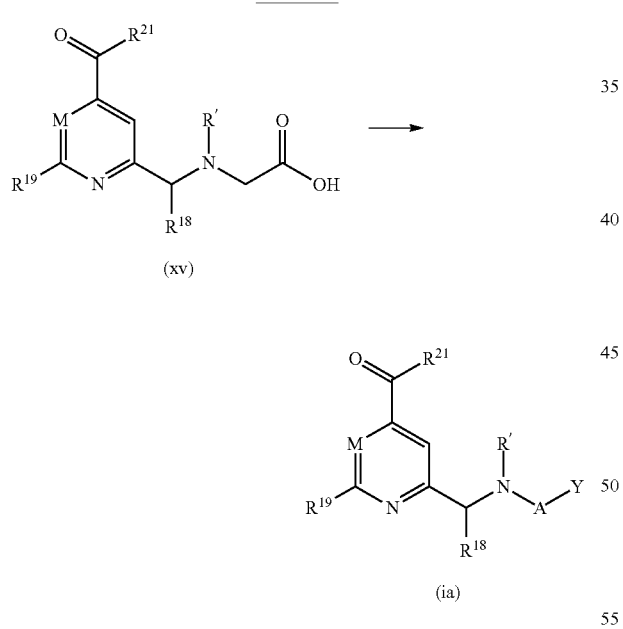

(xv)

(ia)

Scheme 17

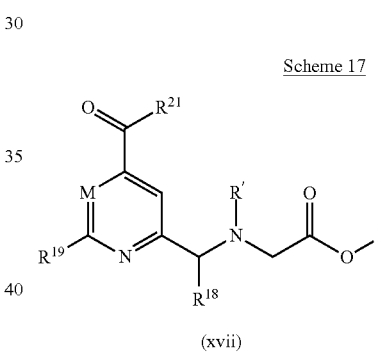

(xvii)

(xv)

Method CC

Intermediates (ia) may be prepared from (xv) according to scheme 15, where R' is a suitable protecting group or $R^1$, by use of a solvent such as DMF or THF, a base such as a hindered tertiary amine, a dehydrating agent such as EDCI or DCC and an amine, and by mixing at or above room temperature for a period up to several hours. Optionally, said protecting group may be removed, and a purification method such as silica gel chromatography is employed if needed.

Method EE

Intermediates (xv) may be prepared according to scheme 17 from (xvii), where R' is a suitable protecting group or $R^1$ and R" is an orthogonal protecting group. R" may be selectively removed, such as by removal of R": tert-Bu in presence of R': $CF_3CO$— by treating with trifluoroacetic acid in a solvent such as dichloromethane at room temperature for several hours. A purification method such as silica gel chromatography is employed if needed.

Scheme 18

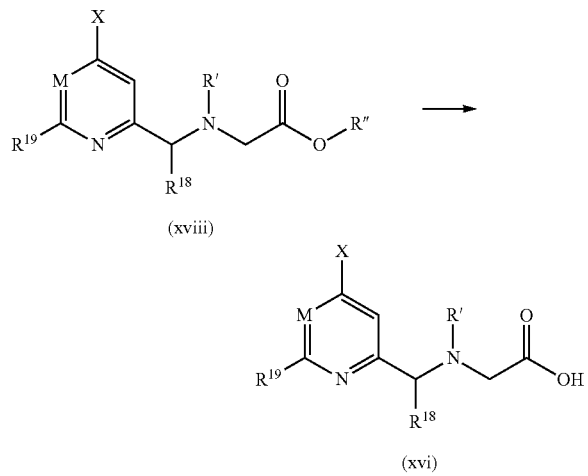

(xviii)

(xvi)

Method FF

Intermediates (xvi) may be prepared from (xviii) according to scheme 18 analogously to Method EE.

Scheme 19

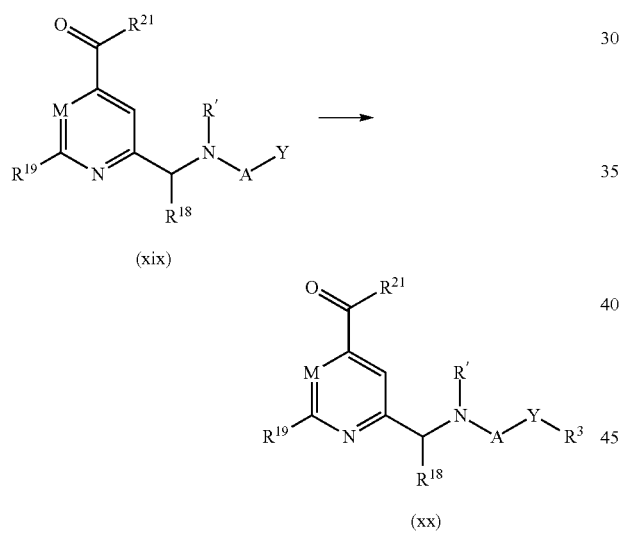

(xix)

(xx)

Method GG

Intermediates (xx) may be prepared from intermediates (xix) according to scheme 19 in one-pot or by a stepwise procedure by mixing the amine (R': $R^1$ or a suitable protecting group) with an aldehyde and a reducing agent such as $NaBH_4$, $NaBH(OAc)_3$, $NaCNBH_3$, or $Et_3SiH$, either at room temperature or by heating for up to several hours in a solvent such as an alcohol, DCE, DCM, water, or toluene, and optionally adding a catalyst such as an acid or a Lewis acid. Optionally, protecting groups may be removed and a purification method such as silica gel chromatography is employed if needed.

Method HH

Intermediates (xx) may be prepared from (xix) according to scheme 19 by use of a solvent such as DMF or THF, optionally a base, and a suitable electrophilic species such as an epoxide, an aliphatic, allylic or benzylic bromide, chloride, or sulfonate. A purification method such as silica gel chromatography is employed if needed.

Scheme 20

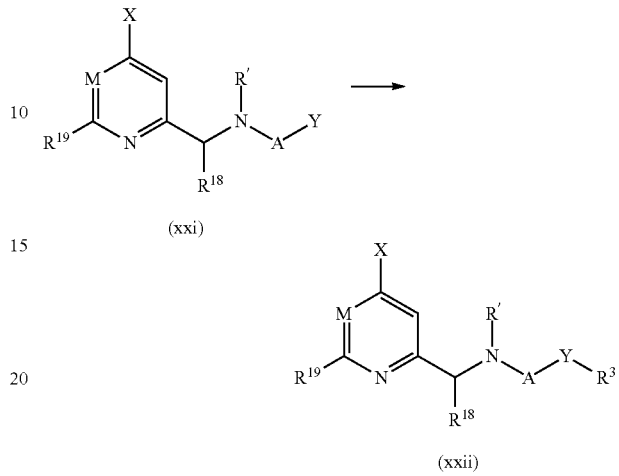

(xxi)

(xxii)

Method II

Intermediates (xxii) may be prepared from (xxi) according to scheme 20 analogously to Method GG.

Method JJ

Intermediates (xxii) may be prepared from (xxi) according to scheme 20 analogously to Method HH.

Scheme 21

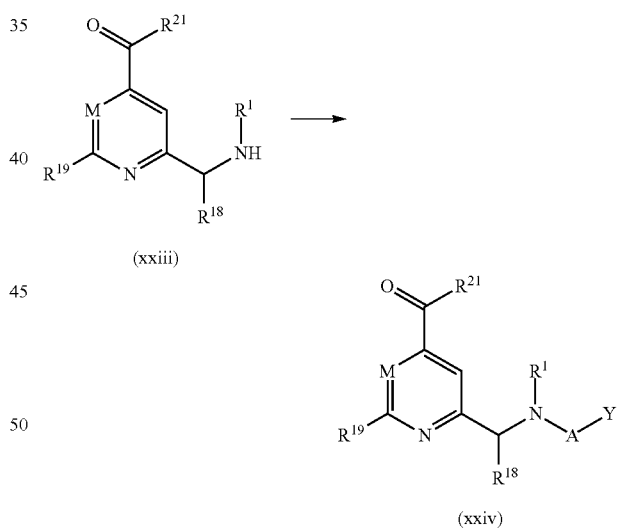

(xxiii)

(xxiv)

Method KK

Intermediates (xxiv) may be prepared from intermediates (xxiii) according to scheme 21 in one-pot or by a stepwise procedure by mixing with an aldehyde or ketone, optionally containing orthogonal protected reactive sites, and a reducing agent such as $NaBH_4$, $NaBH(OAc)_3$, $NaCNBH_3$, or $Et_3SiH$, either at room temperature or by heating for up to several hours in a solvent such as an alcohol, DCE, DCM, water, or toluene, and optionally adding a catalyst such as an acid or a Lewis acid. Optionally, protecting groups may be removed and a purification method such as silica gel chromatography is employed if needed.

Scheme 22

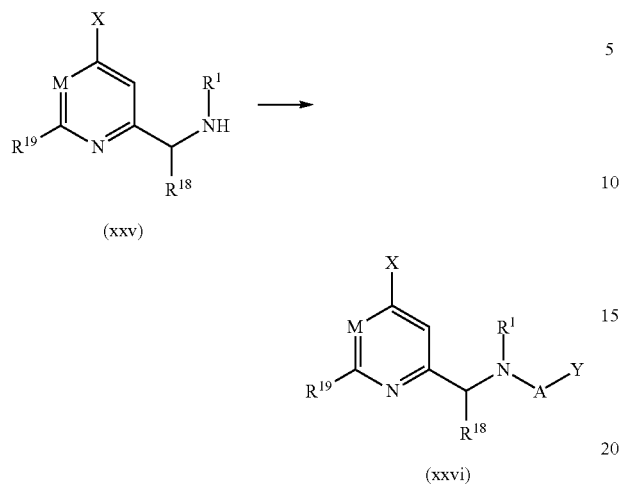

Method LL

Intermediates (xxvi) may be prepared from intermediates (xxv) according to scheme 22 analogously to Method KK.

Scheme 23

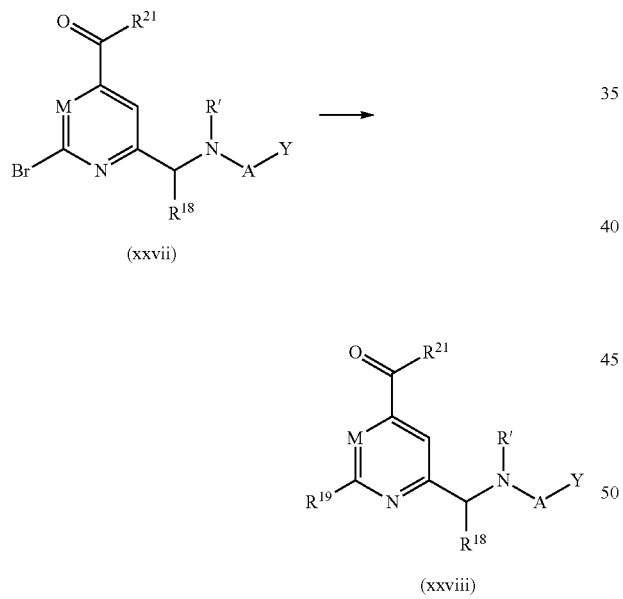

Method MM

Intermediates (xxviii) (R': R¹ or a suitable protecting group) may be prepared from intermediates (xxvii) according to scheme 23 either at room temperature or by heating for up to several hours by use of a solvent such as toluene or tetrahydrofuran, an alkynyl trihalogen borate, a base such as triethylamine, cesium carbonate, or potassium tert-butoxide, and a catalyst such as palladium complex. A purification method such as silica gel chromatography is employed if needed.

Scheme 24

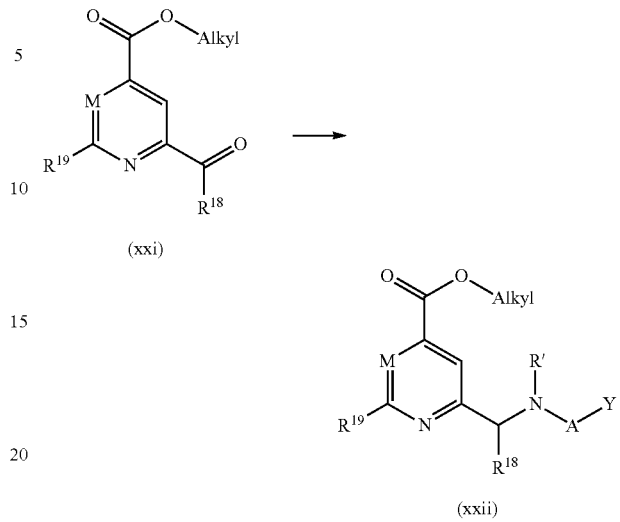

Method NN

Intermediates (xxx) may be prepared from intermediates (xxix) according to scheme 24 analogously to Method D.

Scheme 25

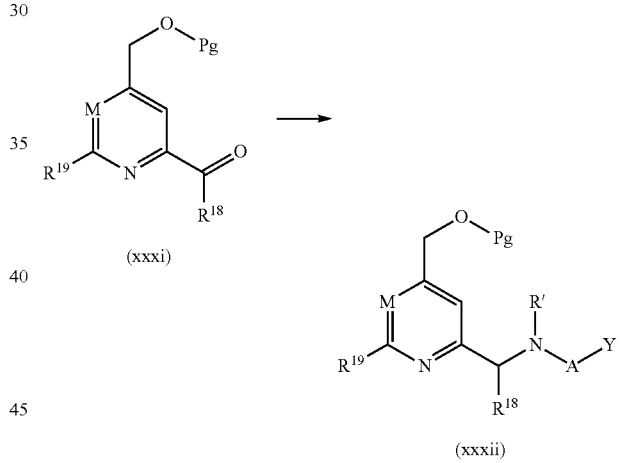

Method OO

Intermediates (xxxii), where Pg designates a suitable protecting group, such as TBMDS or TIPS, may be prepared from intermediates (xxxi) according to scheme 25 analogously to Method D.

Scheme 26

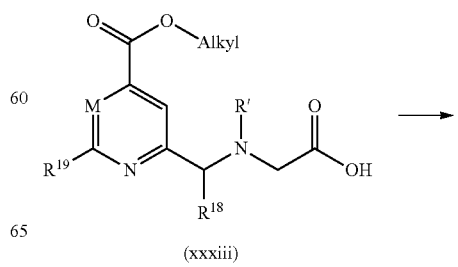

-continued

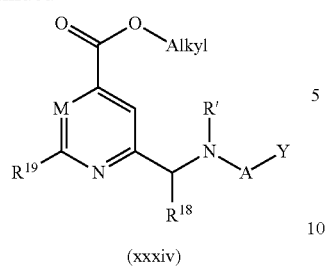

(xxxiv)

Method PP

Intermediates (xxxiv) be prepared according to scheme 26, where R' is a suitable protecting group or R¹, by use of a solvent such as DMF or THF, a base such as a hindered tertiary amine, a dehydrating agent such as EDCI or DCC and an amine, and by mixing at or above room temperature for a period up to several hours. Optionally, the said protecting group may be removed, and a purification method such as silica gel chromatography is employed if needed.

-continued

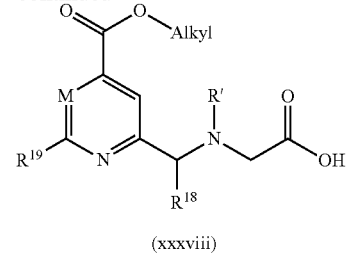

(xxxviii)

Method RR

Intermediates (xxxviii) may be prepared according to scheme 28 from intermediates (xxxvii), where R' is a suitable protecting group or R¹ and R" is an orthogonal protecting group, which may be selectively removed, such as removal of R": tert-Bu in presence of R': $CF_3CO$ by treating with trifluoroacetic acid in a solvent such as dichloromethane at room temperature for several hours. A purification method such as silica gel chromatography is employed if needed.

Scheme 27

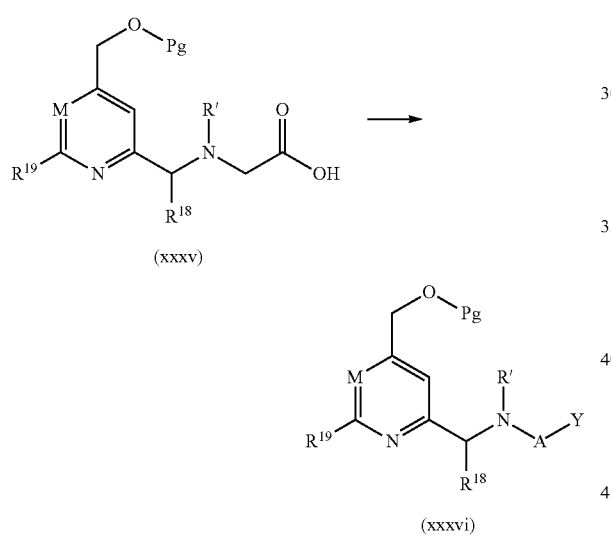

Method QQ

Intermediates (xxxvi) may be prepared according to scheme 27 from intermediates (xxxv) analogously to Method PP.

Scheme 29

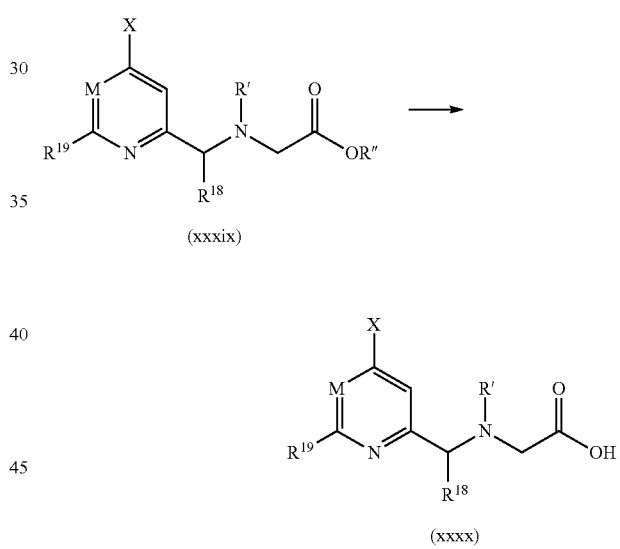

Method SS

Intermediates (xxxx) may be prepared according to scheme 29 analogously to Method RR.

Scheme 28

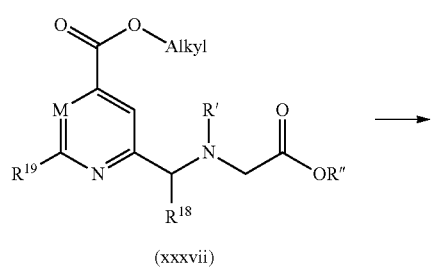

(xxxvii)

Scheme 30

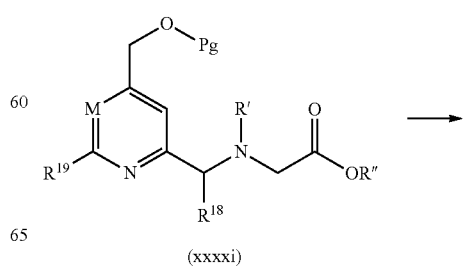

(xxxxi)

-continued

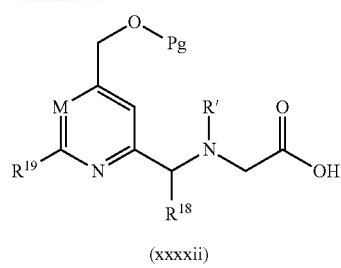

(xxxxii)

Method TT

Intermediates (xxxxii) may be prepared according to scheme 30 analogously to Method RR.

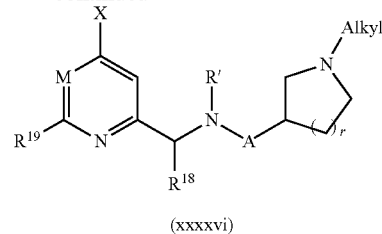

(xxxxvi)

Method VV

Intermediates (xxxxvi) may be prepared according to scheme 32 analogously to Method UU.

Intermediates (xxxxvi) may be prepared according to scheme 32 analogously to Method I.

Scheme 31

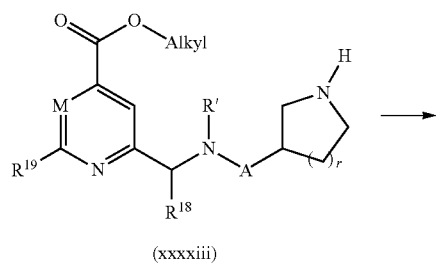

(xxxxiii)

(xxxxiv)

Scheme 33

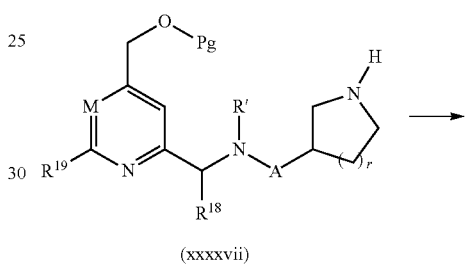

(xxxxvii)

(xxxxviii)

Method UU

Intermediates (xxxxiv) may be prepared from aldehydes and intermediates (xxxxiii) according to scheme 31 analogously to Method D.

Intermediates (xxxxiv) may be prepared according to scheme 31 analogously to Method I.

Method WW

Intermediates (xxxxviii) may be prepared according to scheme 33 analogously to Method UU.

Intermediates (xxxxviii) may be prepared according to scheme 33 analogously to Method I Scheme 32

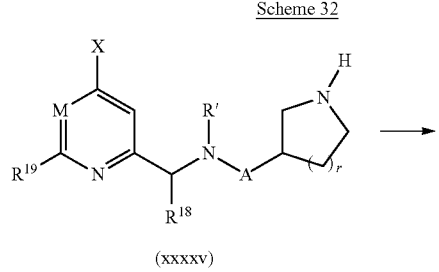

(xxxxv)

Scheme 34

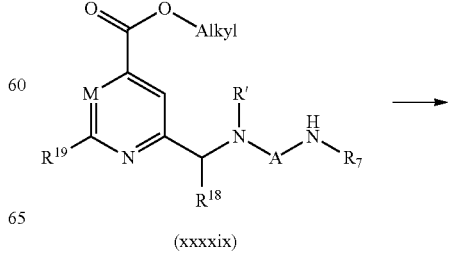

(xxxxix)

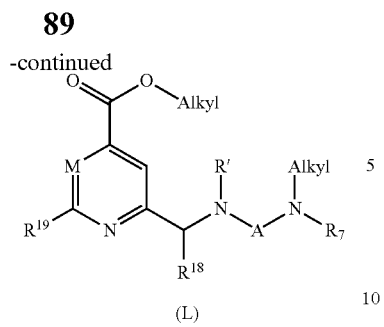

(L)

Method XX

Intermediates (L) may be prepared from aldehydes and intermediates (xxxxix) according to scheme 34 analogously to Method D.

Intermediates (L) may be also prepared according to scheme 34 analogously to Method I.

Scheme 35

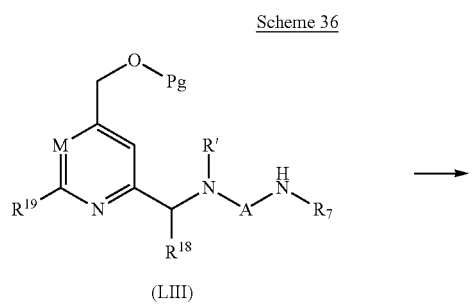

(LI)

(LII)

Method YY

Intermediates (LII) may be prepared from aldehydes according to scheme 35 analogously to Method D.

Intermediates (LII) may be prepared according to scheme 35 analogously to Method I.

Scheme 36

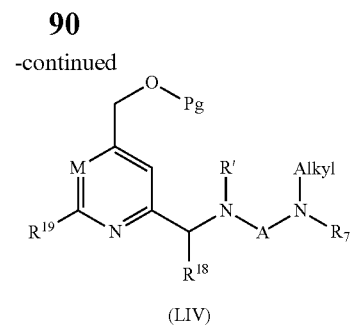

(LIV)

Method ZZ

Intermediates (LIV) may be prepared from aldehydes according to scheme 36 analogously to Method D.

Intermediates (LIV) may be prepared according to scheme 36 analogously to Method I.

Scheme 37

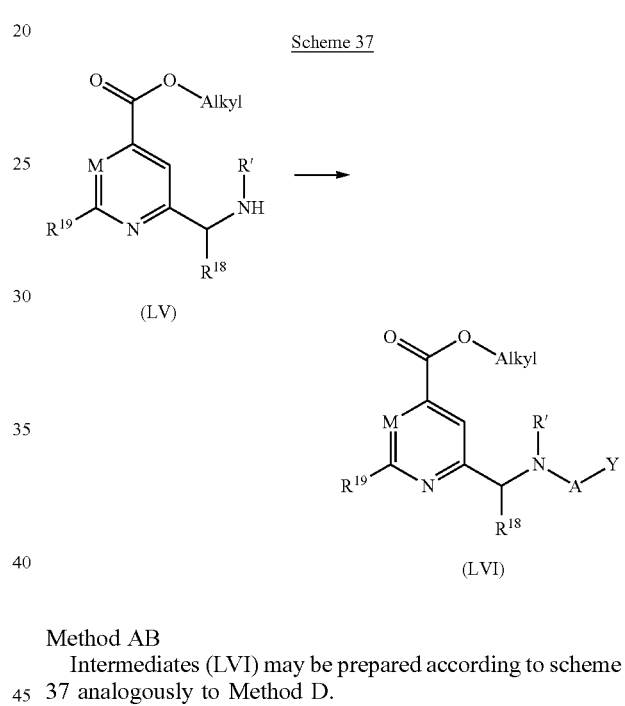

(LV)

(LVI)

Method AB

Intermediates (LVI) may be prepared according to scheme 37 analogously to Method D.

Scheme 38

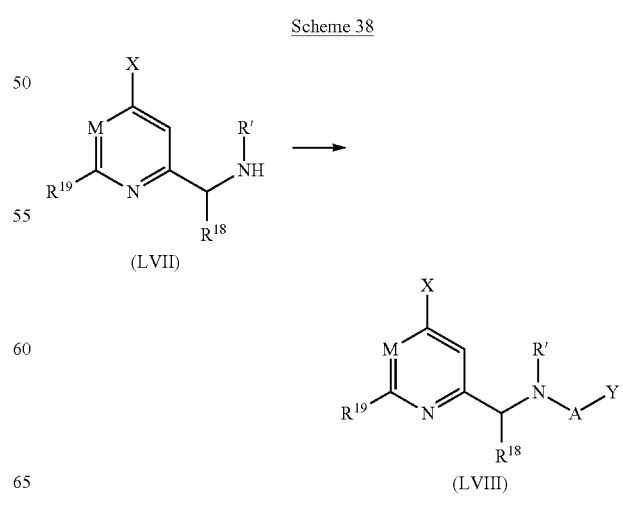

(LVII)

(LVIII)

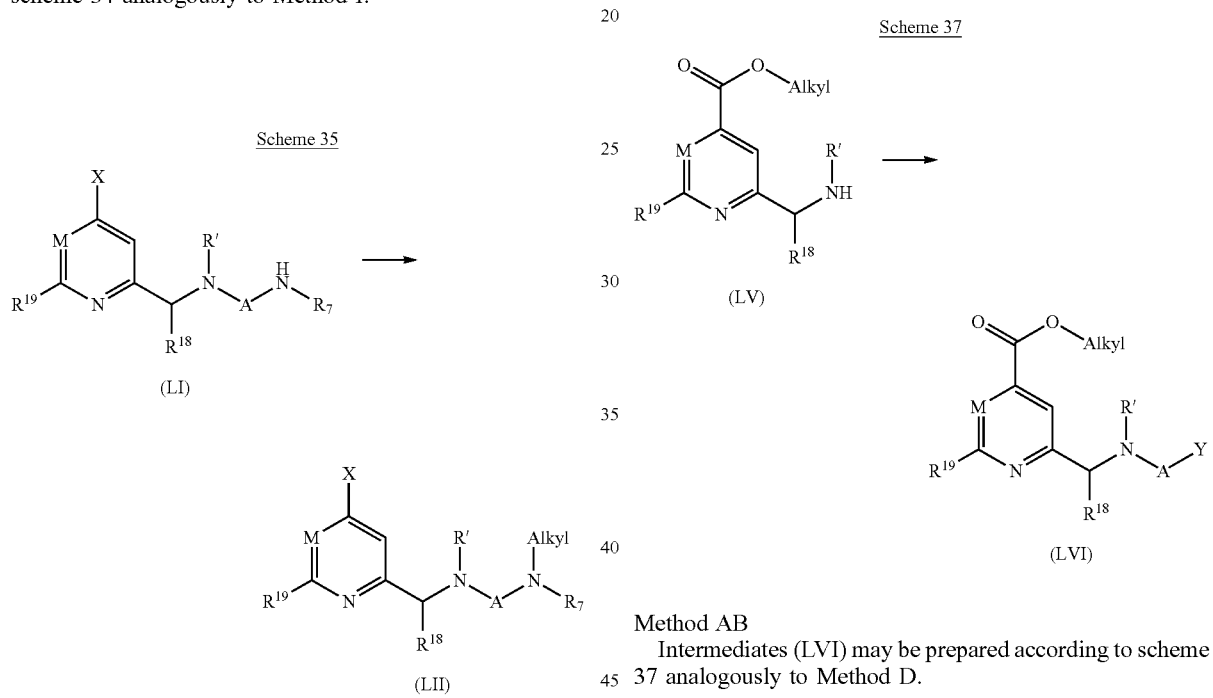

(LIII)

Method AC

Intermediates (LVIII) may be prepared according to scheme 38 analogously to Method D.

Scheme 39

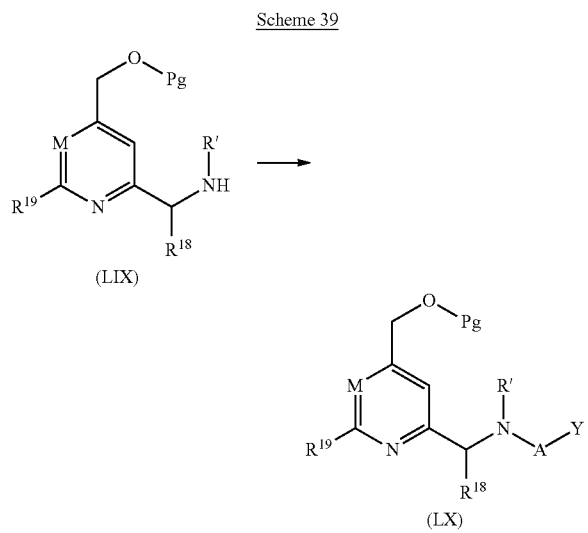

(LIX)

(LX)

Method AD

Intermediates (LX) may be prepared according to scheme 39 analogously to Method D.

Scheme 40

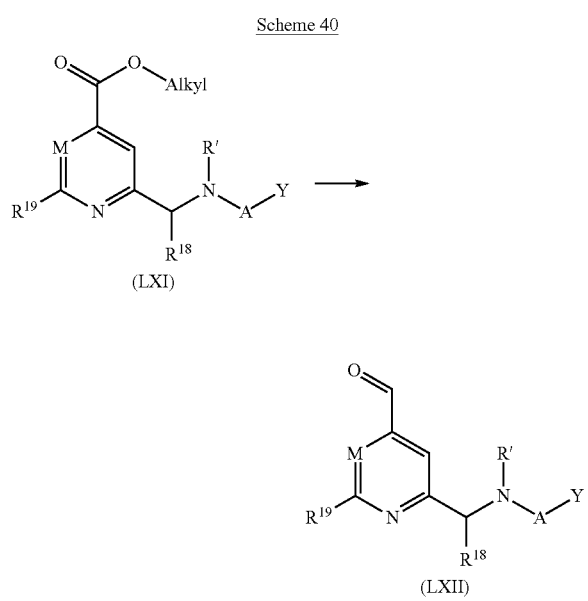

(LXI)

(LXII)

Method AE

Intermediates (LXII) may be prepared from esters (LXI), optionally containing orthogonal protected reactive sites, according to scheme 40, by use of reducing agents, such as DIBAL-H, in a suitable solvent, such as toluene. Optionally, protecting groups may be removed and a purification method such as silica gel chromatography is employed if needed.

Scheme 41

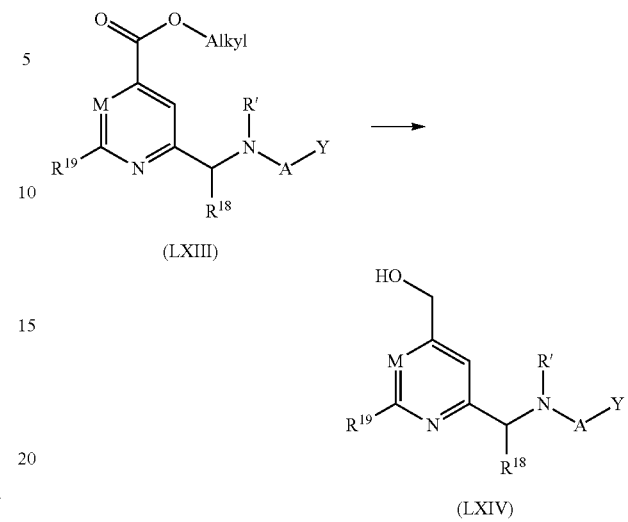

(LXIII)

(LXIV)

Method AF

Intermediates (LXIV) may be prepared from esters (LXIII), optionally containing orthogonal protected reactive sites, according to scheme 41, by use of reducing agents, such as lithium aluminium hydride or borane-complexes, in a suitable solvent, such as an ether or tetrahydrofuran. Optionally, protecting groups may be removed and a purification method such as silica gel chromatography is employed if needed.

Scheme 42

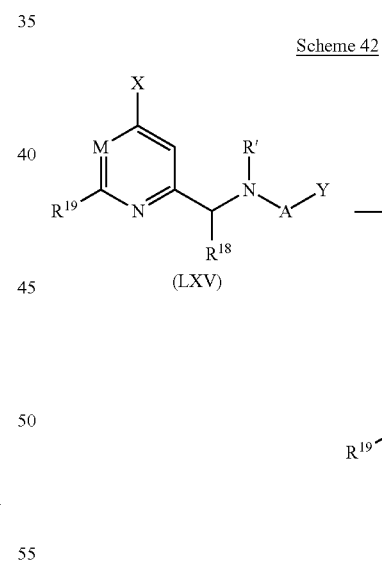

(LXV)

(LXVI)

Method AG

Intermediates (LXVI) may be prepared according to scheme 42 using Method N.

Intermediates (LXVI) may be prepared according to scheme 42 either at room temperature or by heating for several hours by use of a solvent such as toluene or tetrahydrofuran, a base such as cesium carbonate or potassium t-butoxide, a catalyst such as $Pd_2(dba)_3$, optionally a salt such as lithium chloride and the desired nucleophile such as carbon monoxide. A purification method such as silica gel chromatography is employed if needed.

Scheme 43

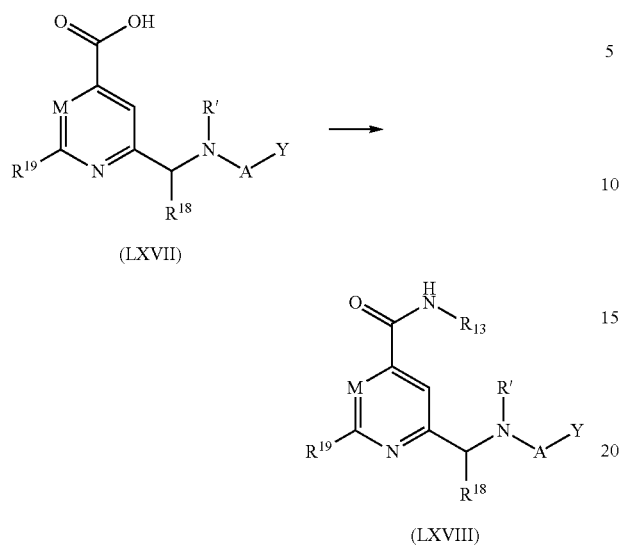

Method AH

Intermediates (LXVIII) may be prepared according to scheme 43 analogously to Method DD.

Scheme 44

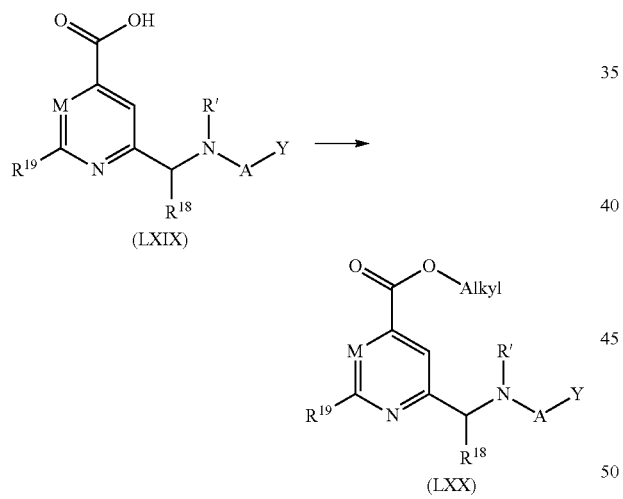

Method AI

Intermediates (LXX) may be prepared according to scheme 44 by use of a solvent such as DMF or THF, a base such as cesium carbonate and an electrophile such as an alkyl halide, heteroaromatic halide, alkenyl halide, etc., and by mixing at or above room temperature for several hours. A purification method such as silica gel chromatography or trituration is employed if needed.

Method AJ

Intermediates (LXX) may be prepared according to scheme 44 by use of acetic catalysis in an alcohol at room temperature or at reflux. A purification method such as silica gel chromatography or trituration is employed if needed.

Scheme 45

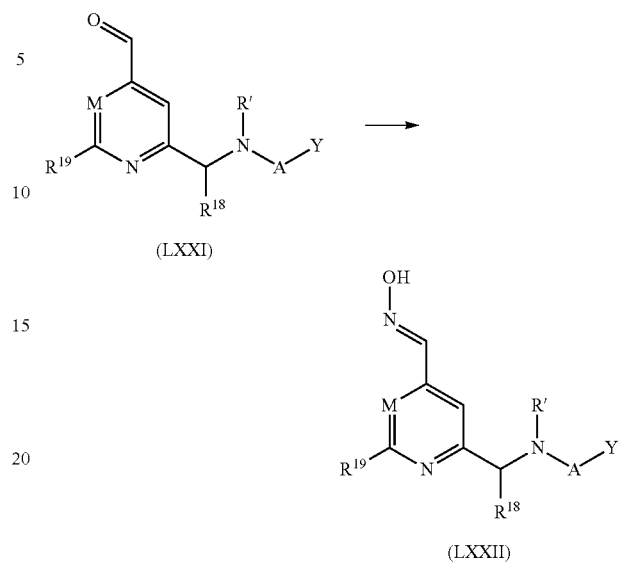

Method AK

Intermediates (LXXII) may be prepared according to scheme 45 from 4-formyl pyridines by reaction with hydroxylamine in a solvent such as an alcohol or water.

Scheme 46

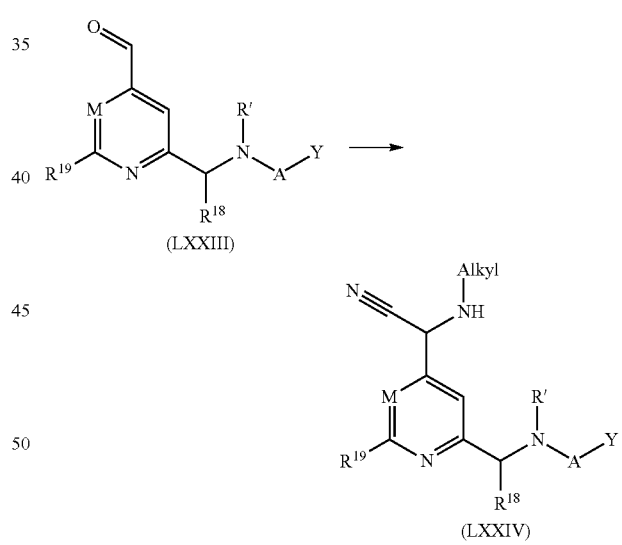

Method AL

Intermediates (LXXIV) may be prepared according to scheme 46 from 4-formyl pyridines by reaction with an amine, optionally containing orthogonally protected reactive sites, either at room temperature or by heating for up to several hours in a solvent such as an alcohol, DCE, DCM, THF water, or toluene, and by optionally adding a catalyst such as a Lewis acid. Subsequently reacting with TMSCN in a solvent such as acetonitrile. Optionally, protecting groups may be removed and a purification method such as silica gel chromatography is employed if needed.

Scheme 47

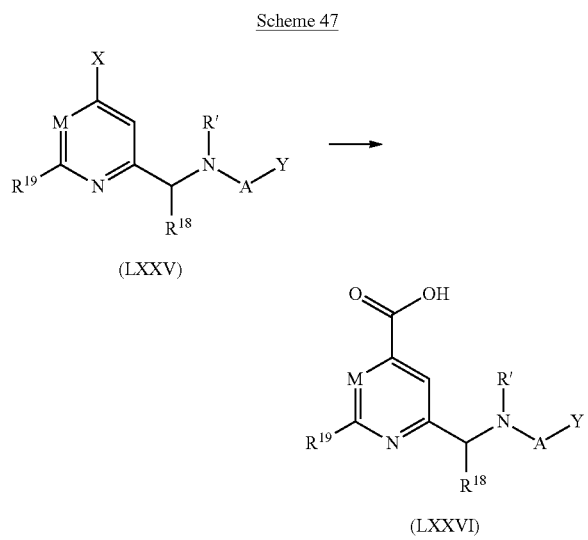

Method AM

Intermediates (LXXVI) may be prepared according to scheme 47 either at room temperature or by heating for several hours by use of a solvent such as wet toluene or tetrahydrofuran, a base such as cesium carbonate or potassium t-butoxide, a catalyst such as $Pd_2(dba)_3$, optionally a salt such as lithium chloride and the desired nucleophile such as carbon monoxide. A purification method such as silica gel chromatography is employed if needed.

Scheme 48

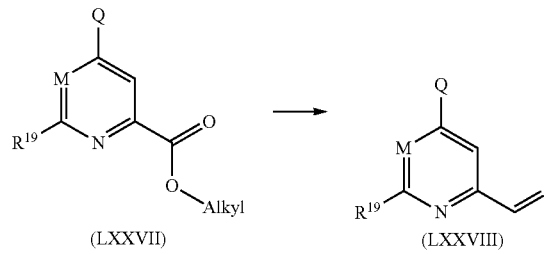

Method AN

Intermediates (LXXVIII) may be prepared according to Scheme 48 from intermediates (LXXVII) analogously to Method M.

Scheme 49

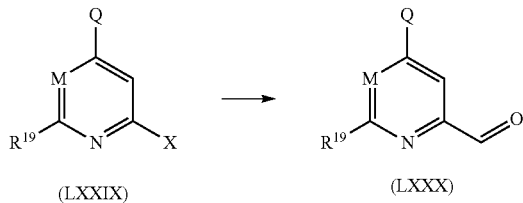

Method AO

Intermediates (LXXX) may be prepared according to scheme 49 from intermediates (LXXIX) analogously to Method N.

Scheme 50

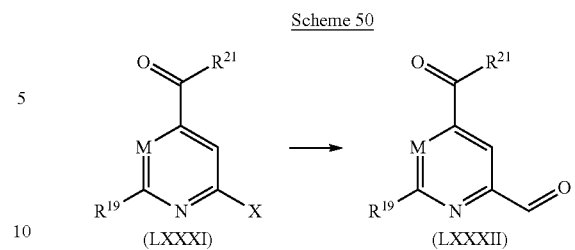

Method AP

Intermediates (LXXXII) may be prepared according to scheme 50 from intermediates (LXXXI) analogously to Method N.

Scheme 51

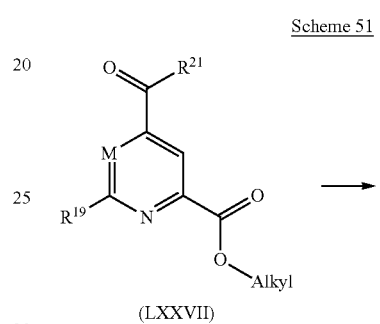

Method AQ

Intermediates (LXXXIV) may be prepared according to Scheme 51 from intermediates (LXXXIII) analogously to Method M.

Scheme 52

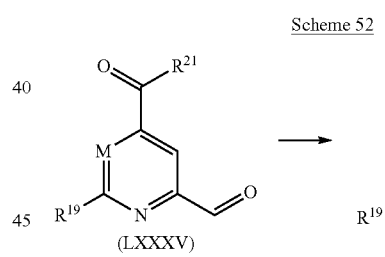

Method AR

Intermediates (LXXXVI) may be prepared according to scheme 52 from intermediate (LXXXV) by reaction with hydroxylamine in a solvent such as an alcohol or water.

Scheme 53

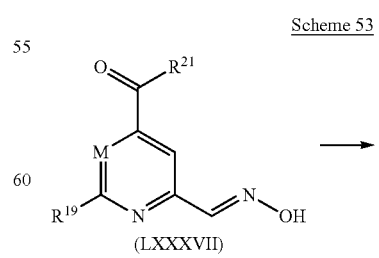

Method AS

Intermediates (LXXXVIII) may be prepared from oximes (LXXXVII), optionally containing orthogonally protected reactive sites, according to scheme 53, by use of reducing agents, such as a hydrogen atmosphere over a suitable catalyst, such as palladium on charcoal, in a suitable solvent, such as an alcohol. Optionally, protecting groups may be removed and a purification method such as silica gel chromatography is employed if needed.

Methods for Biological Assays

The compounds of the application, or a pharmaceutically acceptable salt, or solvate, or prodrug thereof, are tested in an in vitro AlphaLISA assay. Enzymes are dissolved in enzyme buffer and incubated before they are added to DMSO solutions of compounds of the application, or a pharmaceutically acceptable salt, or solvate, or prodrug thereof, in enzyme buffer. The reaction mixture is then incubated for an additional period of time before substrate solution is added and then the resulting mixture again incubated. Acceptor beads and suspended Epigenetic Buffer from stock are added and the suspension is again incubated before a suspension of streptavidin donor beads in Epigenetic Buffer is added. After an additional period of incubation, the plates are read. Results are shown below in Table 1. Compounds 32 and 116 can be metabolized to Compounds 4 and 93, respectively.

TABLE 1

HDME Inhibition**

| Compound # | KDM4C (nM) | KDM2B (nM) | PHF8 (nM) | KDM6A (nM) | KDM5B (nM) |
|---|---|---|---|---|---|
| 1 | >10000 | 431 | 352 | >10000 | >10000 |
| 2 | >10000 | 2939 | >10000 | >10000 | >10000 |
| 3 | >10000 | 4650 | >10000 | >10000 | >10000 |
| 4 | >10000 | 30 | 234 | >10000 | >10000 |
| 5 | >10000 | 1601 | 3761 | >10000 | >10000 |
| 6 | >10000 | 708 | 353 | >10000 | 3348 |
| 7 | >10000 | 7103 | >10000 | >10000 | 1231 |
| 8 | >10000 | 150 | 384 | >10000 | >10000 |
| 9 | 299 | >10000 | >10000 | >10000 | 714 |
| 10 | 1372 | >10000 | >10000 | >10000 | 1280 |
| 11 | >10000 | 1545 | 6928 | >10000 | 5479 |
| 12 | >10000 | 1601 | >10000 | >10000 | 3761 |
| 13 | >10000 | 2273 | 5779 | >10000 | >10000 |
| 14 | >10000 | 3233 | 5604 | >10000 | >10000 |
| 15 | >10000 | 5682 | >6000 | >10000 | >10000 |
| 16 | >10000 | >6800 | 3492 | >9000 | >10000 |
| 17 | >10000 | >10000 | >10000 | >10000 | >10000 |
| 18 | >10000 | 3932 | 3025 | >10000 | >10000 |
| 19 | >10000 | 1153 | 890 | >10000 | 348 |
| 20 | >10000 | 5428 | >10000 | >10000 | >10000 |
| 21 | >10000 | 5354 | >10000 | >10000 | >10000 |
| 22 | >10000 | >10000 | >10000 | >10000 | >10000 |
| 23 | >10000 | >10000 | >10000 | >10000 | >10000 |
| 24 | >10000 | 2226 | nd | 8350 | 262 |
| 25 | >10000 | 1130 | 1210 | >10000 | >10000 |
| 26 | >10000 | 565 | 1030 | >10000 | 3018 |
| 27 | >10000 | 158 | 537 | >10000 | >10000 |
| 28 | >10000 | 462 | 1060 | >10000 | >10000 |
| 29 | >10000 | 1136 | 2655 | >10000 | >10000 |
| 30 | >10000 | 703 | 2219 | >10000 | >10000 |
| 31 | >10000 | 3974 | >10000 | >10000 | >10000 |
| 33 | >10000 | 1024 | 2038 | >10000 | >10000 |
| 34 | >10000 | 1238 | >10000 | >10000 | >10000 |
| 35 | >10000 | 117 | 437 | >10000 | >10000 |
| 36 | >10000 | 248 | 908 | >10000 | >10000 |
| 37 | >10000 | 297 | 489 | >10000 | >10000 |
| 38 | >10000 | 2290 | >10000 | >10000 | 4624 |
| 39 | >10000 | 155 | 472 | >10000 | >10000 |
| 40 | >10000 | 599 | 1532 | >10000 | >10000 |
| 41 | >10000 | 1658 | 6557 | nd | >10000 |
| 42 | >10000 | 659 | 859 | nd | >10000 |
| 43 | >10000 | 442 | 869 | nd | >10000 |
| 44 | >10000 | 2006 | 2375 | nd | >10000 |
| 45 | >10000 | 501 | 491 | nd | >10000 |
| 46 | >10000 | 2270 | 2276 | nd | >10000 |
| 47 | >10000 | 1256 | 391 | nd | 4079 |
| 48 | >10000 | >10000 | >10000 | nd | >10000 |
| 49 | >10000 | 838 | 1109 | nd | >10000 |
| 50 | >10000 | 692 | 1036 | nd | >10000 |
| 51 | >10000 | 2828 | 3879 | nd | >10000 |
| 52 | >10000 | 1727 | 1509 | nd | >10000 |
| 53 | >10000 | 760 | 881 | nd | >10000 |
| 54 | >10000 | 1140 | 1185 | nd | >10000 |
| 55 | >10000 | 656 | 1300 | nd | 1782 |
| 56 | >10000 | 482 | 883 | nd | >10000 |
| 57 | >10000 | 1144 | 1272 | nd | >10000 |
| 58 | nd | >10000 | >10000 | nd | >10000 |
| 59 | nd | 2747 | >10000 | nd | nd |
| 60 | >10000 | 1619 | >10000 | nd | 526 |
| 61 | >10000 | 4181 | 2551 | nd | >10000 |
| 62 | 7370 | 244 | 307 | nd | 231 |
| 63 | >10000 | 333 | 1404 | nd | >10000 |
| 64 | >10000 | 104 | 246 | nd | >10000 |
| 65 | >10000 | 34 | 1009 | nd | 151 |
| 66 | >10000 | 5772 | >10000 | nd | 943 |
| 67 | >10000 | 715 | 791 | nd | >10000 |
| 68 | >10000 | 1683 | 1797 | nd | >10000 |
| 69 | >10000 | 27 | 662 | nd | >10000 |
| 70 | >10000 | 485 | 1749 | nd | 559 |
| 71 | >10000 | 138 | 1775 | nd | >10000 |
| 72 | >10000 | 283 | 529 | nd | >10000 |
| 73 | >10000 | 252 | 1648 | nd | >10000 |
| 74 | nd | 1859 | 3815 | nd | >10000 |
| 75 | >10000 | 587 | 1274 | nd | 431 |
| 76 | nd | 4734 | >10000 | nd | >10000 |
| 77 | >10000 | 379 | 1090 | nd | >10000 |
| 78 | >10000 | 340 | 1136 | nd | 641 |
| 79 | >10000 | >10000 | >10000 | nd | >10000 |
| 80 | >10000 | 683 | 5297 | nd | 1988 |
| 81 | 823 | 140 | 334 | nd | 21 |
| 82 | >10000 | 1403 | 3320 | nd | >10000 |
| 83 | >10000 | 1525 | 4950 | nd | 755 |
| 84 | >10000 | 251 | 673 | nd | 6198 |
| 85 | >10000 | 461 | 1861 | nd | >10000 |
| 86 | >10000 | >10000 | >10000 | nd | >10000 |
| 87 | >10000 | 1703 | 2297 | nd | >10000 |
| 88 | 3468 | 585 | 1273 | nd | 246 |
| 89 | >10000 | 2299 | >10000 | nd | >10000 |
| 90 | >10000 | 2942 | 6969 | nd | >10000 |
| 91 | >10000 | 328 | 1113 | nd | >10000 |
| 92 | >10000 | 53 | 1230 | nd | >10000 |
| 93 | >10000 | 32 | 1480 | nd | >10000 |
| 94 | >10000 | 47 | 2030 | nd | >10000 |
| 95 | >10000 | 389 | 9650 | nd | >10000 |
| 96 | >10000 | 61 | 1810 | nd | >10000 |
| 97 | >10000 | 308 | >10000 | nd | >10000 |
| 98 | 1666 | 530 | >10000 | nd | 8 |
| 99 | >10000 | >10000 | >10000 | nd | 8410 |
| 100 | >10000 | 70 | 1148 | nd | 635 |
| 101 | >10000 | 105 | 1330 | nd | 6108 |
| 102 | 7050 | 240 | >10000 | nd | 20 |
| 103 | >10000 | 56 | 160 | nd | >10000 |
| 104 | nd | 145 | 400 | nd | >10000 |
| 105 | nd | 242 | nd | nd | >10000 |
| 106 | nd | 3100 | 2770 | nd | >10000 |
| 107 | >10000 | 5180 | >10000 | nd | >10000 |
| 108 | >10000 | 133 | 861 | nd | >10000 |
| 109 | >10000 | >10000 | >10000 | nd | >10000 |
| 110 | >10000 | >10000 | >10000 | nd | >10000 |
| 111 | >10000 | 823 | 5100 | nd | 1070 |
| 112 | >10000 | 375 | 3520 | nd | >10000 |
| 113 | >10000 | 2830 | 3000 | nd | >10000 |
| 114 | >10000 | 317 | 1140 | nd | >10000 |
| 115 | >10000 | 53 | 506 | nd | >10000 |

**nd = not determined

The compounds of the application, or a pharmaceutically acceptable salt, or solvate, or prodrug thereof, are tested in histone lysine demethylase immunofluorescence assays for IC$_{50}$ value determination, in transfected and non-transfected cells, to demonstrate the ability of compounds of the application to inhibit demethylation of H3K4 in a human osteosarcoma cancer cell line. U2OS cells are harvested and seeded into multi well plates containing media and a compound of the application. After incubation of cells with compounds, the cells are washed, harvested by fixation, and again washed. Subsequently, the cells are permeabilized and blocking is performed at room temperature. After incubation with aH3K4me3 primary antibody, the cells are washed, incubated with secondary antibody, and washed again. Finally, PBS is added and high throughput imaging and analysis are performed.

The ability of compounds of the application, or a pharmaceutically acceptable salt, or solvate, or prodrug thereof, to inhibit the proliferation of a human breast cancer cell line is tested in a cell proliferation assay in MCF7 cells. Cells are seeded and incubated before addition of compound. Compounds are diluted in complete medium and added to the plates in duplicates. After addition of compounds, the plates are harvested and analyzed. Briefly, ATP lite solution is added to each well, plates are vortexed, followed by incubation in the dark, and then analyzed for luminescence to determine EC$_{50}$ values. The proliferation assay is run with suspension as well as adherent cells.

Compounds of the application, or a pharmaceutically acceptable salt, or solvate, or prodrug thereof, are tested to determine their ability to inhibit demethylation of a specific H3 lysine in a human osteosarcoma cell line transfected to express a specific histone lysine demethylase. U2OS cells are seeded before transfection. After transfection, the cells are harvested and seeded into multi well plates containing media and compound. After incubation of cells with compounds, the cells are washed, harvested by fixation, and again washed. Subsequently, the cells are permeabilized, blocking is performed and the cells are then incubated with primary antibodies. After incubation with primary antibodies, the cells are washed, incubated with secondary antibodies, and washed again 3 times with PBS. Finally, high throughput imaging and analysis are performed on individual cells which are divided into HA+ (transfected cells) and HA− (non-transfected cells) and IC$_{50}$ values are determined.

The compounds of the application, or a pharmaceutically acceptable salt, or solvate, or prodrug thereof, are tested in an in vitro proliferation assay in combination with standard of care active ingredients. Cells are seeded at appropriate densities in a standard medium containing compounds of the application, or a pharmaceutically acceptable salt, or solvate, or prodrug thereof and active ingredients from standard of care. The cells are then incubated for an additional period of time before the medium is optionally replenished with standard medium or optionally replenished with standard medium containing compounds of the application, or a pharmaceutically acceptable salt, or solvate, or prodrug thereof and active ingredients from standard of care. The incubation and replenishment cycle may be repeated a number of times. Cellular growth or drug tolerance is monitored continuously or at certain time points using standard imaging techniques or standard assays for cell number or viability. The proliferation assay is run with suspension as well as adherent cells.

Methods of Treatment

In a further aspect the present application relates to a method of treating a disease in which HDME plays a role in a subject, said method comprises administering to said subject in need thereof a therapeutically effective amount of at least one compound of the application, or a pharmaceutically acceptable salt, or solvate, or prodrug thereof, as defined herein. The disease may be any disease or disorder, as mentioned herein, such as the examples mentioned in the section "HDME-dependent diseases", and the compound may be administered alone or in a pharmaceutical composition, such as the examples mentioned in the section "Pharmaceutical compositions".

Hence, the application also relates to a compound of the application, or a pharmaceutically acceptable salt, or solvate, or prodrug thereof, as defined herein, for use as a medicament useful for the treatment of a HDME-dependent disease.

The term "treating" and "treatment", as used herein, unless otherwise indicated, refers to reversing, alleviating, inhibiting the process of, or preventing the disease, disorder or condition to which such term applies, or one or more symptoms of such disease, disorder or condition and includes the administration of a compound of the application, or a pharmaceutically acceptable salt, or solvate, or prodrug thereof, to prevent the onset of the symptoms or the complications, or alleviating the symptoms or the complications, or eliminating the disease, condition, or disorder. Preferably treatment is curative or ameliorating.

In one embodiment, the present application relates to a method of treating a HDME-dependent disease in a subject in need thereof, wherein said method comprises administering to said subject a therapeutically effective amount of a compound of the application, or a pharmaceutically acceptable salt, or solvate, or prodrug thereof, as defined herein, to a subject in need of such treatment. The HDME-dependent disease may be any HDME-dependent disease as described herein above. Preferably the HDME-dependent disease is squamous cell carcinomas or any other of the cancer conditions mentioned above.

Hence, the application also relates to a compound of the application, or a pharmaceutically acceptable salt, or solvate, or prodrug thereof, as defined herein, for use in the treatment of a HDME-dependent disease, such as for the treatment of cancer.

Further, the application relates to the use of a compound of the application, or a pharmaceutically acceptable salt, or solvate, or prodrug thereof, as defined herein, for the preparation of a pharmaceutical composition for the treatment of a HDME-dependent disease.

In one embodiment, of the method of treatment of a HDME-dependent disease, the compound of the application, or a pharmaceutically acceptable salt, or solvate, or prodrug thereof, as defined herein, is administered in combination with one or more further active substances. The active substances may be any active substances, and preferably an active substance as described herein below in the section "combination treatment". More preferably, the one or more additional active substances are selected from the group consisting of anti-proliferative or anti-neoplastic agents.

Inhibitory Effect

The present application also relates to a compound of the application, or a pharmaceutically acceptable salt, or solvate, or prodrug thereof, in a method for inhibiting the activity of one or more HDMEs. The present application also relates to a compound of the application, or a pharmaceutically acceptable salt, or solvate, or prodrug thereof, for use as a medicament useful for the inhibition of one or more HDMEs. The present application also relates to a compound of the application, or a pharmaceutically acceptable salt, or solvate, or prodrug thereof, for use in the inhibition of one or more HDMEs. The present application also relates to the use of a compound of the application, or a pharmaceutically acceptable salt, or solvate, or prodrug thereof, for the preparation of a pharmaceutical composition for the inhibition of a HDME. In this respect said one or more HDMEs may be any HDME, however preferably the one or more HDMEs are selected from the JmjC (Jumonji) family, more preferably said one or more HDME(s) are HDME of the human JmjC family and even more preferably are HDME belonging to the KDM7, PHF8, KDM6, KDM5, KDM4 or KDM2 families, In one embodiment the HDME is selected from KDM4C, KDM2B, PHF8, KDM6A, and KDM5B. The method includes contacting a cell with a compound of the application, or a pharmaceutically acceptable salt, or solvate, or prodrug thereof. In one embodiment, the method further provides that the compound is present in an amount effective to produce a concentration sufficient to inhibit the demethylation of a histone in the cell.

The compounds of the application can also be selective for one HDME over another HDME. "Selective" is defined as a property of a compound whereby an amount of the compound sufficient to effect a desired response from a particular receptor type, subtype, class or subclass with significantly less or substantially little or no effect upon the activity other receptor types. In one embodiment, a selective compound may have at least a 10-fold greater effect on activity of the desired HDME receptor or receptors than on other HDME receptor types (e.g., KDM7, PHF8, KDM6, KDM5, KDM4, KDM2). In one embodiment, a selective compound may have at least a 20-fold greater effect on activity of the desired receptor than on other receptor types, or at least a 50-fold greater effect, or at least a 100-fold greater effect, or at least a 1,000-fold greater effect, or at least a 10,000-fold greater effect, or at least a 100,000-fold greater effect, or more than a 100,000-fold greater effect. In one embodiment, the compound of the application, or a pharmaceutically acceptable salt, or solvate, or prodrug thereof, is selective for KDM2. In one embodiment, the compound of the application, or a pharmaceutically acceptable salt, or solvate, or prodrug thereof, is selective for PHF8. In one embodiment, the compound of the application, or a pharmaceutically acceptable salt, or solvate, or prodrug thereof, is selective for KDM4. In one embodiment, the compound of the application, or a pharmaceutically acceptable salt, or solvate, or prodrug thereof, is selective for KDM5. In one embodiment, the compound of the application, or a pharmaceutically acceptable salt, or solvate, or prodrug thereof, is selective for KDM6. In one embodiment, the compound of the application, or a pharmaceutically acceptable salt, or solvate, or prodrug thereof, is selective for KDM7.

In one embodiment, in an assay for demethylation of a histone substrate by said HDME, a compound of the application is capable of reducing or preferably inhibiting said demethylation by said HDME. In one embodiment, said histone substrate may be any histone, but preferably is histone H3 or a fragment thereof. In one embodiment, a fragment comprising K4, K9, K27, or K36 of H3. Preferably, said inhibition is determined as the $IC_{50}$ of said compound of the application in respect of the said demethylation assay.

Preferred compounds of the application, or a pharmaceutically acceptable salt, or solvate, or prodrug thereof, which have an $IC_{50}$ at or below 1 μM, more preferably less than 300 nM, for example less than 100 nM, such as less than 50 nM in respect of demethylation of any of said histone substrates by any of said HDME. In one embodiment, a compound of the application, or a pharmaceutically acceptable salt, or solvate, or prodrug thereof, has an $IC_{50}$ at or below 1 μM. In one embodiment, less than 500 nM. In one embodiment, less than 100 nM. In one embodiment, less than 50 nM in respect of demethylation of histone H3 methylated at least on one lysine.

In one embodiment, $IC_{50}$ is determined as described in Example 2 herein below. Thus, in one embodiment, a compound of the application, or a pharmaceutically acceptable salt, or solvate, or prodrug thereof, has an $IC_{50}$ at or below 1 μM. In one embodiment, less than 500 nM. In one embodiment, less than 100 nM. In one embodiment, less than 50 nM when said $IC_{50}$ is determined as described in one of the Examples herein.

Particularly preferred compounds of the application, or a pharmaceutically acceptable salt, or solvate, or prodrug thereof, are compounds that lead to a decreased tumor size and/or decreased number of metastases when tested in a xenograft model (Morton and Houghton, Nature Protocols, 2 (2) 247-250, 2007).

Pharmaceutical Compositions

In one aspect of this application, there is provided a pharmaceutical composition comprising at, as an active ingredient, at least one compound of the application, or a pharmaceutically acceptable salt, or solvate, or prodrug thereof, as defined herein and optionally one or more pharmaceutically acceptable excipients, diluents and/or carriers. The compounds of the application, or a pharmaceutically acceptable salt, or solvate, or prodrug thereof, may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

The pharmaceutical compositions formed by combining a compound of the application, or a pharmaceutically acceptable salt, or solvate, or prodrug thereof, as defined herein with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of the application, or a pharmaceutically acceptable salt, or solvate, or prodrug thereof, as defined herein may suitably be combined with an oral, non-toxic, pharmaceutically acceptable carrier such as ethanol, glycerol, water or the like. Furthermore, suitable binders, lubricants, disintegrating agents, flavoring agents and colorants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum, sodium starch glycolate, crospovidone, croscarmellose sodium or the like. Additional excipients for capsules include macrogols or lipids.

For the preparation of solid compositions such as tablets, the active compound of the application, or a pharmaceutically acceptable salt, or solvate, or prodrug thereof, is mixed with one or more excipients, such as the ones described above, and other pharmaceutical diluents such as water to make a solid pre-formulation composition containing a homogenous mixture of a compound of the application, or a pharmaceutically acceptable salt, or solvate, or prodrug thereof. The term "homogenous" is understood to mean that the compound of the application, or a pharmaceutically acceptable salt, or solvate, or prodrug thereof, is dispersed evenly throughout the composition so that the composition may readily be subdivided into equally effective unit dosage forms such as tablets or capsules.

Liquid compositions for either oral or parenteral administration of the compound of the application, or a pharmaceutically acceptable salt, or solvate, or prodrug thereof, include, e.g., aqueous solutions, syrups, elixirs, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. For parenteral administration, solutions containing a compound of the application, or a pharmaceutically acceptable salt, or solvate, or prodrug thereof, in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

The preparation of all these solutions under sterile conditions is readily accomplished by standard pharmaceutical techniques well known to those skilled in the art.

Depot injectable compositions are also contemplated as being within the scope of the present application.

In addition to the aforementioned ingredients, the compositions of a compound of the application, or a pharmaceutically acceptable salt, or solvate, or prodrug thereof, may include one or more additional ingredients such as diluents, buffers, flavoring agents, colorant, surface active agents, thickeners, preservatives, e.g., methyl hydroxybenzoate (including anti-oxidants), emulsifying agents and the like.

A suitable dosage of the compound of the application, or a pharmaceutically acceptable salt, or solvate, or prodrug thereof, will depend on the age and condition of the patient, the severity of the disease to be treated and other factors well known to the practicing physician. The compound may be administered for example either orally, parenterally or topically according to different dosing schedules, e.g., bi-daily, daily or with intervals, such as weekly intervals. In general a single dose will be in the range from 0.01 to 100 mg/kg body weight, preferably from about 0.05 to 75 mg/kg body weight, more preferably between 0.1 to 50 mg/kg body weight, and most preferably between 0.1 to 25 mg/kg body weight. The compound may be administered as a bolus (i.e. the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

The compounds of the application, or a pharmaceutically acceptable salt, or solvate, or prodrug thereof, may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances, or preferably an active substance as described in the section "combination treatment" herein below.

Clinical Conditions and Other Uses of Compounds

The compounds according to the application, or a pharmaceutically acceptable salt, or solvate, or prodrug thereof, as defined herein are useful for treatment of a HDME-dependent disease, disorder or condition. The treatment may include administering to a mammal, preferably a human, more preferably a human suffering from a HDME-dependent disease, a therapeutically effective amount of a compound according to the application, or a pharmaceutically acceptable salt, or solvate, or prodrug thereof, as defined herein.

Methylation and demethylation of lysine residues on the histone H3 tail constitute important epigenetic marks delineating transcriptionally active and inactive chromatin. For example, methylation of lysine 9 on histone H3 (H3K9) is usually associated with epigenetically silenced chromatin (Fischle, W., et. al. (2003), Curr. Opinion Cell Biol. 15, 172-83; Margueron, R., et al. (2005), Curr. Opinion Genet. Dev. 15, 163-76) while methylation of lysine 4 on histone 3 is associated with transcriptionally active chromatin. Similarly, the lysine 27 histone H3 (H3K27) mark is repressive in its di- and tri-methylated states whereas the lysine 36 histone H3 mark is found in association with gene activation (Barski, A. et al. (2007), Cell, 129, 823-37; Vakoc, C. et al. (2006) Mol. Cell. Biol. 26, 9185-95; Wagner, E. J. & Carpenter, P. B. (2012) Nature Mol. Cell Biol 13, 115-26). There are, however, many exemptions from these general rules of association between methylation states of epigenetic marks and the effect they have on transcription.

As documented by studies of the SUV39H1 knockout mouse, loss of the tri-methyl variant of the H3K9 mark results in chromosomal aberrations and predisposes to cancer (Peters, A. H. et al., Cell 107, 323-37, 2001). The JMJD2C protein (KDM4C, GASC1) has been identified as an eraser of the H3K9 mark (a histone demethylase) and may therefore promote cancer if its expression and activity is not tightly controlled (Cloos, P. et al. (2006), Nature 442, 307-11; Klose, R. J. et al. (2006), Nature 442, 312-16; Liu, G. et al. (2009), Oncogene 28, 4491-500). For example, JMJD2C has been shown to induce transformed phenotypes like growth factor independent growth, anchorage independent growth and mammosphere formation, if it is overexpressed in cells (Liu, G. et al. (2009), Oncogene 28, 4491-500). These findings are supported by the overexpression of JMJD2C in a range of human tumors like squamous cell carcinoma, metastatic lung carcinoma, prostate cancer, breast cancer and several others (Yang, Z. Q. et al. (2000) Cancer Res. 60, 4735-39; Yang, Z. Q. et al. (2001) Jpn. J. Cancer Res. 92, 423-28; Hu, N. et al. (2005) Cancer Res. 65, 2542-46; Liu, G. et al. (2009) Oncogene 28, 4491-500; Wissmann, M. et al. (2007) Nat. Cell Biol. 9, 347-53), indicating the potential importance of JMJD2C as an oncogene.

The JMJD2A protein (KDM4A, JHDM3A) shows similar properties to JMJD2C. JMJD2A shows high sequence identity to JMJD2C in its JmjC catalytic domain, is an eraser of the H3K9 mark and has also been shown to be overexpressed in prostate cancer (Cloos, P. et al., Nature 442, 307-11, 2006). JMJD2A has been shown to interact with the estrogen receptor alpha (ER-alpha) and overexpression of JMJD2A enhances estrogen-dependent transcription and the down-regulation of JMJD2A reduced transcription of a seminal ER-alpha target gene, cyclin D1 (Kawazu et al., (2011) PLoS One 6; Berry et al., (2012) Int. J. Oncol. 41). Additionally, it has been shown that catalytically inactive JMJD2A is compromised in its ability to stimulate ER-alpha mediated transcription, suggesting that inhibitors of JMJD2A may be beneficial for the treatment of ER-alpha positive breast tumors (Berry et al., (2012) Int. J. Oncol. 41).

Likewise, an eraser of the tri-methyl variant of the H3K4 mark, JARID1B (KDM5B, PLU1) has also been identified as potential oncogene. In cancer JARID1B most likely acts as a repressor of tumor repressor genes via removal of the H3K4 tri-methylation leading to decreased transcriptional activation in the affected chromatin regions. The oncogenic potential of JARID1B is demonstrated by its stimulation of proliferation in cell lines and further validated by shRNA knockdown studies of JARID1B expression showing inhibition of proliferation in MCF7 human breast cancer cells, in SW780 and RT4 bladder cancer cells, in A549 and LC319 lung cancer cells and in 4T1 mouse tumor cells in vitro and/or in mouse xenograft experiments (Yamane K. et al. (2007), Mol. Cell 25, 801-12; Hayami S. et al. (2010) Mol. Cancer 9, 59; Catchpole S et al. (2011), Int. J. Oncol. 38, 1267-77). Finally, JARID1B is overexpressed in prostate cancer and is associated with malignancy and poor prognosis (Xiang Y. et al. (2007) PNAS 104). In addition, high activity of JARID1B is associated with poor outcome in patients with estrogen receptor positive breast tumors (Yamamoto S et al. (2014) Cancer Cell 25).

JARID1A (KDM5A, RBP2) is also an eraser of the tri- and di-methyl variant of the H3K4 mark. JARID1A is overexpressed in gastric cancer (Zeng et al., (2010) Gastroenterology 138) and its gene is amplified in cervix carcinoma (Hidalgo et al, (2005) BMC Cancer 5). It has been suggested that JARID1A is fine-tuning progesterone receptor expression control by estrogens (Stratmann and Haendler (2011) FEBS J 278). Together with JARID1B, JARID1A has been implicated in the maintenance of a slow-growing population of cancer cells that are required for continuous tumor growth and that are resistant to cytotoxic and targeted therapy (Roesch, et al, (2010) Cell 141; Sharma, et al., (2010) Cell 141). JARID1A is required for the tumor initiation and progression in Rb+/− and Men1-defective mice (Lin, et al., (2011) PNAS 108). Data from Pasini show that JARID1A binds to Polycomb group protein target genes which are involved in regulating important cellular processes such as embryogenesis, cell proliferation, and stem cell self-renewal through the transcriptional repression of genes determining cell fate decisions (Pasini et al., (2008) Genes & Dev 22). Additionally, JARID1A were also shown to binds the PRC2 complex and being regulator of PRC2 target genes (Pasini et al., (2008) Genes & Dev 22).

Another potential oncogene, an eraser of the di-methyl variant of the H3K36 mark, JHDM1B (KDM2B, FBXL10) has been shown to be highly expressed in human cancers (Tzatsos A et al. (2009), PNAS 106 (8), 2641-6; He, J. et al. (2011), Blood 117 (14), 3869-80). Knock-down of FBXL10 causes senescence in mouse embryonic fibroblasts (MEFs), which can be rescued by expression of catalytic active (but not catalytic inactive) JHDM1B (Pfau R et al. (2008), PNAS 105(6), 1907-12; He J et al. (2008), Nat. Struct. Mol. Biol. 15, 1169-75). JHDM1B demethylates H3K36me2 on the tumor-suppressor gene Ink4b (p15$^{Ink4b}$), and thereby silences the expression of this senescence-mediating gene in MEFs and in leukemic cells (He, J. et al. (2008), Nat. Struct. Mol. Biol. 15, 1169-75; He, J. et al. (2011), Blood 117 (14), 3869-80). The catalytic dependency of JHDM1B is further shown by He et al. as catalytic activity is required for development of leukemia in a mouse AML model.

Inhibitors of the histone demethylase class of epigenetic enzymes, and in particular the potential oncogenes JARID1B, JARID1A, JMJD2C, JMJD2A, and JHDM1B, would present a novel approach for intervention in cancers and other proliferative diseases. Being one of the most devastating diseases, affecting millions of people worldwide, there remains a high need for efficacious and specific compounds against cancer.

Said HDME may be any HDME, however preferably the HDME of the present method is selected from the JmjC (Jumonji) family, as described in Cloos, P. et. al., Genes & Development 22, 1115-1140, 2008 and Højfeldt et al. (2013), Nature Reviews Drug Discovery 12, 917-30, which is incorporated herein by reference, in its entirety. More preferably said HDME is a HDME of the human JmjC family.

The present application also relates to a compound of the application, or a pharmaceutically acceptable salt, or solvate, or prodrug thereof, as defined herein for use in the treatment of a HDME-dependent disease, such as for the treatment of cancer.

By the term "HDME-dependent disease" is meant any disease characterized by elevated HDME expression and/or activity in at least in some instances of the disease, or a disease which is ameliorated by lowering the activity of HDMEs. Thus, the disease to be treated with the inhibitors of HDME, i.e. compounds of the application, or a pharmaceutically acceptable salt, or solvate, or prodrug thereof, may be a proliferative or hyperproliferative disease, which includes benign or malignant tumors, for example a proliferative or hyperproliferative disease selected from the group consisting of a carcinoma of the brain, kidney, liver, adrenal gland, bladder, breast, stomach (for example gastric tumors), ovaries, esophagus, colon, rectum, prostate, pancreas, lung, vagina, thyroid, sarcoma, glioblastomas, multiple myeloma or gastrointestinal cancer, for example, colon carcinoma or colorectal adenoma, or a tumor of the neck and head, an epidermal hyperproliferation, for example, psoriasis, prostate hyperplasia, a neoplasia, including a neoplasia of epithelial character, including mammary carcinoma, and a leukemia.

In one embodiment, compounds of the application, or a pharmaceutically acceptable salt, or solvate, or prodrug thereof, as defined herein are useful in the treatment of one or more cancers. The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the application include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma, (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcorna, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (acute myeloid leukemia, chronic myeloid leukemia, acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

In one embodiment, the compounds of the application, or a pharmaceutically acceptable salt, or solvate, or prodrug thereof, as defined herein are useful in the treatment of one or more cancers selected from the group consisting of: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito-urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In one embodiment, the compounds of the application, or a pharmaceutically acceptable salt, or solvate, or prodrug thereof, as defined herein, are useful for the treatment of squamous cell carcinomas. Preferably said squamous cell carcinomas are cancers of the carcinoma type of squamous epithelium that may occur in many different organs, including the skin, lips, mouth, esophagus, urinary bladder, prostate, lungs, vagina, and cervix; brain cancer, that is neuroblastoma, glioblastoma and other malignant and benign brain tumors; breast cancer, pancreatic cancer, and multiple myeloma.

In one embodiment, the compounds of the application, or a pharmaceutically acceptable salt, or solvate, or prodrug thereof, as defined herein are useful for treatment of brain cancer, tumors of adults such as head and neck cancers (e.g., oral, laryngeal and esophageal), genito-urinary cancers (e.g., prostate, bladder, renal, uterine, ovarian, testicular, rectal and colon), and breast cancer.

Other cancer forms for which the compounds of the application, or a pharmaceutically acceptable salt, or solvate, or prodrug thereof, are useful as treatment can be found in Stedman's Medical Dictionary (Lippincott Williams & Wilkins, $28^{th}$ Ed., 2005), which is incorporated herein by reference in its entirety.

In one embodiment, the disease to be treated by compounds of the application, or a pharmaceutically acceptable salt, or solvate, or prodrug thereof, as defined herein is selected from persistent proliferative or hyperproliferative conditions such as angiogenesis, such as psoriasis; Kaposi's sarcoma; restenosis, e.g., stent-induced restenosis; endometriosis; Hodgkin's disease; leukemia; hemangioma; angiofibroma; eye diseases, such as neovascular glaucoma; renal diseases, such as glomerulonephritis; malignant nephrosclerosis; thrombotic microangiopathic syndromes; transplant rejections and glomerulopathy; fibrotic diseases, such as cirrhosis of the liver; mesangial cell-proliferative diseases; injuries of the nerve tissue; and inhibiting the re-occlusion of vessels after balloon catheter treatment, for use in vascular prosthetics or after inserting mechanical devices for holding vessels open, such as, e.g., stents, as immune-suppressants, as an aid in scar-free wound healing, and treating age spots and contact dermatitis.

The compounds of the application, or a pharmaceutically acceptable salt, or solvate, or prodrug thereof, are suitable as active agents in pharmaceutical compositions that are efficacious particularly for treating cellular proliferative or hyperproliferative ailments and/or ailments associated with dysregulated gene expression. Such pharmaceutical compositions have a therapeutically effective amount of the compound of the application, or a pharmaceutically acceptable salt, or solvate, or prodrug thereof, along with other pharmaceutically acceptable excipients, carriers, and diluents and. The phrase, "therapeutically effective amount" as used herein indicates an amount necessary to administer to a host, or to a cell, tissue, or organ of a host, to achieve a therapeutic effect, such as an ameliorating or alternatively a curative effect, for example an anti-tumor effect, e.g., reduction of or preferably inhibition of proliferation of malignant cancer cells, benign tumor cells or other proliferative cells, or of any other HDME-dependent disease.

Another aspect of the application is a pharmaceutical composition comprising a therapeutically effective amount of at least one compound of the application, or a pharmaceutically acceptable salt, solvate or prodrug thereof, as defined herein, in combination with at least one further anti-neoplastic compound, and a pharmaceutically acceptable excipient, carrier or diluent.

Combination Treatment

A compound of the application, or a pharmaceutically acceptable salt, or solvate, or prodrug thereof, may also be used to advantage in combination with one or more other anti-proliferative or anti-neoplastic agents. Such anti-proliferative agents include, but are not limited to other HDME inhibitors, proteasome inhibitors, including bortezomib (Valcade) and Carfilzomib, aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein tyrosine or serine or threonine kinase activity; compounds targeting/decreasing a lipid kinase activity; compounds targeting/decreasing a carbohydrate kinase activity, and further anti-angiogenic compounds; compounds which target, decrease or inhibit the activity of a protein or lipid phosphatase; gonadorelin agonists; anti-androgens; angiostatic steroids; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL(R)); leucovorin; immune stimulating agents, such as BCG, IL-2 or IFN-a, antibodies, such as anti-CTLA-4 monoclonal antibody ipilimumab (Yervoy), rituximab or herceptin, and cancer vaccines; inhibitors/modulators of mitochondrial activity such as metformin.

A compound of the application, or a pharmaceutically acceptable salt, or solvate, or prodrug thereof, as defined herein, may also be used to advantage in combination with known therapeutic processes, e.g., the administration of hormones or tumor cell damaging approaches, especially ionizing radiation.

A compound of the application, or a pharmaceutically acceptable salt, or solvate, or prodrug thereof, as defined herein, may also be used as a radiosensitizer, including, for example, the treatment of tumors which exhibit poor sensitivity to radiotherapy.

By the term "combination", is meant either a fixed combination in one dosage unit form, or a kit of parts for the combined administration where a compound of the application, or a pharmaceutically acceptable salt, or solvate, or prodrug thereof, and a combination partner may be administered independently at the same time or separately within time intervals that especially allow that the combination partners show a cooperative, e.g., synergistic, effect, or any combination thereof.

The phrase, "aromatase inhibitor" as used herein relates to a compound which inhibits the estrogen production, i.e., the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the application comprising a chemotherapeutic agent which is an aromatase inhibitor is particularly useful for the treatment of hormone receptor positive tumors, e.g., breast tumors.

The term "antiestrogen" as used herein relates to a compound that antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the application comprising a chemotherapeutic agent which is an antiestrogen is particularly useful for the treatment of estrogen receptor positive tumors, e.g., breast tumors.

The term "anti-androgen" as used herein relates to any substance which is capable of inhibiting the biological effects of androgenic hormones and includes, but is not limited to, bicalutamide (CASODEX), which can be formulated, e.g., as disclosed in U.S. Pat. No. 4,636,505.

The phrase, "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The phrase, "topoisomerase I inhibitor" as used herein includes, but is not limited to topotecan, gimatecan, irinotecan, camptothecan and its analogues, 9-nitrocamptothecin and the macromolecular camptothecin conjugate PNU-166148 (compound AI in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The phrase, "topoisomerase II inhibitor" as used herein includes, but is not limited to the anthracyclines such as doxorubicin (including liposomal formulation, e.g., CAELYX), daunorubicin, epirubicin, idarubicin and nemorubicin, the anthraquinones mitoxantrone and Iosoxantrone, and the podophyllotoxins etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The phrase, "microtubule active agent" relates to microtubule stabilizing, microtubule destabilizing agents and microtublin polymerization inhibitors including, but not limited to taxanes, e.g., paclitaxel and docetaxel, vinca alkaloids, e.g., vinblastine, including vinblastine sulfate, vincristine including vincristine sulfate, and vinorelbine, discodermolides, colchicine and epothilones and derivatives thereof, e.g., epothilone B or D or derivatives thereof. Paclitaxel may be administered e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Included are Epothilone A and/or B.

The phrase, "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The phrase, "histone deacetylase inhibitors" or "HDAC inhibitors" relates to compounds which inhibit at least one example of the class of enzymes known as a histone deacetylase, and which compounds generally possess antiproliferative activity. Previously disclosed HDAC inhibitors include compounds disclosed in, e.g., WO 02/22577, including N-hydroxy-3-[4-{[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further includes Suberoylanilide hydroxamic acid (SAHA). Other publicly disclosed HDAC inhibitors include butyric acid and its derivatives, including sodium phenylbutyrate, thalidomide, trichostatin A and trapoxin.

The term "antineoplastic antimetabolite" includes, but is not limited to, 5-Fiuorouracil or 5-FU, capecitabine, gemcitabine, DNA demethylating agents, such as 5-azacytidine and decitabine, methotrexate and edatrexate, and folic acid antagonists such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The phrase, "platin compound" as used herein includes, but is not limited to, carboplatin, cisplatin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

The phrase, "compounds targeting/decreasing a protein tyrosine or serine or threonine kinase activity," as used herein, includes, but is not limited to, gefinitib, erlotinib, lapatinib, foretinib, cabozantinib, vemurafenib or selumetinib (AZD6244). Gefinitib can be administered, e.g., in the form as it is marketed, e.g., under the trademark IRESSA. Erlotinib can be administered, e.g., in the form as it is marketed, e.g., under the trademark TARCEVA. Lapatinib can be administered, e.g., in the form as it is marketed, e.g., under the trademarks TYKERB and TYVERB. Cabozantinib can be administered, e.g., in the form as it is marketed, e.g., under the trademark COMETRIQ. Vemurafenib can be administered, e.g., in the form as it is marketed, e.g., under the trademark CELBORAF. Foretinib can be formulated, e.g., as disclosed in US 2012/0282179. Selumetinib (AZD6244) can be formulated, e.g., as disclosed in US 2008/0177082 and US 2009/0246274. Other suitable protein kinase inhibitors include without limitation Afatanib (Gilotrif, Boeringer Ingelheim), Axitinib (Inlyta, Pfizer), Bosutinib (Bosulif, Wyeth), Crizotinib (Xalkori, Pfizer), Dabrafenib (Tafinlar, GSK), Dasatinib (Sprycel, Bristol-Myers Squib), Elotinib (Tarceva, OSI), Everolimus (Afinitor, Novartis), Gefitinib (Iressa, Astrazeneca), Ibrutinib (Imbruvica, Pharmacyclics and J&J), Idelalisib (Zydelig, Gilead), Imatanib (Gleevec, Novartis), Nilotinib (Tasigna, Novartis), Pazopanib (Votrient, GlaxoSmithKline), Ponatinib (Iclusig, Ariad), Regorafenib (Stivarga, Bayer), Ruxolitinib (Jakafi, Incyte), Sirolimus (Rapamune, Wyeth), Sorafenib (Nexavar, Bayer), Sunitinib (Sutent, Pfizer), Tofacitinib (Xeljanz, Pfizer), Temsirolimus (Torisel, Wyeth), Trametinib (Mekinist, GSK), Vandetanib (Caprelsa, IPR Pharms) as well as other proposed protein kinase inhibitors that can be found in the literature.

Tumor cell damaging approaches refer to approaches such as ionizing radiation. The phrase, "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See, e.g., Hellman, Principles of Radiation Therapy, Cancer, in Principles and Practice of Oncology, Devita et al., Eds., 4th Edition, Vol. 1, pp. 248-275 (1993).

The phrase, "angiostatic steroids" as used herein refers to agents which block or inhibit angiogenesis, such as, e.g., anecortave, triamcinolone, hydrocortisone, 11-[alpha]-epihydrocotisol, cortexolone, 17[alpha]-hydroxyprogesterone, corticosterone, desoxycorticosterone, testosterone, estrone and dexamethasone.

Other chemotherapeutic agents include, but are not limited to, plant alkaloids, hormonal agents and antagonists; biological response modifiers, preferably lymphokines or interferons; antisense oligonucleotides or oligonucleotide derivatives; or miscellaneous agents or agents with other or unknown mechanism of action.

The structure of the active agents identified by code numbers, generic or trade names may be taken from the actual edition of the standard compendium "The Merck Index" or from databases, e.g., Patents International (e.g., IMS World Publications).

The above-mentioned compounds, which can be used in combination with a compound of the application, or a pharmaceutically acceptable salt, or solvate, or prodrug thereof, can be prepared and administered as described in the art such as in the documents cited above.

Furthermore, the compounds of the application may be used in a method of profiling the functional and structural similarity of histone demethylases comprising taking a panel of at least two histone demethylases and a panel of at least two compounds of formula I and determining the extent to which each said compound of formula I inhibits the activity of each of said histone demethylases, and generating a similarity index reflecting the degree of similarity between the histone demethylases in respect of their inhibition by said compounds.

EXAMPLES

Example 1: Preparation of Compounds of the Application

General Methods and Materials

Table 2 below shows examples of compounds according to the application and indicates routes that may be employed in their synthesis. All chemicals were purchased from Sigma-Aldrich, Alfa Aesar, Matrix, Combiblock, Oakwood, and Chembridge Anhydrous solvents were Aldrich Sure/Seal™ brand. All reactions were carried out under a dry nitrogen atmosphere using dry solvents. Reactions were monitored by thin-layer chromatography carried out on Sigma-Aldrich 0.25 mm silica gel plates (60 Å, fluorescent indicator). Spots were visualized under UV light (254 nm). Flash column chromatography was performed on Biotage SNAP Flash System, or silica gel 60 (particle size 0.032-0.063 mm) obtained from Silicycle, Inc. Low-resolution ES (electrospray) mass spectra were obtained using a Micromass Quattro Ultima mass spectrometer in the electrospray positive (ES+) or negative (ES−) ion mode. 1H-NMR spectra were recorded on a Bruker AM-300 spectrometer and were calibrated using residual non-deuterated solvent as internal reference. Spectra were processed using Spinworks version 2.5 (developed by Dr. Kirk Marat, Department of Chemistry, University of Manitoba). Preparative HPLC was performed on Waters 2996 with Photodiode Array Detector, Waters 600 Controller, Waters 100 pump, and Waters 717 auto sampler, with UV detection at 254 and 280 nm. Flow rate: 15 mL/minute, run time 30 minutes. Solvents: 0-100% ($H_2O$-MeOH), with and without added TFA (0.1%). Column used was Supelco C18, 25 cm×21.2 mm, particle size 10 micrometer.

TABLE 2

(#SR = may be prepared analogously to according to synthetic route number listed)

| Structure | # | Name | SR# | NMR |
|---|---|---|---|---|
| 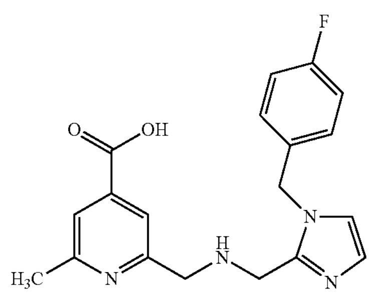 [SMILES: Cc1cc(C(=O)O)cc(CNCc2nccn2Cc2ccc(F)cc2)n1] | 1 | 2-{[({1-[(4-fluorophenyl)methyl]-1H-imidazol-2-yl}methyl)amino]methyl}-6-methylpyridine-4-carboxylic acid | A | 1H-NMR (300 MHz, $CD_3OD$): δ 7.55 (s, 1H), 6.90 (s, 1H), 5.28 (d, 2H), 2.53 (s, 3H). |
| 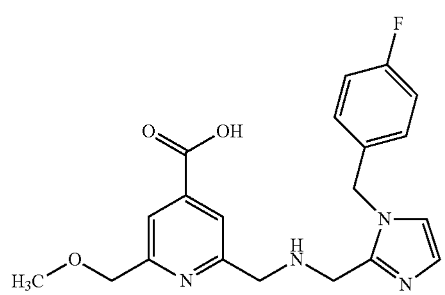 [SMILES: COCc1cc(C(=O)O)cc(CNCc2nccn2Cc2ccc(F)cc2)n1] | 2 | 2-{[({1-[(4-fluorophenyl)methyl]-1H-imidazol-2-yl}methyl)amino]methyl}-6-(methoxymethyl)pyridine-4-carboxylic acid | A | 1H-NMR (300 MHz, $CD_3OD$): δ 7.74 (s, 1H), 6.90 (s, 1H), 5.28 (d, 2H), 4.54 (s, 2H), 3.31 (s, 3H). |
| 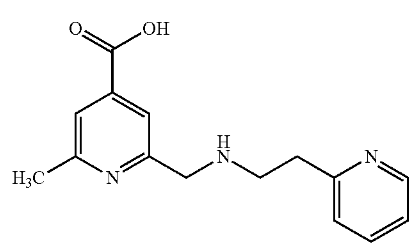 [SMILES: Cc1cc(C(=O)O)cc(CNCCc2ccccn2)n1] | 3 | 2-methyl-6-({[2-(pyridin-2-yl)ethyl]amino}methyl)pyridine-4-carboxylic acid | A | 1H-NMR (300 MHz, $CD_3OD$): δ 8.43 (s, 1H), 7.56 (s, 1H), 4.89 (s, 2H), 2.98 (m, 4H), 2.53 (s, 3H). |

TABLE 2-continued (#SR = may be prepared analogously to according to synthetic route number listed)

| Structure | # | Name | SR# | NMR |
|---|---|---|---|---|
| 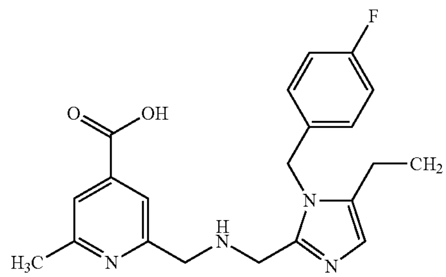 [SMILES: CCc1cnc(CNCc2cc(C(=O)O)cc(C)n2)n1Cc1ccc(F)cc1] | 4 | 2-{[({5-ethyl-1-[(4-fluorophenyl)methyl]-1H-imidazol-2-yl}methyl)amino]methyl}-6-methylpyridine-4-carboxylic acid | A | ¹H-NMR (300 MHz, CD₃OD): δ 7.59 (s, 1H), 5.24 (s, 2H), 3.82 (s, 2H), 2.49 (s, 3H), 1.13 (t, 3H) ppm. |
| 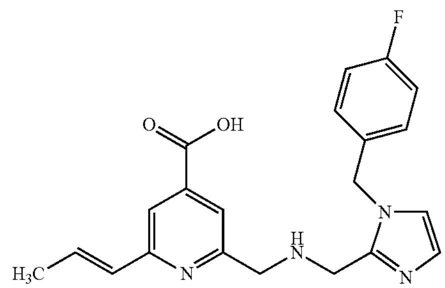 [SMILES: C/C=C/c1cc(C(=O)O)cc(CNCc2nccn2Cc2ccc(F)cc2)n1] | 5 | 2-{[({1-[(4-fluorophenyl)methyl]-1H-imidazol-2-yl}methyl)amino]methyl}-6-[(1E)-prop-1-en-1-yl]pyridine-4-carboxylic acid | B | ¹H-NMR (300 MHz, CD₃OD): δ 8.10 (s, 1H), 6.74 (m, 1H), 5.63 (s, 2H), 4.87 (s, 2H), 2.00 (d, 3H). |
| 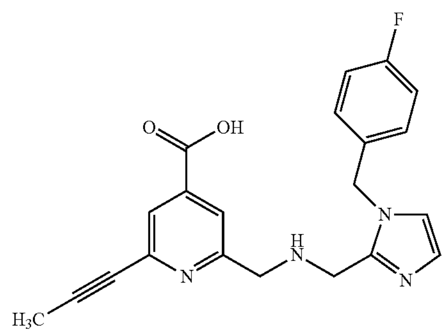 [SMILES: CC#Cc1cc(C(=O)O)cc(CNCc2nccn2Cc2ccc(F)cc2)n1] | 6 | 2-{[({1-[(4-fluorophenyl)methyl]-1H-imidazol-2-yl}methyl)amino]methyl}-6-(prop-1-yn-1-yl)pyridine-4-carboxylic acid | B | ¹H-NMR (300 MHz, CD₃OD): δ 7.90 (s, 1H), 7.21 (s, 1H), 5.75 (s, 2H), 4.77 (s, 2H), 1.92 (s, 3H). |
| 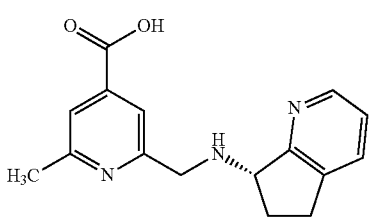 [SMILES: Cc1cc(C(=O)O)cc(CN[C@H]2CCc3cccnc32)n1] | 7 | 2-({[(7S)-5H,6H,7H-cyclopenta[b]pyridin-7-yl]amino}methyl)-6-methylpyridine-4-carboxylic acid | A | ¹H-NMR (300 MHz, CD₃OD): δ 8.34 (d, 1H), 7.21 (m, 1H), 4.22 (t, 1H), 4.03 (s, 2H), 2.56 (s, 3H) ppm. |
| 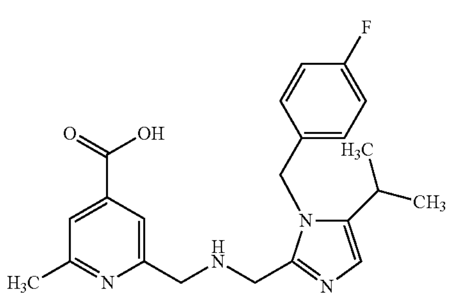 [SMILES: Cc1cc(C(=O)O)cc(CNCc2ncc(C(C)C)n2Cc2ccc(F)cc2)n1] | 8 | 2-{[({1-[(4-fluorophenyl)methyl]-5-(propan-2-yl)-1H-imidazol-2-yl}methyl)amino]methyl}-6-methylpyridine-4-carboxylic acid | A | ¹H-NMR (300 MHz, CD₃OD): δ 7.59 (s, 1H), 6.70 (s, 1H), 5.27 (s, 2H), 1.12 (d, 6H) ppm. |

TABLE 2-continued (#SR = may be prepared analogously to according to synthetic route number listed)

| Structure | # | Name | SR# | NMR |
|---|---|---|---|---|
| 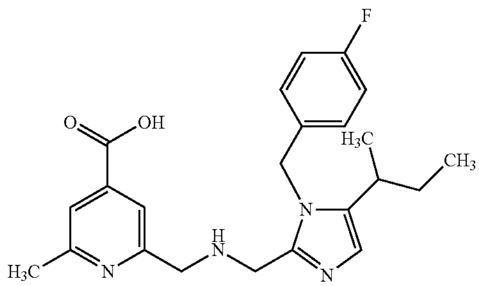 [SMILES: CCC(C)c1cnc(CNCc2cc(C(=O)O)cc(C)n2)n1Cc1ccc(F)cc1] | 9 | 2-[({[5-(butan-2-yl)-1-[(4-fluorophenyl)methyl]-1H-imidazole-2-yl]methyl}amino)methyl]-6-methyl-pyridine-4-carboxylic acid | B | $^{1}$H-NMR (300 MHz, CD$_3$OD): δ 7.60 (s, 1H), 7.51 (s, 1H), 5.27 (s, 2H), 3.82 (s, 2H), 2.48 (s, 3H), 1.92 (s, 3H). |
| 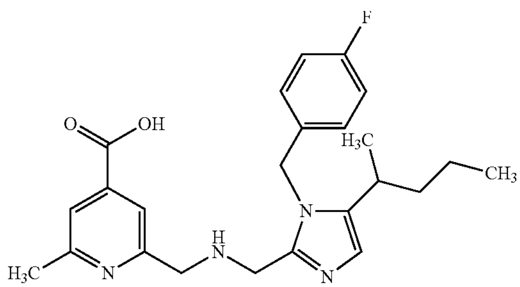 [SMILES: CCCC(C)c1cnc(CNCc2cc(C(=O)O)cc(C)n2)n1Cc1ccc(F)cc1] | 10 | 2-{[({1-[(4-fluorophenyl)methyl]-5-(pentan-2-yl)-1H-imidazole-2-yl}methyl)amino]methyl}-6-methylpyridine-4-carboxylic acid | A | $^{1}$H-NMR (300 MHz, CD$_3$OD): δ 7.62 (s, 1H), 7.53 (s, 1H), 5.29 (s, 2H), 3.84 (s, 2H), 2.50 (s, 3H), 1.92 (s, 3H). |
| 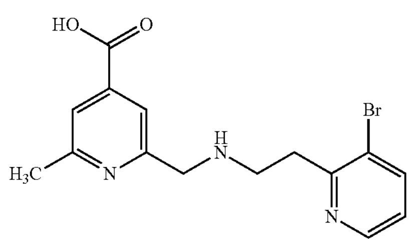 [SMILES: Cc1cc(C(=O)O)cc(CNCCc2ncccc2Br)n1] | 11 | 2-({[2-(3-bromopyridin-2-yl)ethyl]amino}methyl)-6-methylpyridine-4-carboxylic acid | A | $^{1}$H-NMR (300 MHz, CD$_3$OD): δ 8.44 (d, 1H), 7.16 (dd, 1H), 3.18 (t, 2H), 2.53 (s, 3H) ppm |
| 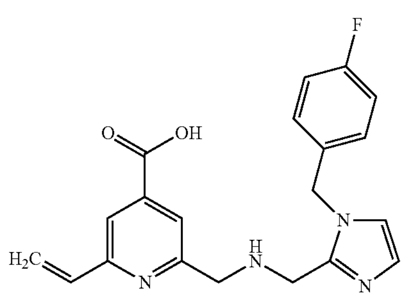 [SMILES: C=Cc1cc(C(=O)O)cc(CNCc2nccn2Cc2ccc(F)cc2)n1] | 12 | 2-ethenyl-6-{[({1-[(4-fluorophenyl)methyl]-1H-imidazol-2-yl}methyl)amino]methyl}pyridine-4-carboxylic acid | B | $^{1}$H-NMR (300 MHz, CD$_3$OD): δ 8.05 (s, 1H), 7.56 (s, 1H), 6.98 (dd, 1H), 5.62 (s, 2H) ppm. |
| 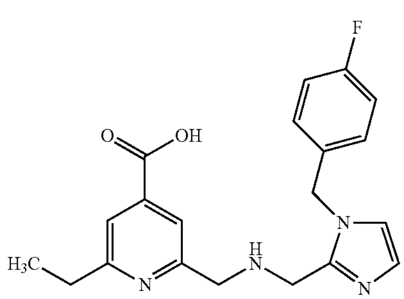 [SMILES: CCc1cc(C(=O)O)cc(CNCc2nccn2Cc2ccc(F)cc2)n1] | 13 | 2-ethyl-6-{[({1-[(4-fluorophenyl)methyl]-1H-imidazol-2-yl}methyl)amino]methyl}pyridine-4-carboxylic acid | C | $^{1}$H-NMR (300 MHz, CD$_3$OD): δ 8.19 (s, 1H), 7.54 (s, 1H), 5.61 (s, 2H), 3.10 (q, 2H) ppm. |

TABLE 2-continued (#SR = may be prepared analogously to according to synthetic route number listed)

| Structure | # | Name | SR# | NMR |
|---|---|---|---|---|
| 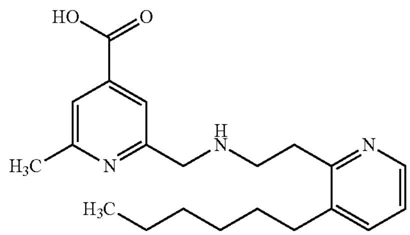 [SMILES: CCCCCCc1cccnc1CCNCc1cc(C(=O)O)cc(C)n1] | 14 | 2-({[2-(3-hexylpyridin-2-yl)ethyl]amino}methyl)-6-methylpyridine-4-carboxylic acid | A | ¹H-NMR (300 MHz, CD₃OD): δ 8.24 (d, 1H), 7.14 (dd, 1H), 3.01 (t, 2H), 2.51 (s, 3H) ppm |
| 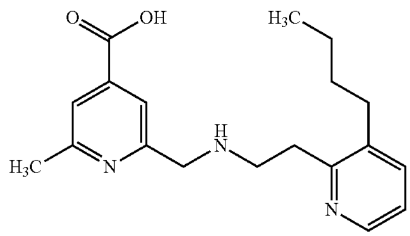 [SMILES: CCCCc1cccnc1CCNCc1cc(C(=O)O)cc(C)n1] | 15 | 2-({[2-(3-butylpyridin-2-yl)ethyl]amino}methyl)-6-methylpyridine-4-carboxylic acid | A | ¹H-NMR (300 MHz, CD₃OD): δ 8.44 (d, 1H), 7.34 (dd, 1H), 3.60 (t, 2H), 2.71 (t, 2H) ppm |
| 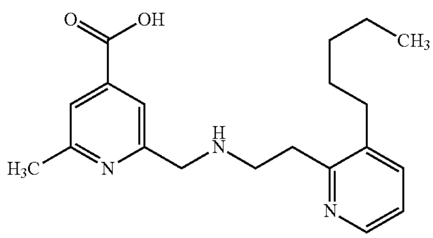 [SMILES: CCCCCc1cccnc1CCNCc1cc(C(=O)O)cc(C)n1] | 16 | 2-methyl-6-({[2-(3-pentylpyridin-2-yl)ethyl]amino}methyl)pyridine-4-carboxylic acid | A | ¹H-NMR (300 MHz, CD₃OD): δ 8.26 (d, 1H), 7.17 (dd,1H), 3.03 (t, 2H), 2.53 (s, 3H) ppm |
| 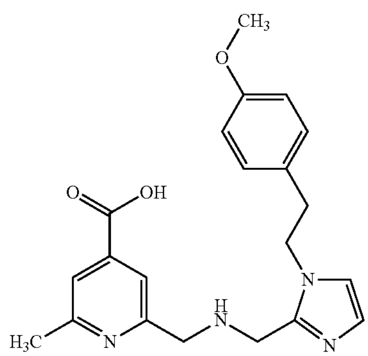 [SMILES: COc1ccc(CCn2ccnc2CNCc2cc(C(=O)O)cc(C)n2)cc1] | 17 | 2-{[({1-[2-(4-methoxyphenyl)ethyl]-1H-imidazol-2-yl}methyl)amino]methyl}-6-methylpyridine-4-carboxylic acid | A | ¹H-NMR (300 MHz, CD₃OD): δ 7.62 (s, 1H), 7.55 (s, 1H), 6.98 (s, 1H), 2.90 (t, 2H), 2.51 (s, 3H) ppm. |
| 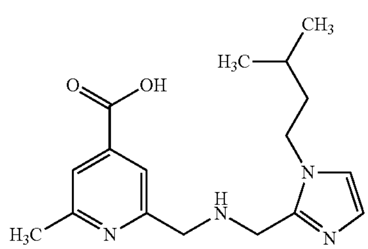 [SMILES: Cc1cc(C(=O)O)cc(CNCc2nccn2CCC(C)C)n1] | 18 | 2-methyl-6-[({[1-(3-methylbutyl)-1H-imidazol-2-yl]methyl}amino)methyl]pyridine-4-carboxylic acid | A | ¹H-NMR (300 MHz, CD₃OD): δ 7.63 (s, 1H), 7.52 (s, 1H), 6.83 (s, 1H), 4.00 (t, 2H), 0.88 (s, 6H) ppm |
| 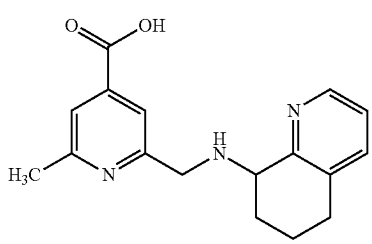 [SMILES: Cc1cc(C(=O)O)cc(CNC2CCCc3cccnc32)n1] | 19 | 2-methyl-6-{[(5,6,7,8-tetrahydroquinolin-8-yl)amino]methyl}pyridine-4-carboxylic acid | A | ¹H-NMR (300 MHz, CD₃OD): δ 7.70 (s, 1H), 7.18 (dd, 1H), 4.02 (q, 2H), 3.81 (t, 1H) ppm. |

TABLE 2-continued (#SR = may be prepared analogously to according to synthetic route number listed)

| Structure | # | Name | SR# | NMR |
|---|---|---|---|---|
| 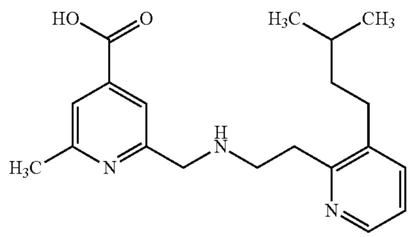 [SMILES: Cc1cc(C(=O)O)cc(CNCCc2ncccc2CCC(C)C)n1] | 20 | 2-methyl-6-[({2-[3-(3-methylbutyl)pyridin-2-yl]ethyl}amino)methyl]pyridine-4-carboxylic acid | A | ¹H-NMR (300 MHz, CD₃OD): δ 8.26 (d, 1H), 7.16 (dd, 1H), 3.03 (t, 2H), 1.61 (m, 1H) ppm |
| 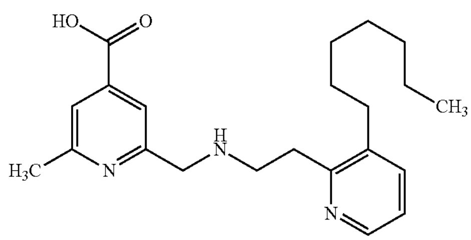 [SMILES: CCCCCCCc1cccnc1CCNCc1cc(C(=O)O)cc(C)n1] | 21 | 2-({[2-(3-heptylpyridin-2-yl)ethyl]amino}methyl)-6-methylpyridine-4-carboxylic acid | A | ¹H-NMR (300 MHz, CD₃OD): δ 8.41 (d, 1H), 7.27 (dd, 1H), 3.26 (t, 2H), 2.67 (t, 2H) ppm |
| 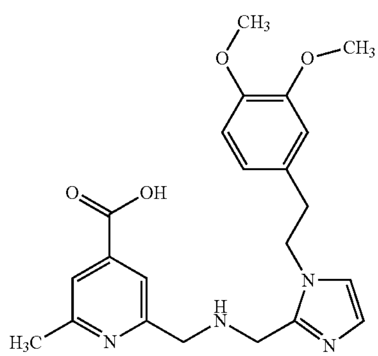 [SMILES: COc1ccc(CCn2ccnc2CNCc2cc(C(=O)O)cc(C)n2)cc1OC] | 22 | 2-{[({1-[2-(3,4-dimethoxyphenyl)ethyl]-1H-imidazol-2-yl}methyl)amino]methyl}-6-methylpyridine-4-carboxylic acid | A | ¹H-NMR (300 MHz, CD₃OD): δ 7.59 (s, 1H), 7.54 (s, 1H), 6.84 (s, 1H), 4.22 (t, 2H), 2.90 (t, 2H) ppm |
| 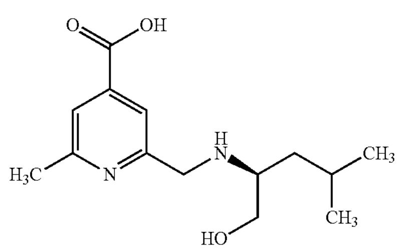 [SMILES: Cc1cc(C(=O)O)cc(CN[C@H](CO)CC(C)C)n1] | 23 | 2-({[(2S)-1-hydroxy-4-methylpentan-2-yl]amino}methyl)-6-methylpyridine-4-carboxylic acid | A | ¹H-NMR (300 MHz, CD₃OD): δ 7.60 (s, 1H), 2.62 (m, 1H), 2.64 (s, 3H), 1.63 (m, 1H) ppm. |
| 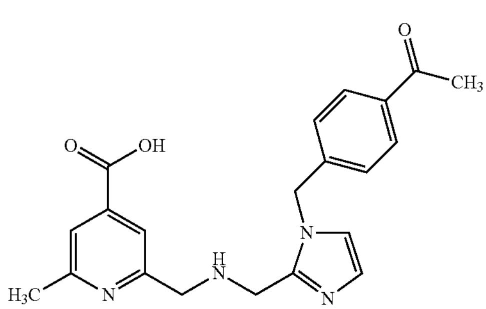 [SMILES: CC(=O)c1ccc(Cn2ccnc2CNCc2cc(C(=O)O)cc(C)n2)cc1] | 24 | 2-{[({1-[(4-acetylphenyl)methyl]-1H-imidazol-2-yl}methyl)amino]methyl}-6-methylpyridine-4-carboxylic acid | A | ¹H-NMR (300 MHz, CD₃OD): δ 7.98 (s, 1H), 7.31 (s, 1H), 2.62 (s, 3H), 2.56 (s, 3H) ppm |

TABLE 2-continued (#SR = may be prepared analogously to according to synthetic route number listed)

| Structure | # | Name | SR# | NMR |
|---|---|---|---|---|
| 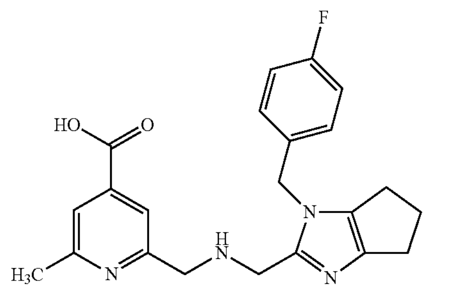 [SMILES: Cc1cc(C(=O)O)cc(CNCc2nc3c(n2Cc2ccc(F)cc2)CCC3)n1] | 25 | 2-{[({1-[(4-fluorophenyl)methyl]-1H,4H,5H,6H-cyclopenta[d]imidazol-2-yl}methyl)amino]methyl}-6-methylpyridine-4-carboxylic acid | A | ¹H-NMR (300 MHz, CD₃OD): δ 7.62 (s, 1H), 5.16 (s, 2H), 3.88 (s, 2H), 3.82 (s, 2H) ppm. |
| 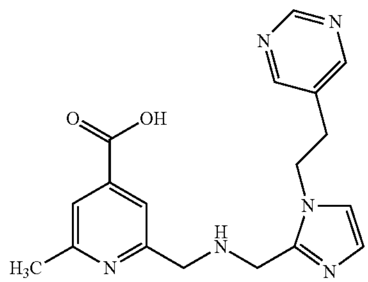 [SMILES: Cc1cc(C(=O)O)cc(CNCc2nccn2CCc2cncnc2)n1] | 26 | 2-methyl-6-{[({1-[2-(pyrimidin-5-yl)ethyl]-1H-imidazol-2-yl}methyl)amino]methyl}pyridine-4-carboxylic acid | A | ¹H-NMR (300 MHz, CD₃OD): δ 9.08 (s, 1H), 7.54 (s, 1H), 4.51 (s, 2H), 2.69 (s, 3H) ppm. |
| 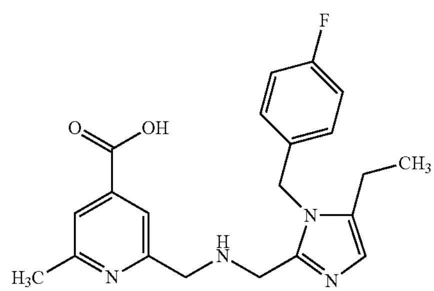 [SMILES: CCc1cnc(CNCc2cc(C(=O)O)cc(C)n2)n1Cc1ccc(F)cc1] | 27 | 2-{[({5-Ethyl-4-[(4-fluorophenyl)methyl]-4H-1,2,4-triazol-3-yl}methyl)amino]methyl}-6-methylpyridine-4-carboxylic acid | A | ¹H-NMR (300 MHz, CD₃OD): δ 7.62 (s, 1H), 5.35 (s, 2H), 2.64 (q, 2H), 2.49 (s, 3H) ppm. |
| 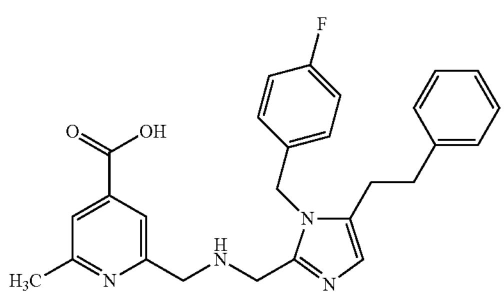 [SMILES: Cc1cc(C(=O)O)cc(CNCc2ncc(CCc3ccccc3)n2Cc2ccc(F)cc2)n1] | 28 | 2-{[({1-[(4-fluorophenyl)methyl]-5-(2-phenylethyl)-1H-imidazol-2-yl}methyl)amino]methyl}-6-methylpyridine-4-carboxylic acid | A | ¹H-NMR (300 MHz, CD₃OD): δ 7.80 (s, 2H), 5.39 (s, 2H), 4.34 (s, 2H), 2.82 (s, 4H), 2.60 (s, 3H) ppm |
| 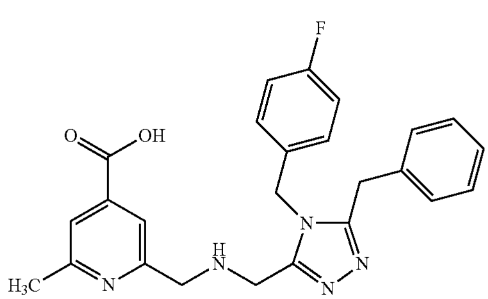 [SMILES: Cc1cc(C(=O)O)cc(CNCc2nnc(Cc3ccccc3)n2Cc2ccc(F)cc2)n1] | 29 | 2-{[({5-benzyl-4-[(4-fluorophenyl)methyl]-4H-1,2,4-triazol-3-yl}methyl)amino]methyl}-6-methylpyridine-4-carboxylic acid | A | ¹H-NMR (300 MHz, CD₃OD): δ 7.58 (s, 1H), 5.23 (s, 2H), 4.06 (s, 2H), 2.44 (s, 3H), ppm |

TABLE 2-continued (#SR = may be prepared analogously to according to synthetic route number listed)

| Structure | # | Name | SR# | NMR |
|---|---|---|---|---|
| 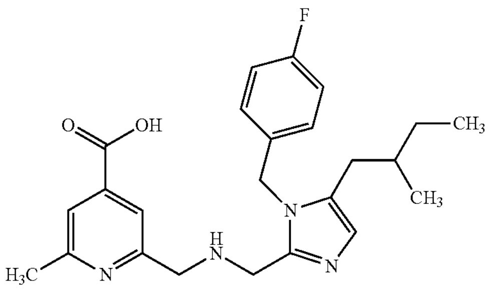 [SMILES: CCC(C)Cc1cnc(CNCc2cc(C(=O)O)cc(C)n2)n1Cc1ccc(F)cc1] | 30 | 2-{[({1-[(4-fluorophenyl)methyl]-5-(2-methylbutyl)-1H-imidazol-2-yl}methyl)amino]methyl}-6-methylpyridine-4-carboxylic acid | A | ¹H-NMR (300 MHz, CD₃OD): δ 7.60 (s, 1H), 7.49 (s, 1H), 6.78 (s, 1H), 2.54 (s, 3H), 2.22-2.12 (m, 1H) ppm |
| 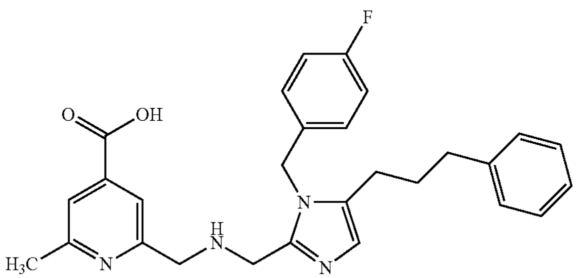 [SMILES: Cc1cc(C(=O)O)cc(CNCc2ncc(CCCc3ccccc3)n2Cc2ccc(F)cc2)n1] | 31 | 2-{[({1-[(4-fluorophenyl)methyl]-5-(3-phenylpropyl)-1H-imidazol-2-yl}methyl)amino]methyl}-6-methylpyridine-4-carboxylic acid | A | ¹H-NMR (300 MHz, CD₃OD): δ 7.60 (s, 1H), 7.51 (s, 1H), 6.70 (s, 1H), 2.57 (t, 2H), 2.48 (s, 2H) ppm |
| 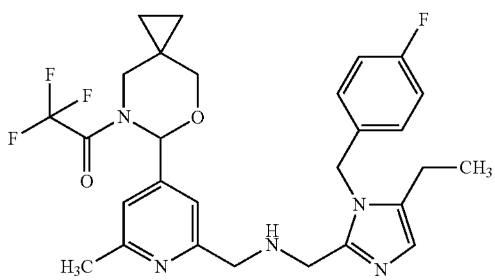 [SMILES: CCc1cnc(CNCc2cc(C3OCC4(CC4)CN3C(=O)C(F)(F)F)cc(C)n2)n1Cc1ccc(F)cc1] | 32 | 1-[6-(2-{[({5-ethyl-1-[(4-fluorophenyl)methyl]-1H-imidazol-2-yl}methyl)amino]methyl}-6-methylpyridin-4-yl)-5-oxa-7-azaspiro[2.5]octan-7-yl]-2,2,2-trifluoroethan-1-one | D | ¹H-NMR (300 MHz, CDCl₃): δ 7.14 (s, 1H), 6.94 (s, 1H), 4.02 (d, 1H), 0.77-0.59 (m, 2H) ppm. |
| 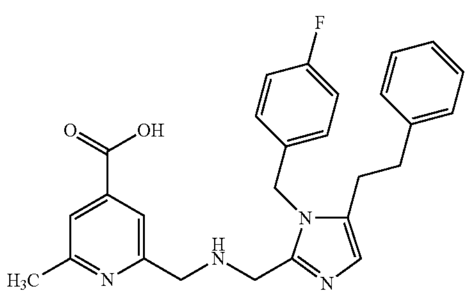 [SMILES: Cc1cc(C(=O)O)cc(CNCc2ncc(CCc3ccccc3)n2Cc2ccc(F)cc2)n1] | 33 | 2-{[({4-[(4-fluorophenyl)methyl]-5-(2-phenylethyl)-4H-1,2,4-triazol-3-yl}methyl)amino]methyl}-6-methylpyridine-4-carboxylic acid | A | ¹H-NMR (300 MHz, CD₃OD): δ 7.58 (s, 1H), 5.16 (s, 2H), 2.87 (s, 2H), 2.45 (s, 3H) ppm. |
| 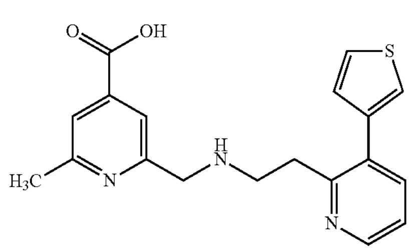 [SMILES: Cc1cc(C(=O)O)cc(CNCCc2ncccc2-c2ccsc2)n1] | 34 | 2-methyl-6-[({2-[3-(thiophen-3-yl)pyridin-2-yl]ethyl}amino)methyl]pyridine-4-carboxylic acid | A | ¹H-NMR (300 MHz, CD₃OD): δ 8.42 (d, 1H), 7.13 (d, 1H), 3.05 (t, 2H), 2.52 (s, 3H) ppm |

TABLE 2-continued (#SR = may be prepared analogously to according to synthetic route number listed)

| Structure | # | Name | SR# | NMR |
|---|---|---|---|---|
| 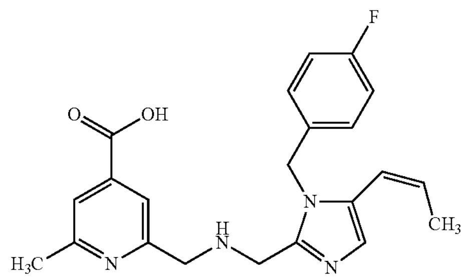 [SMILES: C/C=C\c1cnc(CNCc2cc(C(=O)O)cc(C)n2)n1Cc1ccc(F)cc1] | 35 | 2-{[({1-[(4-fluorophenyl)methyl]-5-[(1Z)-prop-1-en-1-yl]-1H-imidazol-2-yl}methyl)amino]methyl}-6-methylpyridine-4-carboxylic acid | A | $^1$H-NMR (300 MHz, CD$_3$OD): δ 7.63 (s, 1H), 5.32 (s, 2H), 3.87 (s, 2H), 1.84 (d, 3H) ppm. |
| 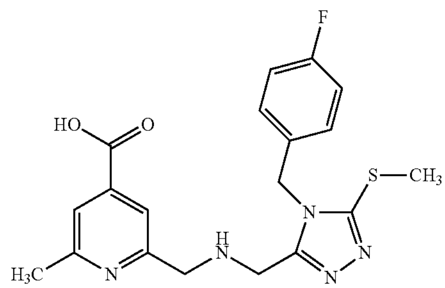 | 36 | 2-{[({4-[(4-fluorophenyl)methyl]-5-(methylsulfanyl)-4H-1,2,4-triazol-3-yl}methyl)amino]methyl}-6-methylpyridine-4-carboxylic acid | A | $^1$H-NMR (300 MHz, CD$_3$OD): δ 7.82 (s, 1H), 5.27 (s, 2H), 4.61 (s, 2H), 2.71 (s, 3H) ppm. |
| 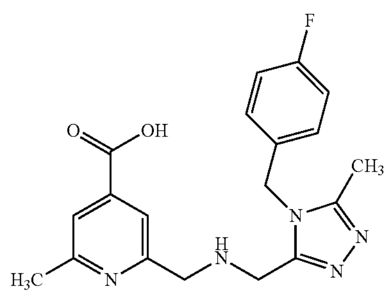 [SMILES: Cc1cc(C(=O)O)cc(CNCc2nnc(C)n2Cc2ccc(F)cc2)n1] | 37 | 2-{[({4-[(4-Fluorophenyl)methyl]-5-methyl-4H-1,2,4-triazol-3-yl}methyl)amino]methyl}-6-methylpyridine-4-carboxylic acid | A | $^1$H-NMR (300 MHz, CD$_3$OD): δ 7.69 (s, 1H), 5.25 (s, 2H), 2.52 (s, 3H), 2.49 (s, 3H) ppm. |
| 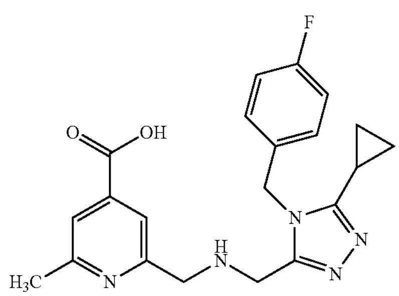 [SMILES: Cc1cc(C(=O)O)cc(CNCc2nnc(C3CC3)n2Cc2ccc(F)cc2)n1] | 38 | 2-{[({5-cyclopropyl-4-[(4-fluorophenyl)methyl]-4H-1,2,4-triazol-3-yl}methyl)amino]methyl}-6-methylpyridine-4-carboxylic acid | A | $^1$H-NMR (300 MHz, CD$_3$OD): δ 7.56 (s, 1H), 5.39 (s, 2H), 2.43 (s, 3H), 0.90-0.82 (m, 4H) ppm. |
| 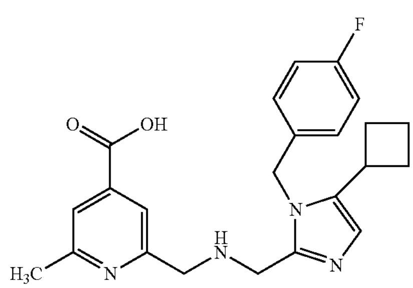 [SMILES: Cc1cc(C(=O)O)cc(CNCc2ncc(C3CCC3)n2Cc2ccc(F)cc2)n1] | 39 | 2-{[({5-cyclobutyl-1-[(4-fluorophenyl)methyl]-1H-imidazol-2-yl}methyl)amino]methyl}-6-methyl pyridine-4-carboxylic acid | A | $^1$H-NMR (300 MHz, CD$_3$OD): δ 7.61 (s, 1H), 5.20 (s, 2H), 3.76 (s, 2H), 2.50 (s, 3H), 1.86-1.74 (m, 2H) ppm. |

TABLE 2-continued (#SR = may be prepared analogously to according to synthetic route number listed)

| Structure | # | Name | SR# | NMR |
|---|---|---|---|---|
| 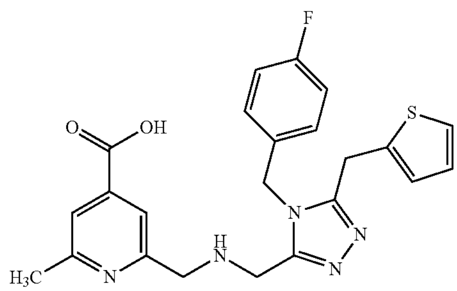 [SMILES: Cc1cc(C(=O)O)cc(CNCc2nnc(Cc3cccs3)n2Cc2ccc(F)cc2)n1] | 40 | 2-{[({4-[(4-fluorophenyl)methyl]-5-(thiophen-2-ylmethyl)-4H-1,2,4-triazol-3-yl}methyl)amino]methyl}-6-methylpyridine-4-carboxylic acid | A | $^1$H-NMR (300 MHz, CD$_3$OD): δ 7.73 (s, 1H), 7.23 (d, 1H), 5.24 (s, 2H), 2.55 (s, 3H) ppm. |
| 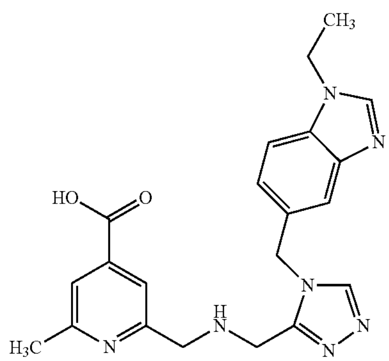 [SMILES: CCn1cnc2cc(Cn3cnnc3CNCc3cc(C(=O)O)cc(C)n3)ccc21] | 41 | 2-{[({4-[(1-ethyl-1H-1,3-benzodiazol-5-yl)methyl]-4H-1,2,4-triazol-3-yl}methyl)amino]methyl}-6-methylpyridine-4-carboxylic acid | A | $^1$H-NMR (300 MHz, CD$_3$OD): δ 8.47 (s, 1H), 8.16 (s, 1H), 3.92 (s, 2H), 3.82 (s, 2H) ppm. |
| 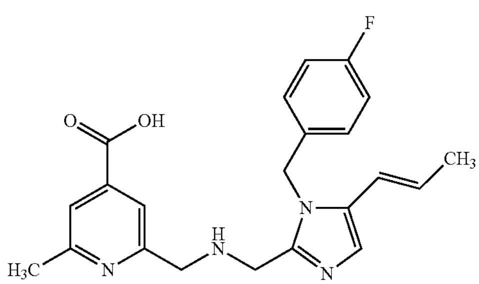 [SMILES: C/C=C/c1cnc(CNCc2cc(C(=O)O)cc(C)n2)n1Cc1ccc(F)cc1] | 42 | 2-{[({1-[(4-fluorophenyl)methyl]-5-[(1E)-prop-1-en-1-yl]-1H-imidazol-2-yl}methyl)amino]methyl}-6-methylpyridine-4-carboxylic acid | A | $^1$H-NMR (300 MHz, CD$_3$OD): δ 7.61 (s, 1H), 7.52 (s, 1H), 6.13-6.00 (m, 2H), 2.49 (s, 3H), 1.76 (d, 3H) ppm. |
| 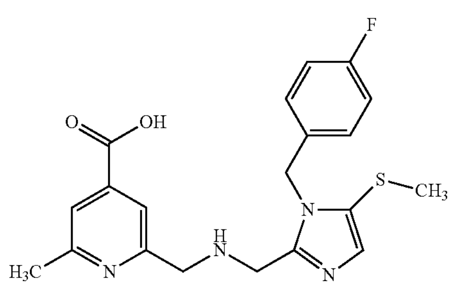 | 43 | 2-{[({1-[(4-fluorophenyl)methyl]-5-(methylsulfanyl)-1H-imidazol-2-yl}methyl)amino]methyl}-6-methyl pyridine-4-carboxylic acid | A | $^1$H-NMR (300 MHz, CD$_3$OD): δ 7.63 (s, 1H), 7.54 (s, 1H), 5.43 (s, 2H), 2.51 (s, 3H), 2.09 (s, 3H) ppm |
| 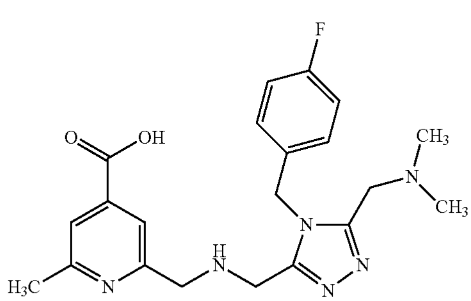 | 44 | 2-{[({5-[(dimethylamino)methyl]-4-[(4-fluorophenyl)methyl]-4H-1,2,4-triazol-3-yl}methyl)amino]methyl}-6-methylpyridine-4-carboxylic acid | A | $^1$H-NMR (300 MHz, CD$_3$OD): δ 7.58 (s, 1H), 5.40 (s, 2H), 2.44 (s, 3H), 2.13 (s, 6H) ppm. |

TABLE 2-continued (#SR = may be prepared analogously to according to synthetic route number listed)

| Structure | # | Name | SR# | NMR |
|---|---|---|---|---|
| 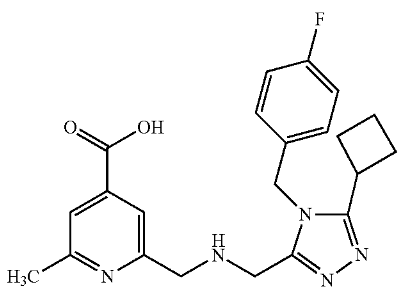 [SMILES: Cc1cc(C(=O)O)cc(CNCc2nnc(C3CCC3)n2Cc2ccc(F)cc2)n1] | 45 | 2-{[({5-cyclobutyl-4-[(4-fluorophenyl)methyl]-4H-1,2,4-triazol-3-yl}methyl)amino]methyl}-6-methylpyridine-4-carboxylic acid | A | $^1$H-NMR (300 MHz, CD$_3$OD): δ 7.50 (s, 1H), 5.15 (s, 2H), 3.37 (m, 1H), 2.36 (s, 3H) ppm. |
| 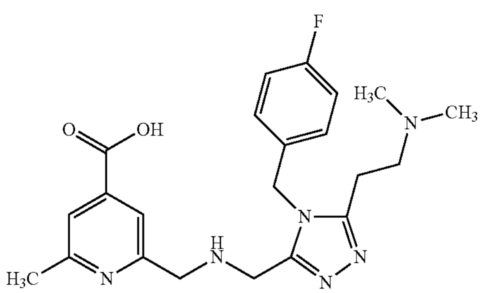 | 46 | 2-{[({5-[2-(dimethylamino)ethyl]-4-[(4-fluorophenyl)methyl]-4H-1,2,4-triazol-3-yl}methyl)amino]methyl}-6-methylpyridine-4-carboxylic acid | A | $^1$H-NMR (300 MHz, CD$_3$OD): δ 7.62 (s, 1H), 5.39 (s, 2H), 2.49 (s, 3H), 2.18 (s, 6H) ppm. |
| 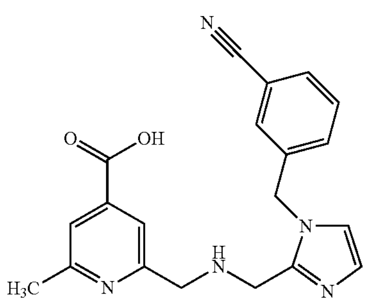 [SMILES: Cc1cc(C(=O)O)cc(CNCc2nccn2Cc2cccc(C#N)c2)n1] | 47 | 2-{[({1-[(3-cyanophenyl)methyl]-1H-imidazol-2-yl}methyl)amino]methyl}-6-methylpyridine-4-carboxylic acid | A | $^1$H-NMR (300 MHz, CD$_3$OD): δ 7.73 (d, 1H), 7.39 (s, 1H), 5.49 (s, 2H), 2.63 (s, 3H). |
| 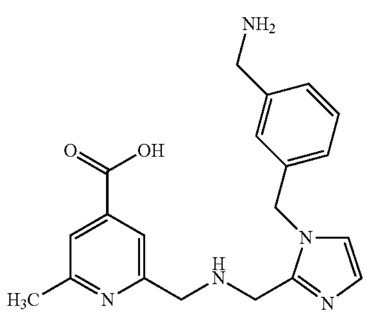 [SMILES: Cc1cc(C(=O)O)cc(CNCc2nccn2Cc2cccc(CN)c2)n1] | 48 | 2-({[(1-{[3-(aminomethyl)phenyl]methyl}-1H-imidazol-2-yl)methyl]amino}methyl)-6-methylpyridine-4-carboxylic acid | C | $^1$H-NMR (300 MHz, CD$_3$OD): δ 7.61 (s, 1H), 6.89 (s, 1H), 3.83 (s, 2H), 2.52 (s, 3H). |

TABLE 2-continued (#SR = may be prepared analogously to according to synthetic route number listed)

| Structure | # | Name | SR# | NMR |
|---|---|---|---|---|
| 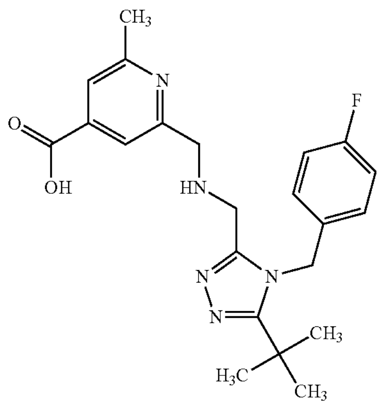 [SMILES: Cc1cc(C(=O)O)cc(CNCc2nnc(C(C)(C)C)n2Cc2ccc(F)cc2)n1] | 49 | 2-{[({5-tert-butyl-4-[(4-fluorophenyl)methyl]-4H-1,2,4-triazol-3-yl}methyl)amino]methyl}-6-methylpyridine-4-carboxylic acid | A | $^1$H-NMR (300 MHz, CD$_3$OD): δ 7.59 (s, 1H), 5.55 (s, 2H), 2.45 (s, 3H), 1.33 (s, 9H) ppm. |
| 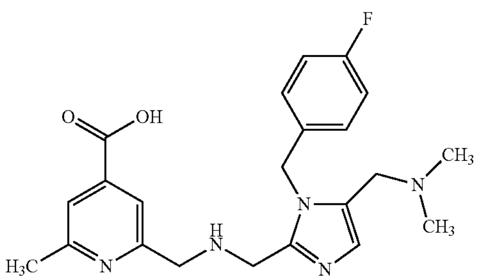 | 50 | 2-{[({5-[(dimethylamino)methyl]-1-[(4-fluorophenyl)methyl]-1H-imidazol-2-yl}methyl)amino]methyl}-6-methylpyridine-4-carboxylic acid | A | $^1$H-NMR (300 MHz, CD$_3$OD): δ 7.59 (s, 1H), 7.51 (s, 1H), 5.36 (s, 2H), 2.47 (s, 3H), 2.11 (s, 6H) ppm. |
| 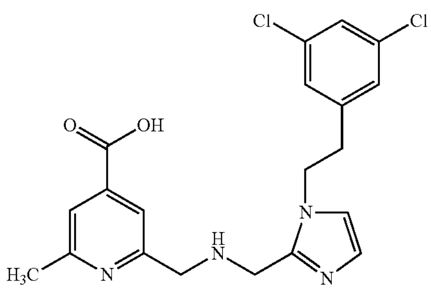 [SMILES: Cc1cc(C(=O)O)cc(CNCc2nccn2CCc2cc(Cl)cc(Cl)c2)n1] | 51 | 2-{[({4-[2-(3,5-dichlorophenyl)ethyl]-4H-1,2,4-triazol-3-yl}methyl)amino]methyl}-6-methylpyridine-4-carboxylic acid | A | $^1$H-NMR (300 MHz, CD$_3$OD): δ 8.32 (s, 1H), 7.10 (s, 2H), 4.42 (d, 2H), 2.52 (s, 3H). |
| 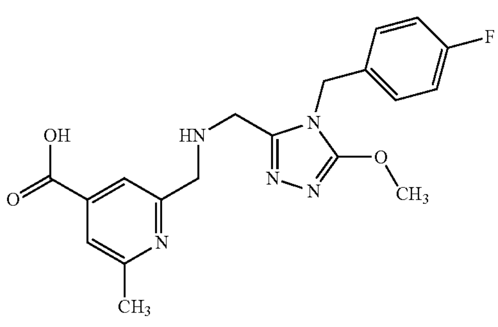 [SMILES: COc1nnc(CNCc2cc(C(=O)O)cc(C)n2)n1Cc1ccc(F)cc1] | 52 | 2-{[(2-{4-[(4-fluorophenyl)methyl]-5-methoxy-4H-1,2,4-triazol-3-yl}ethyl)amino]methyl}-6-methylpyridine-4-carboxylic acid | A | $^1$H-NMR (300 MHz, CD$_3$OD): δ 7.8 (s, 1H), 5.1 (s, 2H), 4.1 (s, 3H), 2.4 (s, 3H) |
| 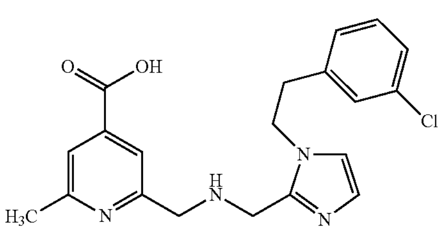 [SMILES: Cc1cc(C(=O)O)cc(CNCc2nccn2CCc2cccc(Cl)c2)n1] | 53 | 2-{[({4-[2-(3-chlorophenyl)ethyl]-4H-1,2,4-triazol-3-yl}methyl)amino]methyl}-6-methylpyridine-4-carboxylic acid | A | $^1$H-NMR (300 MHz, CD$_3$OD): δ 8.57 (s, 1H), 7.08 (m, 1H), 4.32 (s, 2H), 2.68 (s, 3H) ppm |

TABLE 2-continued (#SR = may be prepared analogously to according to synthetic route number listed)

| Structure | # | Name | SR# | NMR |
|---|---|---|---|---|
| 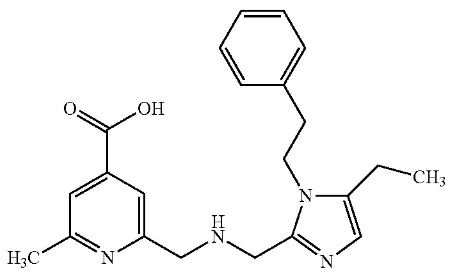 [SMILES: CCc1cnc(CNCc2cc(C(=O)O)cc(C)n2)n1CCc1ccccc1] | 54 | 2-[({[5-ethyl-1-(2-phenylethyl)-1H-imidazol-2-yl]methyl}amino)methyl]-6-methylpyridine-4-carboxylic acid | A | $^1$H-NMR (300 MHz, CD$_3$OD): δ 7.58 (s, 1H), 7.54 (s, 1H), 4.15 (t, 2H), 2.88 (t, 2H), 2.40 (q, 2H) ppm. |
| 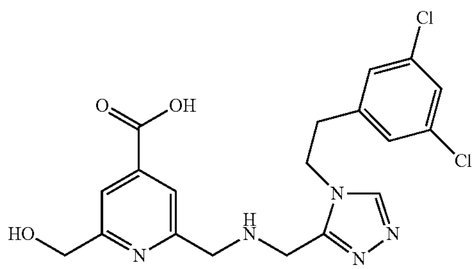 [SMILES: O=C(O)c1cc(CO)nc(CNCc2nncn2CCc2cc(Cl)cc(Cl)c2)c1] | 55 | 2-{[({4-[2-(3,5-dichlorophenyl)ethyl]-4H-1,2,4-triazol-3-yl}methyl)amino]methyl}-6-(hydroxymethyl)pyridine-4-carboxylic acid | A | $^1$H-NMR (300 MHz, CD$_3$OD): δ 8.48 (s, 1H), 7.96 (s, 1H), 7.25 (s, 1H), 3.03 (t, 2H) ppm. |
| 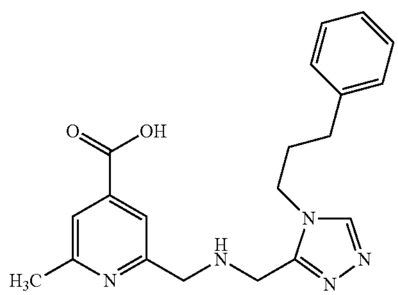 [SMILES: Cc1cc(C(=O)O)cc(CNCc2nncn2CCCc2ccccc2)n1] | 56 | 2-methyl-6-[({[4-(3-phenylpropyl)-4H-1,2,4-triazol-3-yl]methyl}amino)methyl]pyridine-4-carboxylic acid | A | $^1$H-NMR (300 MHz, CD$_3$OD): δ 8.49 (s, 1H), 7.19 (m, 3H), 2.55 (s, 3H), 2.15 (m, 2H) ppm |
| 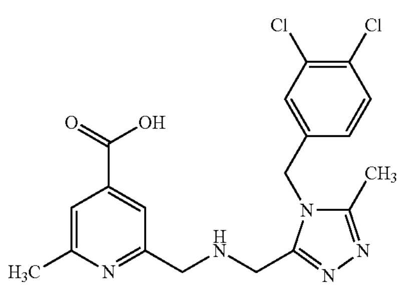 [SMILES: Cc1cc(C(=O)O)cc(CNCc2nnc(C)n2Cc2ccc(Cl)c(Cl)c2)n1] | 57 | 2-{[({4-[(3,4-dichlorophenyl)methyl]-5-methyl-4H-1,2,4-triazol-3-yl}methyl)amino]methyl}-6-methylpyridine-4-carboxylic acid | A | $^1$H-NMR (300 MHz, CD$_3$OD): δ 7.60 (s, 1H), 6.98 (d, 1H), 5.40 (d, 2H), 2.30 (s, 3H). |
| 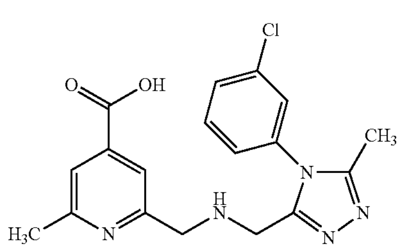 | 58 | 2-[({[4-(3-chlorophenyl)-5-methyl-4H-1,2,4-triazol-3-yl]methyl}amino)methyl]-6-methylpyridine-4-carboxylic acid | A | $^1$H-NMR (300 MHz, CD$_3$OD): δ 7.43 (m, 1H), 3.22 (s, 4H), 2.52 (s, 3H), 2.29 (s, 3H) ppm. |

TABLE 2-continued (#SR = may be prepared analogously to according to synthetic route number listed)

| Structure | # | Name | SR# | NMR |
|---|---|---|---|---|
| 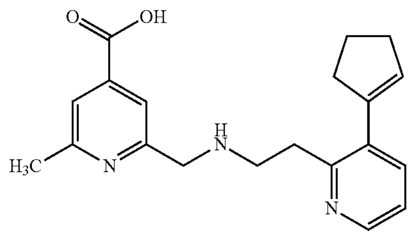 [SMILES: Cc1cc(C(=O)O)cc(CNCCc2ncccc2C2=CCCC2)n1] | 59 | 2-[({2-[3-(cyclopent-1-en-1-yl)pyridin-2-yl]ethyl}amino)methyl]-6-methylpyridine-4-carboxylic acid | A | ¹H-NMR (300 MHz, CD₃OD): δ 8.51 (d, 1H), 5.94 (s, br, 1H), 3.57 (t, 2H), 2.66 (s, 3H) ppm |
| 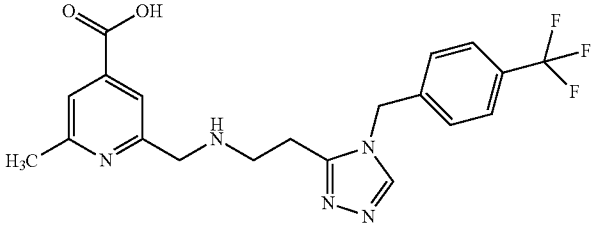 [SMILES: Cc1cc(C(=O)O)cc(CNCCc2nncn2Cc2ccc(C(F)(F)F)cc2)n1] | 60 | 2-methyl-6-({[2-(4-{[4-(trifluoromethyl)phenyl]methyl}-4H-1,2,4-triazol-3-yl)ethyl]amino}methyl)pyridine-4-carboxylic acid | A | ¹H-NMR (300 MHz, CD₃OD): δ 8.8 (s, 1H), 5.4 (s, 2H), 4.4 (s, 2H), 2.5 (s, 3H) |
| 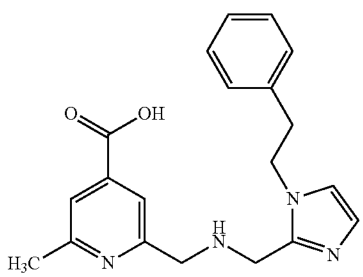 [SMILES: Cc1cc(C(=O)O)cc(CNCc2nccn2CCc2ccccc2)n1] | 61 | 2-methyl-6-[({[1-(2-phenylethyl)-1H-imidazol-2-yl]methyl}amino)methyl]pyridine-4-carboxylic acid | A | ¹H-NMR (300 MHz, CD₃OD): δ 7.61 (s, 1H), 7.55 (s, 1H), 4.24 (t, 2H), 2.98 (t, 2H), 2.51 (s, 3H) ppm. |
| 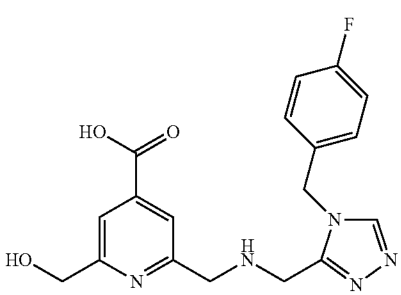 [SMILES: O=C(O)c1cc(CO)nc(CNCc2nncn2Cc2ccc(F)cc2)c1] | 62 | 2-{[({4-[(4-fluorophenyl)methyl]-4H-1,2,4-triazol-3-yl}methyl)amino]methyl}-6-(hydroxymethyl)pyridine-4-carboxylic acid | A | ¹H-NMR (300 MHz, CD₃OD): δ 8.46 (s, 1H, 5.38 (s, 2H, 3.94 (s, 2H), 3.09 (s, 2H) ppm. |
| 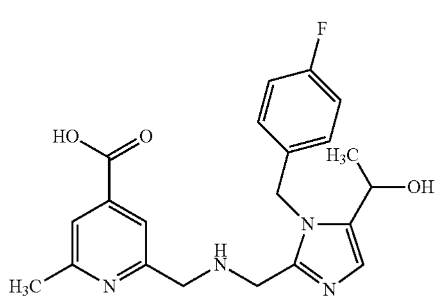 [SMILES: Cc1cc(C(=O)O)cc(CNCc2ncc(C(C)O)n2Cc2ccc(F)cc2)n1] | 63 | 2-{[({1-[(4-fluorophenyl)methyl]-5-(1-hydroxyethyl)-1H-imidazol-2-yl}methyl)amino]methyl}-6-methylpyridine-4-carboxylic acid | A | ¹H-NMR (300 MHz, CD₃OD): δ 7.6 (s, 1H), 5.3 (s, 2H), 4.6 (s, 2H), 3.8 (s, 2H) |

TABLE 2-continued (#SR = may be prepared analogously to according to synthetic route number listed)

| Structure | # | Name | SR# | NMR |
|---|---|---|---|---|
| 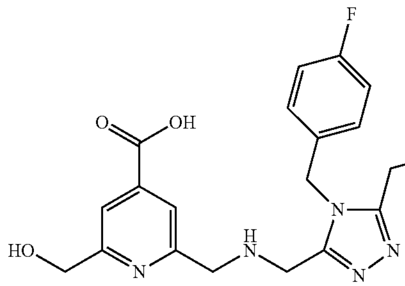 | 64 | 2-{[({5-ethyl-4-[(4-Fluorophenyl)methyl]-4H-1,2,4-triazol-3-yl}methyl)amino]methyl}-6-(hydroxymethyl)pyridine-4-carboxylic acid | A | ¹H-NMR (300 MHz, CD₃OD): δ 7.87 (s, 1H), 5.20 (s, 2H), 4.64 (s, 2H), 2.67 (q, 2H) ppm. |
| 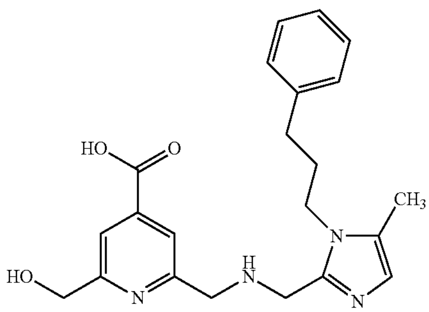 [SMILES: Cc1cnc(CNCc2cc(C(=O)O)cc(CO)n2)n1CCCc1ccccc1] | 65 | 2-(hydroxymethyl)-6-[({[5-methyl-4-(3-phenylpropyl)-4H-1,2,4-triazol-3-yl]methyl}amino)methyl]pyridine-4-carboxylic acid | A | ¹H-NMR (300 MHz, CD₃OD): δ 7.82 (s, 1H), 4.70 (s, 2H), 2.66 (t, 2H), 2.33 (s, 3H) ppm. |
| 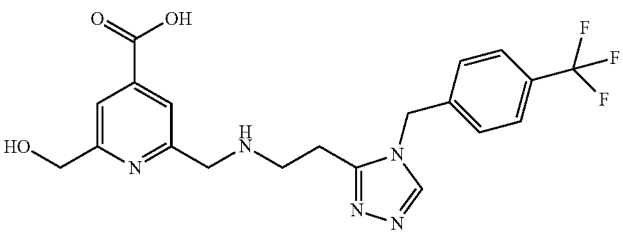 [SMILES: O=C(O)c1cc(CO)nc(CNCCc2nncn2Cc2ccc(C(F)(F)F)cc2)c1] | 66 | 2-(hydroxymethyl)-6-({[2-(4-{[4-(trifluoromethyl)phenyl]methyl}-4H-1,2,4-triazol-3-yl)ethyl]amino}methyl)pyridine-4-carboxylic acid | A | ¹H-NMR (300 MHz, CD₃OD): δ 8.5 (s, 1H), 5.3 (s, 2H), 4.7 (s, 2H), 3.3 (m, 4H) |
| 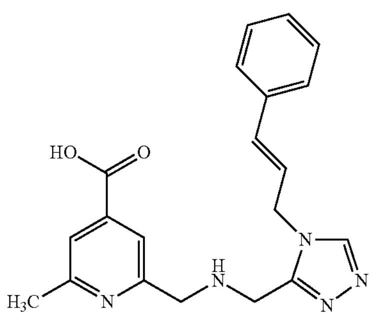 [SMILES: Cc1cc(C(=O)O)cc(CNCc2nncn2C/C=C/c2ccccc2)n1] | 67 | 2-methyl-6-{[({4-[(2E)-3-phenylprop-2-en-1-yl]-4H-1,2,4-triazol-3-yl}methyl)amino]methyl}pyridine-4-carboxylic acid | A | ¹H-NMR (300 MHz, CD₃OD): δ 8.49 (s, 1H), 7.69 (s, 1H), 6.36 (dt, 1H), 4.06 (s, 2H) ppm. |
| 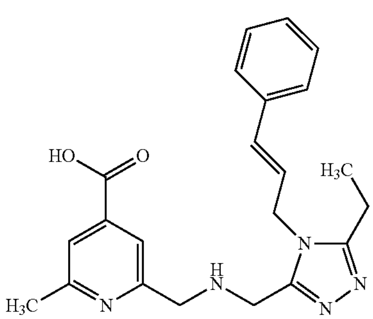 [SMILES: CCc1nnc(CNCc2cc(C(=O)O)cc(C)n2)n1C/C=C/c1ccccc1] | 68 | 2-{[({5-ethyl-4-[(2E)-3-phenylprop-2-en-1-yl]-4H-1,2,4-triazol-3-yl}methyl)amino]methyl}-6-methylpyridine-4-carboxylic acid | A | ¹H-NMR (300 MHz, CD₃OD): δ 7.68 (s, 1H), 4.93 (d, 2H), 4.03 (s, 2H), 2.80 (q, 2H) ppm. |

TABLE 2-continued (#SR = may be prepared analogously to according to synthetic route number listed)

| Structure | # | Name | SR# | NMR |
|---|---|---|---|---|
| 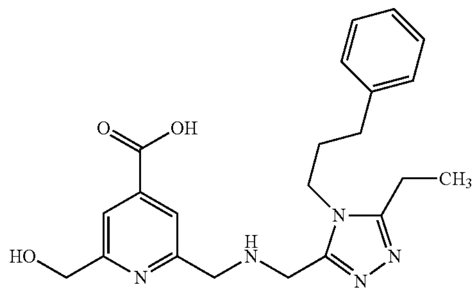 [SMILES: CCc1nnc(CNCc2cc(C(=O)O)cc(CO)n2)n1CCCc1ccccc1] | 69 | 2-[({[5-ethyl-4-(3-phenylpropyl)-4H-1,2,4-triazol-3-yl]methyl}amino)methyl]-6-(hydroxymethyl)pyridine-4-carboxylic acid | A | ¹H-NMR (300 MHz, CD₃OD): δ 7.85 (s, 1H), 7.72 (s, 1H), 4.07 (t, 2H), 2.06 (m, 2H) ppm |
| 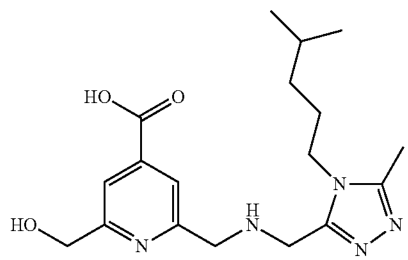 [SMILES: Cc1nnc(CNCc2cc(C(=O)O)cc(CO)n2)n1CCCC(C)C] | 70 | 2-(hydroxymethyl)-6-[({[5-methyl-4-(4-methylpentyl)-4H-1,2,4-triazol-3-yl]methyl}amino)methyl]pyridine-4-carboxylic acid | A | ¹H-NMR (300 MHz, CD₃OD): δ 7.77 (s, 1H), 7.66 (s, 1H), 4.67 (s, 2H), 2.38 (s, 3H), 0.84 (d, 6H). |
| 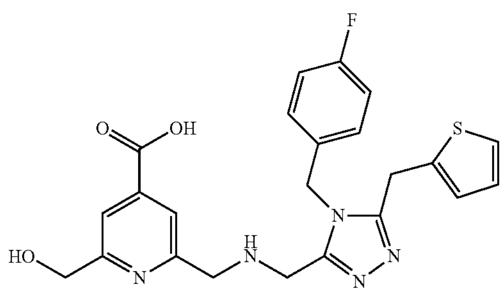 [SMILES: O=C(O)c1cc(CO)nc(CNCc2nnc(Cc3cccs3)n2Cc2ccc(F)cc2)c1] | 71 | 2-{[({4-[(4-Fluorophenyl)methyl]-5-(thiophen-2-ylmethyl)-4H-1,2,4-triazol-3-yl}methyl)amino]methyl}-6-(hydroxymethyl)pyridine-4-carboxylic acid | A | ¹H-NMR (300 MHz, CD₃OD): δ 7.78 (s, 1H), 7.21 (d, 1H), 5.31 (s, 2H), 3.86 (s, 2H) ppm |
| 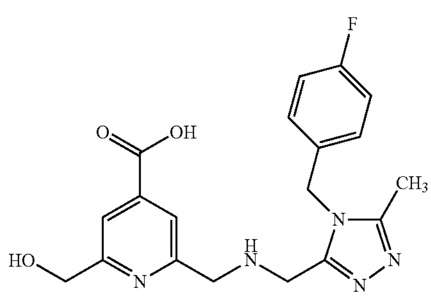 [SMILES: Cc1nnc(CNCc2cc(C(=O)O)cc(CO)n2)n1Cc1ccc(F)cc1] | 72 | 2-{[({4-[(4-fluorophenyl)methyl]-5-methyl-4H-1,2,4-triazol-3-yl}methyl)amino]methyl}-6-(hydroxymethyl)pyridine-4-carboxylic acid | A | ¹H-NMR (300 MHz, CD₃OD): δ 7.81 (s, 1H, 5.37 (s, 2H), 3.92 (s, 2H), 2.32 (s, 3H), ppm. |
| 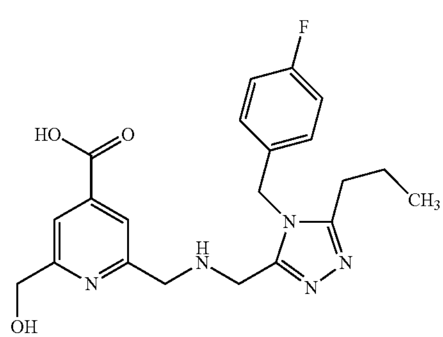 [SMILES: CCCc1nnc(CNCc2cc(C(=O)O)cc(CO)n2)n1Cc1ccc(F)cc1] | 73 | 2-{[({4-[(4-fluorophenyl)methyl]-5-propyl-4H-1,2,4-triazol-3-yl}methyl)amino]methyl}-6-(hydroxymethyl)pyridine-4-carboxylic acid | A | ¹H-NMR (300 MHz, CD₃OD): δ 7.75 (s, 1H), 5.32 (s, 2H), 4.63 (s, 2H), 3.86 (s, 4H) ppm. |

TABLE 2-continued (#SR = may be prepared analogously to according to synthetic route number listed)

| Structure | # | Name | SR# | NMR |
|---|---|---|---|---|
| 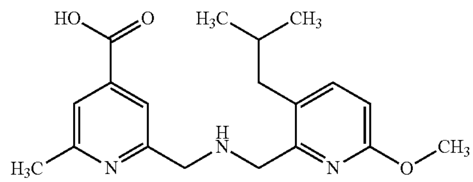 | 74 | 2-[({[6-methoxy-3-(2-methylpropyl)pyridin-2-yl]methyl}amino)methyl]-6-methylpyridine-4-carboxylic acid | A | 1H-NMR (300 MHz, CD3OD): δ 7.65 (s, 1H), 3.83 (s, 2H), 2.52 (s, 3H), 0.88 (m, 6H) ppm. |
| 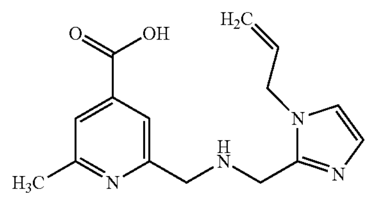 [SMILES: C=CCn1ccnc1CNCc1cc(C(=O)O)cc(C)n1] | 75 | 2-methyl-6-[({[1-(prop-2-en-1-yl)-1H-imidazol-2-yl]methyl}amino)methyl]pyridine-4-carboxylic acid | A | 1H-NMR (300 MHz, CD3OD): δ 7.62 (s, 1H), 6.04-5.84 (m, 1H), 5.15 (d, 1H), 4.69 (d, 2H), 2.52 (s, 3H) ppm. |
| 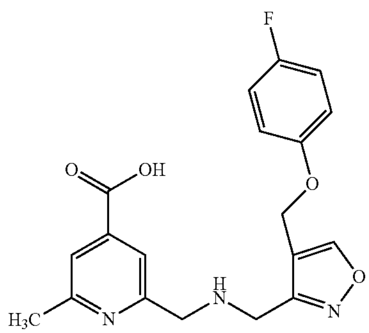 [SMILES: Cc1cc(C(=O)O)cc(CNCc2nocc2COc2ccc(F)cc2)n1] | 76 | 2-[({[4-(4-fluorophenoxymethyl)-1,2-oxazol-3-yl]methyl}amino)methyl]-6-methylpyridine-4-carboxylic acid | A | 1H-NMR (300 MHz, CD3OD): δ 8.59 (s, 1H), 7.59 (s, 1H), 7.47 (s, 1H), 4.97 (s, 2H), 2.45 (s, 3H) ppm. |
| 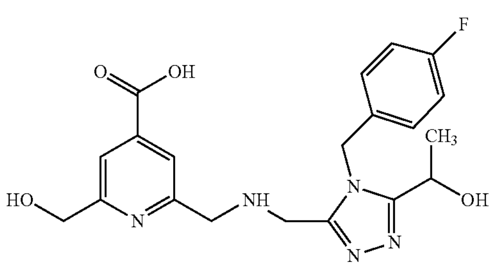 [SMILES: CC(O)c1nnc(CNCc2cc(C(=O)O)cc(CO)n2)n1Cc1ccc(F)cc1] | 77 | 2-{[({4-[(4-fluorophenyl)methyl]-5-(1-hydroxyethyl)-4H-1,2,4-triazol-3-yl}methyl)amino]methyl}-6-(hydroxymethyl)pyridine-4-carboxylic acid | A | 1H-NMR (300 MHz, CD3OD): δ 7.57 (s, 1H), 7.55 (s, 1H), 4.87 (q, 1H), 2.57 (s, 3H) ppm |
| 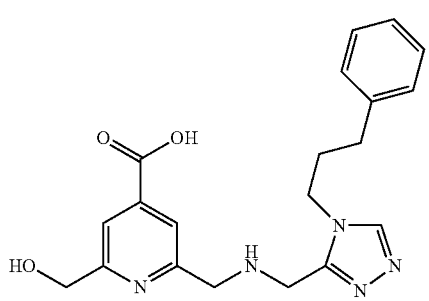 [SMILES: O=C(O)c1cc(CO)nc(CNCc2nncn2CCCc2ccccc2)c1] | 78 | 2-(hydroxymethyl)-6-[({[4-(3-phenylpropyl)-4H-1,2,4-triazol-3-yl]methyl}amino)methyl]pyridine-4-carboxylic acid | A | 1H-NMR (300 MHz, CD3OD): δ 8.44 (s, 1H), 7.69 (s, 1H), 4.13 (t, 2H), 2.70 (t, 2H) ppm |
| 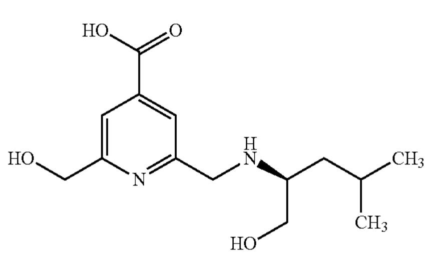 [SMILES: CC(C)C[C@@H](CO)NCc1cc(C(=O)O)cc(CO)n1] | 79 | 2-({[(2S)-1-hydroxy-4-methylpentan-2-yl]amino}methyl)-6-(hydroxymethyl)pyridine-4-carboxylic acid | A | 1H-NMR (300 MHz, CD3OD): δ 7.79 (s, 1H), 4.68 (s, 2H), 2.64 (m, 1H), 0.86 (d, 3H) ppm. |

TABLE 2-continued (#SR = may be prepared analogously to according to synthetic route number listed)

| Structure | # | Name | SR# | NMR |
|---|---|---|---|---|
| 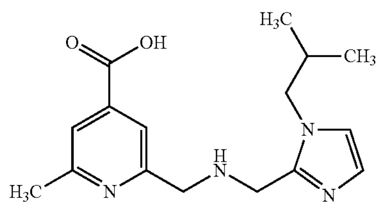 [SMILES: Cc1cc(C(=O)O)cc(CNCc2nccn2CC(C)C)n1] | 80 | 2-methyl-6-[({[1-(2-methylpropyl)-1H-imidazol-2-yl]methyl}amino)methyl]pyridine-4-carboxylic acid | A | ¹H-NMR (300 MHz, CD₃OD): δ 7.67 (s, 1H), 6.88 (s, 1H), 2.56 (s, 3H), 2.09-1.97 (m, 1H). |
| 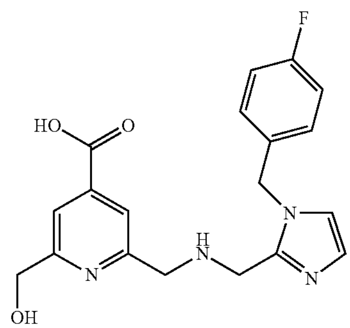 [SMILES: O=C(O)c1cc(CO)nc(CNCc2nccn2Cc2ccc(F)cc2)c1] | 81 | 2-{[({1-[(4-fluorophenyl)methyl]-1H-imidazol-2-yl}methyl)amino]methyl}-6-(hydroxymethyl)pyridine-4-carboxylic acid | A | ¹H-NMR (300 MHz, CD₃OD): δ 7.98 (s, 1H), 5.38 (s, 2H), 4.37 (s, 2H), 4.34 (s, 2H) ppm. |
| 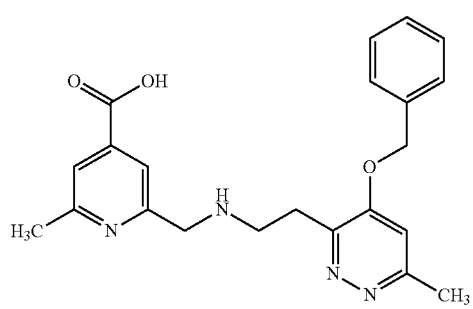 [SMILES: Cc1cc(OCc2ccccc2)c(CCNCc2cc(C(=O)O)cc(C)n2)nn1] | 82 | 2-[({2-[4-(benzyloxy)-6-methylpyridazin-3-yl]ethyl}amino)methyl]-6-methylpyridine-4-carboxylic acid | A | ¹H-NMR (300 MHz, CD₃OD): δ 6.39 (s, 1H), 5.43 (s, 2H), 3.89 (s, 2H), 2.49 (s, 3H) ppm. |
| 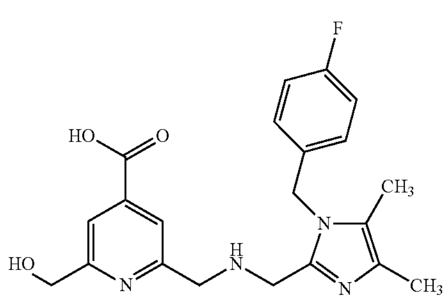 [SMILES: Cc1nc(CNCc2cc(C(=O)O)cc(CO)n2)n(Cc2ccc(F)cc2)c1C] | 83 | 2-{[({1-[(4-fluorophenyl)methyl]-4,5-dimethyl-1H-imidazol-2-yl}methyl)amino]methyl}-6-(hydroxymethyl)pyridine-4-carboxylic acid | A | ¹H-NMR (300 MHz, CD₃OD): δ 7.7 (s, 1H), 5.2 (s, 2H), 4.5 (s, 3H), 2.1 (s, 3H) |
| 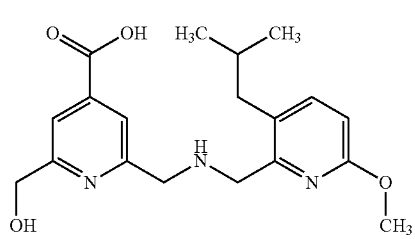 [SMILES: COc1ccc(CC(C)C)c(CNCc2cc(C(=O)O)cc(CO)n2)n1] | 84 | 2-(hydroxymethyl)-6-[({[6-methoxy-3-(2-methylpropyl)pyridin-2-yl]methyl}amino)methyl]pyridine-4-carboxylic acid | A | ¹H-NMR (300 MHz, CD₃OD): δ 8.06 (s, 1H), 4.81 (s, 2H), 4.61 (s, 2H), 0.94 (d, 6H) ppm. |

TABLE 2-continued (#SR = may be prepared analogously to according to synthetic route number listed)

| Structure | # | Name | SR# | NMR |
|---|---|---|---|---|
| 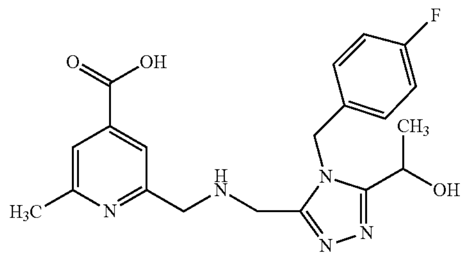 [SMILES: Cc1cc(C(=O)O)cc(CNCc2nnc(C(C)O)n2Cc2ccc(F)cc2)n1] | 85 | 2-{[({4-[(4-fluorophenyl)methyl]-5-(1-hydroxyethyl)-4H-1,2,4-triazol-3-yl}methyl)amino]methyl}-6-methylpyridine-4-carboxylic acid | A | $^1$H-NMR (300 MHz, CD$_3$OD): δ 7.82 (s, 1H), 7.76 (s, 1H), 5.04 (q,1H), 1.68 (d, 3H) ppm |
| 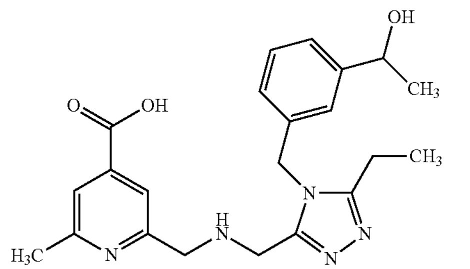 [SMILES: CCc1nnc(CNCc2cc(C(=O)O)cc(C)n2)n1Cc1cccc(C(C)O)c1] | 86 | 2-({[(5-ethyl-4-{[3-(1-hydroxyethyl)phenyl]methyl}-4H-1,2,4-triazol-3-yl)methyl]amino}methyl)-6-methylpyridine-4-carboxylic acid | A | $^1$H-NMR (300 MHz, CD$_3$OD): δ 7.60 (s, 1H), 4.75 (q, 1H), 3.92 (s, 2H), 3.87 (s, 2H) ppm. |
| 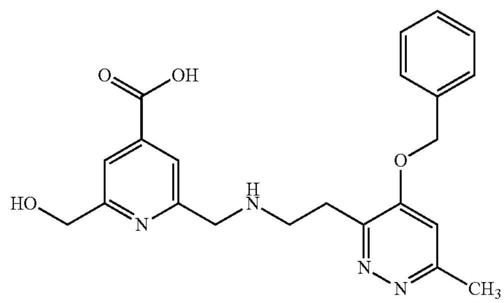 [SMILES: Cc1cc(OCc2ccccc2)c(CCNCc2cc(C(=O)O)cc(CO)n2)nn1] | 87 | 2-[({2-[4-(benzyloxy)-6-methylpyridazin-3-yl]ethyl}amino)methyl]-6-(hydroxymethyl)pyridine-4-carboxylic acid | A | $^1$H-NMR (300 MHz, CD$_3$OD): δ 6.54 (s, 1H), 5.50 (s, 2H), 4.79 (s, 2H), 4.51 (s, 2H) ppm. |
| 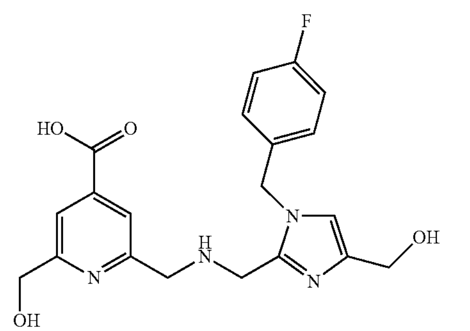 [SMILES: O=C(O)c1cc(CO)nc(CNCc2nc(CO)cn2Cc2ccc(F)cc2)c1] | 88 | 2-{[({1-[(4-fluorophenyl)methyl]-4-(hydroxymethyl)-1H-imidazol-2-yl}methyl)amino]methyl}-6-(hydroxymethyl)pyridine-4-carboxylic acid | A | $^1$H-NMR (300 MHz, CD$_3$OD): δ ppm 8.00 (s, 1H), 5.30 (s, 2H), 4.80 (s, 2H), 4.30 (s, 2H) ppm. |
| 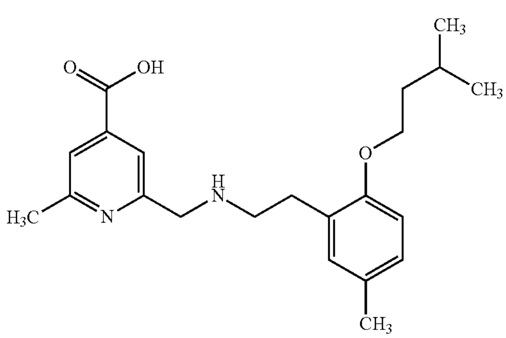 [SMILES: Cc1ccc(OCCC(C)C)c(CCNCc2cc(C(=O)O)cc(C)n2)c1] | 89 | 2-methyl-6-[({2-[5-methyl-2-(3-methylbutoxy)phenyl]ethyl}amino)methyl]pyridine-4-carboxylic acid | A | $^1$H-NMR (300 MHz, CD$_3$OD): δ 7.58 (s, 1H), 3.84 (s, 2H), 2.78 (s, 4H), 0.92 (d, 6H) ppm. |

TABLE 2-continued (#SR = may be prepared analogously to according to synthetic route number listed)

| Structure | # | Name | SR# | NMR |
|---|---|---|---|---|
| 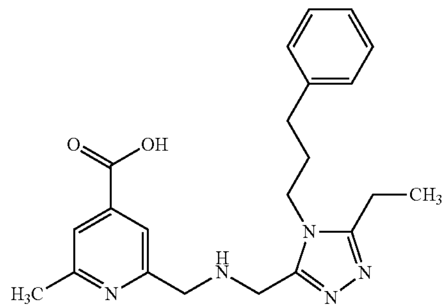 [SMILES: CCc1nnc(CNCc2cc(C(=O)O)cc(C)n2)n1CCCc1ccccc1] | 90 | 2-[({[5-ethyl-4-(3-phenylpropyl)-4H-1,2,4-triazol-3-yl]methyl}amino)methyl]-6-methylpyridine-4-carboxylic acid | A | $^1$H-NMR (300 MHz, CD$_3$OD): δ 7.69 (s, 1H), 2.53 (s, 3H), 2.03 (m, 2H), 1.30 (t, 3H) ppm. |
| 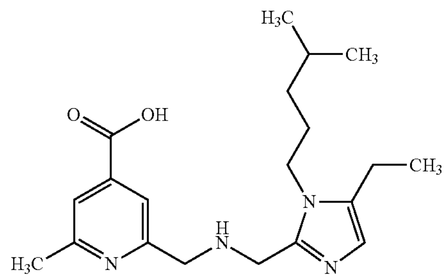 [SMILES: CCc1cnc(CNCc2cc(C(=O)O)cc(C)n2)n1CCCC(C)C] | 91 | 2-[({[5-ethyl-1-(4-methylpentyl)-1H-imidazol-2-yl]methyl}amino)methyl]-6-methylpyridine-4-carboxylic acid | A | $^1$H-NMR (300 MHz, CD$_3$OD): δ 7.86 (s, 1H), 7.26 (s, 1H), 2.75-2.61 (m, 5H), 1.82-1.67 (m, 2H), 0.90 (d, 6H) ppm. |
| 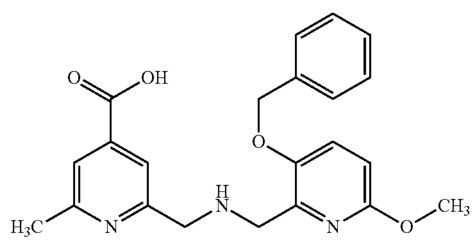 | 92 | 2-[({[3-(benzyloxy)-6-methoxypyridin-2-yl]methyl}amino)methyl]-6-methylpyridine-4-carboxylic acid | A | $^1$H-NMR (300 MHz, CD$_3$OD): δ 7.70 (s, 1H), 6.80 (d, 1H), 4.50 (s, 2H), 2.55 (s, 3H) ppm |
| 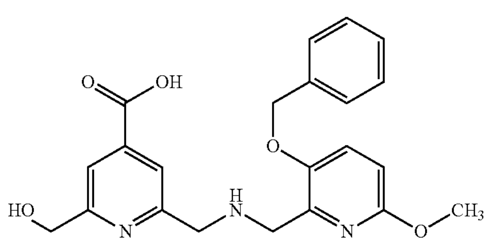 [SMILES: COc1ccc(OCc2ccccc2)c(CNCc2cc(C(=O)O)cc(CO)n2)n1] | 93 | 2-[({[3-(benzyloxy)-6-methoxypyridin-2-yl]methyl}amino)methyl]-6-(hydroxymethyl)pyridine-4-carboxylic acid | A | $^1$H-NMR (300 MHz, CD$_3$OD): δ 7.70 (s, 1H), 6.50 (d, 1H), 3.90 (s, 2H), 3.80 (s, 5H) ppm |
| 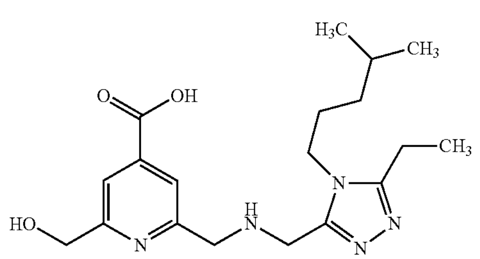 [SMILES: CCc1nnc(CNCc2cc(C(=O)O)cc(CO)n2)n1CCCC(C)C] | 94 | 2-[({[5-ethyl-4-(4-methylpentyl)-4H-1,2,4-triazol-3-yl]methyl}amino)methyl]-6-(hydroxymethyl)pyridine-4-carboxylic acid | A | $^1$H-NMR (300 MHz, CD$_3$OD): δ 8.01 (s, 1H), 4.85 (s, 2H), 4.78 (s, 2H), 0.86 (d, 6H) ppm. |

TABLE 2-continued (#SR = may be prepared analogously to according to synthetic route number listed)

| Structure | # | Name | SR# | NMR |
|---|---|---|---|---|
| 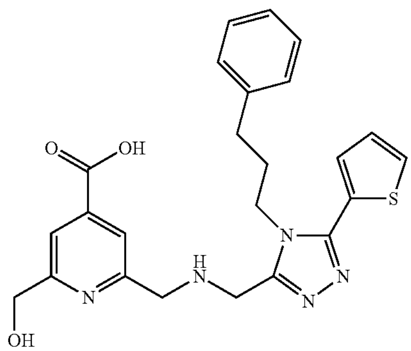 [SMILES: O=C(O)c1cc(CO)nc(CNCc2nnc(-c3cccs3)n2CCCc2ccccc2)c1] | 95 | 2-(hydroxymethyl)-6-[({[4-(3-phenylpropyl)-5-(thiophen-2-yl)-4H-1,2,4-triazol-3-yl]methyl}amino}methyl]pyridine-4-carboxylic acid | A | ¹H-NMR (300 MHz, CD₃OD): δ 7.83 (s, 1H), 4.71 (s, 2H), 3.98 (s, 2H), 2.61 (t, 2H). |
| 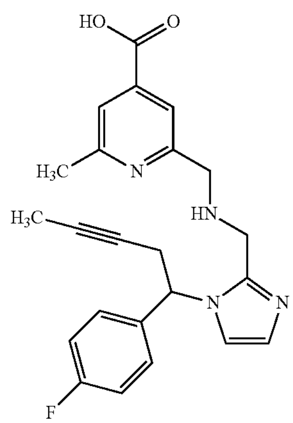 [SMILES: CC#CCC(c1ccc(F)cc1)n1ccnc1CNCc1cc(C(=O)O)cc(C)n1] | 96 | 2-{[({1-[1-(4-fluorophenyl)pent-3-yn-1-yl]-1H-imidazol-2-yl}methyl)amino]methyl}-6-methylpyridine-4-carboxylic acid | A | ¹H-NMR (300 MHz, CD₃OD): δ 7.67 (s, 1H), 5.84 (t, 1H), 2.54 (s, 3H), 1.61 (t, 3H) ppm |
| 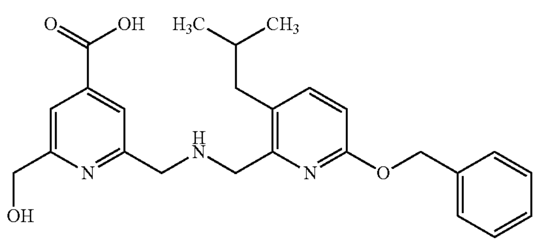 [SMILES: CC(C)Cc1ccc(OCc2ccccc2)nc1CNCc1cc(C(=O)O)cc(CO)n1] | 97 | 2-[({[6-(benzyloxy)-3-(2-methylpropyl)pyridin-2-yl]methyl}amino)methyl]-6-(hydroxymethyl)pyridine-4-carboxylic acid | A | ¹H-NMR (300 MHz, CD₃OD): δ 7.85 (s, 1H), 5.41 (s, 2H), 4.71 (s, 2h), 2.41 (d, 2H) ppm. |
| 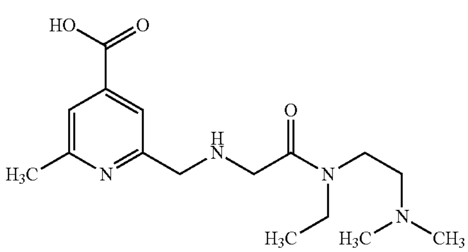 | 98 | 2-{[({[2-(dimethylamino)ethyl](ethyl)carbamoyl}methyl)amino]methyl}-6-methylpyridine-4-carboxylic acid | A | ¹H-NMR (300 MHz, CD₃OD): δ 7.66 (s, 1H), 3.91 (s, 2H), 2.55 (s, 3H), 2.26 (d, 6H). |
| 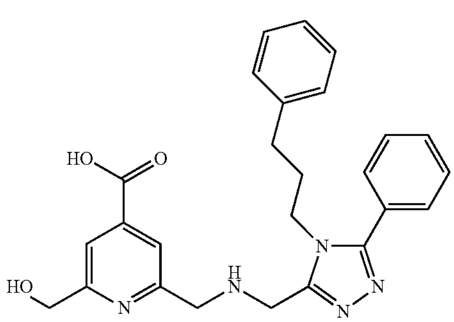 [SMILES: O=C(O)c1cc(CO)nc(CNCc2nnc(-c3ccccc3)n2CCCc2ccccc2)c1] | 99 | 2-(hydroxymethyl)-6-[({[5-phenyl-4-(3-phenylpropyl)-4H-1,2,4-triazol-3-yl]methyl}amino)methyl]pyridine-4-carboxylic acid | A | ¹H-NMR (300 MHz, CD₃OD): δ 7.83 (s, 1H), 6.98 (m, 2H), 4.70 (s, 2H), 2.47 (t, 2H). |

TABLE 2-continued (#SR = may be prepared analogously to according to synthetic route number listed)

| Structure | # | Name | SR# | NMR |
|---|---|---|---|---|
| 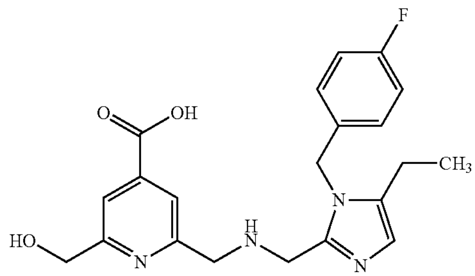 [SMILES: CCc1cnc(CNCc2cc(C(=O)O)cc(CO)n2)n1Cc1ccc(F)cc1] | 100 | 2-{[({5-ethyl-1-[(4-fluorophenyl)methyl]-1H-imidazol-2-yl}methyl)amino]methyl}-6-(hydroxymethyl)pyridine-4-carboxylic acid | A | $^1$H-NMR (300 MHz, CD$_3$OD): δ 7.77 (s, 1H), 4.67 (s, 2H), 3.88 (s, 2H), 2.42 (q, 2H), 1.16 (t, 3H) ppm. |
| 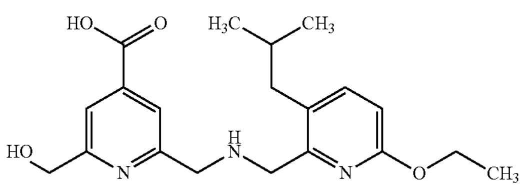 [SMILES: CCOc1ccc(CC(C)C)c(CNCc2cc(C(=O)O)cc(CO)n2)n1] | 101 | 2-[({[6-ethoxy-3-(2-methylpropyl)pyridin-2-yl]methyl}amino)methyl]-6-(hydroxymethyl)pyridine-4-carboxylic acid | A | $^1$H-NMR (300 MHz, CD$_3$OD): δ 7.84 (s, 1H), 4.72 (s, 2H), 4.38 (q, 2H), 0.89 (d, 6H) ppm. |
| 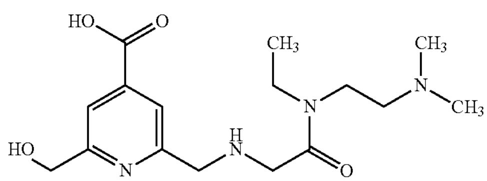 [SMILES: CCN(CCN(C)C)C(=O)CNCc1cc(C(=O)O)cc(CO)n1] | 102 | 2-{[({[2-(dimethylamino)ethyl](ethyl)carbamoyl}methyl)amino]methyl}-6-(hydroxymethyl)pyridine-4-carboxylic acid | A | $^1$H-NMR (300 MHz, CD$_3$OD): δ 7.79 (s, 1H), 4.69 (s, 2H), 2.33 (s, 4H), 1.13 (m, 3H) ppm. |
| 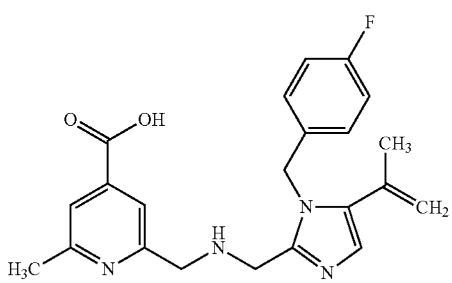 [SMILES: C=C(C)c1cnc(CNCc2cc(C(=O)O)cc(C)n2)n1Cc1ccc(F)cc1] | 103 | 2-{[({1-[(4-fluorophenyl)methyl]-5-(prop-1-en-2-yl)-1H-imidazol-2-yl}methyl)amino]methyl}-6-methylpyridine-4-carboxylic acid | A | $^1$H-NMR (300 MHz, CD$_3$OD): δ 7.83 (d, 2H), 5.47 (s, 2H), 2.56 (s, 3H), 1.91 (s, 3H) ppm. |
| 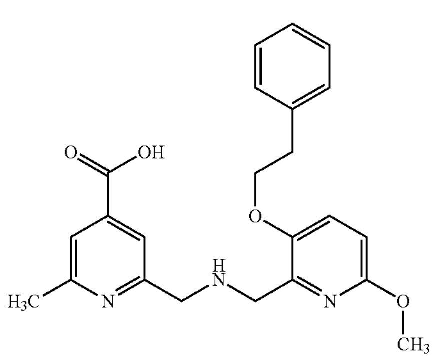 | 104 | 2-[({[6-methoxy-3-(2-phenylethoxy)pyridin-2-yl]methyl}amino)methyl]-6-methylpyridine-4-carboxylic acid | A | $^1$H-NMR (300 MHz, CD$_3$OD): δ 7.60 (s, 1H), 4.15 (t, 2H), 3.86 (s, 3H), 2.52 (s, 3H) ppm. |

TABLE 2-continued (#SR = may be prepared analogously to according to synthetic route number listed)

| Structure | # | Name | SR# | NMR |
|---|---|---|---|---|
| 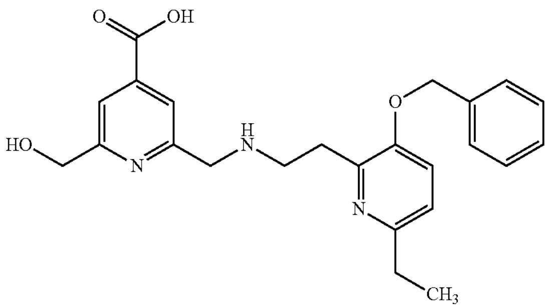 [SMILES: CCc1ccc(OCc2ccccc2)c(CCNCc2cc(C(=O)O)cc(CO)n2)n1] | 105 | 2-[({2-[3-(benzyloxy)-6-methoxypyridin-2-yl]ethyl}amino)methyl]-6-(hydroxymethyl)pyridine-4-carboxylic acid | A | $^1$H-NMR (300 MHz, CD$_3$OD): δ 7.80 (s, 1H), 6.50 (d, 1H), 4.60 (s, 2H), 3.89 (s, 3H) ppm |
| 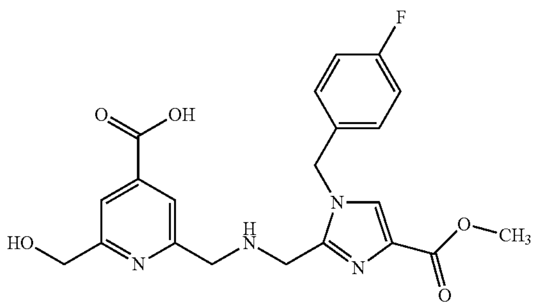 [SMILES: COC(=O)c1cn(Cc2ccc(F)cc2)c(CNCc2cc(C(=O)O)cc(CO)n2)n1] | 106 | 2-{[({1-[(4-fluorophenyl)methyl]-4-(methoxycarbonyl)-1H-imidazol-2-yl}methyl)amino]methyl}-6-(hydroxymethyl)pyridine-4-carboxylic acid | A | $^1$H-NMR (300 MHz, CD$_3$OD): δ 8.03 (s, 1H), 7.91 (s, 1H), 5.32 (s, 2H), 4.81 (s, 2H) ppm |
| 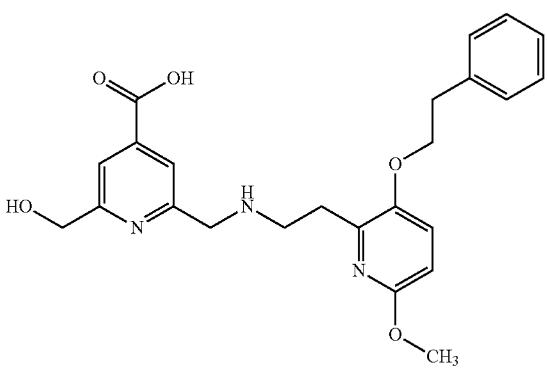 [SMILES: COc1ccc(OCCc2ccccc2)c(CCNCc2cc(C(=O)O)cc(CO)n2)n1] | 107 | 2-(hydroxymethyl)-6-[({2-[6-methoxy-3-(2-phenylethoxy)pyridin-2-yl]ethyl}amino)methyl]pyridine-4-carboxylic acid | A | $^1$H-NMR (300 MHz, CD$_3$OD): δ 8.00 (s, 1H), 6.65 (d, 1H), 4.22 (t, 2H), 3.80 (s, 3H). |
| 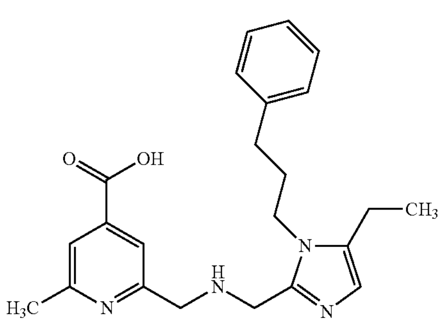 [SMILES: CCc1cnc(CNCc2cc(C(=O)O)cc(C)n2)n1CCCc1ccccc1] | 108 | 2-[({[5-ethyl-1-(3-phenylpropyl)-1H-imidazol-2-yl]methyl}amino)methyl]-6-methylpyridine-4-carboxylic acid | A | $^1$H-NMR (300 MHz, CD$_3$OD): δ 8.19 (s, 1H), 4.64 (s, 4H), 2.15 (t, 2H), 1.28 (t, 3H). |

TABLE 2-continued (#SR = may be prepared analogously to according to synthetic route number listed)

| Structure | # | Name | SR# | NMR |
|---|---|---|---|---|
| 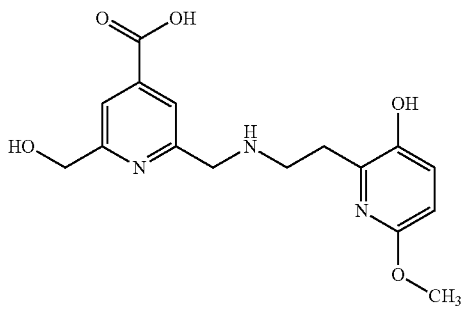 [SMILES: COc1ccc(O)c(CCNCc2cc(C(=O)O)cc(CO)n2)n1] | 109 | 2-({[2-(3-hydroxy-6-methoxypyridin-2-yl)ethyl]amino}methyl)-6-(hydroxymethyl)pyridine-4-carboxylic acid | A | $^1$H-NMR (300 MHz, CD$_3$OD): δ 7.79 (s, 1H), 6.39 (d, 1H), 4.70 (s, 2H), 3.03-2.92 (m, 4H). |
| 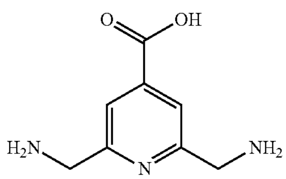 [SMILES: NCc1cc(C(=O)O)cc(CN)n1] | 110 | 2,6-bis(aminomethyl)pyridine-4-carboxylic acid | C | $^1$H-NMR (300 MHz, CD$_3$OD): δ 7.60 (br s, 2H), 4.00-3.80 (br s, 4H). |
| 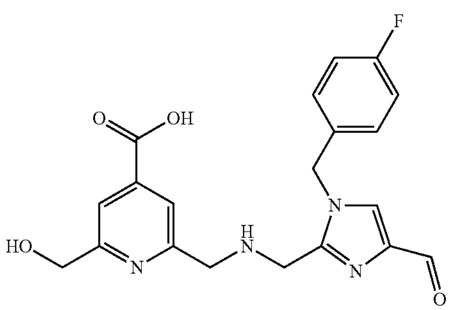 [SMILES: O=Cc1cn(Cc2ccc(F)cc2)c(CNCc2cc(C(=O)O)cc(CO)n2)n1] | 111 | 2-{[({1-[(4-fluorophenyl)methyl]-4-formyl-1H-imidazol-2-yl}methyl)amino]methyl}-6-(hydroxymethyl)pyridine-4-carboxylic acid | A | $^1$H-NMR (300 MHz, CD$_3$OD): δ 9.87 (s, 1H), 8.35 (s, 1H), 8.05 (s, 1H), 5.51 (s, 2H) ppm |
| 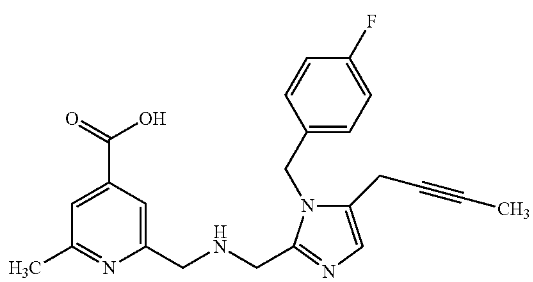 [SMILES: CC#CCc1cnc(CNCc2cc(C(=O)O)cc(C)n2)n1Cc1ccc(F)cc1] | 112 | 2-[({[5-(but-2-yn-1-yl)-1-[(4-fluorophenyl)methyl]-1H-imidazol-2-yl]methyl}amino)methyl]-6-methylpyridine-4-carboxylic acid | A | $^1$H-NMR (300 MHz, CD$_3$OD): δ 7.63 (s, 1H), 6.80 (s, 1H), 4.69 (s, 2H), 2.51 (s, 3H), 1.67 (s, 3H) ppm. |
| 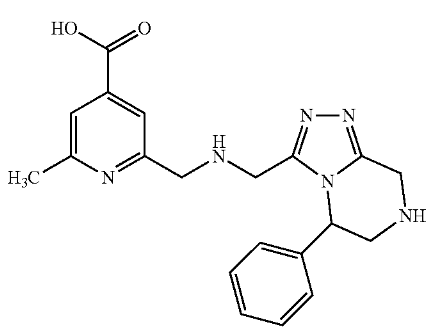 [SMILES: Cc1cc(C(=O)O)cc(CNCc2nnc3n2C(c2ccccc2)CNC3)n1] | 113 | 2-methyl-6-{[({5-phenyl-5H,6H,7H,8H-[1,2,4]triazolo[4,3-a]pyrazin-3-yl}methyl)amino]methyl}pyridine-4-carboxylic acid | C | $^1$H-NMR (300 MHz, CD$_3$OD): δ 7.57 (s, 1H), 5.59 (t, 1H), 4.19 (q, 2H), 3.71 (s, 2H) ppm. |

TABLE 2-continued (#SR = may be prepared analogously to according to synthetic route number listed)

| Structure | # | Name | SR# | NMR |
|---|---|---|---|---|
| (structure) | 114 | 2-[({[5-(2-carbamoylethyl)-1-[(4-fluorophenyl)methyl]-1H-imidazol-2-yl]methyl}amino)methyl]-6-methylpyridine-4-carboxylic acid | A | $^1$H-NMR (300 MHz, CD$_3$OD): δ 7.83 (s, 2H), 4.45 (s, 2H), 2.77 (t, 2H), 2.59 (s, 3H), 2.48 (t, 2H) ppm. |
| (structure) | 115 | 2-[({[5-ethyl-1-(thiophen-2-ylmethyl)-1H-imidazol-2-yl]methyl}amino)methyl]-6-methylpyridine-4-carboxylic acid | A | $^1$H-NMR (300 MHz, CD$_3$OD): δ 7.63 (s, 1H), 6.82 (s, 1H), 6.65 (s, 1H), 3.87 (s, 4H), 1.21 (t, 3H) ppm. |
| (structure) | 116 | 1-(6-{2-[({[3-(benzyloxy)-6-methoxypyridin-2-yl]methyl}amino)methyl]-6-(hydroxymethyl)pyridin-4-yl}-5-oxa-7-azaspiro[2.5]octan-7-yl)-2,2,2-trifluoroethan-1-one | D | $^1$H-NMR (300 MHz, CD$_3$OD): δ 7.58 (d, 1H), 5.13 (s, 2H), 3.92 (s, 3H), 0.72-0.61 (m, 2H), 0.55-0.35 (m, 2H) ppm. |

Illustrative preparations of compounds within Table 2 are as follows.

General Procedures

General Procedure A (Ester Hydrolysis)

The ester was dissolved in a solvent such as MeOH-THF-H$_2$O (1:1:1) and an alkali hydroxide such as KOH (1.0 equivalent (eq)) was added. The reaction mixture was stirred at room temperature. Solvents were removed in vacuo to give the alkali salt of the product. The product was optionally deprotected and purified by chromatography if needed.

General Procedure B (Reductive Amination)

A solution of aldehyde and amine with optionally protected functional groups (1.3 equiv.) in a solvent such as 1,2-dichloroethane was stirred for 1-24 hours at room temperature, before NaBH(AcO)$_3$ (2 equivalents) was added. The mixture was stirred at room temperature. The product was optionally deprotected and purified by chromatography if needed.

General Procedure C (Suzuki-Miyaura Cross Coupling)

[1,1'-Bis(diphenylphosphino)ferrocene]dichloropalladium(II) (Pd(dppf)$_2$Cl$_2$) (0.03 eq), potassium alkynyl trifluoroborate (2.0 eq) and triethylamine (Et$_3$N) (1.5 eq) were added to a solution of a bromide in a solvent such as THF. The reaction mixture was refluxed. Solvents were removed in vacuo and the product was purified by chromatography if needed.

General Procedure D (Boc Protection of Amines)

Di-tert-butylcarbonate (Boc$_2$O) (1.2 eq) and NaHCO$_3$ (4.0 eq) were added to a solution of amine in THF/H$_2$O. The reaction mixture was stirred at room temperature. Evaporation gave the title compound which was purified by chromatography if needed.

General Procedure E (Reduction of Nitriles, Azides, and Oximes)

A slurry of a nitrile, azide, or oxime and Pd/C in a solvent such as MeOH was stirred in the presence of H$_2$. The product was isolated by filtration and purified chromatography if needed.

General Procedure F (Nucleophilic Substitution of Sulfonate)

A nucleophile, such as an azide (2.0 eq), was added to a solution of a sulfonate ester in a solvent such as dimethylformamide and the product was isolated by concentration of the reaction mixture. Trituration with a solvent such as dichloromethane and purification by chromatography if needed.

General Procedure G (Formation of Sulfonate Ester)

An alcohol dissolved in a solvent such as dichloromethane was treated with sulfonyl chloride (2 eq) and triethylamine (2 eq). The product was isolated by aqueous workup and chromatography if needed.

General Procedure H (Formation of Oxime)

Hydroxylamine hydrochloride (1.3 eq) and Na$_2$CO$_3$ (0.5 eq) was added to a suspension of aldehyde in a solvent such as H$_2$O at 0° C. The reaction mixture was stirred at room temperature. Filtration at 0° C. afforded the title compound or the product was isolated after workup and chromatography if needed.

General Procedure I (Oxidation of Benzylic Alcohol)

A mixture of the benzylic alcohol can be oxidized by $MnO_2$, Dess-Martin periodinane, or by Swern Oxidation in a solvent such as toluene or dichloromethane. Filtration, aqueous work-up, and purification by chromatography, if necessary, can afford the title compound.

General Procedure J (Phthalimide to Primary Amine)

Hydrazine monohydrate (1.5 eq) was added to a solution of alkyl phthalimide in a solvent such as EtOH (ethanol). The reaction mixture was refluxed for 3 hours. The mixture was filtered at 0° C. and evaporation of the filtrate gave the title compound, which was purified by chromatography if needed.

General Procedure K (Mitsunobu Reaction)

An azodicarbonyl compound (1.3 eq), such as 1,1'-(azodicarbonyl)dipiperidine, $PPh_3$ (1.3 eq) and a suitable nucleophile such as phthalimide (1.3 eq), were added to a solution of the alcohol in a solvent such as THF. The reaction mixture was stirred at room temperature. The mixture was filtered at 0° C. and workup afforded the title compound which was purified by chromatography if needed.

General Procedure L (2 (or 6)-hydroxymethyl pyridine from 2 (or 6)-methyl pyridine)

m-CPBA (meta-chloroperoxybenzoic acid) (1.2 eq) was added to a solution of 2-methyl pyridine in DCM (dichloromethane) at 0° C. and the resulting mixture was then stirred at room temperature. The resulting residue from an aqueous workup was dissolved in DCM and TFAA (trifluoroacetic anhydride) (10 eq). The mixture was then stirred at room temperature. Aqueous work up afforded the title compound which was purified by chromatography if needed.

General Procedure M (Alkyl Ethers from Alcohols)

NaH (60% in mineral oil, 1.5 eq) and an alkyl halide such as methyl iodide (3.0 eq) were added to a solution of a primary alcohol in DMF (dimethylformamide). The mixture was stirred at room temperature overnight. Aqueous work up gave the title compound which was purified by chromatography if needed.

General Procedure N (Substitution of Aromatic Compounds)

To a solution of the aromatic compound in a solvent such as THF at −78° C. was added n-butyllithium (1 eq) followed by freshly distilled DMF (1 eq) and the resulting mixture was stirred at 0° C. Aqueous work up provided the title compound which was purified by chromatography if needed.

General Procedure O (Synthesis of 1,5-Substituted Imidazoles)

A mixture of alkyl aldehyde, alkylamine, and tosyl methylisocyanide in an anhydrous solvent such as DMF were stirred at room temperature. Aqueous work up provided the title compound, which was purified by chromatography if needed.

General Procedure P (Synthesis of Triazole)

Prepared from literature procedure (Ref: Journal of Medicinal Chemistry, 2007, 50, 1939-1957) from [(t-butoxycarbonyl)amino]acetic acid, amine and other suitable reagents.

General Procedure Q (Removal of Protecting Group)

Acid such as hydrochloric acid, trifluoroacetic acid, or acetic acid was added at room temperature to a solution of the methyl 2-{[(tert-butyldimethylsilyl)oxy]methyl}-6-{[({4-[(4-fluorophenyl)methyl]-4H-1,2,4-triazol-3-yl}methyl)amino]methyl}pyridine-4-carboxylate in solvent such as water, THF, or DCM. The reaction mixture was stirred 1 hour to overnight. The product was isolated by concentration and column chromatography if needed.

General Procedure R (Cyano Insertion)

A compound such as 2-methoxy-5-phenethoxypyridine 1-oxide in a solvent such as DCM was treated with reagents such as dimethylcarbamoyl chloride and trimethylsilyl chloride for 12 h. The product was isolated by aqueous workup and chromatography if needed.

General Procedure S (Formation of N-Oxide)

Oxidizing agent such as m-CPBA (meta-chloroperoxybenzoic acid) was added to a solution of 2-methoxy-5-(2-phenylethoxy)pyridine in solvent such as dichloromethane at 0° C. and the resulting mixture was then stirred at room temperature. The product was isolated by aqueous workup and chromatography if needed.

General Procedure T (N or O-Alkylation)

6-Methoxypyridin-3-ol in a solution such as DMF or THF was added base such as $K_2CO_3$ and (2-bromoethyl)benzene. The mixture can be heated or at room temperature overnight. The product was isolated by aqueous workup and chromatography if needed.

General Procedure U (Formation of Silyl Ether)

Tert-butyldimethylsilyl chloride was added to a solution of alcohol (methyl 2,6-bis(hydroxymethyl)pyridine-4-carboxylate), triethylamine and 4-dimethylaminopyridine in solvent such as dichloromethane at 0° C., stirred at room temperature overnight. The product was isolated by aqueous workup and chromatography if needed.

Synthetic Routes

Synthetic Route A

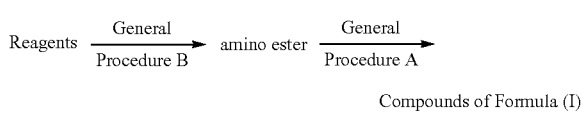

Synthetic Route B

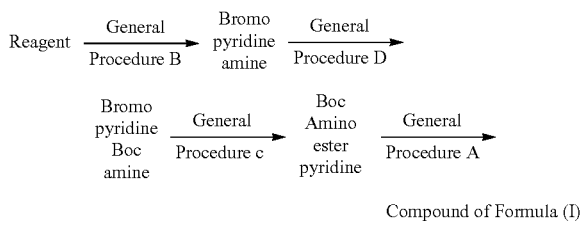

Synthetic Route C

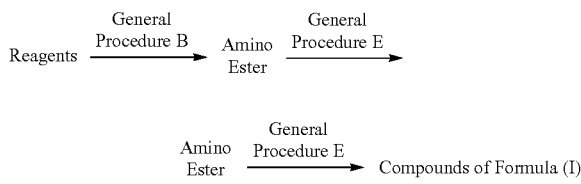

163

Synthetic Route D

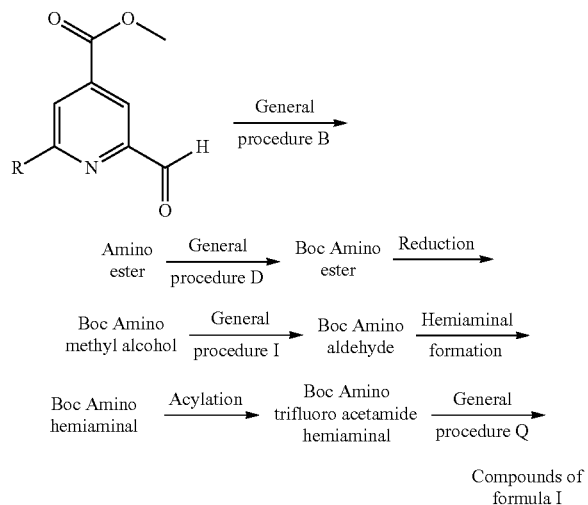

Examples

2-{[({1-[(4-fluorophenyl)methyl]-1H-imidazol-2-yl}methyl)amino]methyl}-6-(prop-1-yn-1-yl)pyridine-4-carboxylic acid (6)

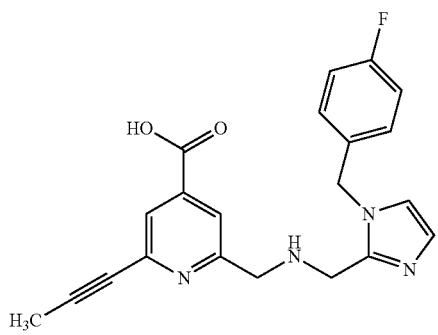

General Procedure A from Methyl 2-({[(tert-butoxy)carbonyl]({1-[(4-fluorophenyl)methyl]-1H-imidazol-2-yl}methyl)amino}methyl)-6-(prop-1-yn-1-yl)pyridine-4-carboxylate provided the title compound as brown solid as a sodium salt after evaporation to dryness. Sodium salt was dissolved in HCl (conc.) and evaporated in vacuo to afford the HCl salt of the title compound as yellow solid. $^1$H-NMR (300 MHz, CD$_3$OD): δ 7.90 (s, 1H), 7.21 (s, 1H), 5.75 (s, 2H), 4.77 (s, 2H), 1.92 (s, 3H). ES-MS: 379 [M+1].

164

(S)-2-[({5H,6H,7H-cyclopenta[b]pyridin-7-yl}amino)methyl]-6-methylpyridine-4-carboxylic acid

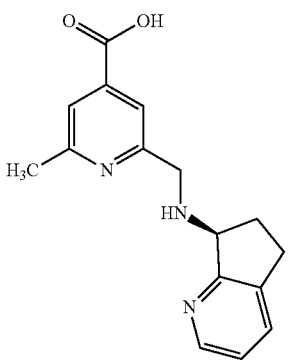

General Procedure A from (S)-methyl 6-[({5H,6H,7H-cyclopenta[b]pyridin-7-yl}amino)methyl]-2-methylpyridine-4-carboxylate provided the title compound as brown solid as a potassium salt after evaporation to dryness. $^1$H-NMR (300 MHz, CD$_3$OD): δ 8.34 (d, 1H), 7.21 (m, 1H), 4.22 (t, 1H), 4.03 (s, 2H), 2.56 (s, 3H) ppm. ES-MS: 282 [M−1].

2-{[({4-[(4-Fluorophenyl)methyl]-4H-1,2,4-triazol-3-yl}methyl)amino]methyl}-6-(hydroxymethyl)pyridine-4-carboxylic acid

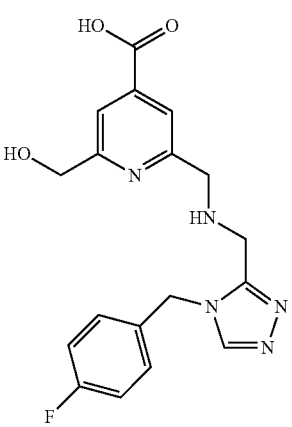

General Procedure A from methyl 2-{[({4-[(4-fluorophenyl)methyl]-4H-1,2,4-triazol-3-yl}methyl)amino]methyl}-6-(hydroxymethyl)pyridine-4-carboxylate. Evaporation to dryness afforded the title compound as white solid as the potassium salt. $^1$H-NMR (300 MHz, CD$_3$OD): δ 8.46 (s, 1H), 7.81 (s, 1H), 7.71 (s, 1H), 7.27 (t, 2H), 7.08 (t, 2H), 5.38 (s, 2H), 4.69 (s, 2H), 3.94 (s, 2H), 3.09 (s, 2H) ppm. ES-MS: 370 [M−1].

165

2-(Hydroxymethyl)-6-[({[5-methyl-4-(3-phenylpropyl)-4H-1,2,4-triazol-3-yl]methyl}amino)methyl]pyridine-4-carboxylic acid

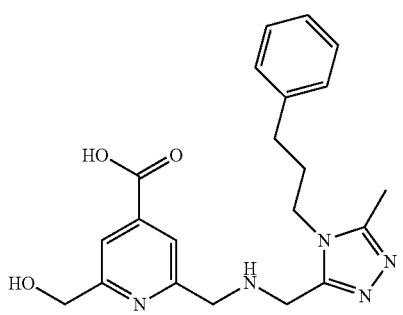

General Procedure A from methyl 2-(hydroxymethyl)-6-[({[5-methyl-4-(3-phenylpropyl)-4H-1,2,4-triazol-3-yl]methyl}amino)methyl]pyridine-4-carboxylate. Evaporation to dryness afforded the title compound as colorless gum as the potassium salt. $^1$H-NMR (300 MHz, CD$_3$OD): δ 7.82 (s, 1H), 7.69 (s, 1H), 7.30-7.21 (m, 3H), 7.20-7.13 (m, 2H), 4.70 (s, 2H), 4.03 (t, 2H), 3.88 (s, 2H), 3.85 (s, 2H), 2.66 (t, 2H), 2.33 (s, 3H), 2.09-1.98 (m, 2H) ppm. ES-MS: 394 [M−1].

2-{[({1-[(4-Fluorophenyl)methyl]-1H-imidazol-2-yl}methyl)amino]methyl}-6-(hydroxymethyl)pyridine-4-carboxylic acid

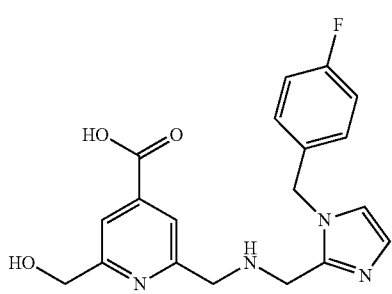

General Procedure A from ethyl 2-{[(tert-butyldimethylsilyl)oxy]methyl}-6-{[({1-[(4-fluorophenyl)methyl]-1H-imidazol-2-yl}methyl)amino]methyl}pyridine-4-carboxylate. Evaporation to dryness afforded the title compound as a potassium salt. Dissolved in HCl (conc.) and evaporated in vacuo to afford the HCl salt. Purification by preparative HPLC gave the title compound as colorless gum as a TFA salt. $^1$H-NMR (300 MHz, CD$_3$OD): δ 7.98 (s, 1H), 7.82 (s, 1H), 7.39-7.26 (m, 4H), 7.16-7.09 (m, 2H), 5.38 (s, 2H), 4.78 (s, 2H), 4.37 (s, 2H), 4.34 (s, 2H) ppm. ES-MS: 371 [M+1].

166

2-[({[6-Methoxy-3-(2-phenylethoxy)pyridin-2-yl]methyl}amino)methyl]-6-methylpyridine-4-carboxylic acid

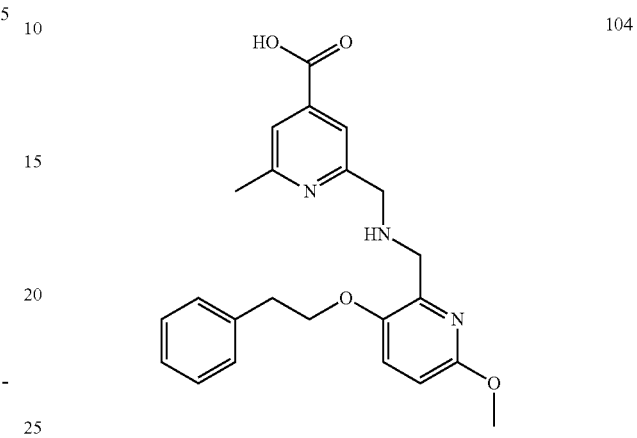

General Procedure A from methyl 6-[({[6-methoxy-3-(2-phenylethoxy)pyridin-2-yl]methyl}amino)methyl]-2-methylpyridine-4-carboxylate. Evaporation to dryness afforded the title compound as white solid as a potassium salt. $^1$H-NMR (300 MHz, CD$_3$OD): δ 7.60 (s, 1H), 7.53 (s, 1H), 7.32-7.14 (m, 6H), 6.57 (d, 1H), 4.15 (t, 2H), 3.86 (s, 3H), 3.80 (s, 2H), 3.73 (s, 2H), 3.04 (t, 2H), 2.52 (s, 3H) ppm. ES-MS: 406 [M−1].

2-(Hydroxymethyl)-6-[({[5-methyl-4-(4-methylpentyl)-4H-1,2,4-triazol-3-yl]methyl}amino)methyl]pyridine-4-carboxylic acid

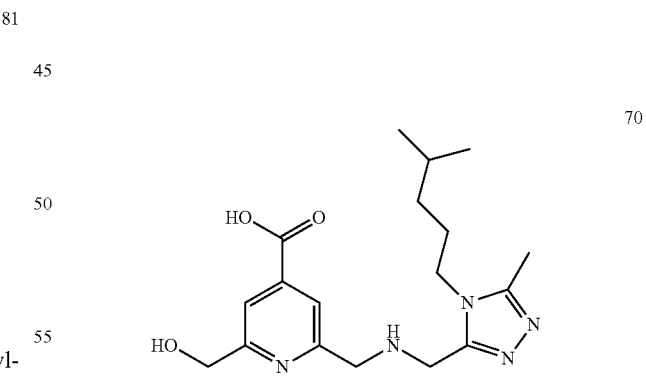

General Procedure A from methyl 2-(hydroxymethyl)-6-[({[5-methyl-4-(4-methylpentyl)-4H-1,2,4-triazol-3-yl]methyl}amino)methyl]pyridine-4-carboxylate. Evaporation to dryness afforded the title compound as a potassium salt. $^1$H-NMR (300 MHz, CD$_3$OD): δ 7.77 (s, 1H), 7.66 (s, 1H), 4.67 (s, 2H), 4.03 (t, 2H), 3.94 (s, 2H), 3.90 (s, 2H), 2.38 (s, 3H), 1.67 (m, 2H), 1.50 (m, 1H), 1.14 (m, 2H), 0.84 (d, 6H). ES-MS: 362 [M+1].

2-{[({1-[(4-Fluorophenyl)methyl]-4-(hydroxymethyl)-1H-imidazol-2-yl}methyl)amino]methyl}-6-(hydroxymethyl)pyridine-4-carboxylic acid

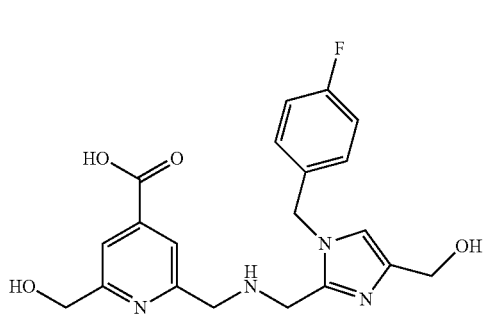

General Procedure A from ethyl 2-{[({1-[(4-fluorophenyl)methyl]-4-(hydroxymethyl)-1H-imidazol-2-yl}methyl)amino]methyl}-6-(hydroxymethyl)pyridine-4-carboxylate. Evaporation to dryness gave the title compound as a potassium salt. Dissolved in HCl (conc.) and evaporated in vacuo to afford the HCl salt. Purification by preparative HPLC gave the title compound as colorless oil as a TFA salt. $^1$H NMR (300 MHz, CD$_3$OD): δ ppm 8.00 (s, 1H), 7.70 (s, 1H), 7.20-6.90 (m, 5H), 5.30 (s, 2H), 4.80 (s, 2H), 4.70 (s, 2H), 4.50 (s, 2H), 4.30 (s, 2H). ES-MS: 401 [M+1].

2-{[({4-[(4-Fluorophenyl)methyl]-5-methyl-4H-1,2,4-triazol-3-yl}methyl)amino]methyl}-6-(hydroxymethyl)pyridine-4-carboxylic acid

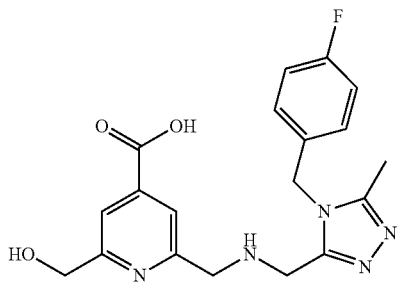

General Procedure A from methyl 2-{[({4-[(4-fluorophenyl)methyl]-5-methyl-4H-1,2,4-triazol-3-yl}methyl)amino]methyl}-6-(hydroxymethyl)pyridine-4-carboxylate. Evaporation to dryness afforded the title compound as potassium salt. $^1$H-NMR (300 MHz, CD$_3$OD): δ 7.81 (s, 1H), 7.61 (s, 1H), 7.18-7.04 (m, 4H), 5.37 (s, 2H), 4.69 (s, 2H), 3.94 (s, 2H), 3.92 (s, 2H), 2.32 (s, 3H) ppm. ES-MS: 386 [M+1].

2-{[({5-Ethyl-4-[(4-fluorophenyl)methyl]-4H-1,2,4-triazol-3-yl}methyl)amino]methyl}-6-methylpyridine-4-carboxylic acid

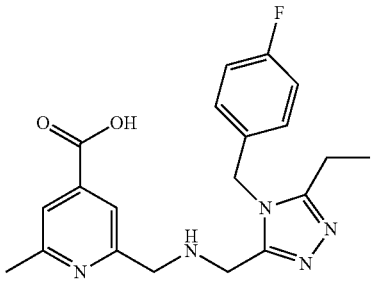

General Procedure A from methyl 6-{[({5-ethyl-4-[(4-fluorophenyl)methyl]-4H-1,2,4-triazol-3-yl}methyl)amino]methyl}-2-methylpyridine-4-carboxylate. Evaporation to dryness afforded the title compound as colorless gum as a potassium salt. $^1$H-NMR (300 MHz, CD$_3$OD): δ 7.62 (s, 1H), 7.52 (s, 1H), 7.12-7.01 (m, 4H), 5.35 (s, 2H), 3.90 (s, 2H), 3.86 (s, 2H), 2.64 (q, 2H), 2.49 (s, 3H), 1.21 (t, 3H) ppm. ES-MS: 384 [M+1].

2-{[({4-[(4-Fluorophenyl)methyl]-5-methyl-4H-1,2,4-triazol-3-yl}methyl)amino]methyl}-6-methylpyridine-4-carboxylic acid

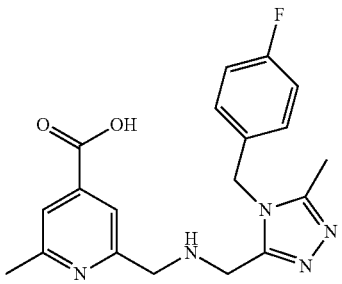

General Procedure A from methyl 6-{[({4-[(4-fluorophenyl)methyl]-5-methyl-4H-1,2,4-triazol-3-yl}methyl)amino]methyl}-2-methylpyridine-4-carboxylate. Evaporation to dryness gave the title compound as colorless gum as a potassium salt. Purification by preparative HPLC afforded the title compound as colorless gum as a TFA salt. $^1$H-NMR (300 MHz, CD$_3$OD): δ 7.69 (s, 1H), 7.66 (s, 1H), 7.11-6.99 (m, 4H), 5.25 (s, 2H), 4.50 (s, 2H), 4.43 (s, 2H), 2.52 (s, 3H), 2.49 (s, 3H) ppm. ES-MS: 370 [M+1].

2-{[({5-Ethyl-4-[(4-Fluorophenyl)methyl]-4H-1,2,4-triazol-3-yl}methyl)amino]methyl}-6-(hydroxymethyl)pyridine-4-carboxylic acid

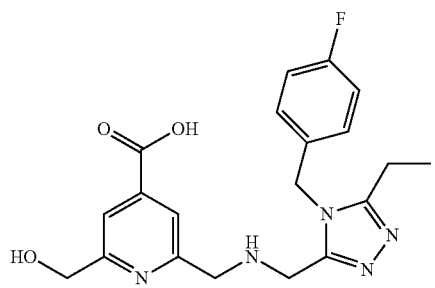

64

General Procedure A from methyl 2-{[({5-ethyl-4-[(4-fluorophenyl)methyl]-4H-1,2,4-triazol-3-yl}methyl)amino]methyl}-6-(hydroxymethyl)pyridine-4-carboxylate. Evaporation to dryness gave the title compound as colorless gum as a potassium salt. Dissolved in aqueous TFA and evaporated in vacuum to give the TFA salt. Purification by preparative HPLC afforded the title compound as colorless gum as a TFA salt. $^1$H-NMR (300 MHz, CD$_3$OD): δ 7.87 (s, 1H), 7.69 (s, 1H), 7.04-6.94 (m, 4H), 5.20 (s, 2H), 4.64 (s, 2H), 4.50 (s, 2H), 4.38 (s, 2H), 2.67 (q, 2H), 3.10 (s, 3H) ppm. ES-MS: 400 [M+1].

2-{[({4-[(4-Fluorophenyl)methyl]-5-(thiophen-2-ylmethyl)-4H-1,2,4-triazol-3-yl}methyl)amino]methyl}-6-(hydroxymethyl)pyridine-4-carboxylic acid

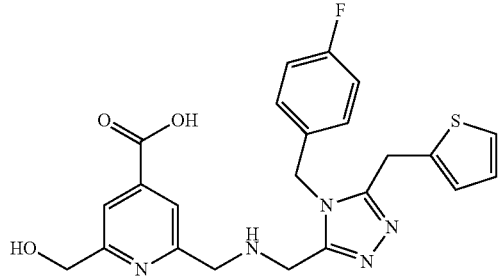

71

General Procedure A from methyl 2-{[({4-[(4-fluorophenyl)methyl]-5-(thiophen-2-ylmethyl)-4H-1,2,4-triazol-3-yl}methyl)amino]methyl}-6-(hydroxymethyl)pyridine-4-carboxylate. Evaporation to dryness afforded the title compound as colorless gum as a potassium salt. $^1$H-NMR (300 MHz, CD$_3$OD): δ 7.78 (s, 1H), 7.65 (s, 1H), 7.21 (d, 1H), 6.97-6.86 (m, 4H), 6.83 (t, 1H), 6.76 (s, 1H), 5.31 (s, 2H), 4.65 (s, 2H), 4.30 (s, 2H), 3.86 (s, 2H), 3.83 (s, 2H) ppm. ES-MS: 468 [M+1].

2-Methyl-6-{[({1-[2-(pyrimidin-5-yl)ethyl]-1H-imidazol-2-yl}methyl)amino]methyl}pyridine-4-carboxylic acid

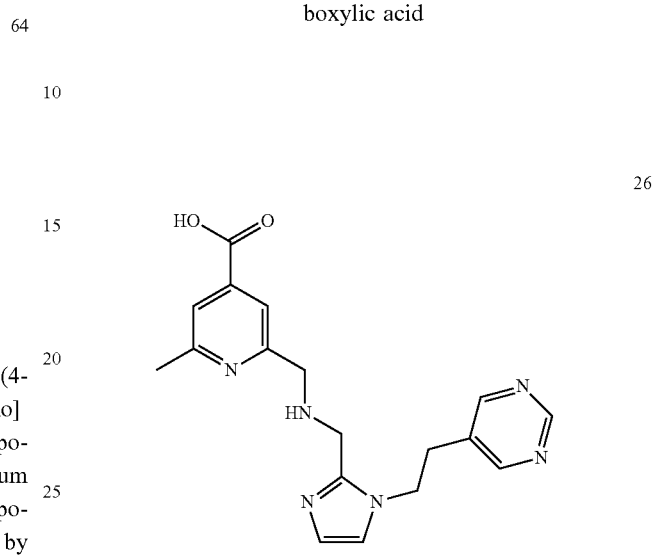

26

General Procedure A from methyl 2-methyl-6-{[({1-[2-(pyrimidin-5-yl)ethyl]-1H-imidazol-2-yl}methyl)amino]methyl}pyridine-4-carboxylate. Evaporation to dryness afforded the title compound as a sodium salt as yellow solid. $^1$H-NMR (300 MHz, CD$_3$OD): δ 9.08 (s, 1H), 8.72 (s, 2H), 7.97 (s, 1H), 7.93 (s, 1H), 7.62 (s, 1H), 7.54 (s, 1H), 4.57 (t, 2H), 4.51 (s, 2H), 4.42 (s, 2H), 3.28 (t, 2H), 2.69 (s, 3H) ppm. ES-MS: 353 [M+1].

2-{[({4-[(4-Fluorophenyl)methyl]-5-(methylsulfanyl)-4H-1,2,4-triazol-3-yl}methyl)amino]methyl}-6-methylpyridine-4-carboxylic acid

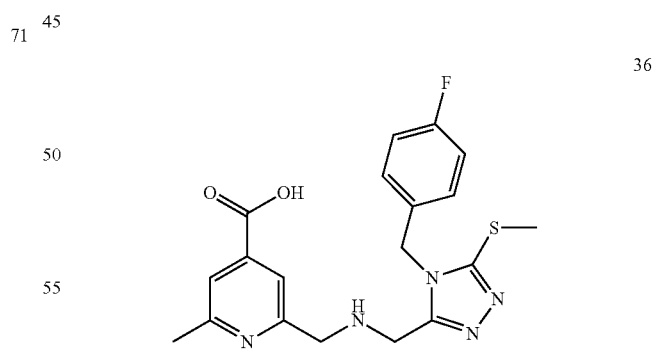

36

General Procedure A from methyl 2-{[({4-[(4-fluorophenyl)methyl]-5-(methylsulfanyl)-4H-1,2,4-triazol-3-yl}methyl)amino]methyl}pyridine-4-carboxylate. Evaporation to dryness afforded the title compound as a potassium salt. $^1$H-NMR (300 MHz, CD$_3$OD): δ 7.82 (s, 1H), 7.78 (s, 1H), 7.14 (d, 2H), 7.22 (t, 2H), 5.27 (s, 2H), 4.61 (s, 2H), 4.52 (s, 2H), 2.71 (s, 3H), 2.65 (s, 3H) ppm.

2-{[({4-[(4-Fluorophenyl)methyl]-5-propyl-4H-1,2,4-triazol-3-yl}methyl)amino]methyl}-6-(hydroxymethyl)pyridine-4-carboxylic acid

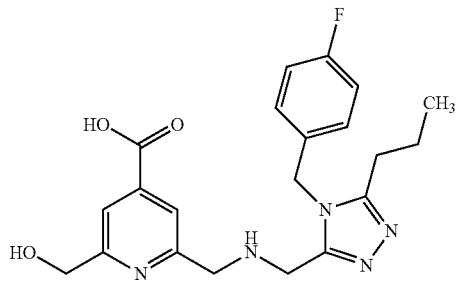

General Procedure A from methyl 2-[(acetyloxy)methyl]-6-{[({4-[(4-fluorophenyl)methyl]-5-propyl-4H-1,2,4-triazol-3-yl}methyl)amino]methyl}pyridine-4-carboxylate. Evaporation to dryness afforded the title compound as a potassium salt. ¹H-NMR (300 MHz, CD₃OD): δ 7.75 (s, 1H), 7.63 (s, 1H), 7.08-6.99 (m, 4H), 5.32 (s, 2H), 4.63 (s, 2H), 3.86 (s, 4H), 2.56 (t, 2H), 1.65-1.53 (m, 2H), 0.87 (t, 3H) ppm.

2-(Hydroxymethyl)-6-[({[6-methoxy-3-(2-methylpropyl)pyridin-2-yl]methyl}amino)methyl]pyridine-4-carboxylic acid

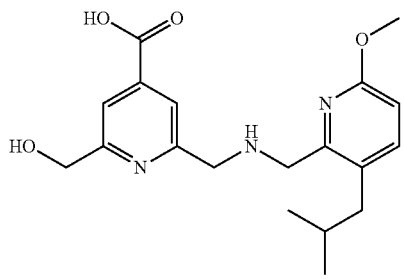

By General Procedure A from methyl 2-[(acetyloxy)methyl]-6-[({[6-methoxy-3-(2-methylpropyl)pyridin-2-yl]methyl}amino)methyl]pyridine-4-carboxylate. Neutralization with trifluoroacetic acid followed by evaporation to dryness afforded the title compound. ¹H-NMR (300 MHz, CD₃OD): δ 8.06 (s, 1H), 7.88 (s, 1H), 7.57 (d, 1H), 6.77 (d, 1H), 4.81 (s, 2H), 4.61 (s, 2H), 4.48 (s, 2H), 3.98 (s, 3H), 2.45 (d, 2H), 1.88-1.75 (m, 1H), 0.94 (d, 6H) ppm.

2-[({5-Ethyl-4-(4-methylpentyl)-4H-1,2,4-triazol-3-yl}methyl}amino)methyl]-6-(hydroxymethyl)pyridine-4-carboxylic acid

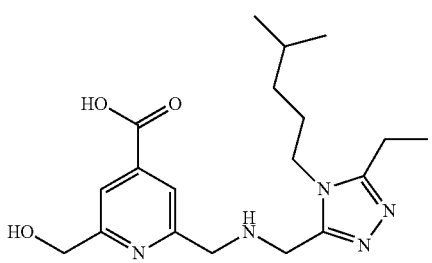

By General Procedure A from methyl 2-[(acetyloxy)methyl]-6-[({[5-ethyl-4-(4-methylpentyl)-4H-1,2,4-triazol-3-yl]methyl}amino)methyl]pyridine-4-carboxylate. Evaporation to dryness afforded the title compound as a sodium salt. Dissolved in HCl and evaporated to afford the title compound as an HCl salt as light yellow solid. ¹H-NMR (300 MHz, CD₃OD): δ 8.01 (s, 1H), 7.90 (s, 1H), 4.85 (s, 2H), 4.78 (s, 2H), 4.71 (s, 2H), 4.17 (t, 2H), 3.11 (q, 2H), 1.81-1.69 (m, 2H), 1.61-1.50 (m, 1H), 1.43 (t, 3H), 1.30-1.20 (m, 2H), 0.86 (d, 6H) ppm.

2-Methyl-6-[({[4-(3-phenylpropyl)-4H-1,2,4-triazol-3-yl]methyl}amino)methyl]pyridine-4-carboxylic acid

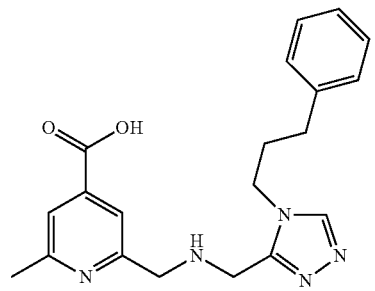

General Procedure A from methyl 2-methyl-6-(((4-(3-phenylpropyl)-4H-1,2,4-triazol-3-yl)methylamino)methyl)pyridine-4-carboxylate afforded the title compound as white solid as a sodium salt. ¹H-NMR (300 MHz, CD3OD): δ 8.49 (s, 1H), 7.68 (s, 1H), 7.59 (s, 1H), 7.27 (m, 2H), 7.19 (m, 3H), 4.18 (t, 2H), 3.97 (s, 2H), 3.89 (s, 2H), 2.66 (t, 2H), 2.55 (s, 3H), 2.15 (m, 2H) ppm. ES-MS: 366 [M+1].

2-(Hydroxymethyl)-6-[({[4-(3-phenylpropyl)-4H-1,2,4-triazol-3-yl]methyl}amino)methyl]pyridine-4-carboxylic acid

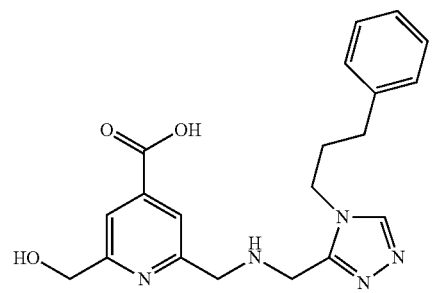

General Procedure A from methyl 2-[(acetyloxy)methyl]-6-[({[4-(3-phenylpropyl)-4H-1,2,4-triazol-3-yl]methyl}amino)methyl]pyridine-4-carboxylate afforded the title compound as white solid as a sodium salt. ¹H-NMR (300 MHz, CD₃OD): δ 8.44 (s, 1H), 7.80 (s, 1H), 7.69 (s, 1H), 7.25-7.13 (m, 5H), 4.68 (s, 2H), 4.13 (t, 2H), 3.92 (s, 2H), 3.87 (s, 2H), 2.70 (t, 2H), 2.12 (m, 2H) ppm. ES-MS: 382 [M+1].

2-[({[5-Ethyl-4-(3-phenylpropyl)-4H-1,2,4-triazol-3-yl]methyl}amino)methyl]-6-(hydroxymethyl)pyridine-4-carboxylic acid

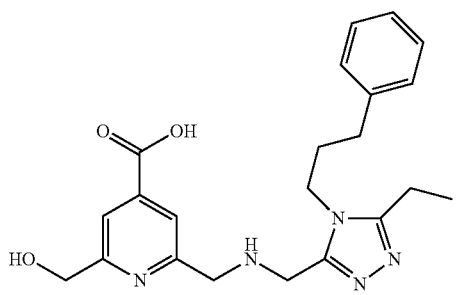

69

General Procedure A from methyl 2-[({[5-ethyl-4-(3-phenylpropyl)-4H-1,2,4-triazol-3-yl]methyl}amino)methyl]-6-(hydroxymethyl)pyridine-4-carboxylate afforded the title compound as white solid as a sodium salt. $^1$H-NMR (300 MHz, CD$_3$OD): δ 7.85 (s, 1H), 7.72 (s, 1H), 7.32-7.20 (m, 5H), 4.72 (s, 2H), 4.07 (t, 2H), 3.90 (m, 4H), 2.68 (m, 4H), 2.06 (m, 2H), 1.32 (s, 3H) ppm. ES-MS: 410 [M+1].

2-{[({4-[(4-Fluorophenyl)methyl]-5-(1-hydroxyethyl)-4H-1,2,4-triazol-3-yl}methyl)amino]methyl}-6-(hydroxymethyl)pyridine-4-carboxylic acid

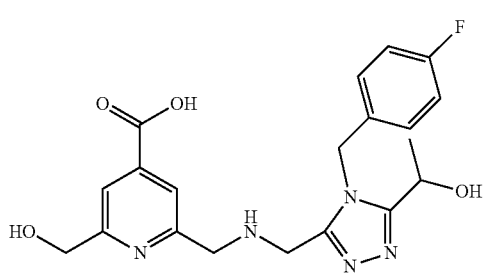

77

General Procedure A from methyl 2-[(acetyloxy)methyl]-6-{[({4-[(4-fluorophenyl)methyl]-5-(1-hydroxyethyl)-4H-1,2,4-triazol-3-yl}methyl)amino]methyl}pyridine-4-carboxylate afforded the title compound as white solid as a sodium salt. $^1$H-NMR (300 MHz, CD$_3$OD): δ 7.81 (s, 1H), 7.68 (s, 1H), 7.20-7.04 (m, 4H), 5.54 (s, 2H), 4.91 (q, 1H), 3.90 (s, 2H), 3.83 (s, 2H), 1.58 (d, 3H) ppm. ES-MS: 416 [M+1].

2-{[({4-[(4-Fluorophenyl)methyl]-5-(1-hydroxyethyl)-4H-1,2,4-triazol-3-yl}methyl)amino]methyl}-6-methylpyridine-4-carboxylic acid

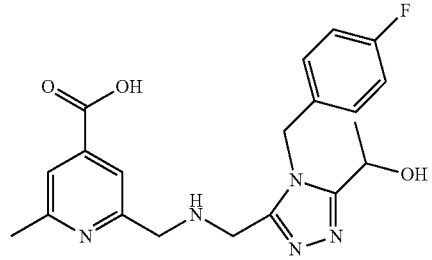

85

General Procedure A from methyl 6-{[({4-[(4-fluorophenyl)methyl]-5-(1-hydroxyethyl)-4H-1,2,4-triazol-3-yl}methyl)amino]methyl}-2-methylpyridine-4-carboxylate afforded the title compound as white solid as a sodium salt. $^1$H-NMR (300 MHz, CD$_3$OD): δ 7.82 (s, 1H), 7.76 (s, 1H), 7.25-7.10 (m, 4H), 5.49 (s, 2H), 5.04 (q, 1H), 4.58 (s, 2H), 4.38 (d, 2H), 2.53 (s, 3H), 1.68 (d, 3H) ppm. ES-MS: 400 [M+1].

2-[({[3-(Benzyloxy)-6-methoxypyridin-2-yl]methyl}amino)methyl]-6-methylpyridine-4-carboxylic acid

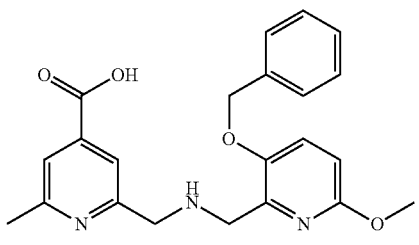

92

General Procedure A from methyl 6-[({[3-(benzyloxy)-6-methoxypyridin-2-yl]methyl}amino)methyl]-2-methylpyridine-4-carboxylate afforded the title compound as white solid as a sodium salt. $^1$H-NMR (300 MHz, CD$_3$OD): δ 7.70 (s, 1H), 7.80 (s, 1H), 7.60 (m, 5H), 7.30 (d, 1H), 6.80 (d, 1H), 4.50 (s, 2H), 3.90 (m, 7H), 2.55 (s, 3H) ppm. ES-MS: 392 [M+1].

2-[({[3-(Benzyloxy)-6-methoxypyridin-2-yl]methyl}amino)methyl]-6-(hydroxymethyl)pyridine-4-carboxylic acid

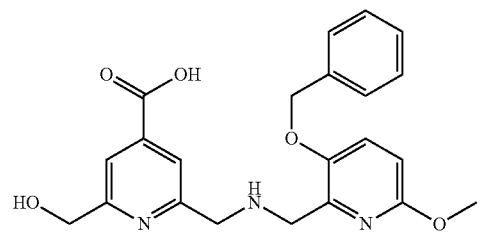

93

General Procedure A from methyl 2-[(acetyloxy)methyl]-6-[({[3-(benzyloxy)-6-methoxypyridin-2-yl]methyl}amino)methyl]pyridine-4-carboxylate afforded the title compound as white solid as a sodium salt. $^1$H-NMR (300 MHz, CD$_3$OD): δ 7.70 (s, 1H) 7.60 (s, 1H), 7.35 (m, 6H), 6.50 (d, 1H), 5.00 (s, 2H), 4.70 (s, 2H), 3.90 (s, 2H), 3.80 (s, 5H) ppm. ES-MS: 410 [M+1].

2-[({2-[3-(Benzyloxy)-6-methoxypyridin-2-yl]ethyl}amino)methyl]-6-(hydroxymethyl)pyridine-4-carboxylic acid

105

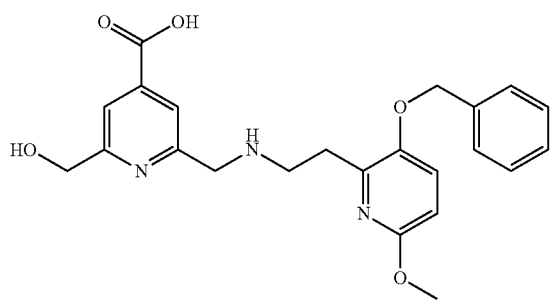

General Procedure A from methyl 2-[(acetyloxy)methyl]-6-[({2-[3-(benzyloxy)-6-methoxypyridin-2-yl]ethyl}amino)methyl]pyridine-4-carboxylate. Evaporation to dryness afforded the title compound as white solid as a sodium salt. $^1$H-NMR (300 MHz, CD$_3$OD): δ 7.80 (s, 1H) 7.60 (s, 1H), 7.30 (m, 6H), 6.50 (d, 1H), 5.00 (s, 2H), 4.60 (s, 2H), 3.90 (s, 2H), 3.80 (s, 3H), 3.00 (s, 4H) ppm. ES-MS: 422 [M+1].

2-{[({1-[(4-Fluorophenyl)methyl]-5-[(1Z)-prop-1-en-1-yl]-1H-imidazol-2-yl}methyl)amino]methyl}-6-methylpyridine-4-carboxylic acid

35

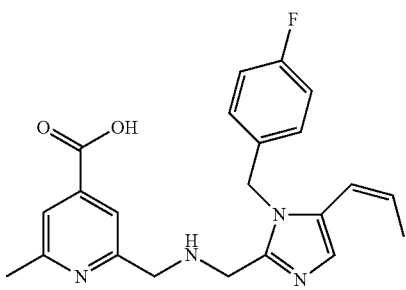

General Procedure A from methyl 6-{[({1-[(4-fluorophenyl)methyl]-5-[(1Z)-prop-1-en-1-yl]-1H-imidazol-2-yl}methyl)amino]methyl}-2-methylpyridine-4-carboxylate. Evaporation to dryness afforded the title compound as a sodium salt. $^1$H-NMR (300 MHz, CD$_3$OD): δ 7.63 (s, 1H), 7.54 (s, 1H), 7.03-6.94 (m, 5H), 6.10 (d, 1H), 5.86-5.76 (m, 1H), 5.32 (s, 2H), 3.87 (s, 2H), 3.83 (s, 2H), 2.51 (s, 3H), 1.84 (d, 3H) ppm. ES-MS: 395 [M+1].

2-{[({5-Cyclobutyl-1-[(4-fluorophenyl)methyl]-1H-imidazol-2-yl}methyl)amino]methyl}-6-methyl pyridine-4-carboxylic acid

39

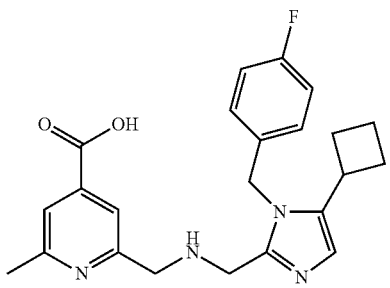

General Procedure A from methyl 6-{[({5-cyclobutyl-1-[(4-fluorophenyl)methyl]-1H-imidazol-2-yl}methyl)amino]methyl}-2-methylpyridine-4-carboxylate. Evaporation to dryness afforded the title compound as brown solid as a sodium salt. $^1$H-NMR (300 MHz, CD$_3$OD): δ 7.61 (s, 1H), 7.52 (s, 1H), 7.01 (t, 2H), 7.12 (s, 1H), 6.93 (t, 2H), 5.20 (s, 2H), 3.84 (s, 2H), 3.76 (s, 2H), 3.37-3.20 (m, 1H), 2.50 (s, 3H), 2.21-1.93 (m, 4H), 1.86-1.74 (m, 2H) ppm. ES-MS: 409 [M+1].

2-{[({1-[(4-Fluorophenyl)methyl]-5-(methylsulfanyl)-1H-imidazol-2-yl}methyl)amino]methyl}-6-methyl pyridine-4-carboxylic acid

43

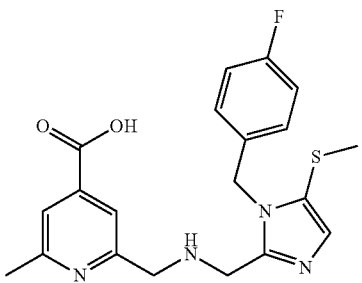

General Procedure A from methyl 6-{[({1-[(4-fluorophenyl)methyl]-5-(methylsulfanyl)-1H-imidazol-2-yl}methyl)amino]methyl}-2-methylpyridine-4-carboxylate. Evaporation to dryness afforded the title compound as brown solid as a sodium salt. $^1$H-NMR (300 MHz, CD$_3$OD): δ 7.63 (s, 1H), 7.54 (s, 1H), 7.12 (s, 1H), 7.01 (d, 4H), 5.43 (s, 2H), 3.84 (s, 2H), 3.77 (s, 2H), 2.51 (s, 3H), 2.09 (s, 3H) ppm. ES-MS: 401 [M+1].

2-[({[5-Ethyl-1-(4-methylpentyl)-1H-imidazol-2-yl]methyl}amino)methyl]-6-methylpyridine-4-carboxylic acid

91

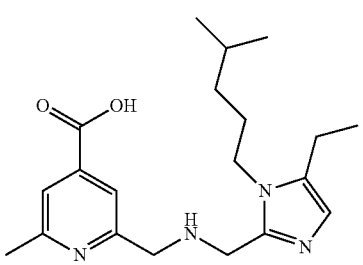

General Procedure A from methyl 6-[({[5-ethyl-1-(4-methylpentyl)-1H-imidazol-2-yl]methyl}amino)methyl]-2-methylpyridine-4-carboxylate. Purification by preparative HPLC afforded the title compound as colorless gum as a TFA salt. $^1$H-NMR (300 MHz, CD$_3$OD): δ 7.86 (s, 1H), 7.82 (s, 1H), 7.26 (s, 1H), 4.35 (s, 2H), 4.24 (s, 2H), 4.14 (t, 2H), 2.75-2.61 (m, 5H), 1.82-1.67 (m, 2H), 1.65-1.50 (m, 1H), 1.38-1.19 (m, 5H), 0.90 (d, 6H) ppm. ES-MS: 359 [M+1].

2-{[({1-[1-(4-Fluorophenyl)pent-3-yn-1-yl]-1H-imidazol-2-yl}methyl)amino]methyl}-6-methylpyridine-4-carboxylic acid

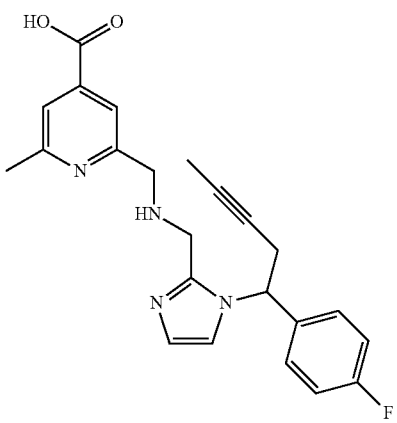

General Procedure A from methyl 6-{[({1-[1-(4-fluorophenyl)pent-3-yn-1-yl]-1H-imidazol-2-yl}methyl)amino]methyl}-2-methylpyridine-4-carboxylate. Evaporation to dryness afforded the title compound as brown solid as a sodium salt. $^1$H-NMR (300 MHz, CD$_3$OD): δ 7.67 (s, 1H), 7.58 (s, 1H), 7.34-7.20 (m, 3H), 7.03 (t, 2H), 6.91 (s, 1H), 5.84 (t, 1H), 4.0-3.77 (m, 4H), 3.06-2.94 (m, 2H), 2.54 (s, 3H), 1.61 (t, 3H) ppm. ES-MS: 407 [M+1].

2-{[({5-Ethyl-1-[(4-fluorophenyl)methyl]-1H-imidazol-2-yl}methyl)amino]methyl}-6-(hydroxymethyl)pyridine-4-carboxylic acid

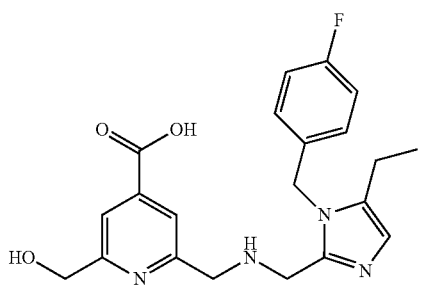

General Procedure A from methyl 2-{[({5-ethyl-1-[(4-fluorophenyl)methyl]-1H-imidazol-2-yl}methyl)amino]methyl}-6-(hydroxymethyl)pyridine-4-carboxylate. Evaporation to dryness afforded the title compound as brown solid as a sodium salt. $^1$H-NMR (300 MHz, CD$_3$OD): δ 7.77 (s, 1H), 7.65 (s, 1H), 7.09-6.88 (m, 4H), 6.68 (s, 1H), 5.26 (s, 2H), 4.67 (s, 2H), 3.88 (s, 2H), 3.78 (s, 2H), 2.42 (q, 2H), 1.16 (t, 3H) ppm. ES-MS: 399 [M+1].

2-{[({1-[(4-Fluorophenyl)methyl]-5-(prop-1-en-2-yl)-1H-imidazol-2-yl}methyl)amino]methyl}-6-methylpyridine-4-carboxylic acid

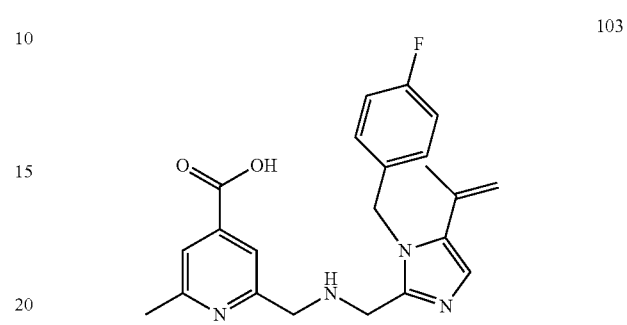

General Procedure A from methyl 6-{[({1-[(4-fluorophenyl)methyl]-5-(prop-1-en-2-yl)-1H-imidazol-2-yl}methyl)amino]methyl}-2-methylpyridine-4-carboxylate. Purification by preparative HPLC gave the title compound as colorless gum as a TFA salt. $^1$H-NMR (300 MHz, CD$_3$OD): δ 7.83 (d, 2H), 7.40 (s, 1H), 7.14-7.00 (m, 4H), 5.47 (s, 2H), 5.34 (s, 1H), 5.10 (s, 1H), 4.39 (s, 2H), 4.36 (s, 2H), 2.56 (s, 3H), 1.91 (s, 3H) ppm. ES-MS: 395 [M+1].

2-[({[5-(2-Carbamoylethyl)-1-[(4-fluorophenyl)methyl]-1H-imidazol-2-yl]methyl}amino)methyl]-6-methylpyridine-4-carboxylic acid

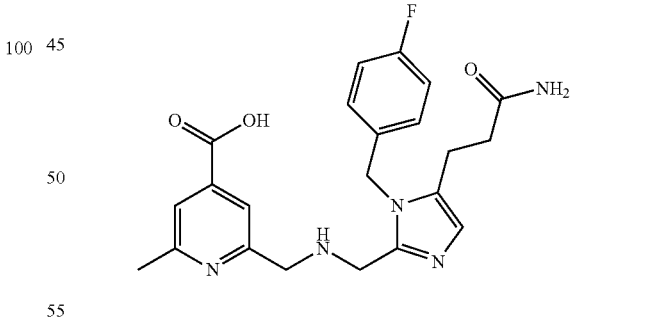

General Procedure A from methyl 6-({[(tert-butoxy)carbonyl]({[5-(2-carbamoylethyl)-1-[(4-fluoro phenyl)methyl]-1H-imidazol-2-yl]methyl})amino}methyl)-2-methylpyridine-4-carboxylate. Evaporation to dryness gave the title compound as colorless solid as a sodium salt. Dissolved in TFA and evaporated to afford the title compound as colorless gum as a TFA salt. $^1$H-NMR (300 MHz, CD$_3$OD): δ 7.83 (s, 2H), 7.33 (s, 1H), 7.17-6.98 (m, 4H), 5.49 (s, 2H), 4.45 (s, 2H), 4.32 (s, 2H), 2.77 (t, 2H), 2.59 (s, 3H), 2.48 (t, 2H) ppm. ES-MS: 426 [M+1].

2-[({[5-Ethyl-1-(thiophen-2-ylmethyl)-1H-imidazol-2-yl]methyl}amino)methyl]-6-methylpyridine-4-carboxylic acid

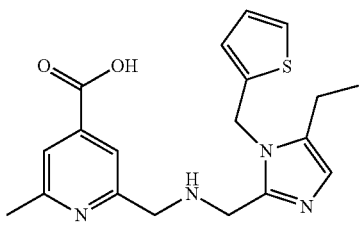

General Procedure A from methyl 6-[({[5-ethyl-1-(thiophen-2-ylmethyl)-1H-imidazol-2-yl]methyl}amino)methyl]-2-methylpyridine-4-carboxylate. Evaporation to dryness afforded the title compound as brown solid as a sodium salt. $^1$H-NMR (300 MHz, CD$_3$OD): δ 7.63 (s, 1H), 7.54 (s, 1H), 7.29 (d, 1H), 6.92 (t, 1H), 6.82 (s, 1H), 6.65 (s, 1H), 5.47 (s, 2H), 3.87 (s, 4H), 2.61-2.50 (m, 5H), 1.21 (t, 3H) ppm. ES-MS: 371 [M+1].

1-[6-(2-{[({5-Ethyl-1-[(4-fluorophenyl)methyl]-1H-imidazol-2-yl}methyl)amino]methyl}-6-methyl pyridin-4-yl)-5-oxa-7-azaspiro[2.5]octan-7-yl]-2,2,2-trifluoroethan-1-one

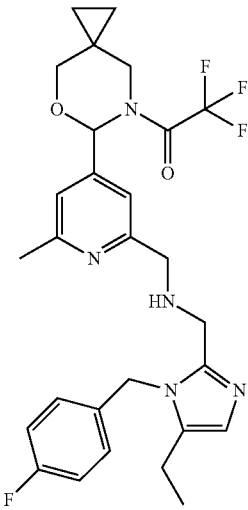

General Procedure Q from tert-butyl N-({5-ethyl-1-[(4-fluorophenyl)methyl]-1H-imidazol-2-yl}methyl)-N-({6-methyl-4-[7-(trifluoroacetyl)-5-oxa-7-azaspiro[2.5]octan-6-yl]pyridin-2-yl}methyl)carbamate. Evaporation to dryness afforded the title compound as brown solid as a TFA salt. $^1$H-NMR (300 MHz, CDCl$_3$): δ 7.48 (s, 1H), 7.30 (s, 1H), 7.14 (s, 1H), 7.09 (t, 2H), 6.99 (t, 2H), 6.94 (s, 1H), 5.45 (s, 2H), 4.51 (s, 2H), 4.41 (s, 2H), 4.02 (d, 1H), 3.72 (d, 1H), 3.25 (t, 2H), 2.71 (s, 3H), 2.56 (q, 2H), 1.30 (t, 3H), 0.77-0.59 (m, 2H), 0.55-0.40 (m, 2H) ppm. ES-MS: 546 [M+1].

1-(6-{2-[({[3-(Benzyloxy)-6-methoxypyridin-2-yl]methyl}amino)methyl]-6-(hydroxymethyl)pyridin-4-yl}-5-oxa-7-azaspiro[2.5]octan-7-yl)-2,2,2-trifluoroethan-1-one

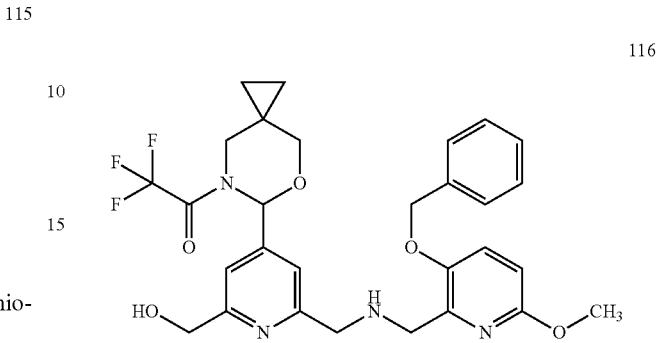

General Procedure Q from tert-butyl N-{[3-(benzyloxy)-6-methoxypyridin-2-yl]methyl}-N-[(6-{[(tert-butyldimethylsilyl)oxy]methyl}-4-[7-(trifluoroacetyl)-5-oxa-7-azaspiro[2.5]octan-6-yl]pyridin-2-yl)methyl]carbamate. Purification by chromatography afforded the title compound as colorless gum as a TFA salt. $^1$H-NMR (300 MHz, CD$_3$OD): δ 7.61-7.26 (m, 7H), 7.58 (d, 1H), 6.96-6.62 (m, 2H), 5.13 (s, 2H), 4.77 (s, 2H), 4.52 (s, 2H), 4.42 (s, 2H), 4.13-3.99 (m, 1H), 3.92 (s, 3H), 3.84-3.72 (m, 1H), 3.40-3.08 (m, 2H), 0.72-0.61 (m, 2H), 0.55-0.35 (m, 2H) ppm. ES-MS: 573 [M+1].

Intermediates

(S)-Methyl-6-[({5H,6H,7H-cyclopenta[b]pyridin-7-yl}amino)methyl]-2-methylpyridine-4-carboxylate

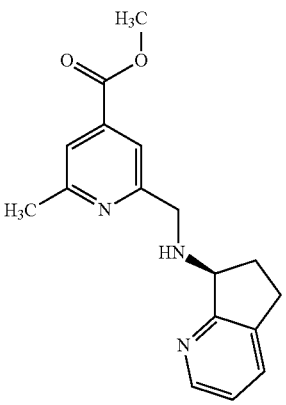 [SMILES: COC(=O)c1cc(C)nc(CN[C@H]2CCc3cccnc32)c1]

General Procedure B from methyl 2-(aminomethyl)-6-methylpyridine-4-carboxylate and (S)-5H,6H,7H-cyclopenta[b]pyridin-7-amine afforded the title compound as yellow oil after purification by chromatography. $^1$H-NMR (300 MHz, CDCl$_3$): δ 8.41 (d, 1H), 7.76 (s, 1H), 7.58 (s, 1H), 7.53 (d, 1H), 7.10 (t, 1H), 4.30 (t, 1H), 4.15 (m, 2H), 3.93 (s, 3H), 3.01 (m, 1H), 2.86 (m, 1H), 2.62 (s, 3H), 2.47 (m, 1H), 1.97 (m, 1H) ppm. ES-MS: 298 [M+1].

181

Methyl 2-(((tert-butoxycarbonyl)((1-(4-fluorobenzyl)-1H-imidazol-2-yl)methyl)amino)methyl)-6-(prop-1-yn-1-yl)isonicotinate

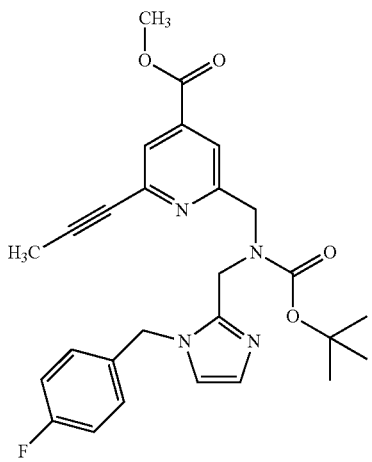 [SMILES: CC#Cc1cc(C(=O)OC)cc(CN(Cc2nccn2Cc2ccc(F)cc2)C(=O)OC(C)(C)C)n1]

General Procedure C from methyl 2-bromo-6-({[(tert-butoxy)carbonyl]({1-[(4-fluorophenyl)methyl]-1H-imidazol-2-yl}methyl)amino}methyl)pyridine-4-carboxylate and potassium propynyltrifluoroborate afforded the title compound as yellow oil after purification by chromatography. $^{1}$H-NMR (300 MHz, CDCl$_3$): δ 7.74 (s, 1H), 7.44 (s, 1H), 7.04 (m, 4H), 6.92 (s, 1H), 6.82 (s, 1H), 5.30 (s, 2H), 4.74 (s, 2H), 4.53 (s, 2H), 3.93 (s, 3H), 2.09 (s, 3H), 1.29 (m, 9H).

Methyl-2-bromo-6-({[(tert-butoxy)carbonyl]({1-[(4-fluorophenyl)methyl]-1H-imidazol-2-yl}methyl)amino}methyl)pyridine-4-carboxylate

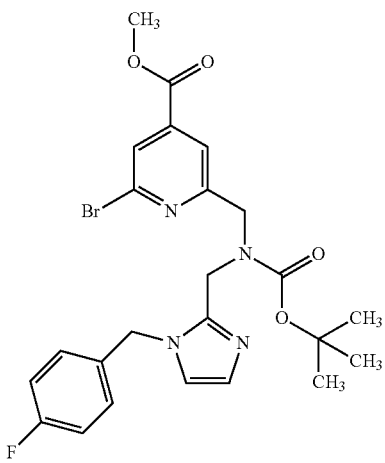 [SMILES: COC(=O)c1cc(Br)nc(CN(Cc2nccn2Cc2ccc(F)cc2)C(=O)OC(C)(C)C)c1]

General Procedure D from methyl 2-bromo-6-{[({1-[(4-fluorophenyl)methyl]-1H-imidazol-2-yl}methyl)amino]methyl}pyridine-4-carboxylate afforded the title compound as yellow oil. $^{1}$H-NMR (300 MHz, CDCl3): δ 7.85 (s, 1H), 7.52 (s, 1H), 7.07 (m, 4H), 6.85 (m, 2H), 5.31 (s, 2H), 4.74 (s, 2H), 4.56 (s, 2H), 3.95 (s, 3H), 1.32 (s, 9H).

182

Methyl-2-bromo-6-{[({1-[(4-fluorophenyl)methyl]-1H-imidazol-2-yl}methyl)amino]methyl}pyridine-4-carboxylate

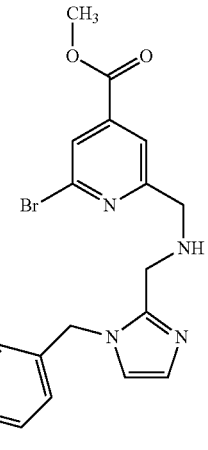

General Procedure B from 1-[(4-fluorophenyl)methyl]-1H-imidazole-2-carbaldehyde and methyl 2-(aminomethyl)-6-bromopyridine-4-carboxylate afforded the title compound as light yellow oil. $^{1}$H-NMR (300 MHz, CDCl$_3$): δ 7.88 (s, 1H), 7.76 (s, 1H), 7.02 (m, 5H), 6.83 (s, 1H), 5.20 (s, 2H), 3.96 (s, 2H), 3.94 (s, 3H), 3.86 (s, 2H).

Methyl 2-{[({4-[(4-fluorophenyl)methyl]-4H-1,2,4-triazol-3-yl}methyl)amino]methyl}-6-(hydroxymethyl)pyridine-4-carboxylate

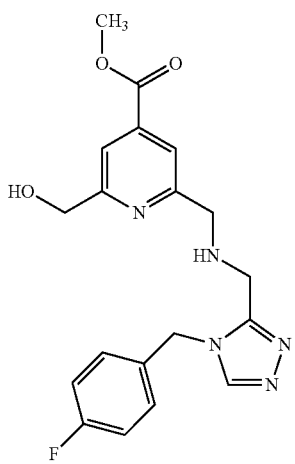 [SMILES: COC(=O)c1cc(CO)nc(CNCc2nncn2Cc2ccc(F)cc2)c1]

General Procedure Q from methyl 2-{[(tert-butyldimethylsilyl)oxy]methyl}-6-{[({4-[(4-fluorophenyl)methyl]-4H-1,2,4-triazol-3-yl}methyl)amino]methyl}pyridine-4-carboxylate. Purification by chromatography afforded the title compound as colorless gum. $^{1}$H-NMR (300 MHz, CDCl$_3$): δ 8.08 (s, 1H), 7.73 (s, 1H), 7.70 (s, 1H), 7.15 (t, 2H), 7.05 (t, 2H), 5.28 (s, 2H), 4.81 (s, 2H), 3.99-3.93 (m, 7H) ppm.

Methyl 2-{[(tert-butyldimethylsilyl)oxy]methyl}-6-{[({4-[(4-fluorophenyl)methyl]-4H-1,2,4-triazol-3-yl}methyl)amino]methyl}pyridine-4-carboxylate

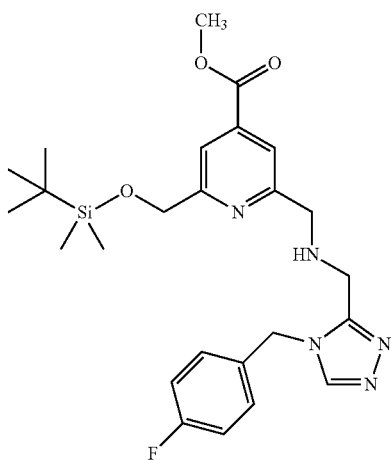 [SMILES: COC(=O)c1cc(CNCc2nncn2Cc2ccc(F)cc2)nc(CO[Si](C)(C)C(C)(C)C)c1]

General Procedure B from methyl 2-{[(tert-butyldimethylsilyl)oxy]methyl}-6-formylpyridine-4-carboxylate and {4-[(4-fluorophenyl)methyl]-4H-1,2,4-triazol-3-yl}methanamine. Purification by chromatography afforded the title compound as colorless gum. $^1$H-NMR (300 MHz, CDCl$_3$): δ 8.08 (s, 1H), 7.95 (s, 1H), 7.65 (s, 1H), 7.14 (t, 2H), 7.05 (t, 2H), 5.29 (s, 2H), 4.86 (s, 2H), 3.98-3.93 (m, 7H), 0.98 (s, 9H), 0.14 (s, 6H) ppm.

Methyl 2-(hydroxymethyl)-6-[({[5-methyl-4-(3-phenylpropyl)-4H-1,2,4-triazol-3-yl]methyl}amino)methyl]pyridine-4-carboxylate

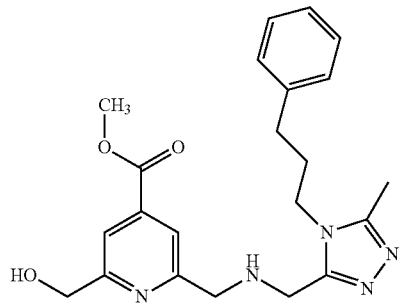 [SMILES: COC(=O)c1cc(CO)nc(CNCc2nnc(C)n2CCCc2ccccc2)c1]

General Procedure Q from methyl 2-{[(tert-butyldimethylsilyl)oxy]methyl}-6-[({[5-methyl-4-(3-phenylpropyl)-4H-1,2,4-triazol-3-yl]methyl}amino)methyl]pyridine-4-carboxylate. Purification by chromatography afforded the title compound as colorless gum. $^1$H-NMR (300 MHz, CDCl$_3$): δ 7.73 (s, 1H), 7.70 (s, 1H), 7.33-7.21 (m, 3H), 7.17-7.11 (m, 2H), 5.47 (brs, 2H), 4.80 (s, 2H), 4.00-3.90 (m, 7H), 2.67 (t, 2H), 2.35 (s, 3H), 2.10-1.97 (m, 2H) ppm.

Methyl 2-{[(tert-butyldimethylsilyl)oxy]methyl}-6-[({[5-methyl-4-(3-phenylpropyl)-4H-1,2,4-triazol-3-yl]methyl}amino)methyl]pyridine-4-carboxylate

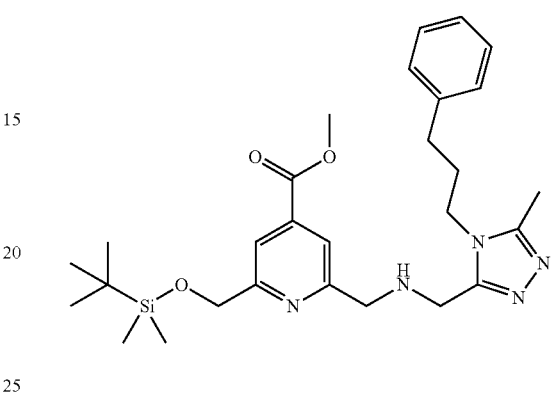

By General Procedure B from methyl 2-{[(tert-butyldimethylsilyl)oxy]methyl}-6-formylpyridine-4-carboxylate and [5-methyl-4-(3-phenylpropyl)-4H-1,2,4-triazol-3-yl]methanamine. Purification by chromatography afforded the title compound as colorless gum. $^1$H-NMR (300 MHz, CDCl$_3$): δ 7.94 (s, 1H), 7.67 (s, 1H), 7.33-7.19 (m, 3H), 7.16-7.11 (m, 2H), 4.85 (s, 2H), 3.99-3.86 (m, 9H), 2.67 (t, 2H), 2.36 (s, 3H), 2.10-1.93 (m, 2H), 0.98 (s, 9H), 0.14 (s, 6H) ppm.

Ethyl 2-{[(tert-butyldimethylsilyl)oxy]methyl}-6-{[({1-[(4-fluorophenyl)methyl]-1H-imidazol-2-yl}methyl)amino]methyl}pyridine-4-carboxylate

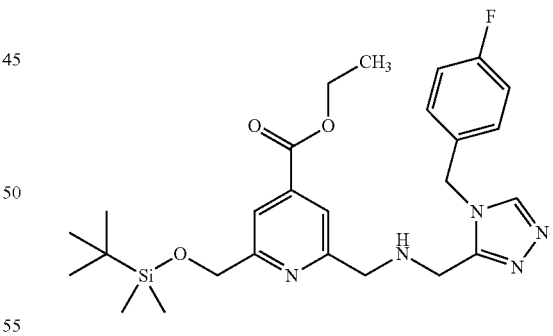

General Procedure B from ethyl 2-(aminomethyl)-6-{[(tert-butyldimethylsilyl)oxy]methyl}pyridine-4-carboxylate and 1-[(4-fluorophenyl)methyl]-1H-imidazole-2-carbaldehyde. Purification by chromatography afforded the title compound as light yellow gum. $^1$H-NMR (300 MHz, CDCl$_3$): δ 7.94 (s, 1H), 7.69 (s, 1H), 7.27 (s, 1H), 7.12-6.95 (m, 4H), 6.84 (s, 1H), 5.21 (s, 2H), 4.84 (s, 2H), 4.41 (q, 2H), 3.94 (s, 2H), 3.87 (s, 2H), 1.41 (t, 3H), 0.98 (s, 9H), 0.14 (s, 6H) ppm.

185

Methyl 6-[({[6-methoxy-3-(2-phenylethoxy)pyridin-2-yl]methyl}amino)methyl]-2-methylpyridine-4-carboxylate

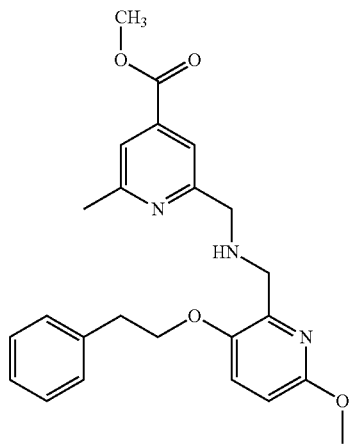 [SMILES: COC(=O)c1cc(C)nc(CNCc2nc(OC)ccc2OCCc2ccccc2)c1]

General Procedure B from methyl 6-formyl-2-methylpyridine-4-carboxylate and [6-methoxy-3-(2-phenylethoxy)pyridin-2-yl]methanamine. Purification by chromatography afforded the title compound as light yellow gum. ¹H-NMR (300 MHz, CDCl₃): δ 7.73 (s, 1H), 7.58 (s, 1H), 7.33-7.20 (m, 5H), 7.12 (d, 1H), 6.55 (d, 1H), 4.13 (t, 2H), 3.95 (s, 2H), 3.94 (s, 3H), 3.90 (s, 3H), 3.89 (s, 2H), 3.07 (t, 2H), 2.61 (s, 3H) ppm.

Methyl-2-(hydroxymethyl)-6-[({[5-methyl-4-(4-methylpentyl)-4H-1,2,4-triazol-3-yl]methyl}amino)methyl]pyridine-4-carboxylate

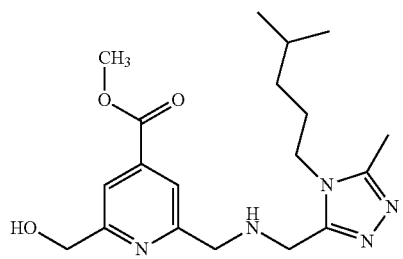 [SMILES: COC(=O)c1cc(CO)nc(CNCc2nnc(C)n2CCCC(C)C)c1]

General Procedure Q from methyl 2-{[(tert-butyldimethylsilyl)oxy]methyl}-6-[({[5-methyl-4-(4-methylpentyl)-4H-1,2,4-triazol-3-yl]methyl}amino)methyl]pyridine-4-carboxylate. Aqueous work up afforded the title compound as colorless gum. ¹H-NMR (300 MHz, CDCl₃): δ 7.8 (brs, 2H), 4.8 (s, 2H), 4.1-3.9 (m, 9H), 2.4 (s, 3H), 1.7 (m, 2H), 1.5 (m, 1H), 1.3 (m, 2H), 0.85 (d, 6H).

186

Methyl 2-{[(tert-butyldimethylsilyl)oxy]methyl}-6-[({[5-methyl-4-(4-methylpentyl)-4H-1,2,4-triazol-3-yl]methyl}amino)methyl]pyridine-4-carboxylate

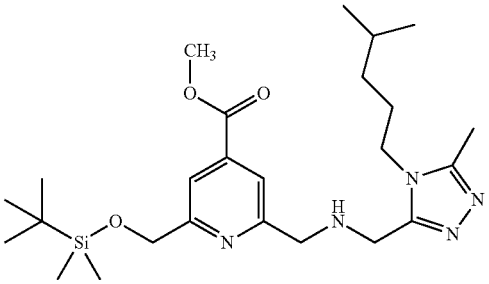 [SMILES: COC(=O)c1cc(CNCc2nnc(C)n2CCCC(C)C)nc(CO[Si](C)(C)C(C)(C)C)c1]

General Procedure B from methyl 2-{[(tert-butyldimethylsilyl)oxy]methyl}-6-formylpyridine-4-carboxylate and [5-methyl-4-(4-methylpentyl)-4H-1,2,4-triazol-3-yl]methanamine. Purification by chromatography afforded the title compound. ¹H-NMR (300 MHz, CDCl₃): δ 7.8 (s, 1H), 7.6 (s, 1H), 4.8 (s, 2H), 4.1-3.9 (m, 9H), 2.4 (s, 3H), 1.6 (m, 2H), 1.5 (m, 1H), 1.3 (m, 2H), 1.0 (s, 9H), 0.85 (d, 6H), 0.1 (s, 6H).

Ethyl 2-{[(tert-butyldimethylsilyl)oxy]methyl}-6-{[({1-[(4-fluorophenyl)methyl]-4-(hydroxymethyl)-1H-imidazol-2-yl}methyl)amino]methyl}pyridine-4-carboxylate

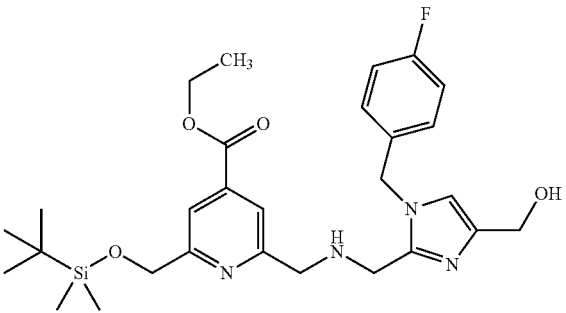 [SMILES: CCOC(=O)c1cc(CNCc2nc(CO)cn2Cc2ccc(F)cc2)nc(CO[Si](C)(C)C(C)(C)C)c1]

General Procedure B from 1-[(4-fluorophenyl)methyl]-4-(hydroxymethyl)-1H-imidazole-2-carbaldehyde and Ethyl 2-(aminomethyl)-6-{[(tert-butyldimethylsilyl)oxy]methyl}pyridine-4-carboxylate Purification by chromatography afforded the title compound as yellow oil. ¹H NMR ¹H NMR (300 MHz, CDCl₃): δ ppm 7.90 (s, 1H), 7.60 (s, 1H), 7.00-6.80 (m, 5H), 5.10, 5.30 (2s, 2H), 4.70 (s, 2H), 4.45 (2s, 2H), 4.40 (q, 2H), 4.00 (s, 2H), 3.80 (2s, 2H), 1.35 (t, 3H), 1.00 (s, 9H), 0.20 (s, 6H).

Methyl 2-{[({4-[(4-fluorophenyl)methyl]-5-methyl-4H-1,2,4-triazol-3-yl}methyl)amino]methyl}-6-(hydroxymethyl)pyridine-4-carboxylate

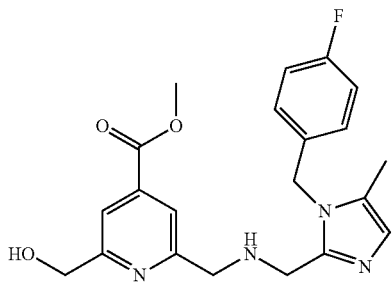 [SMILES: COC(=O)c1cc(CO)nc(CNCc2ncc(C)n2Cc2ccc(F)cc2)c1]

General Procedure Q from methyl 2-{[(tert-butyldimethylsilyl)oxy]methyl}-6-{[({4-[(4-fluorophenyl)methyl]-5-methyl-4H-1,2,4-triazol-3-yl}methyl)amino]methyl}pyridine-4-carboxylate. Purification by chromatography afforded the title compound as colorless gum. $^1$H-NMR (300 MHz, CD$_3$OD): δ 7.89 (s, 1H), 7.72 (s, 1H), 7.19-7.03 (m, 4H), 5.35 (s, 2H), 4.72 (s, 2H), 3.99 (s, 4H), 3.95 (s, 3H), 2.31 (s, 3H).

Methyl 2-{[(tert-butyldimethylsilyl)oxy]methyl}-6-{[({4-[(4-fluorophenyl)methyl]-5-methyl-4H-1,2,4-triazol-3-yl}methyl)amino]methyl}pyridine-4-carboxylate

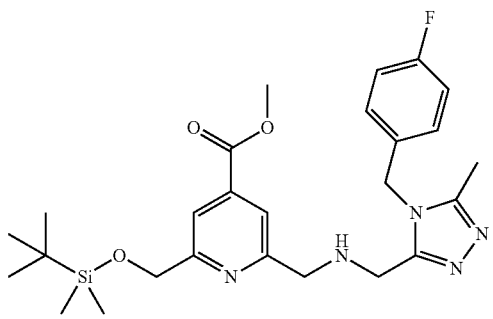 [SMILES: COC(=O)c1cc(CNCc2nnc(C)n2Cc2ccc(F)cc2)nc(CO[Si](C)(C)C(C)(C)C)c1]

General Procedure B from methyl 2-{[(tert-butyldimethylsilyl)oxy]methyl}-6-formylpyridine-4-carboxylate and {4-[(4-fluorophenyl)methyl]-5-methyl-4H-1,2,4-triazol-3-yl}methanamine. Purification by chromatography afforded the title compound as colorless oil. $^1$H-NMR (300 MHz, CD$_3$OD): δ 7.93 (s, 1H), 7.63 (s, 1H), 7.04-6.96 (m, 4H), 5.23 (s, 2H), 4.83 (s, 2H), 3.96 (s, 3H), 3.94 (s, 2H), 3.92 (s, 2H), 2.34 (s, 3H), 0.98 (s, 9H), 0.14 (s, 6H) ppm.

Methyl 6-{[({5-ethyl-4-[(4-fluorophenyl)methyl]-4H-1,2,4-triazol-3-yl}methyl)amino]methyl}-2-methylpyridine-4-carboxylate

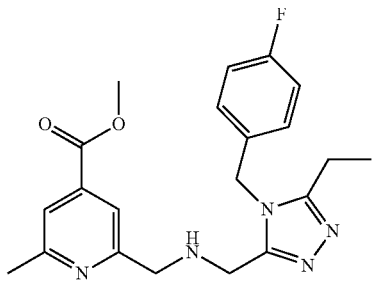 [SMILES: CCc1nnc(CNCc2cc(C(=O)OC)cc(C)n2)n1Cc1ccc(F)cc1]

General Procedure B from methyl 6-formyl-2-methylpyridine-4-carboxylate and {5-Ethyl-4-[(4-fluorophenyl)methyl]-4H-1,2,4-triazol-3-yl}methanamine. Purification by chromatography afforded the title compound as colorless gum. $^1$H-NMR (300 MHz, CDCl$_3$): δ 7.55 (s, 2H), 7.03-6.93 (m, 4H), 5.22 (s, 2H), 3.94-3.84 (m, 7H), 2.60 (q, 2H), 2.56 (s, 3H), 1.28 (t, 3H) ppm.

Methyl 6-{[({4-[(4-fluorophenyl)methyl]-5-methyl-4H-1,2,4-triazol-3-yl}methyl)amino]methyl}-2-methylpyridine-4-carboxylate

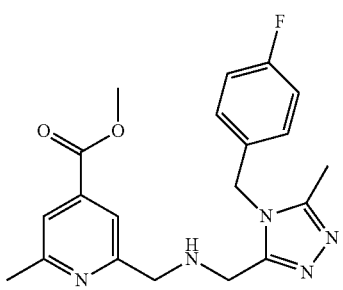 [SMILES: COC(=O)c1cc(C)nc(CNCc2nnc(C)n2Cc2ccc(F)cc2)c1]

General Procedure B from methyl 6-formyl-2-methylpyridine-4-carboxylate and {4-[(4-fluorophenyl)methyl]-5-methyl-4H-1,2,4-triazol-3-yl}methanamine. Purification by chromatography afforded the title compound as colorless gum. $^1$H-NMR (300 MHz, CDCl$_3$): δ 7.56 (s, 1H), 7.55 (s, 1H), 7.00 (s, 2H), 6.98 (s, 2H), 5.23 (s, 2H), 3.96-3.86 (m, 4H), 3.91 (s, 3H), 2.56 (s, 3H), 2.32 (s, 3H) ppm.

Methyl 2-{[({5-ethyl-4-[(4-fluorophenyl)methyl]-4H-1,2,4-triazol-3-yl}methyl)amino]methyl}-6-(hydroxymethyl)pyridine-4-carboxylate

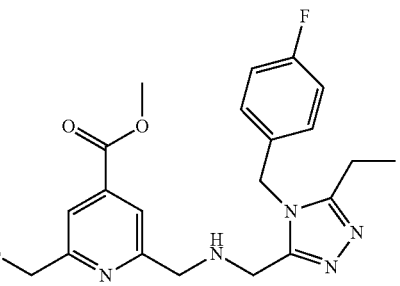

General Procedure Q from methyl 2-{[(tert-butyldimethylsilyl)oxy]methyl}-6-{[({5-ethyl-4-[(4-fluorophenyl)methyl]-4H-1,2,4-triazol-3-yl}methyl)amino]methyl}pyridine-4-carboxylate. Purification by chromatography afforded the title compound as colorless gum. $^1$H-NMR (300 MHz, CDCl$_3$): δ 7.76 (s, 1H), 7.59 (s, 1H), 6.99-6.92 (m, 4H), 5.21 (s, 2H), 4.76 (s, 2H), 3.91-3.86 (m, 4H), 3.87 (s, 3H), 2.58 (q, 2H), 1.25 (t, 3H) ppm.

189

Methyl 2-{[(tert-butyldimethylsilyl)oxy]methyl}-6-{[({5-ethyl-4-[(4-fluorophenyl)methyl]-4H-1,2,4-triazol-3-yl}methyl)amino]methyl}pyridine-4-carboxylate

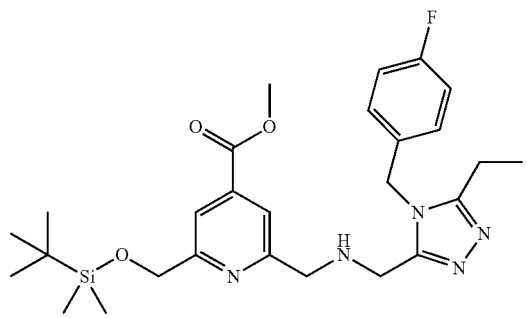 [SMILES: CCc1nnc(CNCc2cc(C(=O)OC)cc(CO[Si](C)(C)C(C)(C)C)n2)n1Cc1ccc(F)cc1]

General Procedure B from methyl 2-{[(tert-butyldimethylsilyl)oxy]methyl}-6-formylpyridine-4-carboxylate and {5-Ethyl-4-[(4-fluorophenyl)methyl]-4H-1,2,4-triazol-3-yl}methanamine. Purification by chromatography afforded the title compound as colorless gum. $^1$H-NMR (300 MHz, CDCl$_3$): δ 7.89 (s, 1H), 7.60 (s, 1H), 7.01-6.93 (m, 4H), 5.21 (s, 2H), 4.79 (s, 2H), 3.93 (s, 3H), 3.90 (s, 2H), 3.88 (s, 2H), 2.59 (q, 2H), 1.28 (t, 3H), 0.95 (s, 9H), 0.10 (s, 6H) ppm.

Methyl 2-{[({4-[(4-fluorophenyl)methyl]-5-(thiophen-2-ylmethyl)-4H-1,2,4-triazol-3-yl}methyl)amino]methyl}-6-(hydroxymethyl)pyridine-4-carboxylate

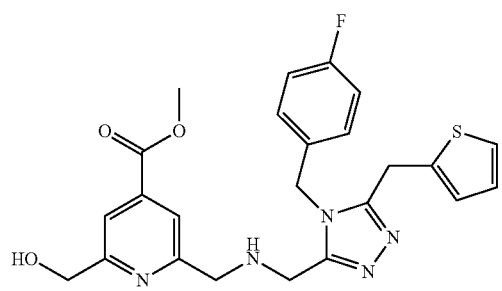 [SMILES: COC(=O)c1cc(CO)nc(CNCc2nnc(Cc3cccs3)n2Cc2ccc(F)cc2)c1]

General Procedure Q from methyl 2-{[(tert-butyldimethylsilyl)oxy]methyl}-6-{[({4-[(4-fluorophenyl)methyl]-5-(thiophen-2-ylmethyl)-4H-1,2,4-triazol-3-yl}methyl)amino]methyl}pyridine-4-carboxylate. Purification by chromatography afforded the title compound as colorless gum. $^1$H-NMR (300 MHz, CDCl$_3$): δ 7.73 (s, 1H), 7.63 (s, 1H), 7.15 (d, 1H), 6.97-6.83 (m, 5H), 6.75 (s, 1H), 5.14 (s, 2H), 4.77 (s, 2H), 4.21 (s, 2H), 3.96-3.87 (m, 5H), 3.82 (s, 2H) ppm.

190

Methyl 2-{[(tert-butyldimethylsilyl)oxy]methyl}-6-{[({4-[(4-fluorophenyl)methyl]-5-(thiophen-2-ylmethyl)-4H-1,2,4-triazol-3-yl}methyl)amino]methyl}pyridine-4-carboxylate

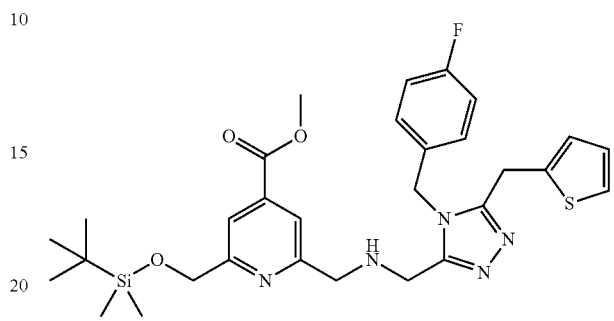

General Procedure B from methyl 2-{[(tert-butyldimethylsilyl)oxy]methyl}-6-formylpyridine-4-carboxylate and {4-[(4-fluorophenyl)methyl]-5-(thiophen-2-ylmethyl)-4H-1,2,4-triazol-3-yl}methanamine. Purification by chromatography afforded the title compound as colorless gum. $^1$H-NMR (300 MHz, CDCl$_3$): δ 7.91 (s, 1H), 7.60 (s, 1H), 7.15 (d, 1H), 6.97-6.83 (m, 5H), 6.76 (s, 1H), 5.14 (s, 2H), 4.80 (s, 2H), 4.21 (s, 2H), 3.93 (s, 3H), 3.91 (s, 2H), 3.88 (s, 2H), 0.96 (s, 9H), 0.12 (s, 6H) ppm.

Methyl 2-methyl-6-{[({1-[2-(pyrimidin-5-yl)ethyl]-1H-imidazol-2-yl}methyl)amino]methyl}pyridine-4-carboxylate

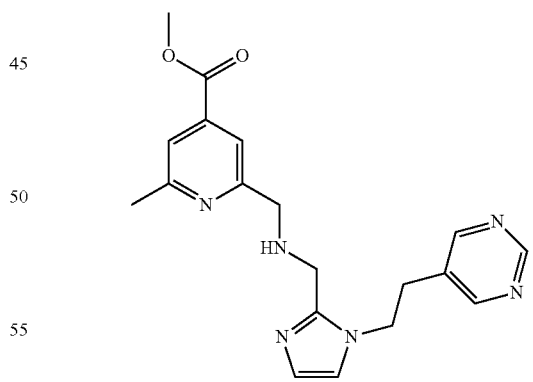

General Procedure B from 1-[2-(pyrimidin-5-yl)ethyl]-1H-imidazole-2-carbaldehyde and methyl 2-(aminomethyl)-6-methylpyridine-4-carboxylate. Purification by chromatography gave the title compound as light yellow oil. $^1$H-NMR (300 MHz, CDCl$_3$): δ 9.08 (s, 1H), 8.43 (s, 2H), 7.27 (s, 1H), 6.96 (s, 1H), 6.93 (s, 1H). 6.75 (s, 1H), 4.28 (t, 2H), 3.90 (s, 3H), 3.81 (s, 2H), 3.45 (s, 2H), 3.09 (t, 2H), 2.58 (s, 3H) ppm.

Methyl 6-{[({4-[(4-fluorophenyl)methyl]-5-(methylsulfanyl)-4H-1,2,4-triazol-3-yl}methyl)amino]methyl}-2-methylpyridine-4-carboxylate

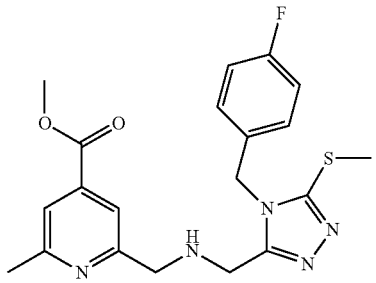

General Procedure B from methyl 6-formyl-2-methylpyridine-4-carboxylate and {4-[(4-fluorophenyl)methyl]-5-(methylsulfanyl)-4H-1,2,4-triazol-3-yl}methanamine. Purification by chromatography afforded the title compound. $^1$H-NMR (300 MHz, CDCl$_3$): δ 7.58 (s, 1H), 7.56 (s, 1H), 7.14 (d, 2H), 7.22 (t, 2H), 5.33 (s, 2H), 4.81 (s, 2H), 4.78 (s, 2H), 3.90 (s, 3H), 2.75 (s, 3H), 2.73 (s, 3H) ppm.

Methyl 2-[(acetyloxy)methyl]-6-{[({4-[(4-fluorophenyl)methyl]-5-propyl-4H-1,2,4-triazol-3-yl}methyl)amino]methyl}pyridine-4-carboxylate

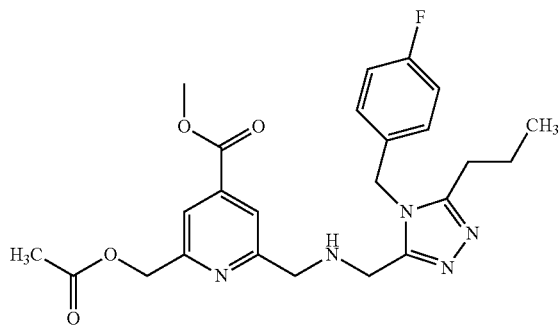 [SMILES: CCCc1nnc(CNCc2cc(C(=O)OC)cc(COC(C)=O)n2)n1Cc1ccc(F)cc1]

General Procedure B from {4-[(4-fluorophenyl)methyl]-5-propyl-4H-1,2,4-triazol-3-yl}methanamine and methyl 2-[(acetyloxy)methyl]-6-formylpyridine-4-carboxylate. Purification by chromatography afforded the title compound. $^1$H-NMR (300 MHz, CDCl$_3$), δ ppm: 7.73 (s, 1H), 7.67 (s, 1H), 7.02-6.93 (m, 4H), 5.22 (s, 2H), 5.19 (s, 2H), 3.93 (s, 5H), 3.88 (s, 2H), 2.56 (t, 2H), 2.24 (bs, 1H), 2.16 (s, 3H), 1.77-1.65 (m, 2H), 0.94 (t, 3H) ppm.

Methyl 2-[(acetyloxy)methyl]-6-[({[6-methoxy-3-(2-methylpropyl)pyridin-2-yl]methyl}amino)methyl]pyridine-4-carboxylate

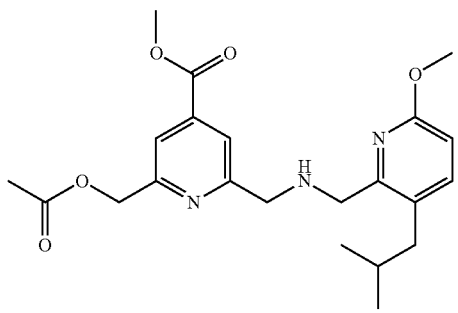 [SMILES: COC(=O)c1cc(CNCc2nc(OC)ccc2CC(C)C)nc(COC(C)=O)c1]

By General Procedure B from [6-methoxy-3-(2-methylpropyl)pyridin-2-yl]methanamine and methyl 2-[(acetyloxy)methyl]-6-formylpyridine-4-carboxylate. Purification by chromatography afforded the title compound. $^1$H-NMR (300 MHz, CDCl$_3$): δ 7.92 (s, 1H), 7.76 (s, 1H), 7.30 (d, 1H), 6.56 (d, 1H), 5.26 (s, 2H), 4.07 (s, 2H), 3.96 (s, 3H), 3.94 (s, 3H), 3.88 (s, 2H), 2.38 (d, 2H), 2.18 (s, 3H), 1.83-1.68 (m, 1H), 0.88 (d, 6H) ppm.

Methyl 2-[(acetyloxy)methyl]-6-[({[5-ethyl-4-(4-methylpentyl)-4H-1,2,4-triazol-3-yl]methyl}amino)methyl]pyridine-4-carboxylate

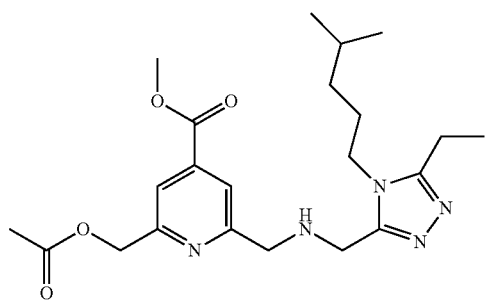 [SMILES: CCc1nnc(CNCc2cc(C(=O)OC)cc(COC(C)=O)n2)n1CCCC(C)C]

By General Procedure B from [5-ethyl-4-(4-methylpentyl)-4H-1,2,4-triazol-3-yl]methanamine and methyl 2-[(acetyloxy)methyl]-6-formylpyridine-4-carboxylate. Purification by chromatography afforded the title compound as a yellow oil. $^1$H-NMR (300 MHz, CDCl$_3$): δ 7.78 (s, 2H), 5.26 (s, 2H), 4.01 (s, 2H), 3.99 (s, 2H), 3.97 (s, 3H), 3.92 (t, 2H), 2.72 (q, 2H), 2.31 (s, 1H), 2.20 (s, 3H), 1.74-1.63 (m, 2H), 1.58-1.48 (m, 1H), 1.42 (t, 3H), 1.23-1.15 (m, 2H), 0.87 (d, 6H) ppm.

Methyl 2-methyl-6-[({[4-(3-phenylpropyl)-4H-1,2,4-triazol-3-yl]methyl}amino)methyl]pyridine-4-carboxylate

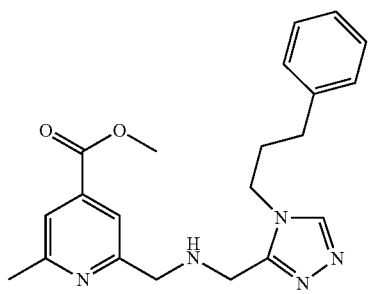 [SMILES: COC(=O)c1cc(C)nc(CNCc2nncn2CCCc2ccccc2)c1]

General Procedure B from methyl (2-formyl-6-methyl)pyridine-4-carboxylate and (4-(3-phenylpropyl)-4H-1,2,4-triazol-3-yl)methanamine. Purification by chromatography afforded the title compound as white solid. $^1$H-NMR (300 MHz, CDCl$_3$): δ 8.09 (s, 1H), 7.61 (s, 2H), 7.27 (m, 3H), 7.13 (d, 2H), 4.07 (t, 2H), 4.00 (s, 2H), 3.93 (m, 7H), 2.66 (t, 2H), 2.61 (s, 3H), 2.15 (m, 2H) ppm.

193

Methyl 2-[(acetyloxy)methyl]-6-[({[4-(3-phenylpropyl)-4H-1,2,4-triazol-3-Yl]methyl}amino)methyl]pyridine-4-carboxylate

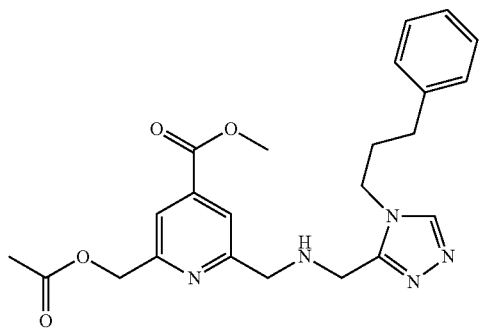 [SMILES: COC(=O)c1cc(CNCc2nncn2CCCc2ccccc2)nc(COC(C)=O)c1]

General Procedure B from methyl 2-(acetoxymethyl)-6-formyl-4-carboxylate and (4-(3-phenylpropyl)-4H-1,2,4-triazol-3-yl)methanamine. Purification by chromatography afforded the title compound as colorless oil. $^1$H-NMR (300 MHz, CDCl$_3$): δ 8.11 (s, 1H), 7.78 (s, 1H), 7.76 (s, 1H), 7.32-7.13 (m, 5H), 5.26 (s, 2H), 4.08 (t, 2H), 3.95 (s, 3H), 3.99 (d, 2H), 3.80 (s, 2H), 2.67 (t, 2H), 2.19 (s, 3H), 2.12 (m, 2H) ppm.

Methyl 2-[({[5-ethyl-4-(3-phenylpropyl)-4H-1,2,4-triazol-3-yl]methyl}amino)methyl]-6-(hydroxymethyl)pyridine-4-carboxylate

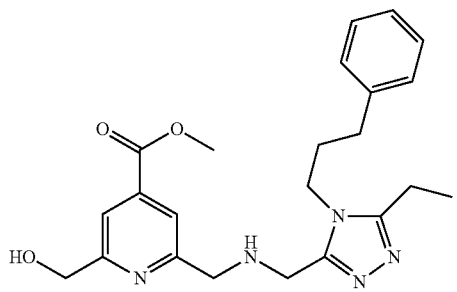 [SMILES: CCc1nnc(CNCc2cc(C(=O)OC)cc(CO)n2)n1CCCc1ccccc1]

General Procedure Q from methyl-2-{[(tert-butyldimethylsilyl)oxy]methyl}-6-[({[5-ethyl-4-(3-phenylpropyl)-4H-1,2,4-triazol-3-yl]methyl}amino)methyl]pyridine-4-carboxylate afforded the title compound. $^1$H-NMR (300 MHz, CDCl$_3$): δ 7.74 (s, 1H), 7.70 (s, 1H), 7.32-7.13 (m, 5H), 4.81 (s, 2H), 3.97-3.88 (m, 9H), 2.14 (m, 4H), 2.04 (m, 2H), 1.36 (s, 3H) ppm.

194

Methyl 2-{[(tert-butyldimethylsilyl)oxy]methyl}-6-[({[5-ethyl-4-(3-phenylpropyl)-4H-1,2,4-triazol-3-yl]methyl}amino)methyl]pyridine-4-carboxylate

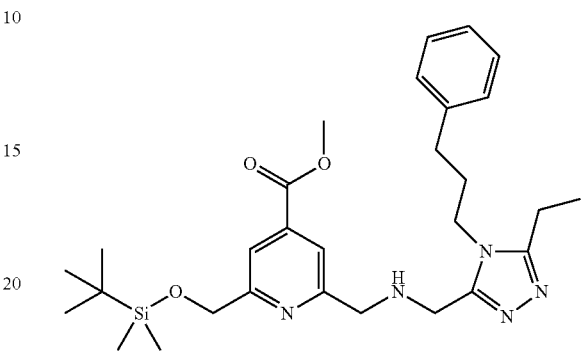

General Procedure B from methyl 2-((tert-butyldimethylsilyloxy)methyl)-6-formylpyridine-4-carboxylate and (5-ethyl-4-(3-phenylpropyl)-4H-1,2,4-triazol-3-yl)methanamine. Purification by preparative TLC afforded the title compound as colorless oil. $^1$H-NMR (300 MHz, CDCl$_3$): δ 7.94 (s, 1H), 7.66 (s, 1H), 7.31-7.12 (m, 5H), 4.82 (s, 2H), 3.98-3.84 (m, 9H), 2.66 (m, 4H), 2.02 (m, 2H), 1.368 (s, 3H), 0.98 (s, 9H), 0.12 (s, 6H) ppm.

Methyl 2-[(acetyloxy)methyl]-6-{[({4-[(4-fluorophenyl)methyl]-5-(1-hydroxyethyl)-4H-1,2,4-triazol-3-yl}methyl)amino]methyl}pyridine-4-carboxylate

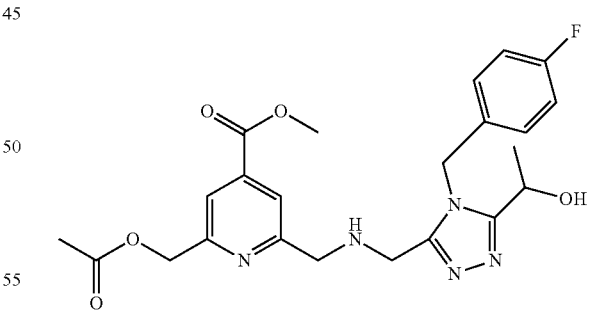

General Procedure B from methyl 2-(acetoxymethyl)-6-formyl-4-carboxylate and 1-[5-(aminomethyl)-4-[(4-fluorophenyl)methyl]-4H-1,2,4-triazol-3-yl]ethan-1-ol. Purification by preparative TLC afforded the title compound as colorless oil. $^1$H-NMR (300 MHz, CDCl$_3$): δ 7.73 (s, 1H), 7.69 (s, 1H), 7.07-6.94 (m, 4H), 5.20 (s, 2H), 4.87 (q, 1H), 3.94 (s, 3H), 3.92 (s, 2H), 3.80 (s, 2H), 2.17 (s, 3H), 1.58 (d, 3H) ppm.

Methyl 6-{[({4-[(4-fluorophenyl)methyl]-5-(1-hydroxyethyl)-4H-1,2,4-triazol-3-yl}methyl)amino]methyl}-2-methylpyridine-4-carboxylate

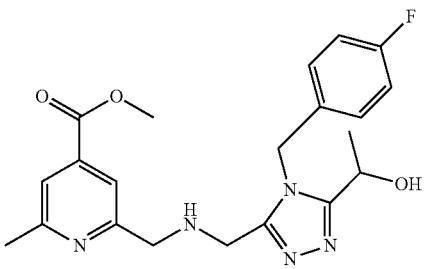 [SMILES: COC(=O)c1cc(C)nc(CNCc2nnc(C(C)O)n2Cc2ccc(F)cc2)c1]

General Procedure B from methyl 2-formyl-6-methylpyridine-4-carboxylate and 1-(5-(aminomethyl)-4-(4-fluorobenzyl)-4H-1,2,4-triazol-3-yl)ethanol. Purification by chromatography afforded the title compound as colorless oil. ¹H-NMR (300 MHz, CD₃OD): δ 7.57 (s, 1H), 7.55 (s, 1H), 7.08-6.95 (m, 4H), 5.47 (s, 2H), 4.87 (q, 1H), 3.93 (s, 3H), 3.89 (s, 2H), 3.81 (s, 2H), 2.57 (s, 3H), 1.60 (d, 3H) ppm.

Methyl 6-[({[3-(benzyloxy)-6-methoxypyridin-2-yl]methyl}amino)methyl]-2-methylpyridine-4-carboxylate

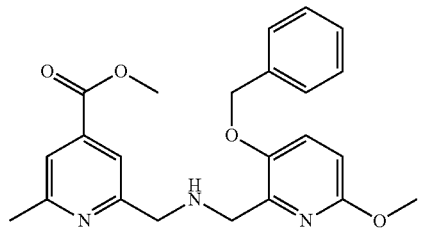

General Procedure B from methyl 2-formyl-6-methylpyridine-4-carboxylate and (3-(benzyloxy)-6-methoxypyridin-2-yl)methanamine. Purification by chromatography afforded the title compound as colorless oil. ¹H-NMR (300 MHz, CDCl₃): δ 7.75 (s, 1H), 7.57 (s, 1H), 7.38-7.32 (m, 5H), 7.20 (d, 2H), 5.02 (s, 2H), 4.02 (s, 2H), 4.01 (s, 2H), 3.92 (s, 3H), 3.91 (s, 3H), 2.59 (s, 3H) ppm.

Methyl 2-[(acetyloxy)methyl]-6-[({[3-(benzyloxy)-6-methoxypyridin-2-yl]methyl}amino)methyl]pyridine-4-carboxylate

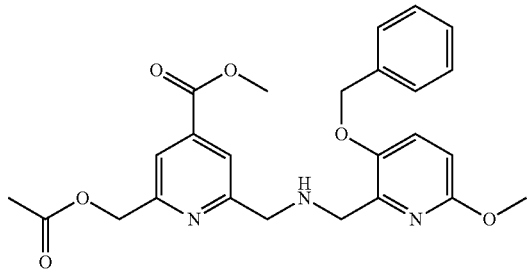 [SMILES: COC(=O)c1cc(CNCc2nc(OC)ccc2OCc2ccccc2)nc(COC(C)=O)c1]

General Procedure B from methyl 2-(acetoxymethyl)-6-formylpyridine-4-carboxylate and (3-(benzyloxy)-6-methoxypyridin-2-yl)methanamine. Purification by chromatography afforded the title compound as colorless oil. ¹H-NMR (300 MHz, CDCl₃): δ 7.90 (s, 1H) 7.75 (s, 1H), 7.35 (m, 5H), 7.10 (d, 1H), 6.50 (d, 1H), 5.20 (s, 2H), 5.00 (s, 2H), 4.05 (s, 2H), 4.00 (s, 2H), 3.90 (s, 3H), 3.80 (s, 3H), 2.20 (s, 3H) ppm.

Methyl 2-[(acetyloxy)methyl]-6-[({2-[3-(benzyloxy)-6-methoxypyridin-2-yl]ethyl}amino)methyl]pyridine-4-carboxylate

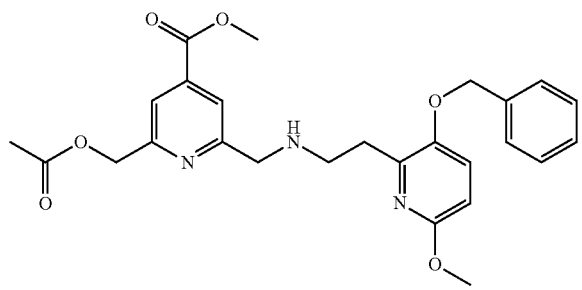 [SMILES: COC(=O)c1cc(CNCCc2nc(OC)ccc2OCc2ccccc2)nc(COC(C)=O)c1]

General Procedure B from methyl 2-(acetoxymethyl)-6-formylpyridine-4-carboxylate and 2-(3-(benzyloxy)-6-methoxypyridin-2-yl)ethan-1-amine. Purification by chromatography afforded the title compound as colorless oil. ¹H-NMR (300 MHz, CDCl₃): δ 7.82 (s, 1H), 7.77 (s, 1H), 7.40-7.32 (m, 5H), 7.21 (d, 1H), 6.55 (d, 1H), 5.22 (s, 2H), 5.02 (s, 2H), 4.08 (s, 2H), 3.96 (s, 3H), 3.88 (s, 3H), 3.12 (m, 4H), 2.19 (s, 3H) ppm.

Methyl 6-{[({1-[(4-fluorophenyl)methyl]-5-[(1Z)-prop-1-en-1-yl]-1H-imidazol-2-yl}methyl)amino]methyl}-2-methylpyridine-4-carboxylate

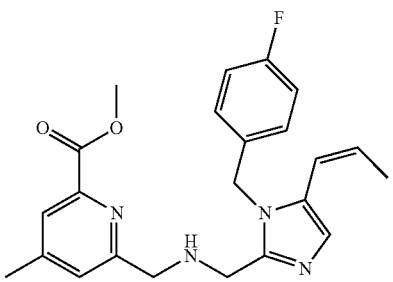 [SMILES: C/C=C\c1cnc(CNCc2cc(C)cc(C(=O)OC)n2)n1Cc1ccc(F)cc1]

General Procedure B from 1-[(4-fluorophenyl)methyl]-5-[(1Z)-prop-1-en-1-yl]-1H-imidazole-2-carbaldehyde and methyl 6-(aminomethyl)-2-methylpyridine-4-carboxylate. Purification by chromatography afforded the title compound. ¹H-NMR (300 MHz, CDCl₃): δ 7.59 (s, 1H), 7.56 (s, 1H), 7.06 (s, 1H), 7.00-6.90 (m, 4H), 5.99 (d, 1H), 5.82-5.71 (m, 1H), 5.24 (s, 2H), 3.93 (m, 5H), 3.87 (s, 2H), 2.58 (s, 3H), 1.88 (d, 3H) ppm.

Methyl 6-{[({5-cyclobutyl-1-[(4-fluorophenyl)methyl]-1H-imidazol-2-yl}methyl)amino]methyl}-2-methylpyridine-4-carboxylate

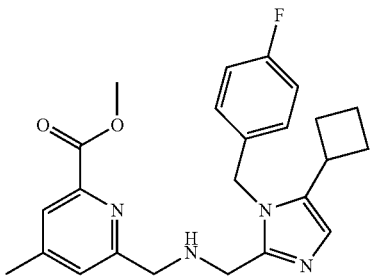 [SMILES: COC(=O)c1cc(C)cc(CNCc2ncc(C3CCC3)n2Cc2ccc(F)cc2)n1]

General Procedure B from methyl 6-(aminomethyl)-2-methylpyridine-4-carboxylate and 5-cyclobutyl-1-[(4-fluorophenyl)methyl]-1H-imidazole-2-carbaldehyde. Purification by chromatography afforded the title compound as yellow oil. $^1$H-NMR (300 MHz, CD$_3$OD): δ 7.58 (s, 1H), 7.55 (s, 1H), 7.05-6.84 (m, 4H), 6.76 (s, 1H), 5.11 (s, 2H), 3.92 (s, 3H), 3.91 (s, 2H), 3.79 (s, 2H), 3.26-3.11 (m, 1H), 2.57 (s, 3H), 2.20-1.75 (m, 6H) ppm.

Methyl 6-{[({1-[(4-fluorophenyl)methyl]-5-(methylsulfanyl)-1H-imidazol-2-yl}methyl)amino]methyl}-2-methylpyridine-4-carboxylate

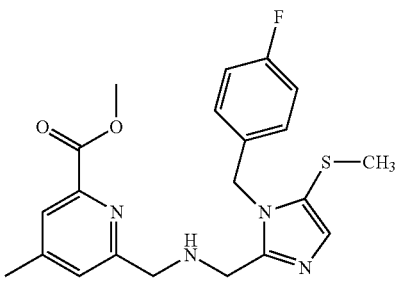

General Procedure B from methyl 6-(aminomethyl)-2-methylpyridine-4-carboxylate and 1-[(4-fluorophenyl)methyl]-5-(methylsulfanyl)-1H-imidazole-2-carbaldehyde. Purification by chromatography gave the title compound as yellow oil. $^1$H-NMR (300 MHz, CD$_3$OD): δ 7.60 (s, 1H), 7.56 (s, 1H), 7.19 (S, 1H), 6.98 (d, 4H), 5.37 (s, 2H), 3.94 (s, 3H), 3.92 (s, 2H), 3.81 (s, 2H), 2.59 (s, 3H), 2.07 (s, 3H) ppm.

Methyl 6-[({[5-ethyl-1-(4-methylpentyl)-1H-imidazol-2-yl]methyl}amino)methyl]-2-methylpyridine-4-carboxylate

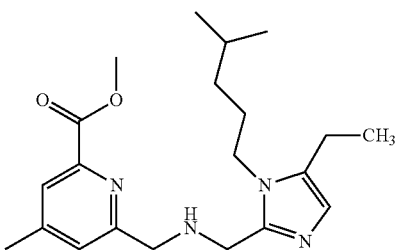 [SMILES: CCc1cnc(CNCc2cc(C)cc(C(=O)OC)n2)n1CCCC(C)C]

General Procedure B from methyl 6-(aminomethyl)-2-methylpyridine-4-carboxylate and 5-ethyl-1-(4-methylpentyl)-1H-imidazole-2-carbaldehyde. Purification by chromatography gave the title compound as yellow oil. $^1$H-NMR (300 MHz, CD$_3$OD): δ 7.68 (s, 1H), 7.58 (s, 1H), 6.68 (s, 1H), 3.99 (s, 2H), 3.94 (s, 3H), 3.89 (s, 2H), 3.84 (t, 2H), 2.60 (s, 3H), 2.52 (q, 2H), 1.79-1.44 (m, 4H), 1.35-1.11 (m, 4H), 0.90 (d, 6H) ppm.

Methyl 6-{[({1-[1-(4-fluorophenyl)pent-3-yn-1-yl]-1H-imidazol-2-yl}methyl)amino]methyl}-2-methyl pyridine-4-carboxylate

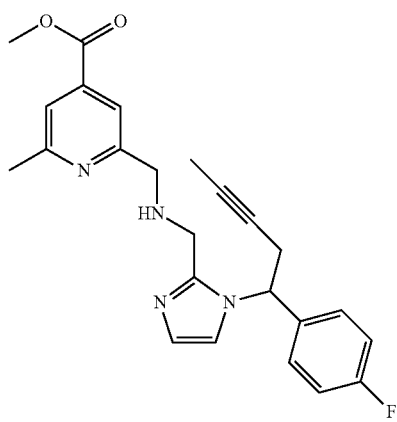 [SMILES: CC#CCC(c1ccc(F)cc1)n1ccnc1CNCc1cc(C(=O)OC)cc(C)n1]

General Procedure B from methyl 6-(aminomethyl)-2-methylpyridine-4-carboxylate and 1-[1-(4-fluorophenyl)pent-3-yn-1-yl]-1H-imidazole-2-carbaldehyde. Purification by chromatography gave the title compound as yellow oil. $^1$H-NMR (300 MHz, CD$_3$OD): δ 7.67 (s, 1H), 7.58 (s, 1H), 7.34-7.20 (m, 3H), 7.03 (t, 2H), 6.91 (s, 1H), 5.84 (t, 1H), 4.0-3.77 (m, 7H), 3.06-2.94 (m, 2H), 2.54 (s, 3H), 1.61 (t, 3H) ppm.

Methyl 2-{[({5-ethyl-1-[(4-fluorophenyl)methyl]-1H-imidazol-2-yl}methyl)amino]methyl}-6-(hydroxyl methyl)pyridine-4-carboxylate

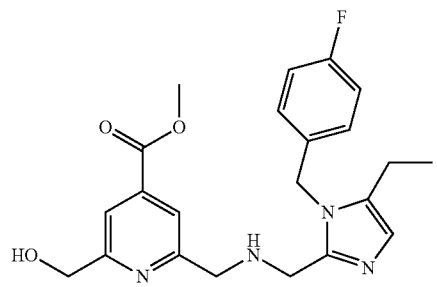 [SMILES: CCc1cnc(CNCc2cc(C(=O)OC)cc(CO)n2)n1Cc1ccc(F)cc1]

General Procedure B from methyl 2-(aminomethyl)-6-(hydroxymethyl)pyridine-4-carboxylate and 5-ethyl-1-[(4-fluorophenyl)methyl]-1H-imidazole-2-carbaldehyde. Purification by chromatography gave the title compound as yellow oil. $^1$H-NMR (300 MHz, CD$_3$OD): δ 7.70 (s, 1H), 7.67 (s, 1H), 7.07-6.87 (m, 4H), 6.78 (s, 1H), 5.31 (s, 2H), 4.80 (s, 2H), 3.99 (s, 2H), 3.95 (s, 3H), 3.82 (s, 2H), 2.39 (q, 2H), 1.20 (t, 3H) ppm.

Methyl 6-{[({1-[(4-fluorophenyl)methyl]-5-(prop-1-en-2-yl)-1H-imidazol-2-yl}methyl)amino]methyl}-2-methylpyridine-4-carboxylate

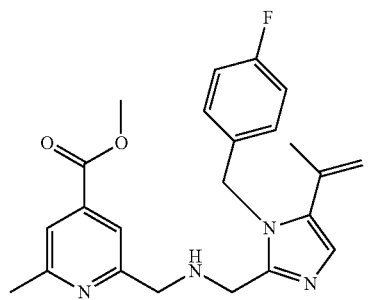 [SMILES: C=C(C)c1cnc(CNCc2cc(C(=O)OC)cc(C)n2)n1Cc1ccc(F)cc1]

General Procedure B from methyl 2-(aminomethyl)-6-methylpyridine-4-carboxylate and 1-[(4-fluoro phenyl)methyl]-5-(prop-1-en-2-yl)-1H-imidazole-2-carbaldehyde. Purification by chromatography gave the title compound as yellow oil. $^1$H-NMR (300 MHz, CD$_3$OD): δ 7.59 (s, 1H), 7.55 (s, 1H), 7.09-6.82 (m, 5H), 5.30 (s, 2H), 5.01 (s, 1H), 4.82 (s, 1H), 3.93 (s, 3H), 3.91 (s, 2H), 3.78 (s, 2H), 2.58 (s, 3H), 2.01 (s, 3H) ppm.

Methyl 6-({[(tert-butoxy)carbonyl]({[5-(2-carbamoylethyl)-1-[(4-fluorophenyl)methyl]-1H-imidazol-2-yl]methyl})amino}methyl)-2-methylpyridine-4-carboxylate

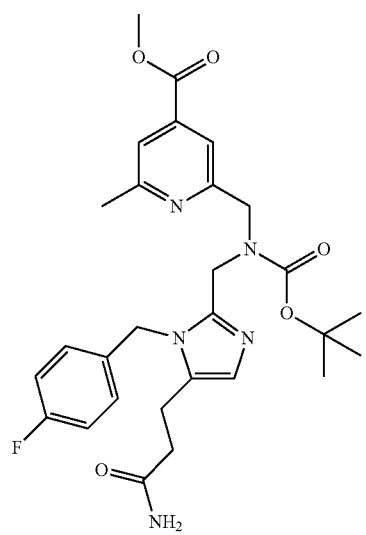 [SMILES: COC(=O)c1cc(C)nc(CN(Cc2ncc(CCC(N)=O)n2Cc2ccc(F)cc2)C(=O)OC(C)(C)C)c1]

General Procedure D from Methyl 6-[({[5-(2-carbamoylethyl)-1-[(4-fluorophenyl)methyl]-1H-imidazol-2-yl]methyl}amino)methyl]-2-methylpyridine-4-carboxylate. Purification by chromatography gave the title compound as yellow oil. $^1$H-NMR (300 MHz, CD$_3$OD): δ 7.55 (s, 1H), 7.38 (s, 1H), 7.00 (t, 2H), 6.88 (t, 2H), 6.76 (s, 1H), 5.31 (s, 2H), 4.71 (s, 2H), 4.46 (s, 2H), 3.93 (s, 3H), 2.71 (t, 2H), 2.58 (s, 3H), 2.45 (t, 2H), 1.22 (s, 9H) ppm.

Methyl 6-[({[5-(2-carbamoylethyl)-1-[(4-fluorophenyl)methyl]-1H-imidazol-2-yl]methyl}amino)methyl]-2-methylpyridine-4-carboxylate

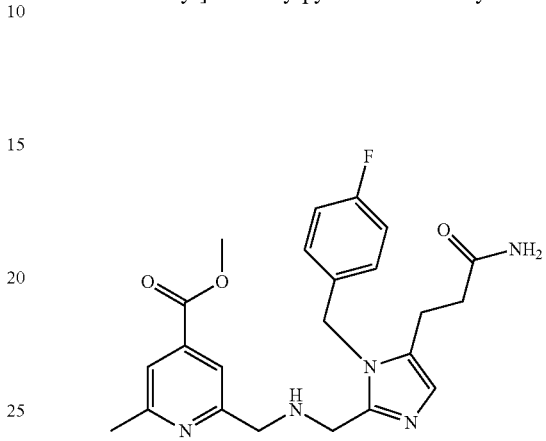

General Procedure B from methyl 2-(aminomethyl)-6-methylpyridine-4-carboxylate and 3-{1-[(4-fluorophenyl)methyl]-2-formyl-1H-imidazol-5-yl}propanamide. Purification by chromatography gave the title compound as yellow oil. $^1$H-NMR (300 MHz, CD$_3$OD): δ 7.55 (s, 1H), 7.37 (s, 1H), 6.99 (t, 2H), 6.87 (t, 2H), 6.76 (s, 1H), 5.31 (s, 2H), 3.97 (s, 2H), 3.92 (s, 2H), 3.93 (s, 3H), 2.71 (t, 2H), 2.58 (s, 3H), 2.45 (t, 2H) ppm.

Methyl 6-[({[5-ethyl-1-(thiophen-2-ylmethyl)-1H-imidazol-2-yl]methyl}amino)methyl]-2-methyl pyridine-4-carboxylate

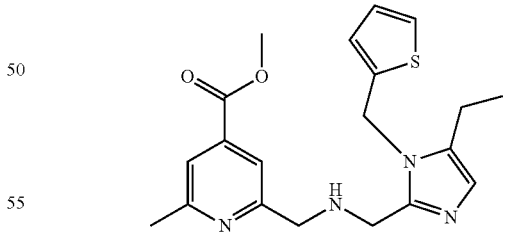

General Procedure B from methyl 2-(aminomethyl)-6-methylpyridine-4-carboxylate and 5-ethyl-1-(thiophen-2-ylmethyl)-1H-imidazole-2-carbaldehyde. Purification by chromatography gave the title compound as yellow oil. $^1$H-NMR (300 MHz, CDCl$_3$): δ 7.63 (S, 1H), 7.57 (s, 1H), 7.24 (d, 1H), 6.94 (t, 1H), 6.83 (s, 1H), 6.73 (s, 1H), 5.37 (s, 2H), 3.96 (s, 2H), 3.93 (s, 3H), 3.92 (s, 2H), 2.59 (s, 3H), 2.53 (q, 2H), 1.24 (t, 3H) ppm.

201

Tert-butyl N-({5-ethyl-1-[(4-fluorophenyl)methyl]-1H-imidazol-2-yl}methyl)-N-({6-methyl-4-[7-(trifluoroacetyl)-5-oxa-7-azaspiro[2.5]octan-6-yl]pyridin-2-yl}methyl)carbamate

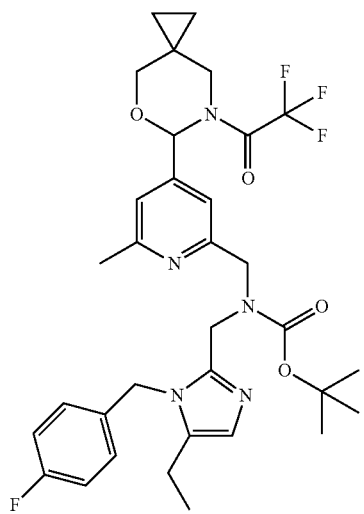 [SMILES: CCc1cnc(CN(Cc2cc(C3OCC4(CC4)CN3C(=O)C(F)(F)F)cc(C)n2)C(=O)OC(C)(C)C)n1Cc1ccc(F)cc1]

To a solution of tert-butyl N-({5-ethyl-1-[(4-fluoro phenyl)methyl]-1H-imidazol-2-yl}methyl)-N-[(6-methyl-4-{5-oxa-7-azaspiro[2.5]octan-6-yl}pyridin-2-yl)methyl]carbamate in 1,2-dichloroethane was added trifluoroacetic anhydride. The reaction mixture was stirred at room temperature for 5 hours. Purification by chromatography afforded the title compound as brown solid. ¹H-NMR (300 MHz, CDCl₃): δ 7.08-6.92 (m, 3H), 7.90-6.70 (m, 5H), 5.28 (s, 2H), 4.72 (s, 2H), 4.46 (s, 2H), 4.08 (d, 1H), 3.74 (d, 1H), 3.24-2.95 (m, 2H), 2.54 (s, 3H), 2.36 (q, 2H), 1.42-1.07 (m, 12H), 0.78-0.57 (m, 2H), 0.52-0.29 (m, 2H) ppm.

Tert-butyl N-({5-ethyl-1-[(4-fluoro phenyl)methyl]-1H-imidazol-2-yl}methyl)-N-[(6-methyl-4-{5-oxa-7-azaspiro[2.5]octan-6-yl}pyridin-2-yl)methyl]carbamate

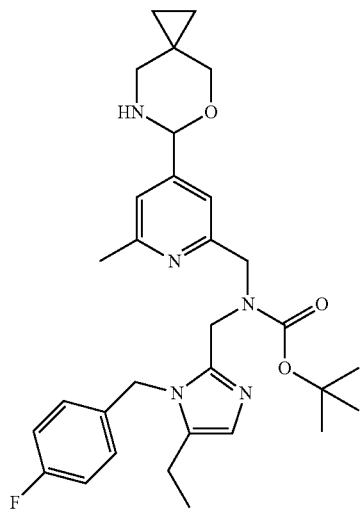 [SMILES: CCc1cnc(CN(Cc2cc(C3NCC4(CC4)CO3)cc(C)n2)C(=O)OC(C)(C)C)n1Cc1ccc(F)cc1]

202

A mixture of tert-butyl N-({5-ethyl-1-[(4-fluorophenyl)methyl]-1H-imidazol-2-yl}methyl)-N-[(4-formyl-6-methylpyridin-2-yl)methyl]carbamate and [1-(aminomethyl)cyclopropyl]methanol in 1,2-dichloroethane was stirred at room temperature for 3 hour and concentrated to afford the title compound. ¹H-NMR (300 MHz, CDCl₃): δ 7.08-6.92 (m, 3H), 7.90-6.70 (m, 5H), 5.28 (s, 2H), 4.72 (s, 2H), 4.46 (s, 2H), 4.08 (d, 1H), 3.74 (d, 1H), 3.24-2.95 (m, 2H), 2.54 (s, 3H), 2.36 (q, 2H), 1.42-1.07 (m, 12H), 0.78-0.57 (m, 2H), 0.52-0.29 (m, 2H) ppm.

Tert-butyl N-({5-ethyl-1-[(4-fluorophenyl)methyl]-1H-imidazol-2-yl}methyl)-N-[(4-formyl-6-methylpyridin-2-yl)methyl]carbamate

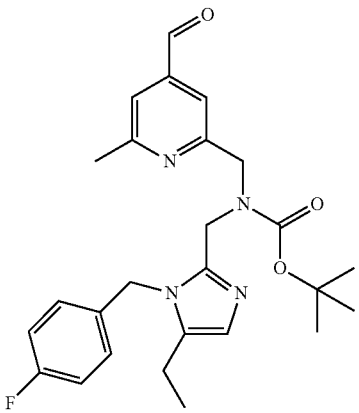 [SMILES: CCc1cnc(CN(Cc2cc(C=O)cc(C)n2)C(=O)OC(C)(C)C)n1Cc1ccc(F)cc1]

General Procedure I from tert-butyl N-({5-ethyl-1-[(4-fluorophenyl)methyl]-1H-imidazol-2-yl}methyl)-N-{[4-(hydroxymethyl)-6-methylpyridin-2-yl]methyl}carbamate gave the title product as colorless oil. ¹H-NMR (300 MHz, CDCl₃): 9.96 (s, 1H), 7.35 (s, 1H), 7.19 (s, 1H), 6.97 (t, 2H), 6.84 (t, 2H), 6.71 (s, 1H), 5.27 (s, 2H), 4.69 (s, 2H), 4.47 (s, 2H), 2.58 (s, 3H), 2.31 (q, 2H), 1.40-1.07 (m, 12H) ppm.

Tert-butyl N-({5-ethyl-1-[(4-fluorophenyl)methyl]-1H-imidazol-2-yl}methyl)-N-{[4-(hydroxymethyl)-6-methylpyridin-2-yl]methyl}carbamate

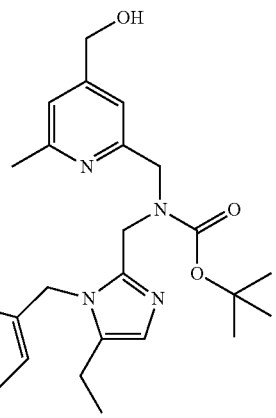

General Procedure D from tert-butyl N-({5-ethyl-1-[(4-fluorophenyl)methyl]-1H-imidazol-2-yl}methyl)-N-{[4-

(hydroxymethyl)-6-methylpyridin-2-yl]methyl}carbamate afforded the title compound as colorless oil. $^{1}$H-NMR (300 MHz, CDCl$_3$): δ 6.98-6.90 (m, 3H), 6.84-6.77 (m, 2H), 6.73 (s, 1H), 6.68 (s, 1H), 5.20 (s, 2H), 4.62 (s, 2H), 4.49 (s, 2H), 4.26 (s, 2H), 2.39 (s, 3H), 2.30 (q, 2H), 1.31-1.09 (m, 12H) ppm.

(2-{[({5-Ethyl-1-[(4-fluorophenyl)methyl]-1H-imidazol-2-yl}methyl)amino]methyl}-6-methylpyridin-4-yl)methanol

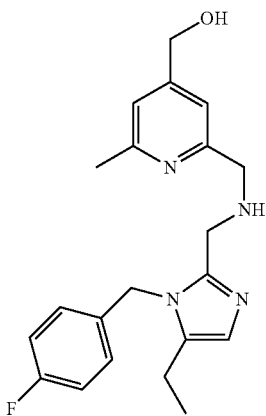 [SMILES: CCc1cnc(CNCc2cc(CO)cc(C)n2)n1Cc1ccc(F)cc1]

To a solution of methyl 6-{[({5-ethyl-1-[(4-fluorophenyl)methyl]-1H-imidazol-2-yl}methyl)amino]methyl}-2-methylpyridine-4-carboxylate in ethanol was added NaBH$_4$ and refluxed for 2 hours. Purification by chromatography afforded the title compound as colorless oil. $^{1}$H-NMR (300 MHz, CDCl$_3$): δ 7.01-6.85 (m, 6H), 6.70 (s, 1H), 5.19 (s, 2H), 4.57 (s, 2H), 3.74 (s, 2H), 3.71 (s, 2H), 2.45 (s, 3H), 2.36 (q, 2H), 1.17 (t, 3H) ppm.

Methyl 6-{[({5-ethyl-1-[(4-fluorophenyl)methyl]-1H-imidazol-2-yl}methyl)amino]methyl}-2-methyl-pyridine-4-carboxylate

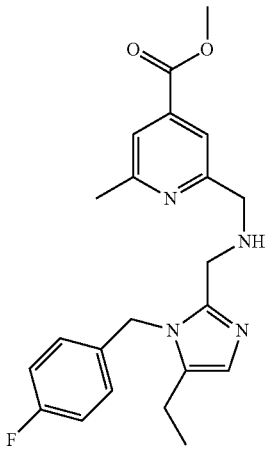 [SMILES: CCc1cnc(CNCc2cc(C(=O)OC)cc(C)n2)n1Cc1ccc(F)cc1]

General Procedure B from 5-ethyl-1-[(4-fluorophenyl)methyl]-1H-imidazole-2-carbaldehyde and methyl 6-(aminomethyl)-2-methylpyridine-4-carboxylate. Purification by chromatography afforded the title compound as yellow oil. $^{1}$H-NMR (300 MHz, CDCl$_3$): δ 7.57 (s, 1H), 7.54 (s, 1H), 7.00-6.85 (m, 4H), 6.74 (s, 1H), 5.17 (s, 2H), 3.91 (m, 5H), 3.80 (s, 2H), 2.56 (s, 3H), 2.36 (q, 2H), 1.17 (t, 3H) ppm.

Tert-butyl N-{[3-(benzyloxy)-6-methoxypyridin-2-yl]methyl}-N-[(6-{[(tert-butyldimethylsilyl)oxy]methyl}-4-[7-(trifluoroacetyl)-5-oxa-7-azaspiro[2.5]octan-6-yl]pyridin-2-yl)methyl]carbamate

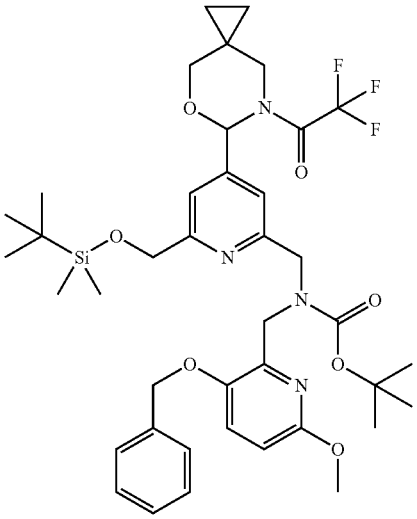 [SMILES: COc1ccc(OCc2ccccc2)c(CN(Cc2cc(C3OCC4(CC4)CN3C(=O)C(F)(F)F)cc(CO[Si](C)(C)C(C)(C)C)n2)C(=O)OC(C)(C)C)n1]

To a solution of tert-butyl N-{[3-(benzyloxy)-6-methoxypyridin-2-yl]methyl}-N-[(6-{[(tert-butyldimethylsilyl)oxy]methyl}-4-{5-oxa-7-azaspiro[2.5]octan-6-yl}pyridin-2-yl)methyl]carbamate in 1,2 dichloroethane was added trifluoroacetic anhydride. The reaction mixture was stirred at room temperature for 5 hours. Purification by chromatography gave the title compound as a colorless oil. $^{1}$H-NMR (300 MHz, CDCl$_3$): δ 7.40-7.03 (m, 9H), 6.55 (d, 1H), 4.99 (s, 2H), 4.85-4.49 (m, 6H), 4.17-4.01 (m, 1H), 3.87 (s, 3H), 3.83-3.70 (m, 1H), 3.39-3.12 (m, 1H), 3.07-2.97 (m, 1H), 1.44-1.36 (m, 9H), 0.94 (s, 9H), 0.77-0.60 (m, 2H), 0.45-0.28 (m, 2H), 0.10 (d, 6H) ppm.

Tert-butyl N-{[3-(benzyloxy)-6-methoxypyridin-2-yl]methyl}-N-[(6-{[(tert-butyldimethylsilyl)oxy]methyl}-4-{5-oxa-7-azaspiro[2.5]octan-6-yl}pyridin-2-yl)methyl]carbamate

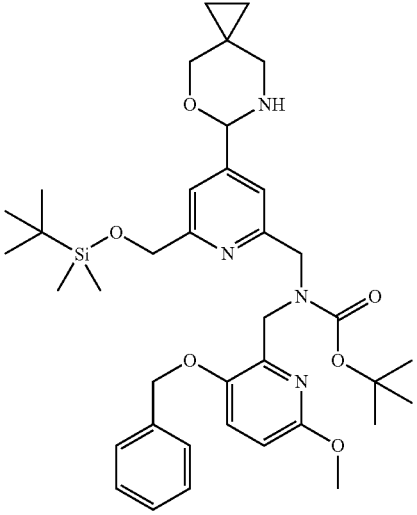 [SMILES: COc1ccc(OCc2ccccc2)c(CN(Cc2cc(C3NCC4(CC4)CO3)cc(CO[Si](C)(C)C(C)(C)C)n2)C(=O)OC(C)(C)C)n1]

A mixture of tert-butyl N-{[3-(benzyloxy)-6-methoxypyridin-2-yl]methyl}-N-[(6-{[(tert-butyldimethylsilyl)oxy]methyl}-4-formylpyridin-2-yl)methyl]carbamate and [1-(aminomethyl)cyclopropyl]methanol in 1,2-dichloroethane was stirred at room temperature for 3 hour and concentrated to afford the title compound as colorless oil as a 1:1 mixture of closed form (title compound) and opened form (imine). ¹H-NMR (300 MHz, CDCl₃): δ 8.19 (s, 0.5H), 7.66 (d, 0.5H), 7.52 (d, 0.5H), 7.44 (s, 0.5H), 7.39-7.28 (m, 5.5H), 7.17-7.11 (m, 1H), 6.56-6.51 (m, 1H), 5.18 (d, 0.5H), 5.00-4.96 (m, 2H), 4.81-4.75 (m, 3H), 4.73-4.69 (m, 1H), 4.65-4.61 (m, 1H), 4.58-4.52 (m, 1H), 4.24 (d, 0.5H), 3.89 (s, 1.5H), 3.88 (s, 1.5H), 3.67-3.64 (m, 2H), 3.47 (d, 0.5H), 3.36 (d, 0.5H), 2.42 (d, 0.5H), 1.44-1.36 (m, 9H), 0.97 (s, 4.5H), 0.96 (s, 4.5H), 0.66-0.34 (m, 4H), 0.13 (s, 3H), 0.11 (s, 3H) ppm.

Tert-butyl N-{[3-(benzyloxy)-6-methoxypyridin-2-yl]methyl}-N-[(6-{[(tert-butyldimethylsilyl)oxy]methyl}-4-formylpyridin-2-yl)methyl]carbamate

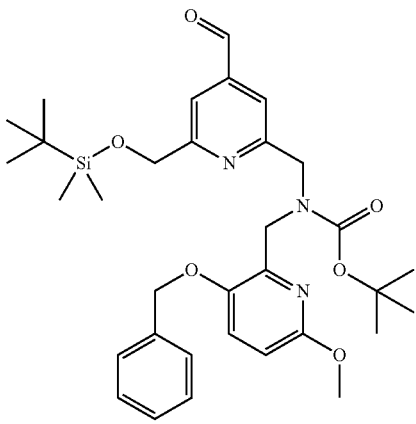 [SMILES: COc1ccc(OCc2ccccc2)c(CN(Cc2cc(C=O)cc(CO[Si](C)(C)C(C)(C)C)n2)C(=O)OC(C)(C)C)n1]

General Procedure I from tert-butyl N-{[3-(benzyloxy)-6-methoxypyridin-2-yl]methyl}-N-[(6-{[(tert-butyldimethylsilyl)oxy]methyl}-4-(hydroxymethyl)pyridin-2-yl)methyl]carbamate to afford the title compound as colorless oil. ¹H-NMR (300 MHz, CDCl₃): 10.05 (d, 1H), 7.76 (s, 1H), 7.58 (d, 1H), 7.39-7.27 (m, 5H), 7.15 (d, 1H), 6.53 (d, 1H), 4.98 (d, 2H), 4.84 (s, 2H), 4.80 (s, 1H), 4.74 (s, 1H), 4.67 (s, 1H), 4.59 (s, 1H), 3.86 (s, 3H), 1.40 (s, 9H), 0.97 (s, 9H), 0.14 (s, 6H) ppm.

Tert-butyl N-{[3-(benzyloxy)-6-methoxypyridin-2-yl]methyl}-N-[(6-{[(tert-butyldimethylsilyl)oxy]methyl}-4-(hydroxymethyl)pyridin-2-yl)methyl]carbamate

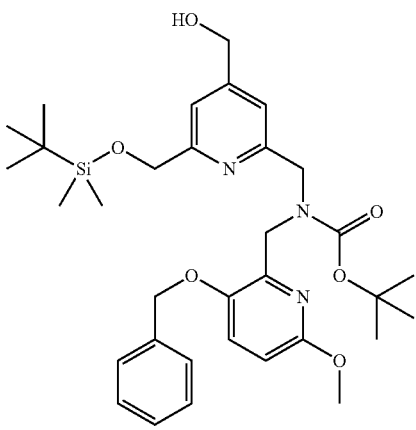 [SMILES: COc1ccc(OCc2ccccc2)c(CN(Cc2cc(CO)cc(CO[Si](C)(C)C(C)(C)C)n2)C(=O)OC(C)(C)C)n1]

To a solution of methyl 2-[({[3-(benzyloxy)-6-methoxypyridin-2-yl]methyl}[(tert-butoxy)carbonyl]amino)methyl]-6-{[(tert-butyldimethylsilyl)oxy]methyl}pyridine-4-carboxylate in ethanol was added NaBH₄ and refluxed for 2 hours. Purification by chromatography afforded the title compound as a colorless oil. ¹H-NMR (300 MHz, CDCl₃): δ 7.38-7.28 (m, 6H), 7.19 (d, 1H), 7.14 (dd, 1H), 6.53 (d, 1H), 4.97 (s, 2H), 4.77 (s, 2H), 4.74-4.68 (m, 4H), 4.61 (s, 1H), 4.55 (s, 1H), 3.87 (s, 3H), 2.27-2.15 (m, 1H), 1.40 (d, 9H), 0.96 (s, 9H), 0.11 (s, 6H) ppm.

Methyl 2-[({[3-(benzyloxy)-6-methoxypyridin-2-yl]methyl}[(tert-butoxy)carbonyl]amino)methyl]-6-{[(tert-butyldimethylsilyl)oxy]methyl}pyridine-4-carboxylate

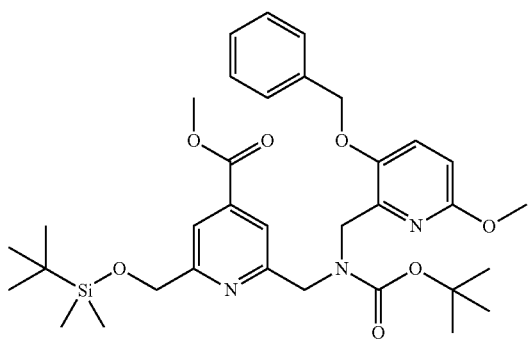 [SMILES: COC(=O)c1cc(CO[Si](C)(C)C(C)(C)C)nc(CN(Cc2nc(OC)ccc2OCc2ccccc2)C(=O)OC(C)(C)C)c1]

General Procedure D from methyl 2-[({[3-(benzyloxy)-6-methoxypyridin-2-yl]methyl}amino)methyl]-6-{[(tert-butyldimethylsilyl)oxy]methyl}pyridine-4-carboxylate. Purification by chromatography gave the title compound as a colorless oil. ¹H-NMR (300 MHz, CDCl₃): δ 7.90 (s, 1H), 7.72 (s, 1H), 7.38-7.30 (m, 5H), 7.15 (d, 1H), 6.54 (d, 1H), 4.99 (s, 2H), 4.81 (s, 2H), 4.78 (s, 1H), 4.73 (s, 1H), 4.65 (s, 1H), 4.57 (s, 1H), 3.95 (s, 3H), 3.88 (s, 3H), 1.41 (d, 9H), 0.97 (s, 9H), 0.13 (s, 6H) ppm.

Methyl 2-[({[3-(benzyloxy)-6-methoxypyridin-2-yl]methyl}amino)methyl]-6-{[(tert-butyldimethylsilyl)oxy]methyl}pyridine-4-carboxylate

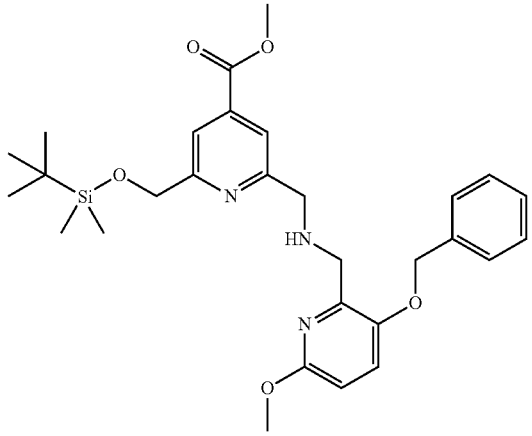 [SMILES: COC(=O)c1cc(CNCc2nc(OC)ccc2OCc2ccccc2)nc(CO[Si](C)(C)C(C)(C)C)c1]

General Procedure B from [3-(benzyloxy)-6-methoxy-pyridin-2-yl]methanamine and methyl 2-{[(tert-butyldimethylsilyl)oxy]methyl}-6-formylpyridine-4-carboxylate. Purification by chromatography afforded the title compound as a yellow oil. $^1$H-NMR (300 MHz, CDCl$_3$): δ 7.92 (s, 1H), 7.81 (s, 1H), 7.38-7.30 (m, 5H), 7.20 (d, 1H), 6.56 (d, 1H), 5.02 (s, 2H), 4.86 (s, 2H), 4.02 (s, 2H), 4.00 (s, 2H), 3.94 (s, 3H), 3.91 (s, 3H), 0.98 (s, 9H), 0.13 (s, 6H) ppm.

Reagents (S)-5H,6H,7H-cyclopenta[b]pyridin-7-amine

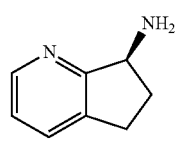

General Procedure E from (S)-7-azido-5H,6H,7H-cyclopenta[b]pyridine afforded the title compound. The title product can be used as reagent in one or more of the Synthetic Routes described herein. Used in the next step without characterization.

(S)-7-azido-5H,6H,7H-cyclopenta[b]pyridine

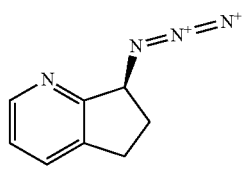

General Procedure F from (R)-5H,6H,7H-cyclopenta[b]pyridin-7-yl methanesulfonate afforded the title compound. Used in the next step without purification.

(R)-5H,6H,7H-cyclopenta[b]pyridin-7-yl methanesulfonate

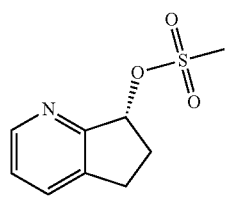

General Procedure G from (R)-5H,6H,7H-cyclopenta[b]pyridin-7-ol afforded the title compound. Used in the next step without purification. $^1$H-NMR (300 MHz, CDCl$_3$): δ 8.51 (d, 1H), 7.61 (d, 1H), 7.19 (m, 1H), 5.37 (m, 1H), 3.23 (m, 1H), 3.15 (s, 3H), 2.93 (m, 1H), 2.65 (m, 1H), 2.45 (m, 1H) ppm.

(R)-5H,6H,7H-cyclopenta[b]pyridin-7-ol

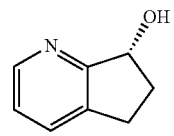

To a solution of (S)-Me-CBS (1 eq) in THF was added borane-THF (1M in THF) (0.2 eq) and the resulting mixture was stirred for 30 min at rt. 5H,6H,7H-cyclopenta[b]pyridin-7-one (1 eq) (prepared from literature procedure (Pereira, C. S., et als., Synlett 2013, 24 (7), 837-838) in THF was then added to the reaction mixture followed by dropwise addition of borane-THF (1M in THF) (1.0 eq). The resulting mixture was stirred overnight and then quenched with methanol. Aqueous work up and purification by column chromatography afforded the title product as brown solid. $^1$H-NMR (300 MHz, CDCl$_3$): δ 8.44 (d, 1H), 7.58 (d, 1H), 7.15 (m, 1H), 5.32-5.22 (m, 1H), 3.05 (m, 1H), 2.86 (m, 1H), 2.56 (m, 1H), 2.07 (m, 1H) ppm.

Methyl 2-(aminomethyl)-6-methylpyridine-4-carboxylate

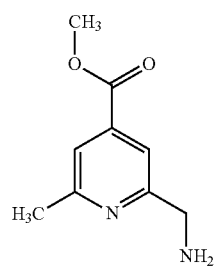

General Procedure E from methyl 2-[(hydroxyimino)methyl]-6-methylpyridine-4-carboxylate provided the title compound as yellow oil. The title compound can be used as reagent in one or more of the Synthetic Routes described herein. $^1$H-NMR (300 MHz, CDCl$_3$): δ 7.61 (s, 1H), 7.54 (s, 1H), 3.97 (s, 2H), 3.91 (s, 3H), 2.58 (s, 3H), 2.12 (s (br), 2H).

Methyl 2-[(hydroxyimino)methyl]-6-methylpyridine-4-carboxylate

General Procedure H from methyl 2-formyl-6-methylpyridine-4-carboxylate afforded the title compound as a white solid. $^1$H-NMR (300 MHz, CDCl$_3$): δ 8.30 (s, 1H), 8.18 (s (br), 1H), 8.13 (s, 1H), 7.71 (s, 1H), 3.97 (s, 3H), 2.97 (s, 3H).

Methyl 2-formyl-6-methylpyridine-4-carboxylate

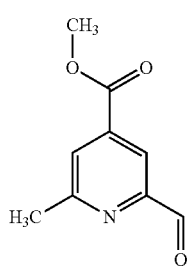

General procedure I from methyl 2-(hydroxymethyl)-6-methylpyridine-4-carboxylate afforded the title compound as a white solid. The title compound can be used as reagent in one or more of the Synthetic Routes described herein. $^1$H-NMR (300 MHz, CDCl$_3$): δ 10.07 (s, 1H), 8.26 (s, 1H), 7.93 (s, 1H), 3.96 (s, 3H), 2.72 (s, 3H).

Methyl 2-(hydroxymethyl)-6-methylpyridine-4-carboxylate

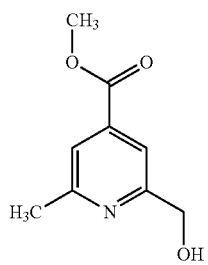

A solution of (NH$_4$)$_2$S$_2$O$_8$ in water was added to a solution of methyl 2-methylpyridine-4-carboxylate in methanol at reflux. The resulting reaction mixture was then stirred at reflux. Aqueous work up and recrystallization from DCM afforded the title compound as white solid. $^1$H-NMR (300 MHz, CDCl$_3$): δ 7.60 (s, 2H), 4.78 (s, 2H), 3.93 (s, 3H), 3.81 (s (br), 1H), 2.61 (s, 3H).

Methyl 2-(aminomethyl)-6-bromopyridine-4-carboxylate

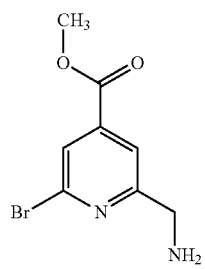

General Procedure J from methyl 2-bromo-6-[(1,3-dioxo-2,3-dihydro-1H-isoindol-2-yl)methyl]pyridine-4-carboxylate afforded the title compound as yellow oil. The title compound can be used as reagent in one or more of the Synthetic Routes described herein. $^1$H-NMR (300 MHz, CDCl$_3$): δ 7.84 (s, 1H), 7.76 (s, 1H), 3.97 (s, 2H), 3.91 (s, 3H), 2.65 (s (br), 2H).

Methyl 2-bromo-6-[(1,3-dioxo-2,3-dihydro-1H-isoindol-2-yl)methyl]pyridine-4-carboxylate

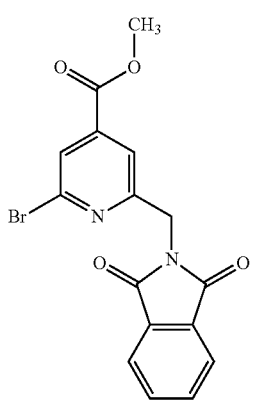

General Procedure K from methyl 2-bromo-6-(hydroxymethyl)pyridine-4-carboxylate and phthalimide afforded the title compound as white solid. $^1$H-NMR (300 MHz, CDCl$_3$): δ 7.89 (m, 3H), 7.78 (m, 2H), 7.70 (s, 1H), 4.72 (s, 2H), 3.93 (s, 3H).

Methyl 2-bromo-6-(hydroxymethyl)pyridine-4-carboxylate

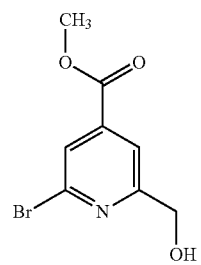

General Procedure L from methyl 6-bromo-2-methylpyridine-4-carboxylate afforded the title compound as light yellow oil. $^1$H-NMR (300 MHz, CDCl$_3$): δ 7.91 (s, 1H), 7.85 (s, 1H), 4.81 (s, 2H), 3.96 (s, 3H).

Methyl 2-(aminomethyl)-6-(methoxymethyl)pyridine-4-carboxylate

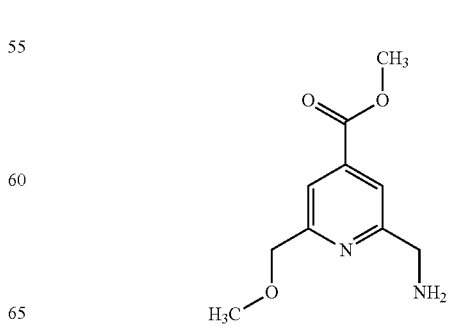

General Procedure E from methyl 2-[(hydroxyimino)methyl]-6-(methoxymethyl)pyridine-4-carboxylate afforded the title compound as yellow oil. The title compound can be used as reagent in one or more of the Synthetic Routes described herein. ¹H-NMR (300 MHz, CDCl₃): δ 7.83 (s, 1H), 7.74 (s, 1H), 4.62 (s, 2H), 4.03 (s, 2H), 3.95 (s, 3H), 3.50 (s, 3H), 2.03 (s (br), 2H).

Methyl 2-[(hydroxyimino)methyl]-6-(methoxymethyl)pyridine-4-carboxylate

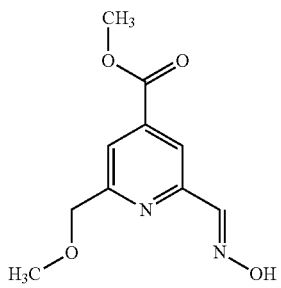 [SMILES: COCc1cc(C(=O)OC)cc(/C=N/O)n1]

General Procedure H from methyl 2-formyl-6-(methoxymethyl)pyridine-4-carboxylate afforded the title compound as a white solid. ¹H-NMR (300 MHz, CDCl₃): δ 8.29 (s, 1H), 8.23 (s, 1H), 7.98 (s, 1H), 7.86 (s (br), 1H), 4.67 (s, 2H), 3.98 (s, 3H), 3.53 (s, 3H).

Methyl 2-formyl-6-(methoxymethyl)pyridine-4-carboxylate

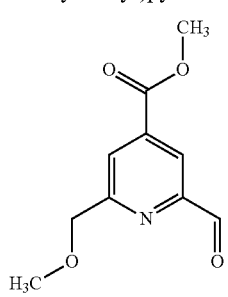

General Procedure I from 2-(hydroxymethyl)-6-(methoxymethyl)pyridine-4-carboxylate afforded the title compound as a yellow solid. The title compound can be used as reagent in one or more of the Synthetic Routes described herein. ¹H-NMR (300 MHz, CDCl₃): δ 10.06 (s, 1H), 8.32 (s, 1H), 8.17 (s, 1H), 4.68 (s, 2H), 3.96 (s, 3H), 3.51 (s, 3H).

Methyl 2-(hydroxymethyl)-6-(methoxymethyl)pyridine-4-carboxylate

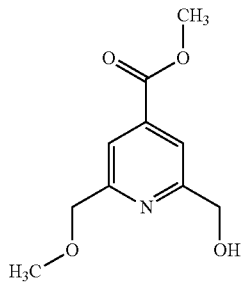

General Procedure L from methyl 2-(methoxymethyl)-6-methylpyridine-4-carboxylate afforded the title compound as light yellow oil. ¹H-NMR (300 MHz, CDCl₃): δ 7.86 (s, 1H), 7.74 (s, 1H), 4.80 (s, 2H), 4.61 (s, 2H), 3.94 (s, 3H), 3.49 (s, 3H).

Methyl 2-(methoxymethyl)-6-methylpyridine-4-carboxylate

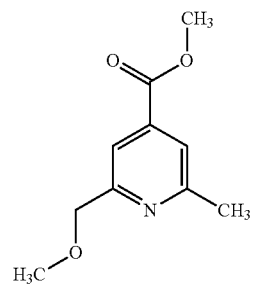

General Procedure M from methyl 2-(hydroxymethyl)-6-methylpyridine-4-carboxylate afforded the title compound as colorless oil. ¹H-NMR (300 MHz, CDCl₃): δ 7.77 (s, 1H), 7.62 (s, 1H), 4.60 (s, 2H), 3.94 (s, 3H), 3.50 (s, 3H), 2.61 (s, 3H).

5-Ethyl-1-[(4-fluorophenyl)methyl]-1H-imidazole-2-carbaldehyde

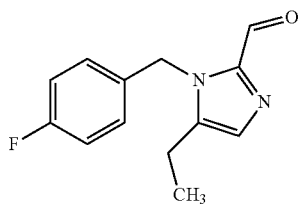 [SMILES: CCc1cnc(C=O)n1Cc1ccc(F)cc1]

General Procedure N from 5-ethyl-1-[(4-fluorophenyl)methyl]-1H-imidazole afforded the title product as colorless oil. The title product can be used as reagent in one or more of the Synthetic Routes described herein. ¹H-NMR (300 MHz, CDCl₃): δ 9.73 (s, 1H), 7.12 (s, 1H), 7.03-6.86 (m, 4H), 5.58 (s, 2H), 2.50 (q, 2H), 1.22 (t, 3H) ppm. ES-MS: 233 [M+1].

5-Ethyl-1-[(4-fluorophenyl)methyl]-1H-imidazole

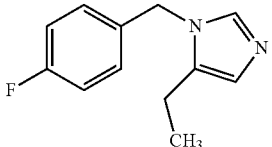

General Procedure O from propionaldehyde and 4-fluorobenzylamine afforded the title product as yellow oil. ¹H-NMR (300 MHz, CDCl₃): δ 7.38 (s, 1H), 6.99-6.80 (m, 4H), 6.74 (s, 1H), 4.93 (s, 2H), 2.31 (q, 2H), 1.08 (t, 3H) ppm. ES-MS: 205 [M+1].

1-[(4-Fluorophenyl)methyl]-5-(propan-2-yl)-1H-imidazole-2-carbaldehyde

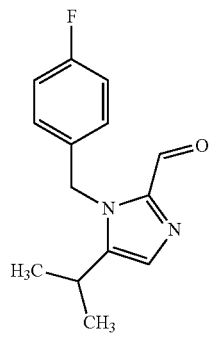

General Procedure N from 1-[(4-fluorophenyl)methyl]-5-(propan-2-yl)-1H-imidazole afforded the title product as colorless oil. The title compound can be used as reagent in one or more of the Synthetic Routes described herein. $^1$H-NMR (300 MHz, CDCl$_3$): δ 9.75 (s, 1H), 7.20 (s, 1H), 7.06-6.90 (m, 4H), 5.63 (s, 2H), 2.94-2.77 (m, 1H), 1.22 (d, 6H) ppm. ES-MS: 247 [M+1].

1-[(4-fluorophenyl)methyl]-5-(propan-2-yl)-1H-imidazole

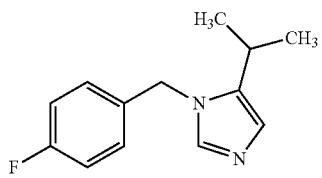 [SMILES: CC(C)c1cncn1Cc1ccc(F)cc1]

General Procedure O from iso-butyraldehyde and 4-fluorobenzylamine gave the title product as yellow oil. $^1$H-NMR (300 MHz, CDCl$_3$): δ 7.41 (s, 1H), 7.02 (d, 4H), 6.87 (s, 1H), 5.07 (s, 2H), 2.79-2.64 (m, 1H), 1.19 (d, 6H) ppm. ES-MS: 219 [M+1].

5-(butan-2-yl)-1-[(4-fluorophenyl)methyl]-1H-imidazole-2-carbaldehyde

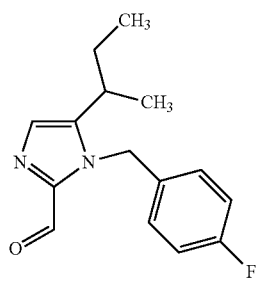 [SMILES: CCC(C)c1cnc(C=O)n1Cc1ccc(F)cc1]

General Procedure N from 5-(butan-2-yl)-1-[(4-fluorophenyl)methyl]-1H-imidazole afforded the title product as colorless oil. The title product can be used as reagent in one or more of the Synthetic Routes described herein. $^1$H-NMR (300 MHz, CDCl$_3$): δ 9.77 (s, 1H), 7.18 (s, 1H), 7.08-6.92 (m, 4H), 5.63 (s, 2H), 2.71-2.55 (m, 1H), 1.69-1.48 (m, 2H), 1.17 (d, 3H), 0.82 (t, 3H) ppm. ES-MS: 261 [M+1].

5-(butan-2-yl)-1-[(4-fluorophenyl)methyl]-1H-imidazole

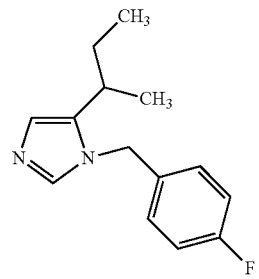 [SMILES: CCC(C)c1cncn1Cc1ccc(F)cc1]

General Procedure O from 2-methylbutyraldehyde and 4-fluorobenzylamine afforded the title product as yellow oil. $^1$H-NMR (300 MHz, CDCl$_3$): δ 7.41 (s, 1H), 7.02 (d, 4H), 6.85 (s, 1H), 5.05 (s, 2H), 2.56-2.41 (m, 1H), 1.67-1.48 (m, 2H), 1.14 (d, 3H), 0.82 (t, 3H) ppm. ES-MS: 233 [M+1].

1-[(4-fluorophenyl)methyl]-5-(pentan-2-yl)-1H-imidazole-2-carbaldehyde

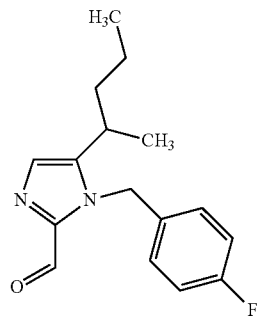 [SMILES: CCCC(C)c1cnc(C=O)n1Cc1ccc(F)cc1]

General Procedure N from 1-[(4-fluorophenyl)methyl]-5-(pentan-2-yl)-1H-imidazole afforded the title product as colorless oil. The title product can be used as reagent in one or more of the Synthetic Routes described herein. $^1$H-NMR (300 MHz, CDCl$_3$): δ 9.77 (s, 1H), 7.18 (s, 1H), 7.06-6.92 (m, 4H), 5.64 (s, 2H), 2.78-2.63 (m, 1H), 1.61-1.44 (m, 2H), 1.30-1.13 (m, 5H), 0.80 (t, 3H) ppm. ES-MS: 275 [M+1].

1-[(4-fluorophenyl)methyl]-5-(pentan-2-yl)-1H-imidazole

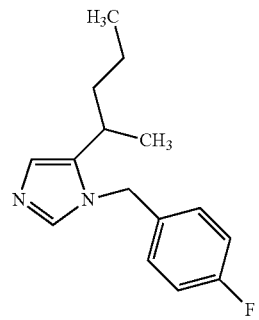 [SMILES: CCCC(C)c1cncn1Cc1ccc(F)cc1]

General Procedure O from 2-Methylvaleraldehyde and 4-fluorobenzylamine afforded the title product as yellow oil. $^1$H-NMR (300 MHz, CDCl$_3$): δ 7.42 (s, 1H), 7.02 (d, 4H), 6.84 (s, 1H), 5.05 (s, 2H), 2.63-2.49 (m, 1H), 1.60-1.35 (m, 2H), 1.31-1.15 (m, 2H), 1.12 (d, 3H), 0.82 (t, 3H) ppm. ES-MS: 247 [M+1].

{4-[(4-Fluorophenyl)methyl]-4H-1,2,4-triazol-3-yl}methanamine

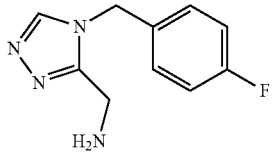

General Procedure P from [(t-butoxycarbonyl)amino]acetic acid and (4-fluorophenyl)methanamine to afford the title compound as colorless gum. ¹H-NMR (300 MHz, CDCl₃): δ 8.08 (s, 1H), 7.20-7.02 (m, 4H), 5.23 (s, 2H), 3.97 (s, 2H), 1.60 (br s, 2H) ppm.

[5-Methyl-4-(3-phenylpropyl)-4H-1,2,4-triazol-3-yl]methanamine

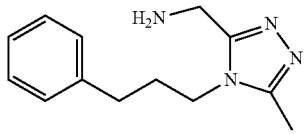 [SMILES: Cc1nnc(CN)n1CCCc1ccccc1]

¹H-NMR (300 MHz, CDCl₃): δ 7.37-7.16 (m, 5H), 3.94-3.85 (m, 4H), 2.70 (t, 2H), 2.35 (s, 3H), 2.10-1.99 (m, 2H), 1.51 (br s, 2H) ppm.

[6-Methoxy-3-(2-phenylethoxy)pyridin-2-yl]methanamine

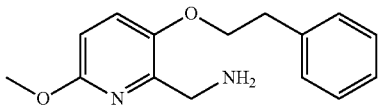 [SMILES: COc1ccc(OCCc2ccccc2)c(CN)n1]

General Procedure E from 6-methoxy-3-(2-phenylethoxy)pyridine-2-carbonitrile. Purification by chromatography if needed to afford the title compound as light yellow gum. ¹H-NMR (300 MHz, CD₃OD): δ 7.49 (d, 1H), 7.35-7.20 (m, 5H), 7.76 (d, 1H), 4.29 (t, 2H), 4.03 (s, 2H), 3.92 (s, 3H), 3.10 (t, 2H) ppm.

6-Methoxy-3-(2-phenylethoxy)pyridine-2-carbonitrile

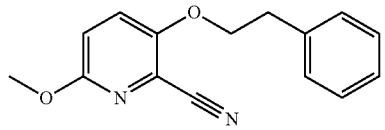 [SMILES: COc1ccc(OCCc2ccccc2)c(C#N)n1]

General Procedure R from 2-methoxy-5-(2-phenylethoxy)pyridin-1-ium-1-olate. Purification by chromatography afforded the title compound as orange solid. ¹H-NMR (300 MHz, CDCl₃): δ 7.38-7.22 (m, 6H), 6.89 (d, 1H), 4.25 (t, 2H), 3.91 (s, 3H), 3.16 (t, 2H) ppm.

2-Methoxy-5-(2-phenylethoxy)pyridin-1-ium-1-olate

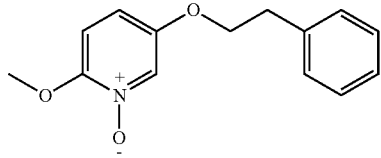

General Procedure S from 2-methoxy-5-(2-phenylethoxy)pyridine. Purification by chromatography gave the title compound as light yellow solid. ¹H-NMR (300 MHz, CDCl₃): δ 8.02 (d, 1H), 7.36-7.23 (m, 5H), 6.89 (m, 1H), 6.79 (d, 1H), 4.14 (t, 2H), 4.03 (s, 3H), 3.08 (t, 2H) ppm.

2-Methoxy-5-(2-phenylethoxy)pyridine

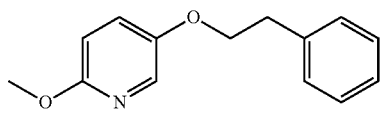 [SMILES: COc1ccc(OCCc2ccccc2)cn1]

General Procedure T from 6-methoxypyridin-3-ol. Purification by chromatography afforded the title compound as brown oil. ¹H-NMR (300 MHz, CDCl₃): δ 7.81 (d, 1H), 7.37-7.17 (m, 6H), 6.68 (d, 1H), 4.17 (t, 2H), 3.90 (s, 3H), 3.09 (t, 2H) ppm.

[5-Methyl-4-(4-methylpentyl)-4H-1,2,4-triazol-3-yl]methanamine

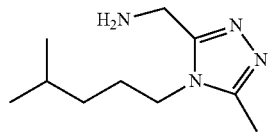

General Procedure P from tert-butyl N-{[(4-methylpentyl)carbamothioyl]methyl}carbamate and acetohydrazide. Purification by chromatography afforded the title compound. ¹H-NMR (300 MHz, CDCl₃): δ 4.4 (brs, 2H), 3.8 (t, 2H), 2.4 (s, 3H), 1.6 (m, 2H), 1.5 (m, 1H), 1.2 (m, 2H), 1.4 (s, 9H), 1.2 (m, 2H), 0.85 (d, 6H).

1-[(4-Fluorophenyl)methyl]-4-(hydroxymethyl)-1H-imidazole-2-carbaldehyde

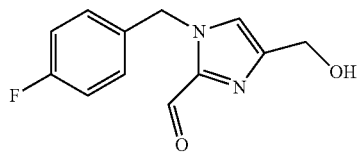 [SMILES: O=Cc1nc(CO)cn1Cc1ccc(F)cc1]

General Procedure N from {1-[(4-fluorophenyl)methyl]-1H-imidazol-4-yl}methanol. Aqueous work up and purification by chromatography afforded the title compound as yellow oil. $^1$H NMR (300 MHz, CDCl$_3$): δ ppm 9.80 (s, 1H), 6.90-7.20 (m, 5H), 5.50 (s, 2H), 4.55 (s, 2H).

{1-[(4-Fluorophenyl)methyl]-1H-imidazol-4-yl}methanol

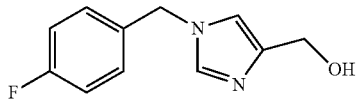 [SMILES: OCc1cn(Cc2ccc(F)cc2)cn1]

General Procedure T from 1H-imidazol-4-ylmethanol and 1-(bromomethyl)-4-fluorobenzene. Purification by chromatography afforded the title compound as yellow oil. $^1$H NMR (300 MHz, CDCl$_3$): δ ppm 7.40 (s, 1H), 6.90-7.20 (m, 4H), 6.80 (s, 1H), 5.00 (s, 2H), 4.50 (s, 2H).

Ethyl 2-(aminomethyl)-6-{[(tert-butyldimethylsilyl)oxy]methyl}pyridine-4-carboxylate

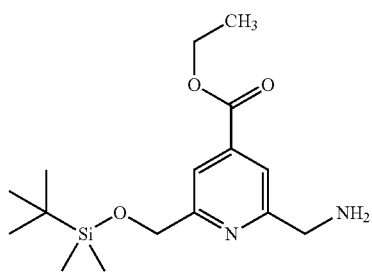 [SMILES: CCOC(=O)c1cc(CN)nc(CO[Si](C)(C)C(C)(C)C)c1]

General Procedure E from ethyl 2-{[(tert-butyldimethylsilyl)oxy]methyl}-6-cyanopyridine-4-carboxylate. Purification by chromatography afforded the title compound as colorless oil. $^1$H NMR (300 MHz, CDCl$_3$): δ ppm 8.00 (s, 1H), 7.80 (s, 1H), 4.80 (s, 2H), 4.50 (s, 2H), 4.35 (m, 2H), 1.35 (t, 3H), 1.00 (s, 9H), 0.20 (s, 6H).

Ethyl 2-{[(tert-butyldimethylsilyl)oxy]methyl}-6-cyanopyridine-4-carboxylate

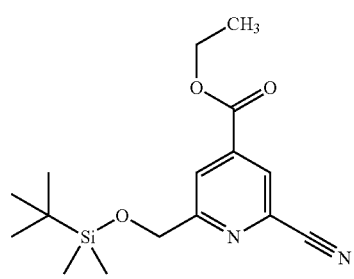 [SMILES: CCOC(=O)c1cc(C#N)nc(CO[Si](C)(C)C(C)(C)C)c1]

General Procedure R from 2-{[(tert-butyldimethylsilyl)oxy]methyl}-4-(ethoxycarbonyl)pyridin-1-ium-1-olate. Purification by chromatography afforded the title compound as colorless oil. $^1$H NMR (300 MHz, CDCl$_3$): δ ppm 8.25 (s, 1H), 8.00 (s, 1H), 4.90 (s, 2H), 4.30 (m, 2H), 1.35 (t, 3H), 1.00 (s, 9H), 0.20 (s, 6H).

2-{[(Tert-butyldimethylsilyl)oxy]methyl}-4-(ethoxycarbonyl)pyridin-1-ium-1-olate

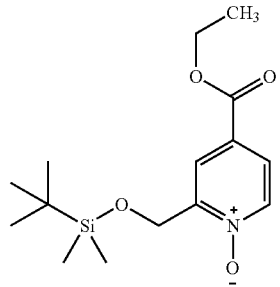 [SMILES: CCOC(=O)c1cc[n+]([O-])c(CO[Si](C)(C)C(C)(C)C)c1]

General Procedure S from 2-{[(tert-butyldimethylsilyl)oxy]methyl}-4-(ethoxycarbonyl)pyridin-1-ium-1-olate Purification by chromatography afforded the title compound as white solid. $^1$H NMR (300 MHz, CDCl$_3$): δ ppm 8.10 (m, 2H), 7.70 (d, 1H), 4.90 (s, 2H), 4.30 (m, 2H), 1.35 (t, 3H), 1.00 (s, 9H), 0.20 (s, 6H).

{4-[(4-Fluorophenyl)methyl]-5-methyl-4H-1,2,4-triazol-3-yl}methanamine

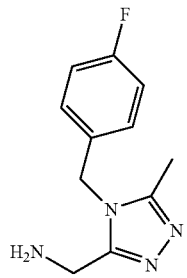 [SMILES: Cc1nnc(CN)n1Cc1ccc(F)cc1]

General Procedure P from [(t-butoxycarbonyl)amino]acetic acid, (4-fluorophenyl)methanamine and acetohydrazide to get the title compound as yellow gum. $^1$H-NMR (300 MHz, CDCl$_3$): δ 6.97 (s, 2H), 6.95 (s, 2H), 5.14 (s, 2H), 3.87 (s, 2H), 2.26 (s, 3H) ppm.

{5-Ethyl-4-[(4-fluorophenyl)methyl]-4H-1,2,4-triazol-3-yl}methanamine

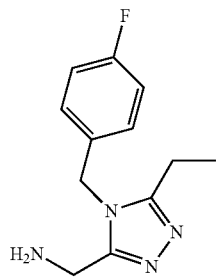 [SMILES: CCc1nnc(CN)n1Cc1ccc(F)cc1]

General Procedure P from [(t-butoxycarbonyl)amino]acetic acid, (4-fluorophenyl)methanamine and propane hydrazide to afford the title compound as yellow gum. ¹H-NMR (300 MHz, CDCl₃): δ 6.98 (s, 2H), 6.95 (s, 2H), 5.15 (s, 2H), 3.86 (s, 2H), 2.58 (q, 2H), 1.21 (t, 3H) ppm.

Methyl 2-{[(tert-butyldimethylsilyl)oxy]methyl}-6-formylpyridine-4-carboxylate

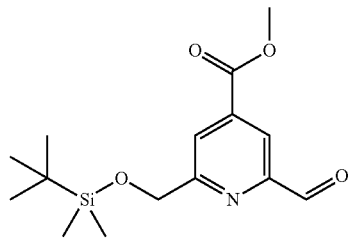 [SMILES: COC(=O)c1cc(C=O)nc(CO[Si](C)(C)C(C)(C)C)c1]

By General Procedure I from methyl 2-{[(tert-butyldimethylsilyl)oxy]methyl}-6-(hydroxymethyl)pyridine-4-carboxylate. Purification by chromatography afforded the title compound as colorless gum. ¹H-NMR (300 MHz, CDCl₃): δ 10.07 (s, 1H), 8.34 (s, 1H), 8.29 (s, 1H), 4.96 (s, 2H), 3.99 (s, 3H), 0.98 (s, 9H), 0.16 (s, 6H) ppm.

Methyl 2-{[(tert-butyldimethylsilyl)oxy]methyl}-6-(hydroxymethyl)pyridine-4-carboxylate

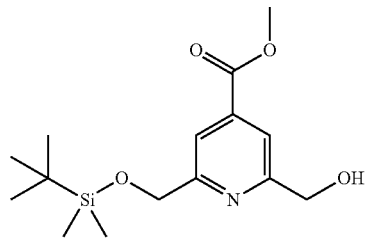 [SMILES: COC(=O)c1cc(CO)nc(CO[Si](C)(C)C(C)(C)C)c1]

General Procedure U from methyl 2,6-bis(hydroxymethyl)pyridine-4-carboxylate. Purification by chromatography gave the title compound as colorless oil. ¹H-NMR (300 MHz, CDCl₃): δ 7.96 (s, 1H), 7.69 (s, 1H), 4.88 (s, 2H), 4.80 (s, 2H), 3.97 (s, 3H), 3.69 (s, 1H), 0.98 (s, 9H), 0.15 (s, 6H) ppm.

Methyl 2,6-bis(hydroxymethyl)pyridine-4-carboxylate

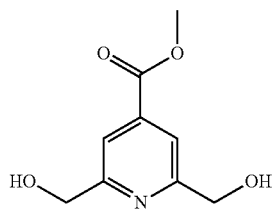

Synthesized from literature procedure (Ref: Org. Lett. 2014, 16, 2787-2789). A solution of (NH₄)₂S₂O₈ in water was added to a solution of methyl pyridine-4-carboxylate in methanol at reflux. Aqueous work up and column chromatography afforded the title compound as colorless gum. ¹H-NMR (300 MHz, CDCl₃): δ 7.23 (s, 2H), 4.16 (s, 4H), 3.24 (s, 3H) ppm.

{4-[(4-Fluorophenyl)methyl]-5-(thiophen-2-ylmethyl)-4H-1,2,4-triazol-3-yl}methanamine

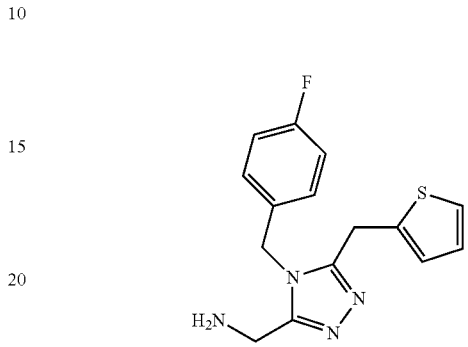

General Procedure P from [(t-butoxycarbonyl)amino]acetic acid, (4-fluorophenyl)methanamine and 2-(thiophen-2-yl)acetohydrazide to afford the title compound as yellow gum. ¹H-NMR (300 MHz, CDCl₃): δ 7.06 (d, 1H), 6.92-6.77 (m, 5H), 6.70 (s, 1H), 5.05 (s, 2H), 4.15 (s, 2H), 3.81 (s, 2H), 1.60 (s, 2H) ppm.

1-[2-(Pyrimidin-5-yl)ethyl]-1H-imidazole-2-carbaldehyde

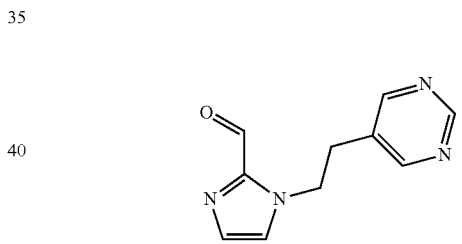

General Procedure T from 1H-imidazole-2-carbaldehyde and 5-(2-chloroethyl)pyrimidine. Purification by chromatography afforded the title compound as colorless oil. ¹H-NMR (300 MHz, CDCl₃): δ 9.83 (s, 1H), 9.11 (s, 1H), 8.52 (s, 2H), 7.28 (s, 1H), 6.97 (s, 1H), 4.64 (t, 2H), 3.11 (t, 2H) ppm.

5-(2-Chloroethyl)pyrimidine

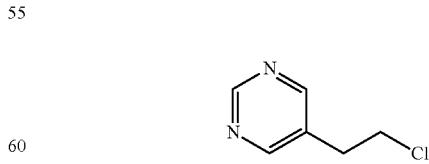

To a solution of 2-(pyrimidin-5-yl)ethan-1-ol in DCM was added SOCl₂ at 0° C. and stirred at room temperature for 2 hours. Concentrated to afford the title compound as yellow oil. ¹H-NMR (300 MHz, CDCl₃): δ 9.13 (s, 1H), 8.65 (s, 2H), 3.75 (t, 2H), 3.08 (t, 2H) ppm.

{4-[(4-Fluorophenyl)methyl]-5-(methylsulfanyl)-4H-1,2,4-triazol-3-yl}methanamine

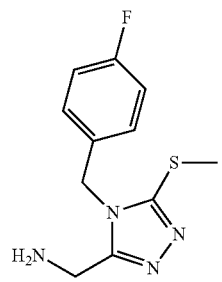

General procedure Q from tert-butyl (4-(4-fluorobenzyl)-5-(methylthio)-4H-1,2,4-triazol-3-yl)methylcarbamate to afford the title compound which was used in the next step without further characterization.

Tert-butyl (4-(4-fluorobenzyl)-5-(methylthio)-4H-1,2,4-triazol-3-yl)methylcarbamate

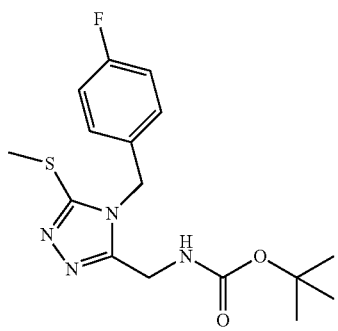 [SMILES: CSc1nnc(CNC(=O)OC(C)(C)C)n1Cc1ccc(F)cc1]

A solution of tert-butyl (4-(4-fluorobenzyl)-5-mercapto-4H-1,2,4-triazol-3-yl)methylcarbamate in ethanol was added 1N NaOH followed by a solution of MeI in EtOH at 0° C., stirred at room temperature for 12 hours. Aqueous work up and chromatography if needed afforded the title compound. $^1$H-NMR (300 MHz, CDCl$_3$): δ 7.12 (t, 2H), 7.04 (t, 2H), 5.16 (s, 2H), 5.15-5.08 (br s, 1H), 4.45 (s, 2H), 2.70 (s, 3H), 1.40 (s, 9H) ppm.

Tert-butyl N-({4-[(4-fluorophenyl)methyl]-5-sulfanyl-4H-1,2,4-triazol-3-yl}methyl)carbamate

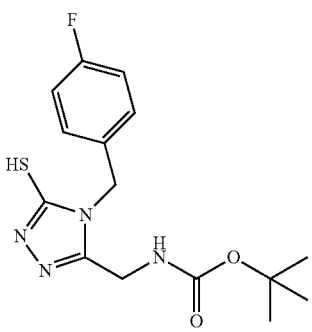 [SMILES: CC(C)(C)OC(=O)NCc1nnc(S)n1Cc1ccc(F)cc1]

The title compound was obtained from the general procedure outlined in Pct. Int. Appl., 2011130661, 20 Oct. 2011. $^1$H-NMR (300 MHz, CD$_3$OD): δ 7.38 (t, 2H), 7.10 (t, 2H), 5.34 (s, 2H), 4.22 (s, 2H), 1.40 (s, 9H) ppm.

{4-[(4-Fluorophenyl)methyl]-5-propyl-4H-1,2,4-triazol-3-yl}methanamine

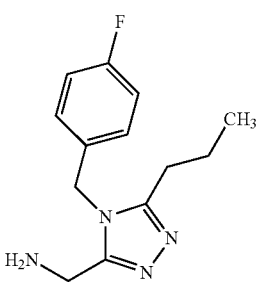 [SMILES: CCCc1nnc(CN)n1Cc1ccc(F)cc1]

General Procedure P from [(t-butoxycarbonyl)amino]acetic acid, (4-fluorophenyl)methanamine and butanehydrazide to afford the title compound, which was used in the next step without further characterization.

[6-Methoxy-3-(2-methylpropyl)pyridin-2-yl]methanamine

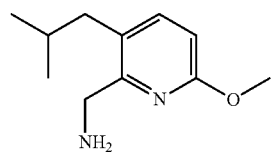

General Procedure E from 6-methoxy-3-(2-methylpropyl)pyridine-2-carbonitrile. Purification by chromatography afforded the title compound. $^1$H-NMR (300 MHz, CDCl$_3$): δ 7.31 (d, 1H), 6.56 (d, 1H), 3.95 (s, 3H), 3.88 (s, 2H), 2.40 (d, 2H), 1.86-1.70 (m, 3H), 0.91 (d, 6H) ppm.

6-Methoxy-3-(2-methylpropyl)pyridine-2-carbonitrile

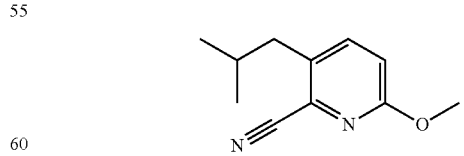

General Procedure R from 2-methoxy-5-(2-methylpropyl)pyridin-1-ium-1-olate. Purification by chromatography afforded the title compound. $^1$H-NMR (300 MHz, CDCl$_3$): δ 7.48 (d, 1H), 6.90 (d, 1H), 3.95 (s, 3H), 2.65 (d, 2H), 2.01-1.87 (m, 1H), 0.97 (d, 6H) ppm.

2-Methoxy-5-(2-methylpropyl)pyridin-1-ium-1-olate

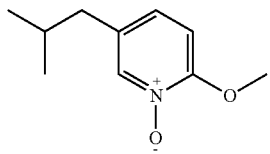

General Procedure S from 2-methoxy-5-(2-methylpropyl)pyridine. Purification by chromatography afforded the title compound. $^1$H-NMR (300 MHz, CDCl$_3$): δ 8.12 (s, 1H), 7.10 (d, 1H), 6.83 (d, 1H), 4.07 (s, 3H), 2.39 (d, 2H), 1.91-1.77 (m, 1H), 0.92 (d, 6H) ppm.

2-Methoxy-5-(2-methylpropyl)pyridine

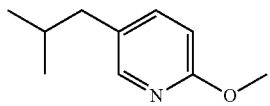

General Procedure C from 5-bromo-2-methoxypyridine and isobutyl boronic acid. Purification by chromatography afforded the title compound. $^1$H-NMR (300 MHz, CDCl$_3$): δ 7.94 (s, 1H), 7.37 (dd, 1H), 6.68 (d, 1H), 3.93 (s, 3H), 2.40 (d, 2H), 1.88-1.74 (m, 1H), 0.91 (d, 6H) ppm.

[5-Ethyl-4-(4-methylpentyl)-4H-1,2,4-triazol-3-yl]methanamine

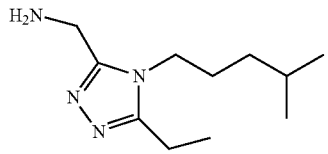

General Procedure P from 4-methylpentan-1-amine, N-Boc glycine, and propanehydrazide afforded the title compound as a yellow liquid. $^1$H-NMR (300 MHz, CDCl$_3$): δ 4.00 (s, 2H), 3.87 (t, 2H), 2.73 (q, 2H), 1.75-1.51 (m, 5H), 1.41 (t, 3H), 1.27-1.18 (m, 2H), 0.90 (d, 6H) ppm.

[4-(3-Phenylpropyl)-4H-1,2,4-triazol-3-yl]methanamine

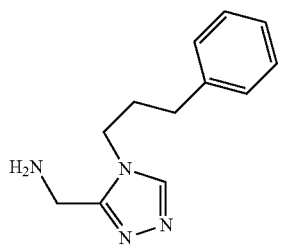 [SMILES: NCc1nncn1CCCc1ccccc1]

General Procedure P from [(t-butoxycarbonyl)amino]acetic acid, 3-phenylpropan-1-amine and N-Boc glycine and formohydrazide to afford the title compound. $^1$H-NMR (300 MHz, CDCl$_3$): δ 8.09 (s, 1H), 7.34-7.15 (m, 5H), 4.00 (m, 4H), 2.68 (t, 2H), 2.16 (m, 2H) ppm.

[5-Ethyl-4-(3-phenylpropyl)-4H-1,2,4-triazol-3-yl]methanamine

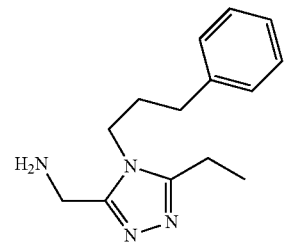 [SMILES: CCc1nnc(CN)n1CCCc1ccccc1]

General Procedure P from [(t-butoxycarbonyl)amino]acetic acid, 3-phenylpropan-1-amine and N-Boc glycine and propanehydrazide to afford the title compound. $^1$H-NMR (300 MHz, CDCl$_3$): δ 7.32-7.15 (m, 5H), 4.05 (s, 2H), 3.98 (t, 2H), 2.68 (t, 2H), 2.58 (q, 2H), 2.02 (m, 2H), 1.31 (t, 3H) ppm.

Methyl 2-[(acetyloxy)methyl]-6-formylpyridine-4-carboxylate

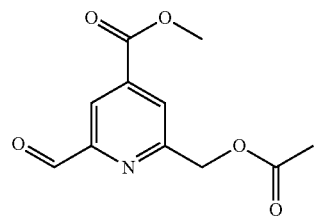 [SMILES: COC(=O)c1cc(C=O)nc(COC(C)=O)c1]

General Procedure I from methyl 2-[(acetyloxy)methyl]-6-(hydroxymethyl)pyridine-4-carboxylate afforded the title compound as an off white solid. $^1$H-NMR (300 MHz, CDCl$_3$): δ 10.12 (s, 1H), 8.41 (s, 1H), 8.13 (s, 1H), 5.38 (s, 2H), 4.01 (s, 3H), 2.22 (s, 3H) ppm.

Methyl 2-[(acetyloxy)methyl]-6-(hydroxymethyl)pyridine-4-carboxylate

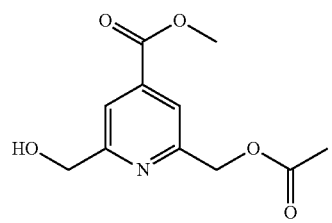 [SMILES: COC(=O)c1cc(CO)nc(COC(C)=O)c1]

General Procedure L from methyl 6-[(acetyloxy)methyl]-2-methylpyridine-4-carboxylate afforded the title compound. $^1$H-NMR (300 MHz, CDCl$_3$): δ 7.78 (s, 2H), 5.27 (s, 2H), 4.82 (s, 2H), 3.96 (s, 3H), 2.18 (s, 3H) ppm.

225

Methyl 6-[(acetyloxy)methyl]-2-methylpyridine-4-carboxylate

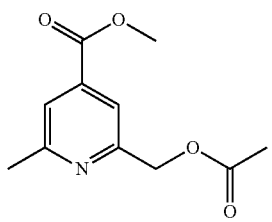 [SMILES: COC(=O)c1cc(C)nc(COC(C)=O)c1]

Methyl 6-(hydroxymethyl)-2-methylpyridine-4-carboxylate was treated with acetic anhydride and triethylamine in DCM at room temperature. Aqueous work up afforded the title compound. $^1$H-NMR (300 MHz, CDCl$_3$): δ 7.65 (s, 1H), 7.61 (s, 1H), 5.20 (s, 2H), 3.92 (s, 3H), 2.59 (s, 3H), 2.15 (s, 3H) ppm.

1-[5-(Aminomethyl)-4-[(4-fluorophenyl)methyl]-4H-1,2,4-triazol-3-yl]ethan-1-ol

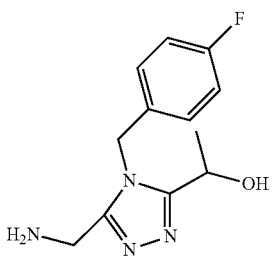

General Procedure P from 4-methylpentan-1-amine, N-Boc glycine, and propanehydrazide afforded the title compound as a yellow liquid $^1$H-NMR (300 MHz, CDCl$_3$): δ 7.06 (m, 4H), 5.42 (s, 2H), 4.90 (q, 1H), 3.79 (s, 2H), 1.61 (d, 3H) ppm.

2-[(Tert-butyldimethylsilyl)oxy]propanehydrazide

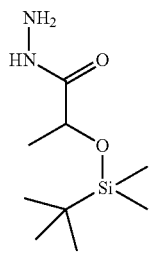

Methyl 2-[(tert-butyldimethylsilyl)oxy]propanoate, hydrazine and ethanol were heated to reflux. Purification by chromatography afforded the title compound as colorless oil. $^1$H-NMR (300 MHz, CDCl$_3$): δ 7.70 (br, 1H), 4.31 (m, 1H), 3.84 (br s, 2H), 1.41 (d, 3H), 0.93 (s, 9H), 0.12 (s, 3H), 0.11 (s, 3H) ppm.

226

Methyl 2-[(tert-butyldimethylsilyl)oxy]propanoate

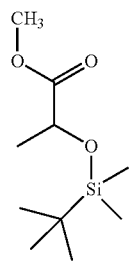

General Procedure U from methyl 2-hydroxypropanoate afforded the title compound as colorless oil. $^1$H-NMR (300 MHz, CDCl$_3$): δ 4.31 (m, 1H), 3.71 (s, 3H), 1.39 (d, 3H), 0.89 (s, 9H), 0.09 (s, 3H), 0.06 (s, 3H) ppm.

(3-(Benzyloxy)-6-methoxypyridin-2-yl)methanamine

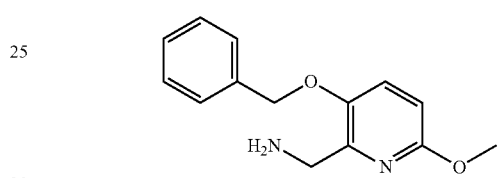

General Procedure E from 3-(benzyloxy)-6-methoxypyridine-2-carbonitrile afforded the title compound as an off white solid. $^1$H NMR (300 MHz, CDCl$_3$): δ 7.30 (m, 6H) 7.15 (d, 1H) 6.50 (d, 1H), 5.00 (s, 2H), 3.90 (s, 2H), 3.80 (s, 3H) ppm.

3-(Benzyloxy)-6-methoxypyridine-2-carbonitrile

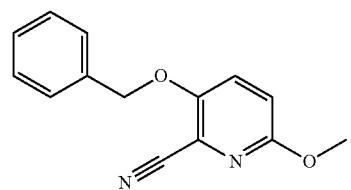 [SMILES: COc1ccc(OCc2ccccc2)c(C#N)n1]

General Procedure R from 5-(benzyloxy)-2-methoxypyridin-1-ium-1-olate afforded the title compound. $^1$H NMR (300 MHz, CDCl$_3$): δ 7.30 (m, 6H) 6.85 (d, 1H), 5.00 (s, 2H), 3.90 (s, 3H) ppm.

5-(Benzyloxy)-2-methoxypyridin-1-ium-1-olate

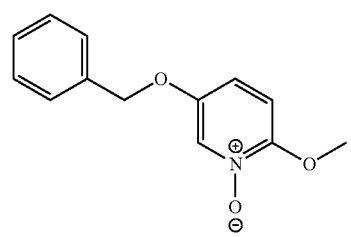 [SMILES: COc1ccc(OCc2ccccc2)c[n+]1[O-]]

General Procedure S from 5-(benzyloxy)-2-methoxypyridine afforded the title compound as yellow solid. ¹H NMR (300 MHz, CDCl₃): δ 8.10 (d, 1H) 7.40 (m, 5H), 6.95 (dd, 1H), 6.80 (d, 1H), 5.00 (s, 2H), 4.10 (s, 3H) ppm.

5-(Benzyloxy)-2-methoxypyridine

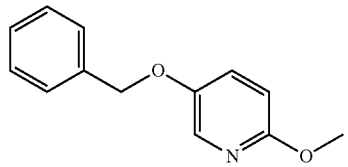 [SMILES: COc1ccc(OCc2ccccc2)cn1]

General Procedure T from 6-methoxypyridin-3-ol afforded the title compound. ¹H NMR (300 MHz, CDCl₃): δ 7.80 (s, 1H) 7.30 (m, 6H), 6.70 (d, 1H), 5.00 (s, 2H), 3.90 (s, 3H) ppm.

2-[3-(Benzyloxy)-6-methoxypyridin-2-yl]ethan-1-amine

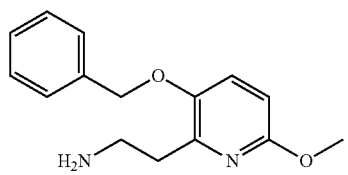 [SMILES: COc1ccc(OCc2ccccc2)c(CCN)n1]

General Procedure E from 2-(3-(benzyloxy)-6-methoxypyridin-2-yl)acetonitrile afforded the title compound as an off white solid. ¹H NMR (300 MHz, CDCl₃): δ 7.40 (m, 5H), 7.20 (d, 1H), 6.60 (d, 1H), 5.00 (s, 2H), 3.90 (s, 3H), 3.20 (m, 2H), 3.00 (m, 2H) ppm.

2-(3-(benzyloxy)-6-methoxypyridin-2-yl)acetonitrile

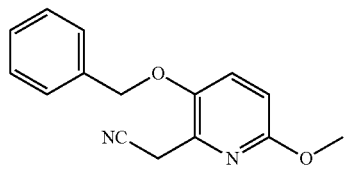 [SMILES: COc1ccc(OCc2ccccc2)c(CC#N)n1]

To a solution of 3-(benzyloxy)-2-(chloromethyl)-6-methoxypyridine in DMSO was added NaCN and heated at 60° C. for 4 hours. Aqueous workup and purification afforded the title compound as yellow solid. ¹H NMR (300 MHz, CDCl3): δ 7.40 (m, 5H), 7.30 (d, 1H), 6.70 (d, 1H), 5.05 (s, 2H), 3.90 (s, 3H), 3.80 (s, 2H) ppm.

3-(Benzyloxy)-2-(chloromethyl)-6-methoxypyridine

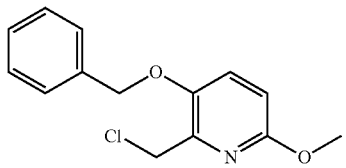 [SMILES: COc1ccc(OCc2ccccc2)c(CCl)n1]

To a solution of (3-(benzyloxy)-6-methoxypyridin-2-yl)methanol in DCM was added trimethylamine. SOCl₂ was added dropwise at 0° C. The reaction mixture was stirred at room temperature for 2 hours. Aqueous workup afforded the title compound as an off white solid. ¹H NMR (300 MHz, CDCl3): δ 7.40 (m, 5H), 7.30 (d, 1H), 6.60 (d, 1H), 5.10 (s, 2H), 4.70 (s, 2H), 3.90 (s, 3H) ppm.

[3-(Benzyloxy)-6-methoxypyridin-2-yl]methanol

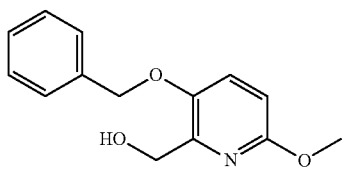 [SMILES: COc1ccc(OCc2ccccc2)c(CO)n1]

General Procedure L from 3-(benzyloxy)-6-methoxy-2-methylpyridine afforded the title compound. ¹H NMR (300 MHz, CDCl3): δ 7.39 (m, 5H), 7.24 (d, 1H), 6.61 (d, 1H), 5.07 (s, 2H), 4.76 (s, 2H), 3.94 (s, 3H) ppm.

3-(Benzyloxy)-6-methoxy-2-methylpyridine

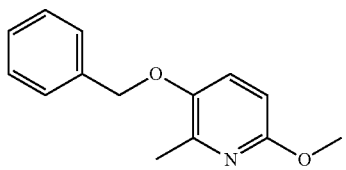 [SMILES: COc1ccc(OCc2ccccc2)c(C)n1]

The mixture of 3-bromo-6-methoxy-2-methylpyridine, benzyl alcohol, CuI, 1,10-phenanthroline, Cs₂CO₃ in toluene was stirred at 100° C. for 48 hours. Purification by chromatography afforded the title compound as colorless oil. ¹H NMR (300 MHz, CDCl3): δ 7.35 (m, 5H) 7.15 (d, 1H), 6.50 (d, 1H), 5.00 (s, 2H), 3.89 (s, 2H), 2.50 (s, 3H) ppm.

1-[(4-Fluorophenyl)methyl]-5-[(1Z)-prop-1-en-1-yl]-1H-imidazole-2-carbaldehyde

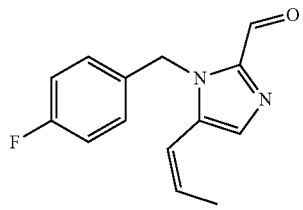 [SMILES: C/C=C\c1cnc(C=O)n1Cc1ccc(F)cc1]

General Procedure Q from 2-(1,3-dioxolan-2-yl)-1-[(4-fluorophenyl)methyl]-5-[(1Z)-prop-1-en-1-yl]-1H-imidazole. ¹H-NMR (300 MHz, CDCl₃): δ 9.81 (s, 1H), 7.41 (s, 1H), 7.09-6.96 (m, 4H), 6.19-6.03 (m, 2H), 5.62 (s, 2H), 1.95 (d, 3H) ppm.

2-(1,3-Dioxolan-2-yl)-1-[(4-fluorophenyl)methyl]-5-[(1Z)-prop-1-en-1-yl]-1H-imidazole

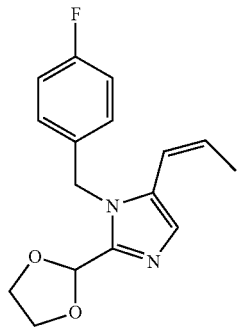 [SMILES: C/C=C\c1cnc(C2OCCO2)n1Cc1ccc(F)cc1]

Prepared from literature procedure (Ref: J. Org. Chem. 2007, 72, 3741-3749) from 2-(1,3-dioxolan-2-yl)-1-[(4-fluorophenyl)methyl]-5-iodo-1H-imidazole and tributyl (1Z)-prop-1-en-1-ylstannane in DMF. Purification by chromatography gave the title compound.
¹H-NMR (300 MHz, CDCl₃): δ 7.11 (s, 1H), 7.06-6.97 (m, 4H), 5.97-5.89 (m, 1H), 5.94 (s, 1H), 5.85-5.73 (m, 1H), 5.24 (s, 2H), 4.11-3.97 (m, 4H), 1.86 (d, 3H) ppm.

2-(1,3-Dioxolan-2-yl)-1-[(4-fluorophenyl)methyl]-5-iodo-1H-imidazole

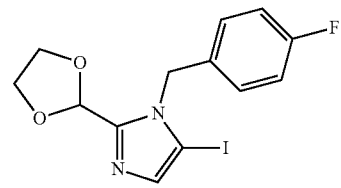 [SMILES: Fc1ccc(Cn2c(I)cnc2C2OCCO2)cc1]

General Procedure N from 2-(1,3-dioxolan-2-yl)-1-[(4-fluorophenyl)methyl]-1H-imidazole and iodine. ¹H-NMR (300 MHz, CDCl₃): δ 7.19 (s, 1H), 7.08-6.98 (m, 4H), 5.88 (s, 1H), 5.29 (s, 2H), 4.08-3.96 (m, 4H) ppm.

5-Cyclobutyl-1-[(4-fluorophenyl)methyl]-1H-imidazole-2-carbaldehyde

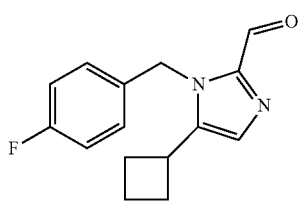 [SMILES: O=Cc1ncc(C2CCC2)n1Cc1ccc(F)cc1]

By General Procedure N from 5-cyclobutyl-1-[(4-fluorophenyl)methyl]-1H-imidazole afforded the title compound as colorless oil. ¹H-NMR (300 MHz, CD₃OD): δ 9.76 (s, 1H), 7.23 (s, 1H), 7.05-6.89 (m, 4H), 5.52 (s, 2H), 3.43-3.26 (m, 1H), 2.32-1.84 (m, 6H) ppm.

5-Cyclobutyl-1-[(4-fluorophenyl)methyl]-1H-imidazole

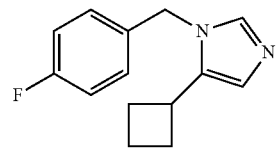 [SMILES: Fc1ccc(Cn2cncc2C2CCC2)cc1]

General Procedure O from propionaldehyde and 4-methylpentan-1-amine gave the title product as yellow oil. ¹H-NMR (300 MHz, CD₃OD): δ 7.43 (s, 1H), 7.01 (d, 4H), 6.90 (s, 1H), 4.96 (s, 2H), 3.30-3.14 (m, 1H), 2.23-1.76 (m, 6H) ppm.

1-[(4-Fluorophenyl)methyl]-5-(methylsulfanyl)-1H-imidazole-2-carbaldehyde

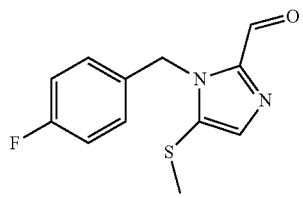

General Procedure Q from 2-(1,3-dioxolan-2-yl)-1-[(4-fluorophenyl)methyl]-5-(methylsulfanyl)-1H—. ¹H-NMR (300 MHz, CD₃OD): δ 9.73 (s, 1H), 7.31 (s, 1H), 7.21-7.08 (m, 2H), 7.07-6.94 (m, 2H), 5.64 (s, 2H), 2.54 (s, 3H), 2.13 (s, 3H) ppm.

2-(1,3-Dioxolan-2-yl)-1-[(4-fluorophenyl)methyl]-5-(methylsulfanyl)-1H-imidazole

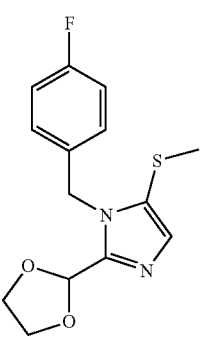 [SMILES: CSc1cnc(C2OCCO2)n1Cc1ccc(F)cc1]

General procedure N from 2-(1,3-dioxolan-2-yl)-1-[(4-fluorophenyl)methyl]-1H-imidazole and dimethyl sulfide. ¹H-NMR (300 MHz, CD₃OD): δ 7.17-7.07 (m, 2H), 7.06-6.96 (m, 2H), 6.71 (s, 1H), 5.88 (s, 1H), 5.37 (s, 2H), 4.14-3.93 (m, 4H), 2.07 (s, 3H) ppm.

5-Ethyl-1-(4-methylpentyl)-1H-imidazole-2-carbaldehyde

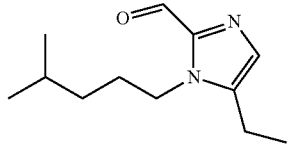

General Procedure N from 5-ethyl-1-(4-methylpentyl)-1H-imidazole afforded the title product as colorless oil. $^1$H-NMR (300 MHz, CD$_3$OD): δ 9.70 (s, 1H), 7.07 (s, 1H), 4.24 (t, 2H), 2.61 (q, 2H), 1.75-1.60 (m, 2H), 1.61-1.48 (m, 2H), 1.32 (t, 3H), 1.26-1.15 (m, 1H), 0.86 (d, 6H) ppm.

5-Ethyl-1-(4-methylpentyl)-1H-imidazole

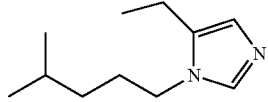

General Procedure O from propionaldehyde and 4-methylpentan-1-amine gave the title product as yellow oil. $^1$H-NMR (300 MHz, CD$_3$OD): δ 7.43 (s, 1H), 6.76 (s, 1H), 3.80 (t, 2H), 2.54 (q, 2H), 1.80-1.65 (m, 2H), 1.63-1.47 (m, 2H), 1.28 (t, 3H), 1.25-1.14 (m, 1H), 0.89 (d, 6H) ppm.

1-[1-(4Fluorophenyl)pent-3-yn-1-yl]-1H-imidazole-2-carbaldehyde

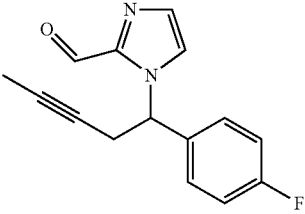 [SMILES: CC#CCC(c1ccc(F)cc1)n1ccnc1C=O]

General Procedure Q from 2-(1,3-dioxolan-2-yl)-1-[1-(4-fluorophenyl)pent-3-yn-1-yl]-1H-imidazole. $^1$H-NMR (300 MHz, CD$_3$OD): δ 9.83 (s, 1H), 7.34 (s, 1H), 7.32 (s, 1H), 7.27 (t, 2H), 7.05 (t, 2H), 6.57 (t, 1H), 3.03-2.95 (m, 2H), 1.69 (t, 3H) ppm.

2-(1,3-Dioxolan-2-yl)-1-[1-(4-fluorophenyl)pent-3-yn-1-yl]-1H-imidazole

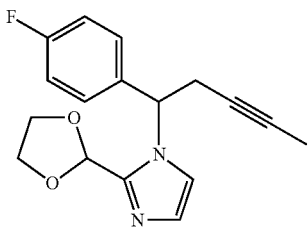 [SMILES: CC#CCC(c1ccc(F)cc1)n1ccnc1C1OCCO1]

TMEDA and n-butyllithium was added to a solution of the 2-(1,3-dioxolan-2-yl)-1-[(4-fluorophenyl)methyl]-1H-imidazole in a solvent such as THF at −78° C. Stirred at the same temperature for 3 min, 1-bromobut-2-yne was added and stirring continued at same temperature for 1 hour then the reaction mixture warmed to room temperature. Aqueous work up gave the title compound which was purified by chromatography if needed. $^1$H-NMR (300 MHz, CD$_3$OD): δ 7.34 (s, 1H), 7.32 (s, 1H), 7.27 (t, 2H), 7.05 (t, 2H), 5.97 (s, 1H), 5.77 (t, 1H), 4.23-3.97 (m, 4H), 3.03-2.93 (m, 2H), 1.71 (t, 3H) ppm.

5-Ethyl-1-[(4-fluorophenyl)methyl]-1H-imidazole-2-carbaldehyde

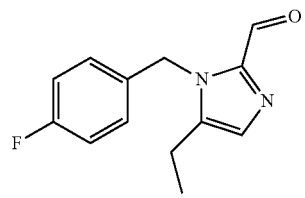 [SMILES: CCc1cnc(C=O)n1Cc1ccc(F)cc1]

General Procedure N from 5-ethyl-1-[(4-fluorophenyl)methyl]-1H-imidazole. 1H-NMR (300 MHz, CDCl3): δ 9.77 (s, 1H), 7.16 (s, 1H), 7.00 (d, 4H), 5.60 (s, 2H), 2.54 (q, 2H), 1.26 (t, 3H) ppm.

5-Ethyl-1-[(4-fluorophenyl)methyl]-1H-imidazole

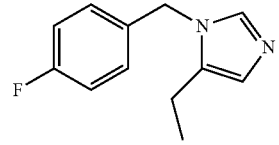

General Procedure O from propionaldehyde and 4-fluorobenzylamine. 1H-NMR (300 MHz, CDCl3): δ 7.38 (s, 1H), 6.99-6.80 (m, 4H), 6.74 (s, 1H), 4.93 (s, 2H), 2.31 (q, 2H), 1.08 (t, 3H) ppm.

1-[(4-Fluorophenyl)methyl]-5-(prop-1-en-2-yl)-1H-imidazole-2-carbaldehyde

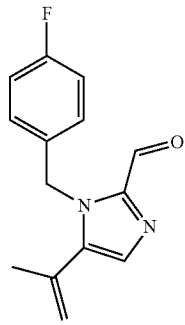 [SMILES: C=C(C)c1cnc(C=O)n1Cc1ccc(F)cc1]

General Procedure N from 1-[(4-fluorophenyl)methyl]-5-(prop-1-en-2-yl)-1H-imidazole. $^1$H-NMR (300 MHz, CD$_3$OD): δ 9.76 (s, 1H), 7.29-7.19 (m, 2H), 7.06-6.92 (m, 3H), 5.67 (s, 2H), 5.32 (s, 1H), 5.08 (s, 1H), 2.03 (s, 3H) ppm.

1-[(4-Fluorophenyl)methyl]-5-(prop-1-en-2-yl)-1H-imidazole

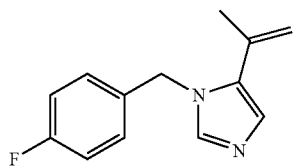

General Procedure O from 2-methylprop-2-enal and 4-fluorobenzylamine gave the title product as yellow oil. $^1$H-NMR (300 MHz, CD$_3$OD): δ 7.46 (s, 1H), 7.37-7.14 (m, 2H), 7.13-6.89 (m, 3H), 5.21 (s, 2H), 5.05 (s, 1H), 4.90 (s, 1H), 2.03 (s, 3H) ppm.

3-{1-[(4-Fluorophenyl)methyl]-2-formyl-1H-imidazol-5-yl}propanamide

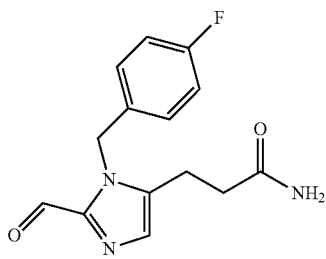 [SMILES: NC(=O)CCc1cnc(C=O)n1Cc1ccc(F)cc1]

General Procedure N from 3-{1-[(4-fluorophenyl)methyl]-1H-imidazol-5-yl}propanamide. $^1$H-NMR (300 MHz, CD$_3$OD): δ 9.83 (s, 1H), 7.19 (s, 1H), 7.05-6.99 (m, 4H), 5.68 (s, 2H), 2.73 (t, 2H), 2.47 (t, 2H) ppm.

3-{1-[(4-Fluorophenyl)methyl]-1H-imidazol-5-yl}propanamide

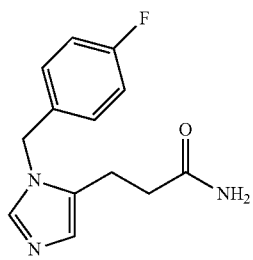 [SMILES: NC(=O)CCc1cncn1Cc1ccc(F)cc1]

A mixture of methyl 3-{1-[(4-fluorophenyl)methyl]-1H-imidazol-5-yl}propanoate in 7N ammonia in MeOH was heated to 85° C. for 12 hours in a sealed vessel. Purification by column chromatography gave the title compound as colorless oil. $^1$H-NMR (300 MHz, CD$_3$OD): δ 7.43 (s, 1H), 7.08-6.92 (m, 4H), 6.79 (s, 1H), 6.66 (br s, 1H), 5.95 (br s, 1H), 5.03 (s, 2H), 2.73 (t, 2H), 2.45 (t, 2H) ppm.

Methyl 3-{1-[(4-fluorophenyl)methyl]-1H-imidazol-5-yl}propanoate

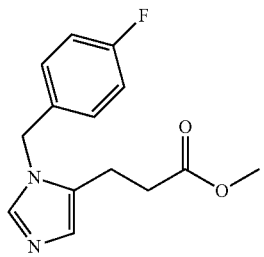 [SMILES: COC(=O)CCc1cncn1Cc1ccc(F)cc1]

General Procedure O from methyl 4-oxobutanoate and 4-fluorobenzylamine. $^1$H-NMR (300 MHz, CD$_3$OD): δ 7.48 (s, 1H), 7.04 (d, 4H), 6.85 (s, 1H), 5.08 (s, 2H), 3.67 (s, 3H), 2.74 (t, 2H), 2.57 (t, 2H) ppm.

5-Ethyl-1-(thiophen-2-ylmethyl)-1H-imidazole-2-carbaldehyde

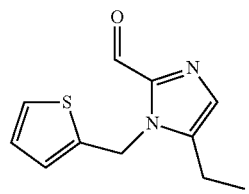

General Procedure I from [5-ethyl-1-(thiophen-2-ylmethyl)-1H-imidazol-2-yl]methanol gave the title product as colorless oil. $^1$H-NMR (300 MHz, CDCl$_3$): δ 9.73 (s, 1H), 7.19 (d, 1H), 7.08 (s, 1H), 6.92 (s, 1H), 6.88 (t, 1H), 5.71 (s, 2H), 2.67 (q, 2H), 1.29 (t, 3H) ppm.

[5-Ethyl-1-(thiophen-2-ylmethyl)-1H-imidazol-2-yl]methanol

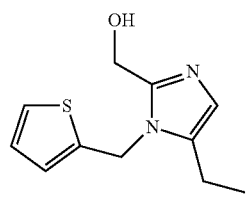

A mixture of methyl 5-ethyl-1-(thiophen-2-ylmethyl)-1H-imidazole, paraformaldehyde, and powdered molecular sieves in anhydrous DMSO was heated at 140° C. for 15 hours in a sealed vessel. Aqueous work up and purification by chromatography afforded the title compound as colorless oil. $^1$H-NMR (300 MHz, CDCl$_3$): δ 7.21 (d, 1H), 6.92 (t, 1H), 6.82 (s, 1H), 6.63 (s, 1H), 5.36 (s, 2H), 4.63 (s, 2H), 2.50 (q, 2H), 1.21 (t, 3H) ppm.

5-Ethyl-1-(thiophen-2-ylmethyl)-1H-imidazole

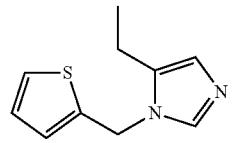

General Procedure O from propionaldehyde and thiophen-2-yl-methanamine. $^1$H-NMR (300 MHz, CDCl$_3$): δ 7.48 (s, 1H), 7.27 (d, 1H), 6.96 (t, 1H), 6.88 (s, 1H), 6.82 (s, 1H), 5.19 (s, 2H), 2.54 (q, 2H), 1.25 (t, 3H) ppm.

Example 2: Histone Lysine Demethylase AlphaLISA Assays for IC$_{50}$ Value Determination The ability of compounds of the application to inhibit the histone lysine demethylase activity in vitro of different enzymes was determined. (TABLE 3).

Assays were performed analogously to the protocol described by PerkinElmer (Roy et al. PerkinElmer Technical Note: AlphaLISA #12, April 2011). Enzymes (final assay concentration 0.1-2.5 nM) were dissolved in enzyme buffer and incubated for 10 min before 5 µL was added to 5 µL 3% DMSO solutions of compounds in enzyme buffer. The reaction mixture was incubated for another 10 minutes before 5 µL of substrate solution was added and the resulting mixture was then incubated at room temperature. 10 µL acceptor beads and suspended Epigenetic Buffer (Perkin Elmer AL008) were added from stock and the suspension was incubated in the dark at room temperature before a 10 µL suspension of streptavidin donor beads (Perkin Elmer 6760002) in Epigenetic Buffer was added. After incubation at room temperature in the dark, the plates were read. Results are shown in Table 1. Compounds 32 and 116 can be metabolized to Compounds 4 and 93, respectively.

TABLE 3

| Protein name | Vendor/source | Sequence | Expression organism |
|---|---|---|---|
| KDM2B (FBXL10) | BPS, Bioscience, US | 1-650 | Bac |
| KDM4C (JMJD2C) | BRIC, Denmark | 1-349 | E. coli |
| KDM5B (PLU-1) | BRIC | 1-809 | E. coli |
| KDM6A (UTX) | BRIC | 919-1401 | E. coli |
| KDM7 (PHF8) | BRIC | 1-1322 | Bac |

Substrates:

BK9M2:
(SEQ ID.: 1)
Biotin-ARTKQTAR(KMe$_2$)STGGKAPRKQ-NH$_2$
(AnaSpec 64359)

BK9M3:
(SEQ ID.: 2)
Biotin-ARTKQTAR(KMe$_3$)STGGKAPRKQ-NH$_2$
(Caslo, Denmark)

H3K4M3B:
(SEQ ID.: 3)
H-ART(Kme$_3$)QTARKSTGGKAPRKQLA-NH-Biotin
(Caslo, Denmark)

BK27M3:
(SEQ ID.: 4)
Biotin-ATKAAR(Kme$_3$)SAPATGGVKKPHRY-NH$_2$
(Caslo, Denmark)

BH3K36M2:
(SEQ ID.: 5)
RKAAPATGGVK(Me$_2$)KPHRYRPGTVK-(BIOTIN)
(Anaspec)

Substrate solution: Substrate (final assay concentration 50-200 nM), 50 mM Hepes (pH 7.4-8.0), 0.003% Tween-20, 0.1% BS, 25 µM L-Asc, 10 µM α-KG. Enzyme Buffer: 50 mM Hepes (pH 7.4-8.0), 0.003-0.01% Tween-20, 0.1% BSA; 5 µM (NH$_4$)$_2$Fe(SO$_4$)$_2$.

TABLE 1

HDME Inhibition**

| Compound # | KDM4C (nM) | KDM2B (nM) | PHF8 (nM) | KDM6A (nM) | KDM5B (nM) |
|---|---|---|---|---|---|
| 1 | >10000 | 431 | 352 | >10000 | >10000 |
| 2 | >10000 | 2939 | >10000 | >10000 | >10000 |
| 3 | >10000 | 4650 | >10000 | >10000 | >10000 |
| 4 | >10000 | 30 | 234 | >10000 | >10000 |
| 5 | >10000 | 1601 | 3761 | >10000 | >10000 |
| 6 | >10000 | 708 | 353 | >10000 | 3348 |
| 7 | >10000 | 7103 | >10000 | >10000 | 1231 |
| 8 | >10000 | 150 | 384 | >10000 | >10000 |
| 9 | 299 | >10000 | >10000 | >10000 | 714 |
| 10 | 1372 | >10000 | >10000 | >10000 | 1280 |
| 11 | >10000 | 1545 | 6928 | >10000 | 5479 |
| 12 | >10000 | 1601 | >10000 | >10000 | 3761 |
| 13 | >10000 | 2273 | 5779 | >10000 | >10000 |
| 14 | >10000 | 3233 | 5604 | >10000 | >10000 |
| 15 | >10000 | 5682 | >6000 | >10000 | >10000 |
| 16 | >10000 | >6800 | 3492 | >9000 | >10000 |
| 17 | >10000 | >10000 | >10000 | >10000 | >10000 |
| 18 | >10000 | 3932 | 3025 | >10000 | >10000 |
| 19 | >10000 | 1153 | 890 | >10000 | 348 |
| 20 | >10000 | 5428 | >10000 | >10000 | >10000 |
| 21 | >10000 | 5354 | >10000 | >10000 | >10000 |
| 22 | >10000 | >10000 | >10000 | >10000 | >10000 |
| 23 | >10000 | >10000 | >10000 | >10000 | >10000 |
| 24 | >10000 | 2226 | nd | 8350 | 262 |
| 25 | >10000 | 1130 | 1210 | >10000 | >10000 |
| 26 | >10000 | 565 | 1030 | >10000 | 3018 |
| 27 | >10000 | 158 | 537 | >10000 | >10000 |
| 28 | >10000 | 462 | 1060 | >10000 | >10000 |
| 29 | >10000 | 1136 | 2655 | >10000 | >10000 |
| 30 | >10000 | 703 | 2219 | >10000 | >10000 |
| 31 | >10000 | 3974 | >10000 | >10000 | >10000 |
| 33 | >10000 | 1024 | 2038 | >10000 | >10000 |
| 34 | >10000 | 1238 | >10000 | >10000 | >10000 |
| 35 | >10000 | 117 | 437 | >10000 | >10000 |
| 36 | >10000 | 248 | 908 | >10000 | >10000 |
| 37 | >10000 | 297 | 489 | >10000 | >10000 |
| 38 | >10000 | 2290 | >10000 | >10000 | 4624 |
| 39 | >10000 | 155 | 472 | >10000 | >10000 |
| 40 | >10000 | 599 | 1532 | >10000 | >10000 |
| 41 | >10000 | 1658 | 6557 | nd | >10000 |
| 42 | >10000 | 659 | 859 | nd | >10000 |
| 43 | >10000 | 442 | 869 | nd | >10000 |
| 44 | >10000 | 2006 | 2375 | nd | >10000 |
| 45 | >10000 | 501 | 491 | nd | >10000 |
| 46 | >10000 | 2270 | 2276 | nd | >10000 |
| 47 | >10000 | 1256 | 391 | nd | 4079 |
| 48 | >10000 | >10000 | >10000 | nd | >10000 |
| 49 | >10000 | 838 | 1109 | nd | >10000 |
| 50 | >10000 | 692 | 1036 | nd | >10000 |
| 51 | >10000 | 2828 | 3879 | nd | >10000 |
| 52 | >10000 | 1727 | 1509 | nd | >10000 |
| 53 | >10000 | 760 | 881 | nd | >10000 |
| 54 | >10000 | 1140 | 1185 | nd | >10000 |
| 55 | >10000 | 656 | 1300 | nd | 1782 |
| 56 | >10000 | 482 | 883 | nd | >10000 |

TABLE 1-continued

HDME Inhibition**

| Compound # | KDM4C (nM) | KDM2B (nM) | PHF8 (nM) | KDM6A (nM) | KDM5B (nM) |
|---|---|---|---|---|---|
| 57 | >10000 | 1144 | 1272 | nd | >10000 |
| 58 | nd | >10000 | >10000 | nd | >10000 |
| 59 | nd | 2747 | >10000 | nd | nd |
| 60 | >10000 | 1619 | >10000 | nd | 526 |
| 61 | >10000 | 4181 | 2551 | nd | >10000 |
| 62 | 7370 | 244 | 307 | nd | 231 |
| 63 | >10000 | 333 | 1404 | nd | >10000 |
| 64 | >10000 | 104 | 246 | nd | >10000 |
| 65 | >10000 | 34 | 1009 | nd | 151 |
| 66 | >10000 | 5772 | >10000 | nd | 943 |
| 67 | >10000 | 715 | 791 | nd | >10000 |
| 68 | >10000 | 1683 | 1797 | nd | >10000 |
| 69 | >10000 | 27 | 662 | nd | >10000 |
| 70 | >10000 | 485 | 1749 | nd | 559 |
| 71 | >10000 | 138 | 1775 | nd | >10000 |
| 72 | >10000 | 283 | 529 | nd | >10000 |
| 73 | >10000 | 252 | 1648 | nd | >10000 |
| 74 | nd | 1859 | 3815 | nd | >10000 |
| 75 | >10000 | 587 | 1274 | nd | 431 |
| 76 | nd | 4734 | >10000 | nd | >10000 |
| 77 | >10000 | 379 | 1090 | nd | >10000 |
| 78 | >10000 | 340 | 1136 | nd | 641 |
| 79 | >10000 | >10000 | >10000 | nd | >10000 |
| 80 | >10000 | 683 | 5297 | nd | 1988 |
| 81 | 823 | 140 | 334 | nd | 21 |
| 82 | >10000 | 1403 | 3320 | nd | >10000 |
| 83 | >10000 | 1525 | 4950 | nd | 755 |
| 84 | >10000 | 251 | 673 | nd | 6198 |
| 85 | >10000 | 461 | 1861 | nd | >10000 |
| 86 | >10000 | >10000 | >10000 | nd | >10000 |
| 87 | >10000 | 1703 | 2297 | nd | >10000 |
| 88 | 3468 | 585 | 1273 | nd | 246 |
| 89 | >10000 | 2299 | >10000 | nd | >10000 |
| 90 | >10000 | 2942 | 6969 | nd | >10000 |
| 91 | >10000 | 328 | 1113 | nd | >10000 |
| 92 | >10000 | 53 | 1230 | nd | >10000 |
| 93 | >10000 | 32 | 1480 | nd | >10000 |
| 94 | >10000 | 47 | 2030 | nd | >10000 |
| 95 | >10000 | 389 | 9650 | nd | >10000 |
| 96 | >10000 | 61 | 1810 | nd | >10000 |
| 97 | >10000 | 308 | >10000 | nd | >10000 |
| 98 | 1666 | 530 | >10000 | nd | 8 |
| 99 | >10000 | >10000 | >10000 | nd | 8410 |
| 100 | >10000 | 70 | 1148 | nd | 635 |
| 101 | >10000 | 105 | 1330 | nd | 6108 |
| 102 | 7050 | 240 | >10000 | nd | 20 |
| 103 | >10000 | 56 | 160 | nd | >10000 |
| 104 | nd | 145 | 400 | nd | >10000 |
| 105 | nd | 242 | nd | nd | >10000 |
| 106 | nd | 3100 | 2770 | nd | >10000 |
| 107 | >10000 | 5180 | >10000 | nd | >10000 |
| 108 | >10000 | 133 | 861 | nd | >10000 |
| 109 | >10000 | >10000 | >10000 | nd | >10000 |
| 110 | >10000 | >10000 | >10000 | nd | >10000 |
| 111 | >10000 | 823 | 5100 | nd | 1070 |
| 112 | >10000 | 375 | 3520 | nd | >10000 |
| 113 | >10000 | 2830 | >10000 | nd | >10000 |
| 114 | >10000 | 317 | 1140 | nd | >10000 |
| 115 | >10000 | 53 | 506 | nd | >10000 |

**nd = not determined

Example 3: Histone Lysine Demethylase Immunofluorescence Assays for IC$_{50}$ Value Determination in Cells The ability of compounds of the application, or a pharmaceutically acceptable salt, or solvate, or prodrug thereof, to inhibit demethylation of H3K4 in a human osteosarcoma cancer cell line is determined as described herein.

U2OS cells are harvested and seeded into multi well plates into media containing compound. The media used is DMEM containing 5% FBS and pen/strep. 20 hours after incubation of cells with compounds, the cells are washed once in PBS, harvested by fixation with formaldehyde 4% aqueous solution, and washed 2 times in PBS. Subsequently, the cells are permeabilized in PBS with 0.2% Triton X-100 for 10 min at room temperature. Blocking is performed in PBS with 0.2% Triton X-100 and 5% FBS for 45 min at room temperature. The cells are incubated with aH3K4me3 primary antibody (Cell Signaling, #9751S) diluted 1:1000 in blocking solution over night at 4° C. After incubation with primary antibody, the cells are washed 3 times with PBS, incubated with secondary antibody diluted 1:1000 (Alexa fluor 594 goat anti rabbit IgG, Invitrogen, A11012) and Hoechst, 20 µg/ml (Sigma, 33342) in blocking solution, and washed again 3 times with PBS. Finally, PBS is added and high throughput imaging and analysis are performed by an IN Cell Analyzer 1000 (GE Healthcare). The IC$_{50}$ values are based on an average measure of the staining of the H3K4me3 mark in cells.

Example 4: Cell Proliferation Assays for EC$_{50}$ Value Determination

The ability of the compounds of the application to inhibit the proliferation of a human breast cancer cell line is determined as described herein.

MCF7 cells are seeded at 1250 cells/well in 50 µl medium/well in black 96 well plates. Cells are incubated for 24 hours before addition of a compound of the application. Compounds are diluted in complete medium (50 µl/well) and added to the plates in duplicates. The total volume of medium in the wells was 100 µL, and the final concentration of DMSO 0.5%. Complete medium used is DMEM with GlutaMAX containing 10% FBS and pen/strep.

120 hours after addition of compounds, the plates are harvested and analyzed by ATPlite 1 Step (Perkin Elmer, cat no 6016739) according to the manufactures recommendation. Briefly, 100 µl ATP lite solution is added to each well, plates are vortexed at 700 rpm 2 minutes, followed by 20 minutes incubation in the dark, and then analyzed for luminescence on EnSpire 2300 Multilabel reader (Perkin Elmer). EC$_{50}$ values are calculated using GraphPad Prism 6.

Example 5: Histone Lysine Demethylase Immunofluorescence Assays for IC50 Value Determination in Cells The ability of the compounds of the application, or a pharmaceutically acceptable salt, or solvate, or prodrug thereof, to inhibit demethylation of a specific H3 lysine in a human osteosarcoma cell line transfected to express a specific histone lysine demethylase is determined as described herein.

U2OS cells are seeded 24 hours before transfection. Transfection is performed with Fugene HD transfection reagent as recommended by the manufacturer. 6 hours after transfection, the cells are harvested and seeded into multi well plates into media containing compound. The media used is DMEM containing 5% FBS and pen/strep. 20 hours after incubation of cells with compounds, the cells are washed once in PBS, harvested by fixation with formaldehyde 4% aqueous solution, and washed 2 times in PBS. Subsequently, the cells are permeabilized in PBS with 0.2% Triton X-100 for 10 min at room temperature. Blocking is performed in PBS with 0.2% Triton X-100 and 5% FBS for 45 min at room temperature. The cells are incubated with primary antibodies diluted 1 µg/ml in blocking solution over night at 4° C. The primary antibodies used in the assays were HA.11 (Covance, MMS-101P) and the antibody detecting the mark specified in the Table 4 below. After incubation with primary antibodies, the cells are washed 3 times with PBS, incubated with secondary antibodies diluted 1:1000 (Alexa fluor 594 goat anti rabbit IgG, Invitrogen, A11012; Alexa flour 488 donkey anti mouse IgG, Invitrogen, A21202) and Hoechst, 20 µg/ml (Sigma, 33342) in blocking solution, and washed again 3 times with PBS. Finally, PBS is added and high throughput imaging and analysis are performed by an IN Cell Analyzer 1000 (GE Healthcare). The robot software analyzes individual cells and divides these into HA+ (transfected cells) and HA− (non-transfected cells). The $IC_{50}$ values are based on an average measure of the staining of the mark specified in the Table 4 below in the transfected cells.

TABLE 4

| Construct name | Vendor/ source | Sequence | Mark detected | Primary antibody used for detection of | Plasmid NCBIID |
|---|---|---|---|---|---|
| pCMVHA JMJD2C | BRIC | Full length | H3K9me3 | Abeam Ab8898 | NM_014663 |
| pCMVHA JMJD2A | BRIC | Full length | H3K9me3 | Abeam Ab8898 | NM_015061 |
| pCMVHA PLUI | BRIC | Fragment (1-752) | H3K4me2 | Millipore 07-030 | NM_006618 |

Example 6: In Vitro Proliferation Assay in Combination with Other Active Therapeutic Agents The compounds of the application, or a pharmaceutically acceptable salt, or solvate, or prodrug thereof, are tested in an in vitro proliferation assay in combination with standard of care active ingredients. Cells are seeded at appropriate densities in a standard medium containing compounds and active ingredients. The cells are then incubated for an additional period of time before the medium is optionally replenished with standard medium or optionally replenished with standard medium containing compounds and active ingredients. The incubation and replenishment cycle may be repeated a number of times. Cellular growth or drug tolerance is monitored continuously or at certain time points using standard imaging techniques or standard assays for cell number or viability.

EQUIVALENTS

The application can be embodied in other specific forms without departing from the spirit or essential characteristics thereof. The foregoing embodiments are therefore to be considered in all respects illustrative rather than limiting on the application described herein. Scope of the application is thus indicated by the appended claims rather than by the foregoing description, and all changes that come within the meaning and range of equivalency of the claims are intended to be embraced therein.

The invention claimed is:
1. A compound being of Formula (I):

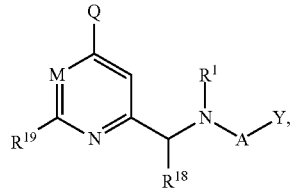

wherein:
Q is selected from $CO_2H$, $CO_2R^{20}$, —CH=$NR^{12}$, —W, —$CH_2NHR^{13}$, —CH=O and —$CH(OR^{17})_2$;
M is CH or N;
A is selected from —$C(R^2)_2C(O)$—, —$C(R^2)_2C(R^2)_2C(O)$—, $C_{3-10}$ alkyl, —Z—$C_{3-10}$ cycloalkylene, —Z-heterocyclylene, —Z-heteroarylene and —Z-arylene, wherein the $C_{3-10}$ alkyl, —Z-cycloalkylene, —Z-heterocyclylene, —Z-heteroarylene and —Z-arylene are optionally substituted with one or more $R^3$, or A and Y form a $C_{3-10}$ cycloalkyl or heterocyclic ring;
Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, wherein the alkyl, alkenyl, alkynyl, cycloalkyl, heterocyclyl, heteroaryl and aryl are optionally substituted with one or more $R^3$;
$R^1$ is selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —$NR^6R^7$, —F and $C_{3-6}$ cycloalkyl; or $R^1$, together with A-Y and the nitrogen atom to which it is attached, forms a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl; or $R^1$ and $R^{18}$, together with the atoms to which they are attached, form a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl;
Each $R^2$ is independently selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; or two $R^2$ substituents on adjacent carbon atoms, together with the carbon atoms to which they are attached, form a $C_{4-10}$ cycloalkyl or heterocyclic ring; or two $R^2$ substituents on the same carbon atom, together with the carbon atom to which they are attached, form a $C_{3-10}$ cycloalkyl or heterocyclic ring; or $R^2$ and Y, together with the carbon atoms to which they are attached, form a $C_{4-10}$ cycloalkyl or heterocyclic ring;
each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; or two $R^3$ on the same carbon atom may, together with the carbon atom to which they are attached, form a $C_{3-10}$ cycloalkyl or heterocyclic ring;
Z is selected from a single bond, $C_{1-4}$ alkylene, heterocyclylene and $C_{3-6}$ cycloalkylene;
each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—$NR^6R^7$, —Z—C(=O)—$NR^6R^7$, —Z—$NR^6$—C(=O)—$R^7$, —Z—C(=O)—$R^7$, —Z—C(=O)—H, —$OR^7$, halogen, —$SR^7$, —$SOR^7$, —$SO_2R^7$, —$SO_2NR^6R^7$, and —$COOR^7$;
each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, —Z—$NR^6R^7$, —Z—C(=O)—$NR^6R^7$, —Z—$NR^6$—C(=O)—$R^7$, —Z—C(=O)—$R^7$, —Z—C(=O)—H, —$SR^7$, —$SOR^7$, —$SO_2R^7$, —$SO_2NR^6R^7$, and —$COOR^7$;
each $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, wherein the alkyl, alkenyl, alkynyl, cycloalkyl, heterocyclyl, heteroaryl and aryl are optionally substituted with one or more $R^8$; or $R^6$ and $R^7$ may, together with the N-atom to which they are attached, form a heterocyclic ring optionally substituted with one or more $R^8$;
each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, wherein the alkyl, alkenyl, alkynyl, cycloalkyl, heterocyclyl, heteroaryl and aryl are optionally substituted with one or more substituents independently selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein the heterocyclyl is optionally substituted with one or more $R^4$ and wherein the heteroaryl and aryl are optionally substituted with one or more $R^5$;
each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the heterocyclyl is optionally substituted with one or more $R^4$ and wherein the heteroaryl and aryl are optionally substituted with one or more $R^5$;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and $C_{6-14}$ aryl, wherein the heterocyclyl is optionally substituted with one or more $R^4$ and wherein the heteroaryl and aryl are optionally substituted with one or more $R^5$; or $R^{10}$ and $R^{11}$ may, together with the N-atom to which they are attached, form a 5- to 7-membered heterocyclic ring optionally substituted with one or more $R^4$;

when Q is —CH═$NR^{12}$, $R^{12}$ is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—$NR^6R^7$, —Z—C(═O)—$NR^6R^7$, —Z—$NR^6$—C(═O)—$R^7$, —Z—C(═O)—$R^7$, —Z—$OR^7$, —Z—$SR^7$, —Z—$SOR^7$, —Z—$SO_2R^7$ and —Z—$COOR^7$, wherein the alkyl, alkenyl, alkynyl, cycloalkyl, heterocyclyl, heteroaryl and aryl are optionally substituted with one or more $R^3$;

when Q is —$CH_2NHR^{13}$, $R^{13}$ is selected from —H, —C(O)$R^7$, —C(O)C(O)$R^7$, —C(O)C(O)$OR^7$, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z—heterocyclyl, and —Z-monocyclic-heteroaryl, wherein the alkyl, alkenyl, alkynyl, cycloalkyl, heterocyclyl, and heteroaryl are optionally substituted with one or more $R^8$; or $R^{13}$ is —$CR^{14}R^{15}NR^6R^7$, —$CR^{14}R^{15}CN$, or —$CR^{14}R^{15}OR^7$, wherein each $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, heterocyclyl, heteroaryl, and $C_{6-14}$ aryl, wherein the alkyl, alkenyl, alkynyl, cycloalkyl, heterocyclyl, heteroaryl and aryl are optionally substituted with one or more $R^3$; or wherein $R^{14}$ and $R^{15}$ together with the intervening carbon atom form a $C_{3-10}$ cycloalkyl or $C_{5-10}$-cycloalkenyl ring optionally substituted with one or more $R^3$;

when Q is W, W is selected from a 1,3-diazacycloalk-2-yl group which is N-substituted with $R^{16}$, optionally further substituted with one or more $R^3$, and optionally containing one or two oxo groups; a 1,3-thiazacycloalk-2-yl group which is N-substituted with $R^{16}$, optionally further substituted with one or more $R^3$ and optionally containing one or two oxo groups; and a 1,3-oxazacycloalk-2-yl group which is N-substituted with $R^{16}$, optionally further substituted with one or more $R^3$, and optionally containing one or two oxo groups, wherein in all three instances two $R^3$ on the same carbon atom may, together with the carbon atom to which they are attached, form a $C_{3-10}$ cycloalkyl or heterocyclic ring;

$R^{16}$ is selected from —H, —C(O)$R^7$, —C(O)C(O)$R^7$ and —C(O)C(O)$OR^7$;

when Q is —CH(O$R^{17}$)$_2$, each $R^{17}$ independently is $R^3$; or wherein two $R^{17}$ together with the intervening —O—CH—O— form a heterocyclic ring optionally substituted with one or more $R^3$ and optionally containing one to two oxo groups;

$R^{18}$ is selected from —H, $C_{1-6}$ alkyl, $C_{1-6}$ fluoroalkyl, $C_{1-6}$ hydroxyalkyl, $C_{2-7}$ alkenyl, $C_{2-7}$ alkynyl, $C_{3-7}$ cycloalkyl, and $C_{3-7}$ oxyalkyl; or $R^{18}$ and A, together with the atoms to which they are attached, form a heterocyclic ring; or $R^{18}$ and Y, together with the atoms to which they are attached, form a heterocyclic ring; or $R^{18}$ and $R^1$, together with the atoms to which they are attached, form a heterocyclic ring;

$R^{19}$ is selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from aryl, $C_{1-6}$ alkoxy, heteroaryl, aryloxy, heteroaryloxy, $C_{3-6}$ cycloalkyl, —Z-heterocyclyl, —Z-aryl, —Z-heteroaryl, —Z—$NR^6R^7$, —Z—C(═O)—$NR^6R^7$, —Z—$NR^6$—C(═O)—$R^7$, —Z—C(═O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; and may optionally form a cyclophane structure by attaching to Y or A; and when Q is $CO_2R^{20}$, $R^{20}$ is selected from $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the $C_{1-8}$ alkyl, $C_{3-10}$ cycloalkyl and heterocyclyl are optionally substituted with one or more $R^4$, and wherein the heteroaryl and aryl are optionally substituted with one or more $R^5$ as defined above;

or a pharmaceutically acceptable salt or solvate thereof.

2. The compound of claim 1, wherein A is selected from —Z-heterocyclylene, —Z-arylene, and —Z-heteroarylene.

3. The compound of claim 1, wherein Y is —H or $C_{1-8}$ alkyl.

4. The compound claim 1, wherein $R^3$ is —Z-aryl.

5. The compound of claim 1, wherein Z is a single bond or $C_{1-4}$ alkylene.

6. The compound claim 1, wherein $R^1$ is —H.

7. The compound claim 1, wherein $R^1$ is —H.

8. The compound of claim 1, wherein $R^{19}$ is $C_{1-8}$ alkyl optionally substituted with one —Z—$OR^7$.

9. The compound of claim 1, wherein Q is $CO_2H$.

10. The compound of claim 1 being of Formula (II),

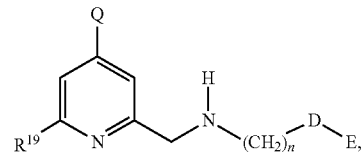

(II)

or a pharmaceutically acceptable salt or solvate thereof, wherein:

D is Z-heteroarylene optionally substituted with one to three $R^{23}$;

E is Z-aryl or Z-heteroaryl optionally substituted with one to three $R^{24}$;

each $R^{23}$ is independently selected from —H, —$NR^6R^7$, $C_{1-8}$ alkyl, $C_{2-8}$ alkenyl, $C_{2-8}$ alkynyl, $C_{3-10}$ cycloalkyl, $C_{5-10}$ heterocyclyl, $C_{5-14}$ heteroaryl and $C_{6-14}$ aryl;

each $R^{24}$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH; and n is 0 to 3.

11. The compound of claim 10, wherein D is imidazolyl optionally substituted with one to three $R^{23}$.

12. The compound of claim 10, wherein D is pyridinyl optionally substituted with one to three $R^{23}$.

13. The compound of claim 10, wherein D is triazolyl optionally substituted with one to three $R^{23}$.

14. The compound of claim 10, wherein E is Z-aryl optionally substituted with one to three $R^{24}$.

15. The compound of claim 10, wherein $R^{19}$ is —$CH_2OH$.

16. The compound of claim 10, wherein $R^{19}$ is methyl.

17. The compound of claim 10, wherein Q is $CO_2H$.

18. The compound of claim 1 being of Formula (III),

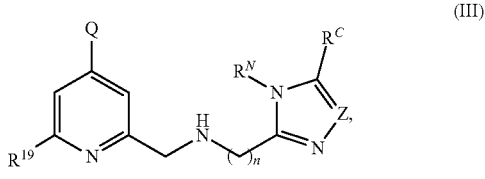

(III)

or a pharmaceutically acceptable salt or solvate thereof, wherein:

Z is N or $CR^Z$;

$R^N$, $R^C$, and $R^Z$ are each independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; and n is 1 or 2.

19. The compound of claim 18, wherein Q is $CO_2H$.

20. The compound of claim 1 being of Formula (IV),

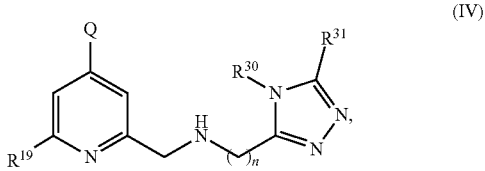

(IV)

or a pharmaceutically acceptable salt or solvate thereof, wherein:

$R^{30}$ and $R^{31}$ are independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; and n is 1 or 2.

21. The compound of claim 20, wherein Q is $CO_2H$.

22. The compound of claim 1 being of Formula (V),

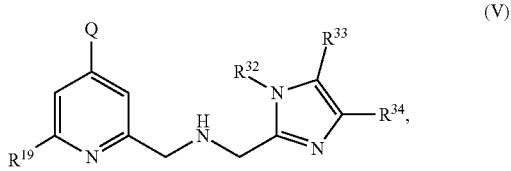

(V)

or a pharmaceutically acceptable salt or solvate thereof, wherein:

$R^{32}$, $R^{33}$, and $R^{34}$ are independently selected from —H, $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$.

23. The compound of claim 22, wherein Q is $CO_2H$.

24. A compound being of Formula (VI):

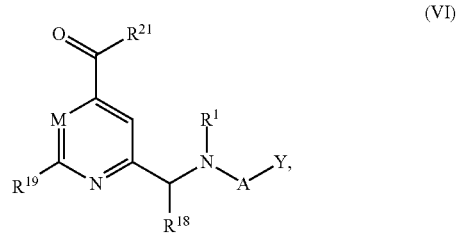

(VI)

or a pharmaceutically acceptable salt or solvate thereof, wherein:

M is CH or N;

A is selected from —$C(R^2)_2C(O)$—, —$C(R^2)_2C(R^2)_2C(O)$—, $C_{3-10}$ alkyl, —Z—$C_{3-10}$cycloalkylene, —Z-heterocyclylene, —Z-heteroarylene and —Z-arylene, wherein the $C_{3-10}$ alkyl, —Z-cycloalkylene, —Z-heterocyclylene, —Z-heteroarylene and —Z-arylene are optionally substituted with one or more $R^3$, or A and Y form a $C_{3-10}$ cycloalkyl or heterocyclic ring;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, wherein the alkyl, alkenyl, alkynyl, cycloalkyl, heterocyclyl, heteroaryl and aryl are optionally substituted with one or more $R^3$;

$R^1$ is selected from —H, $C_{1-8}$ alkyl, $C_{2-8}$alkenyl, $C_{2-8}$ alkynyl, and $C_{3-10}$ cycloalkyl, wherein the alkyl, alkenyl, alkynyl and cycloalkyl are optionally substituted with one or more substituents selected from —OH, aryl, $C_{1-6}$ alkoxy, heteroaryl, aryloxy, heteroaryloxy, —$NR^6R^7$, —F and $C_{3-6}$ cycloalkyl; or $R^1$, together with A-Y and the nitrogen atom to which it is attached, forms a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl; or $R^1$ and $R^{18}$, together with the atoms to which they are attached, form a nitrogen-containing heterocyclic ring optionally substituted with one or more substituents independently selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —$NR^6R^7$, —F and $C_{3-6}$ cycloalkyl;

Each $R^2$ is independently selected from —H, $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from —OH, aryl, $C_{1-6}$ alkoxy, heteroaryl, aryloxy, heteroaryloxy, —F, $C_{3-6}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$; or two $R^2$ substituents on adjacent carbon atoms, together with the carbon atoms to which they are attached, form a $C_{4-10}$ cycloalkyl or heterocyclic ring; or two $R^2$ substituents on the same carbon atom, together with the carbon atom to which they are attached, form a $C_{3-10}$ cycloalkyl or heterocyclic ring; or $R^2$ and Y, together with the carbon atoms to which they are attached, form a $C_{4-10}$ cycloalkyl or heterocyclic ring;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein the heterocyclyl is optionally substituted with one or more $R^4$, and wherein the heteroaryl and aryl are optionally substituted with one or more $R^5$; or two $R^3$ on the same carbon atom may, together with the carbon atom to which they are attached, form a $C_{3-10}$ cycloalkyl or heterocyclic ring;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —Z—$NR^6R^7$, —Z—C(=O)—$NR^6R^7$, —Z—$NR^6$—C(=O)—$R^7$, —Z—C(=O)—$R^7$, —Z—C(=O)—H, —$OR^7$, halogen, —$SR^7$, —$SOR^7$, —$SO_2R^7$, —$SO_2NR^6R^7$, and —$COOR^7$;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, —Z—$NR^6R^7$, —Z—C(=O)—$NR^6R^7$, —Z—$NR^6$—C(=O)—$R^7$, —Z—C(=O)—$R^7$, —Z—C(=O)—H, —$OR^7$, —$SR^7$, —$SOR^7$, —$SO_2R^7$, —$SO_2NR^6R^7$, and —$COOR^7$;

each $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z—aryl, wherein the alkyl, alkenyl, alkynyl, cycloalkyl, heterocyclyl, heteroaryl and aryl are optionally substituted with one or more $R^8$; or $R^6$ and $R^7$ may, together with the N-atom to which they are attached, form a heterocyclic ring optionally substituted with one or more $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, wherein the alkyl, alkenyl, alkynyl, cycloalkyl, heterocyclyl, heteroaryl and aryl are optionally substituted with one or more substituents independently selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein the heterocyclyl is optionally substituted with one or more $R^4$ and wherein the heteroaryl and aryl are optionally substituted with one or more $R^5$;

each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein the heterocyclyl is optionally substituted with one or more $R^4$ and wherein the heteroaryl and aryl are optionally substituted with one or more $R^5$;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and $C_{6-14}$ aryl, wherein the heterocyclyl is optionally substituted with one or more $R^4$ and wherein the heteroaryl and aryl are optionally substituted with one or more $R^5$; or $R^{10}$ and $R^{11}$ may, together with the N-atom to which they are attached, form a 5- to 7-membered heterocyclic ring optionally substituted with one or more $R^4$;

$R^{18}$ is selected from —H, $C_{1-6}$ alkyl, $C_{1-6}$ fluoroalkyl, $C_{1-6}$ hydroxyalkyl, $C_{2-7}$ alkenyl, $C_{2-7}$ alkynyl, $C_{3-7}$ cycloalkyl, and $C_{3-7}$ oxyalkyl; or $R^{18}$ and A, together with the atoms to which they are attached, form a heterocyclic ring; or $R^{18}$ and Y, together with the atoms to which they are attached, form a heterocyclic ring; or $R^{18}$ and $R^1$, together with the atoms to which they are attached, form a heterocyclic ring;

$R^{19}$ is selected from $C_{1-8}$ alkyl, $C_{2-8}$ alkenyl, $C_{2-8}$ alkynyl, and $C_{3-10}$ cycloalkyl, wherein the alkyl, alkenyl, alkynyl and cycloalkyl are optionally substituted with one or more substituents independently selected from aryl, $C_{1-6}$ alkoxy, heteroaryl, aryloxy, heteroaryloxy, $C_{3-6}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$ and may optionally form a cyclophane structure by attaching to Y or A; and wherein:

$R^{21}$ is $(R^{22})_2N$— or $R^{22}O$, wherein $R^{22}$ is $C_{1-8}$ alkyl, $C_{2-8}$ alkenyl, $C_{2-8}$ alkynyl, $C_{3-10}$ cycloalkyl, and aryloxy optionally substituted with one or more substituents independently selected from —OH, aryl, $C_{1-6}$ alkoxy, heteroaryl, aryloxy, heteroaryloxy, —F, a sulfonamide moiety, and $C_{3-6}$ cycloalkyl; wherein one $R^{22}$ in $(R^{22})_2N$—is optionally —H.

25. The compound of claim 24, wherein:

M is CH;

A is selected from —Z-heterocyclylene, —Z-arylene, and —Z-heteroarylene;

Y is selected from —H and $C_{1-8}$ alkyl;

$R^1$ is H;

each $R^3$ is independently selected from —Z-heterocyclyl, —Z-aryl, and —Z-heteroaryl;

$R^{18}$ is H;

Z is selected from a single bond and $C_{1-4}$ alkylene; and $R^{19}$ is methyl.

26. The compound of claim 24, wherein:

M is CH;

A is selected from —Z-heterocyclylene, —Z-arylene, and —Z-heteroarylene;

Y is selected from —H and $C_{1-8}$ alkyl;

R[1] is H;

each R[3] is independently selected from —Z-heterocyclyl, —Z-aryl, and —Z-heteroaryl;

R[18] is H;

Z is selected from a single bond and $C_{1-4}$ alkylene; and

R[19] is —CH$_2$OH.

27. The compound of claim 24, wherein R[21] is $(R^{22})_2N$—.

28. The compound of claim 27, wherein one R[22] is —H, and the other R[22] is $C_{1-8}$ alkyl or $C_{3-10}$ cycloalkyl.

29. The compound of claim 24, wherein R[21] is $R^{22}O$.

30. The compound of claim 29, wherein R[22] is $C_{1-8}$ alkyl optionally substituted with one or more —F.

31. The compound of claim 1 being of Formula (IIIa),

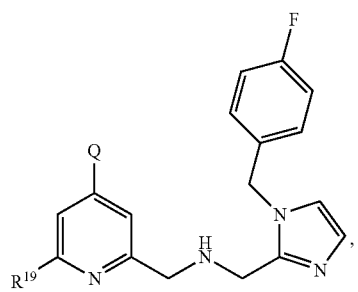

IIIa or a pharmaceutically acceptable salt or solvate thereof.

32. The compound of claim 1 being of Formula (IIIb),

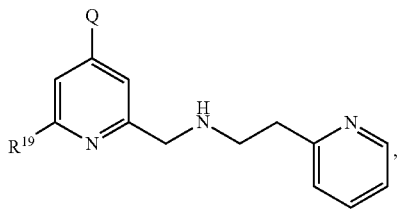

IIIb or a pharmaceutically acceptable salt or solvate thereof.

33. The compound of claim 1 being of Formula (IIIc),

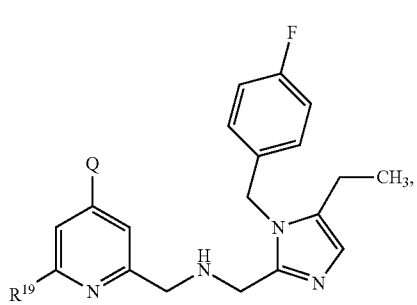

IIIc or a pharmaceutically acceptable salt or solvate thereof.

34. The compound of claim 1 being of Formula (IIId),

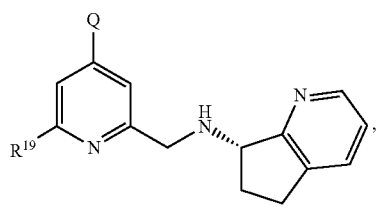

IIId or a pharmaceutically acceptable salt or solvate thereof.

35. The compound of claim 1 being of Formula (IIIe),

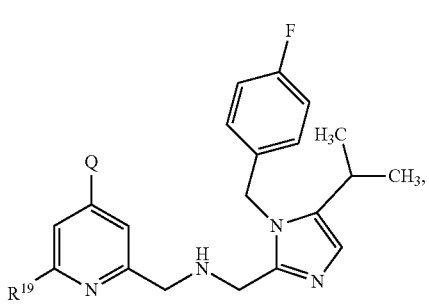

IIIe or a pharmaceutically acceptable salt or solvate thereof.

36. The compound of claim 1 being of Formula (IIIf),

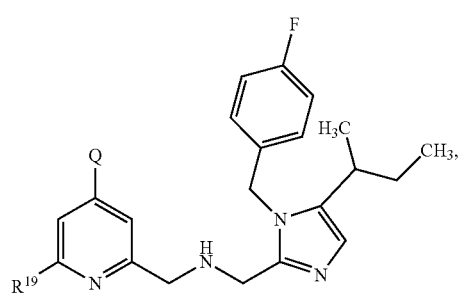

IIIf or a pharmaceutically acceptable salt or solvate thereof.

37. The compound of claim 1 being of Formula (IIIg),

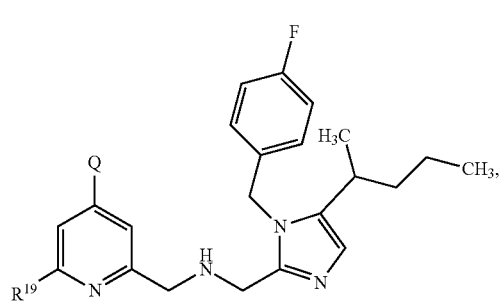

IIIg or a pharmaceutically acceptable salt or solvate thereof.

38. The compound of claim 1, selected from any one of the following:
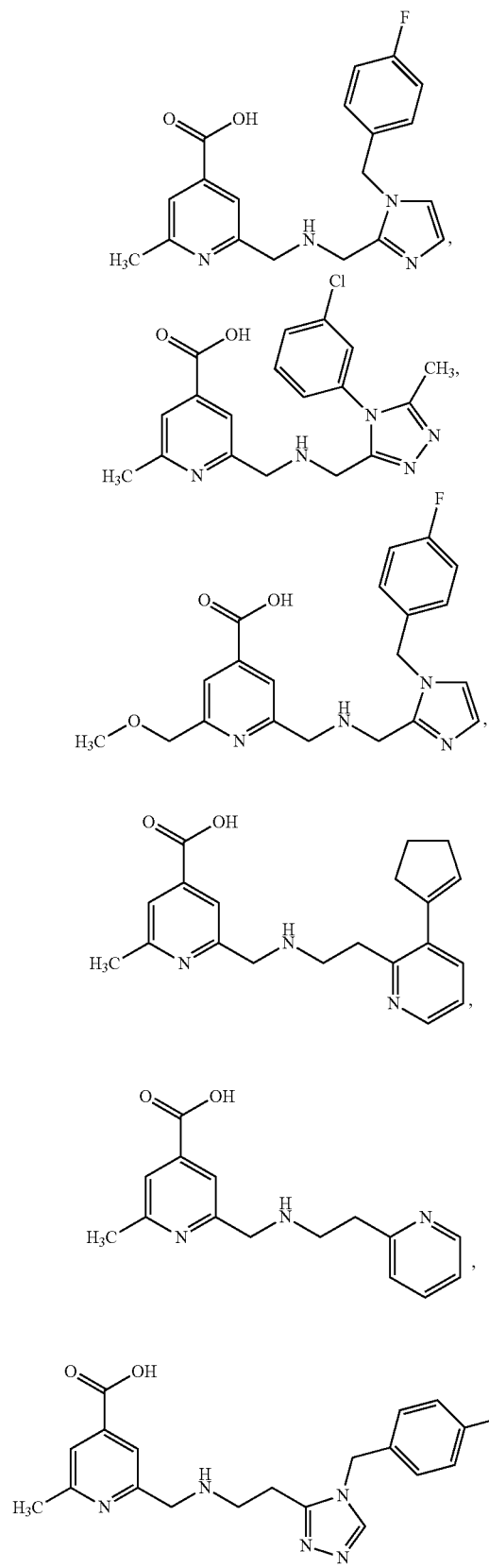
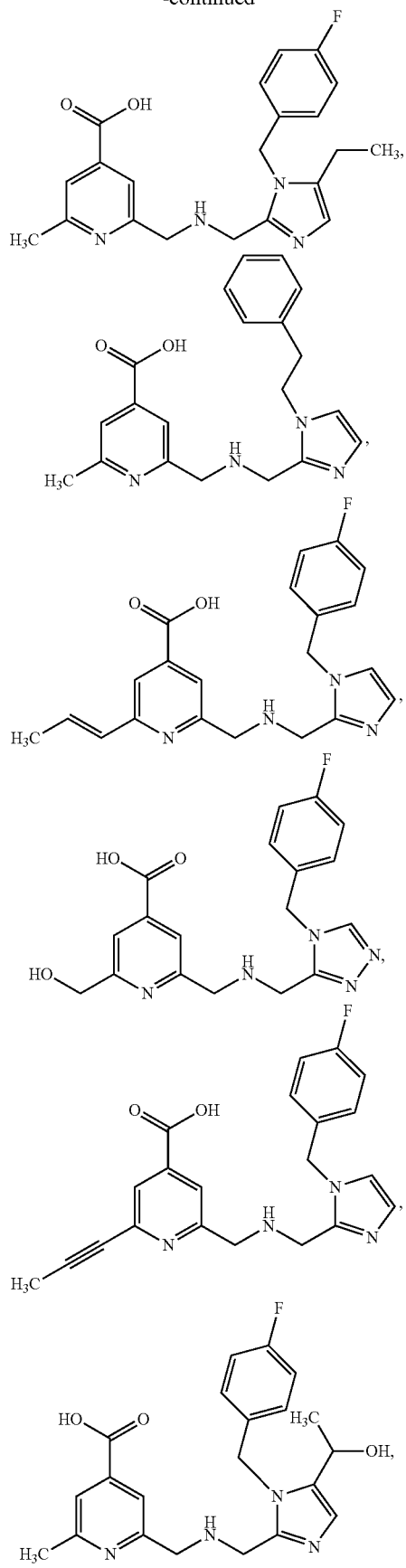

255
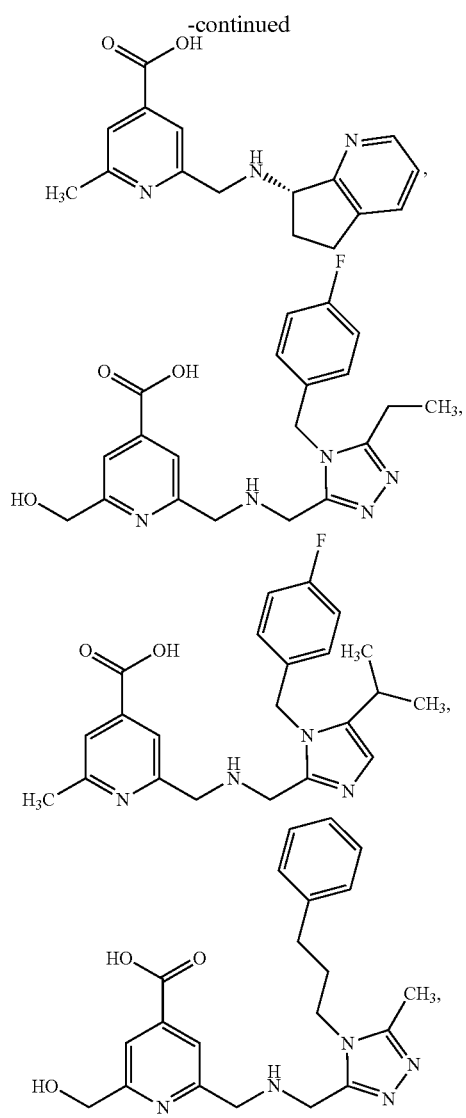
256
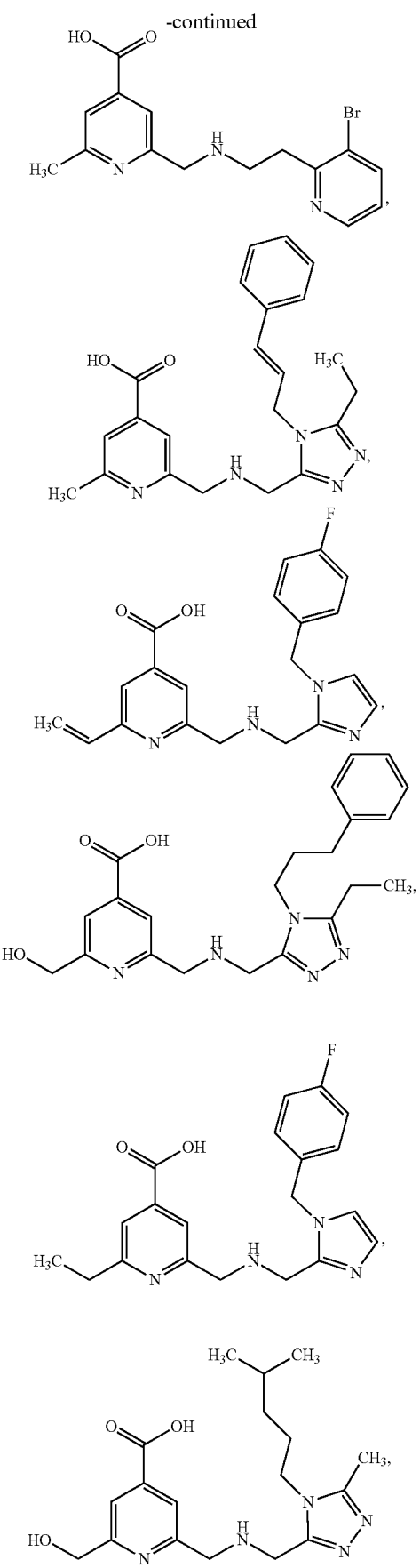

257
-continued
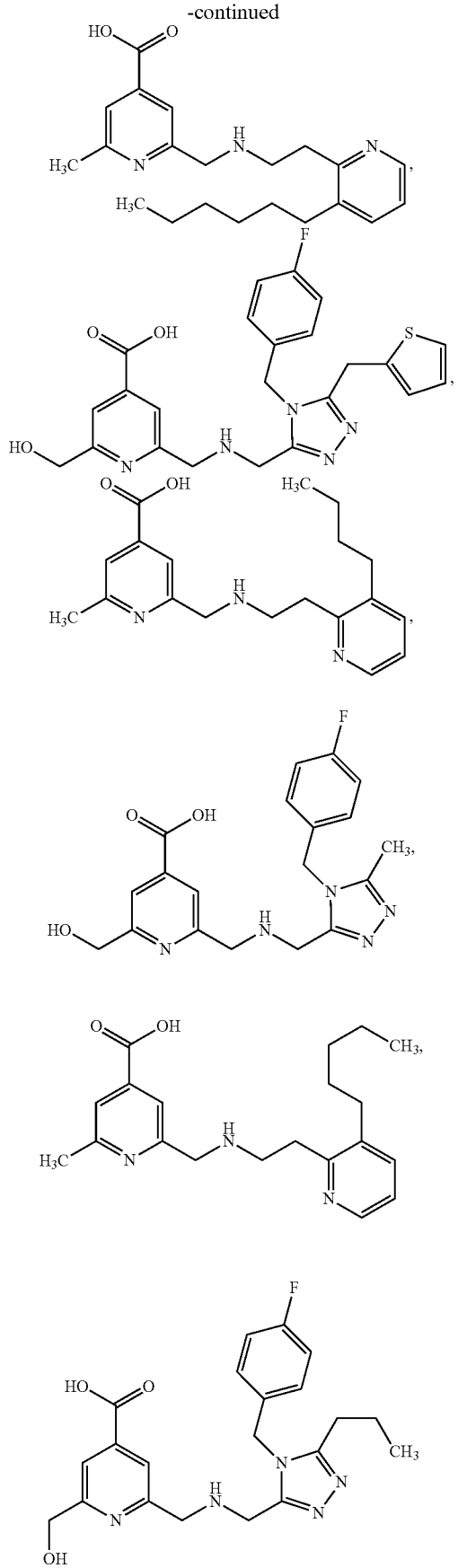
258
-continued
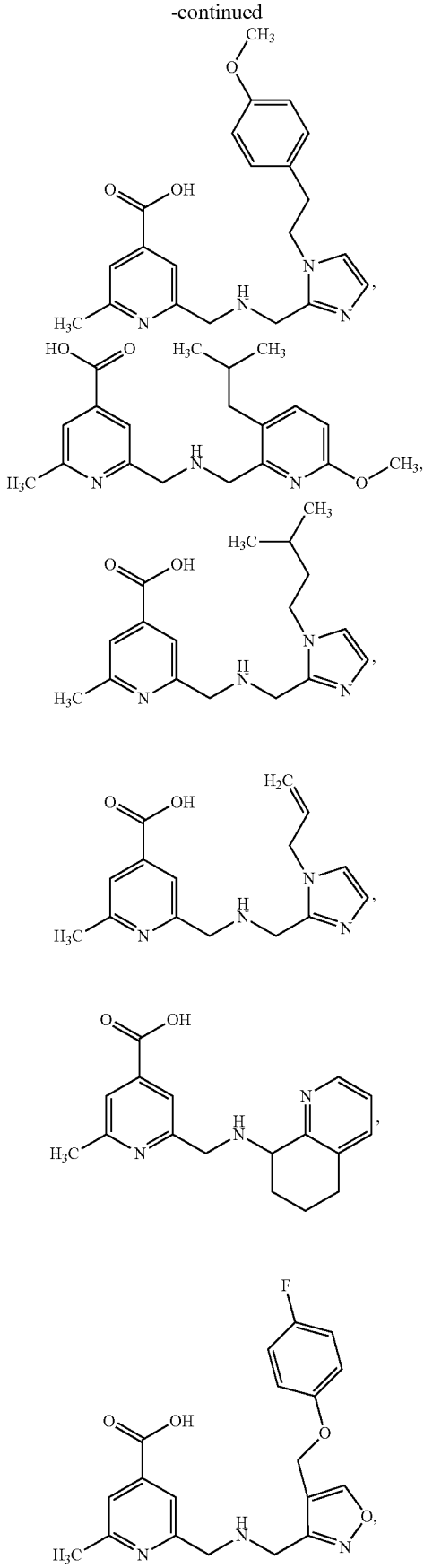

259
-continued
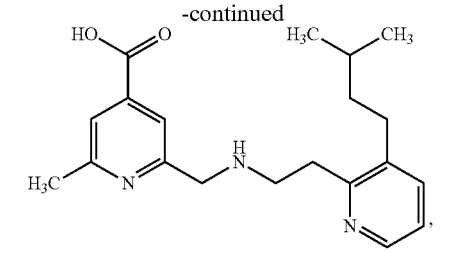
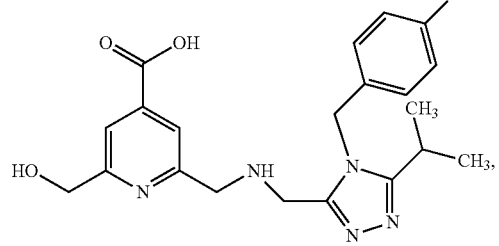
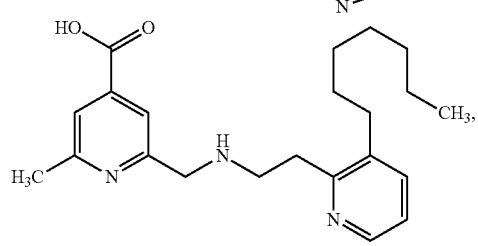
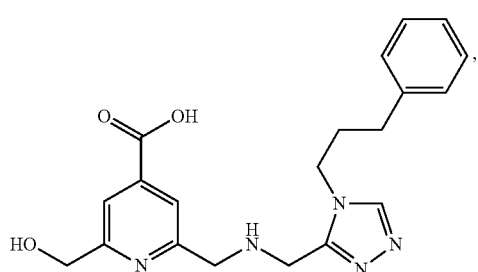
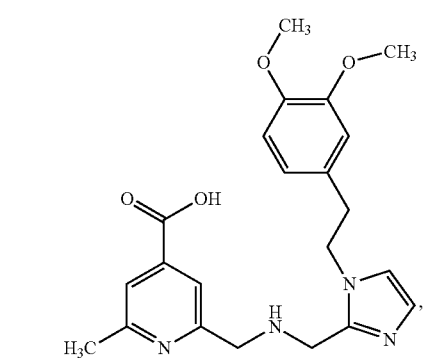
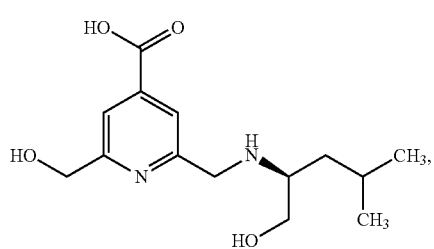
260
-continued
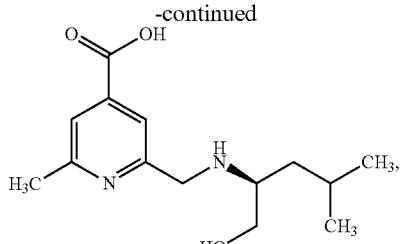
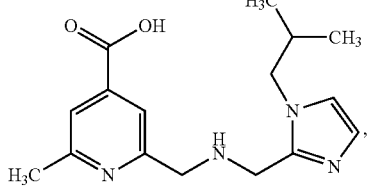
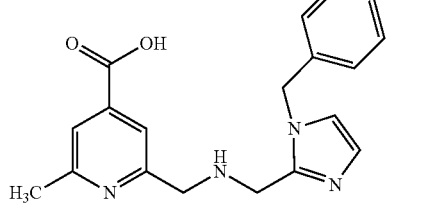
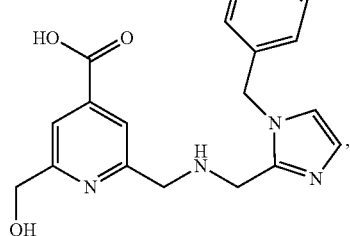
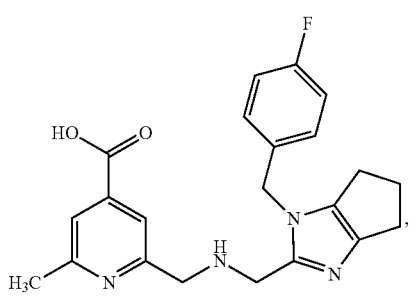
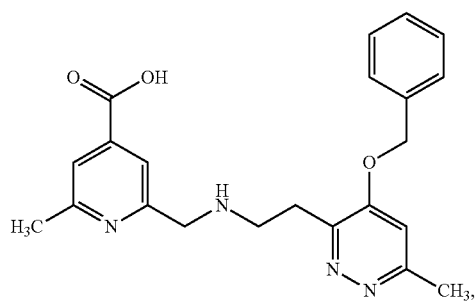

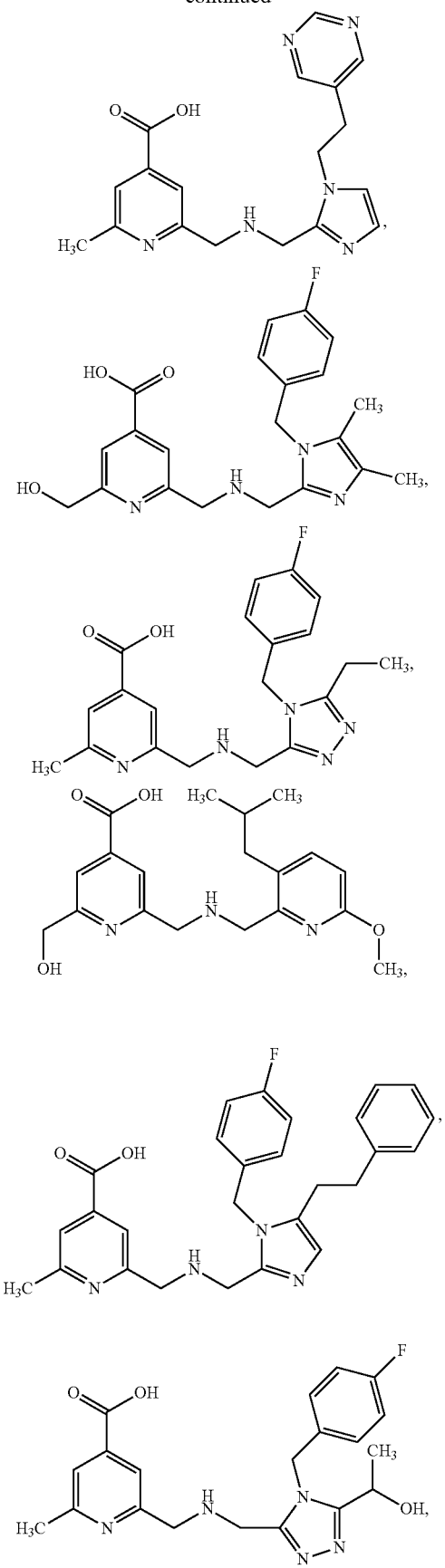
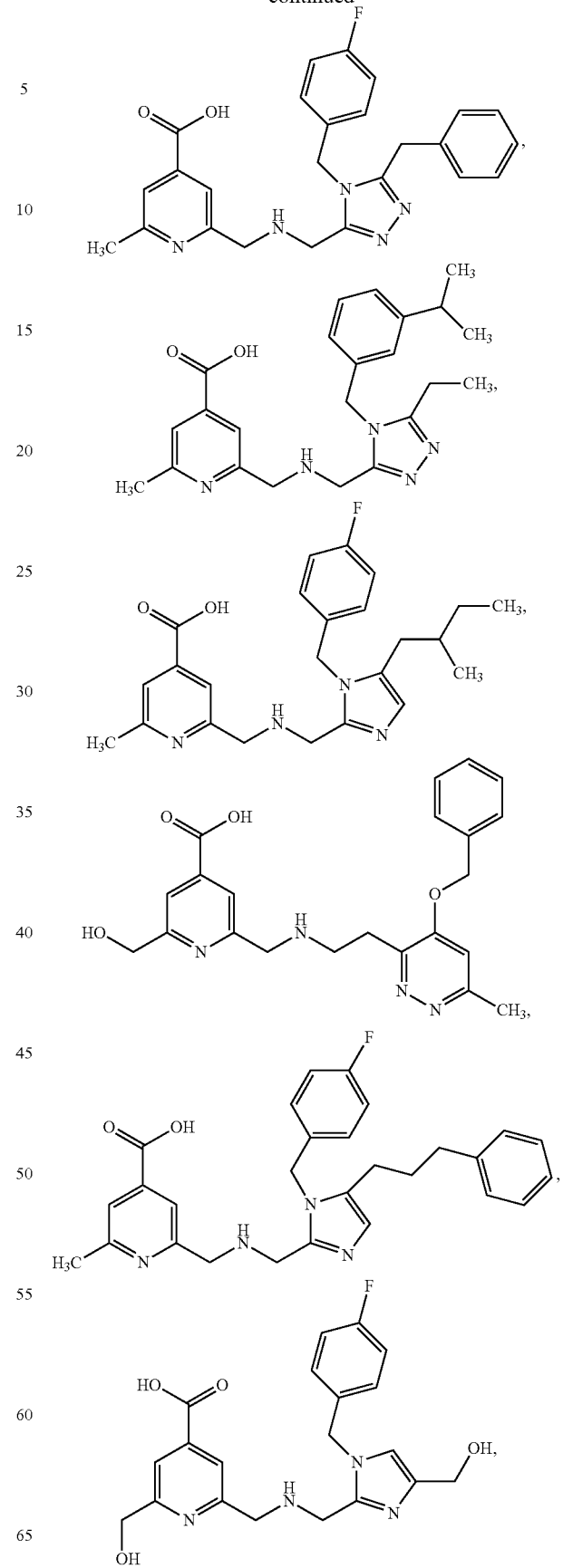

263
-continued
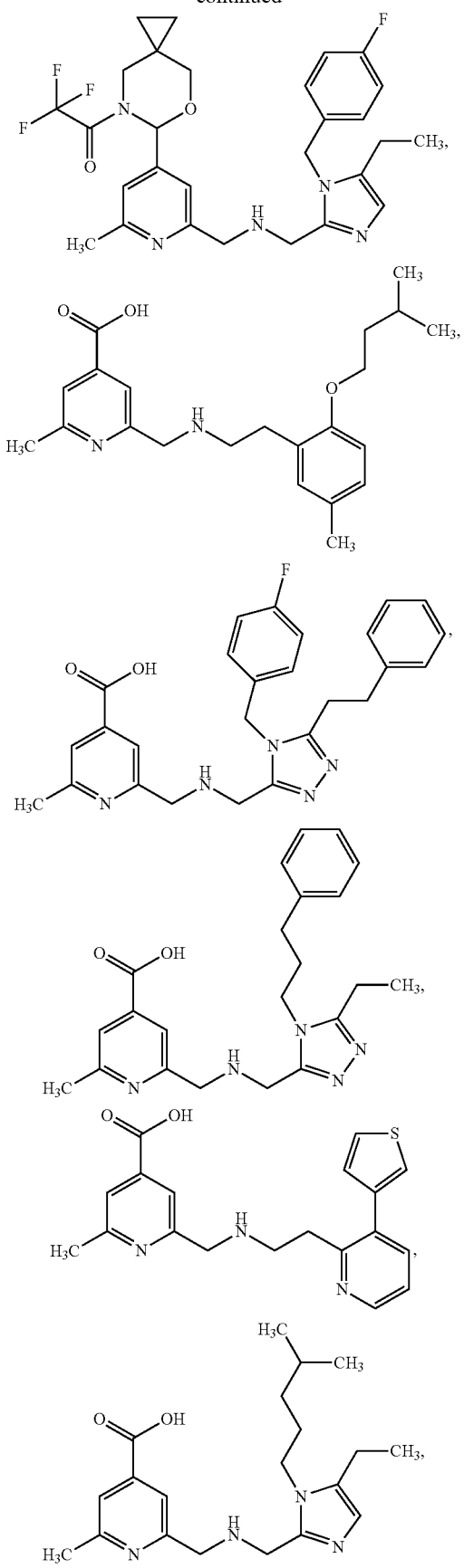
264
-continued
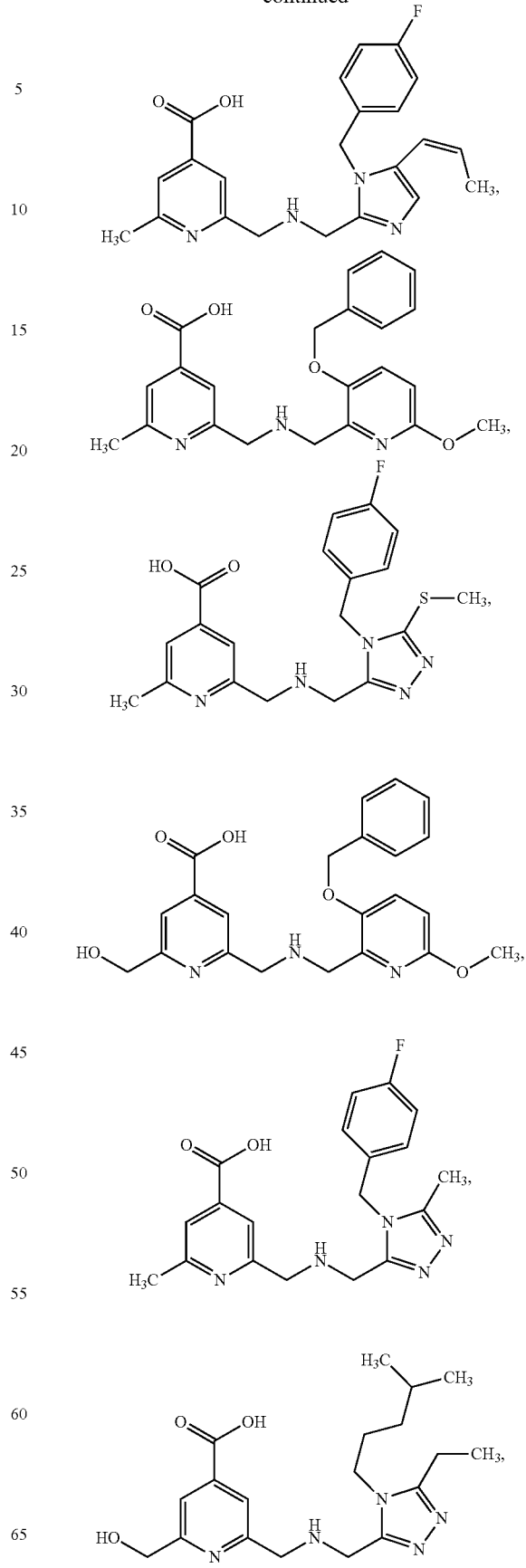

265
-continued
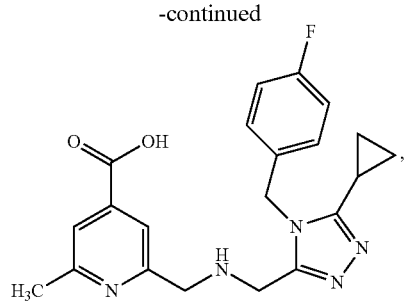
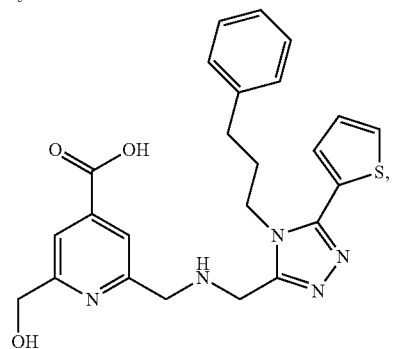
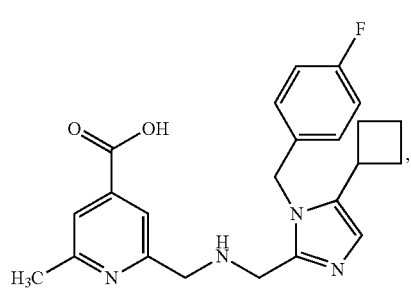
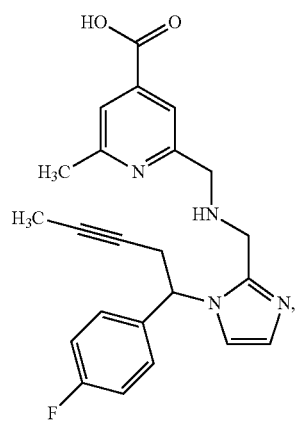
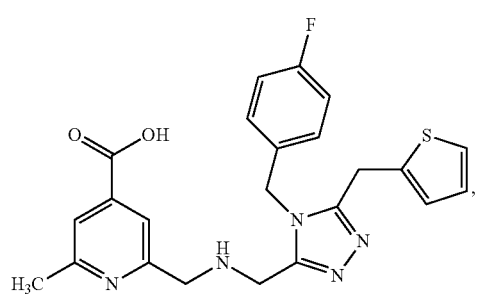
266
-continued
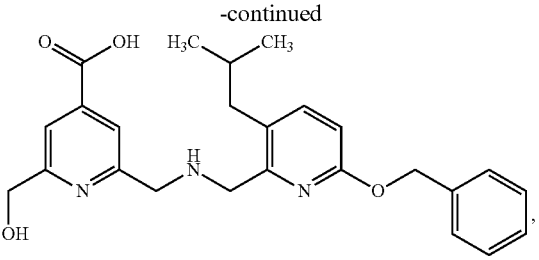
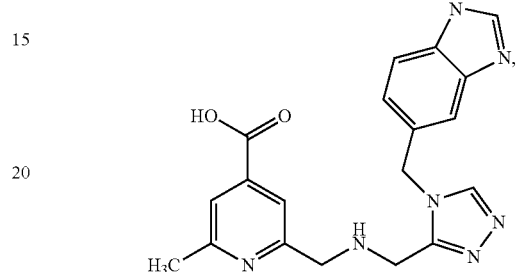
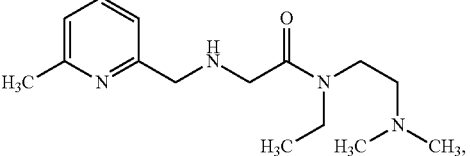
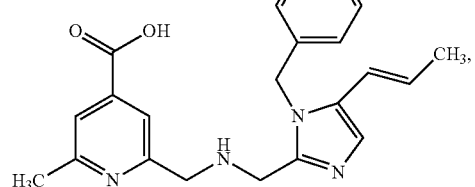
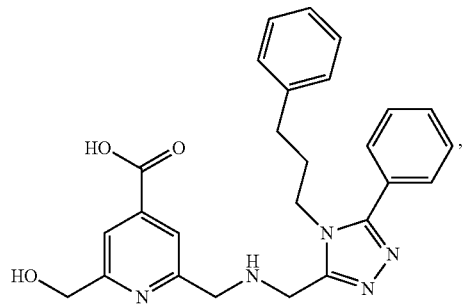
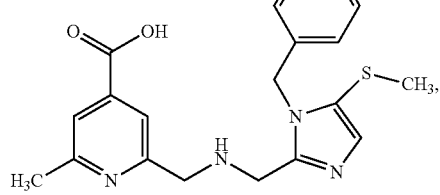

267
-continued
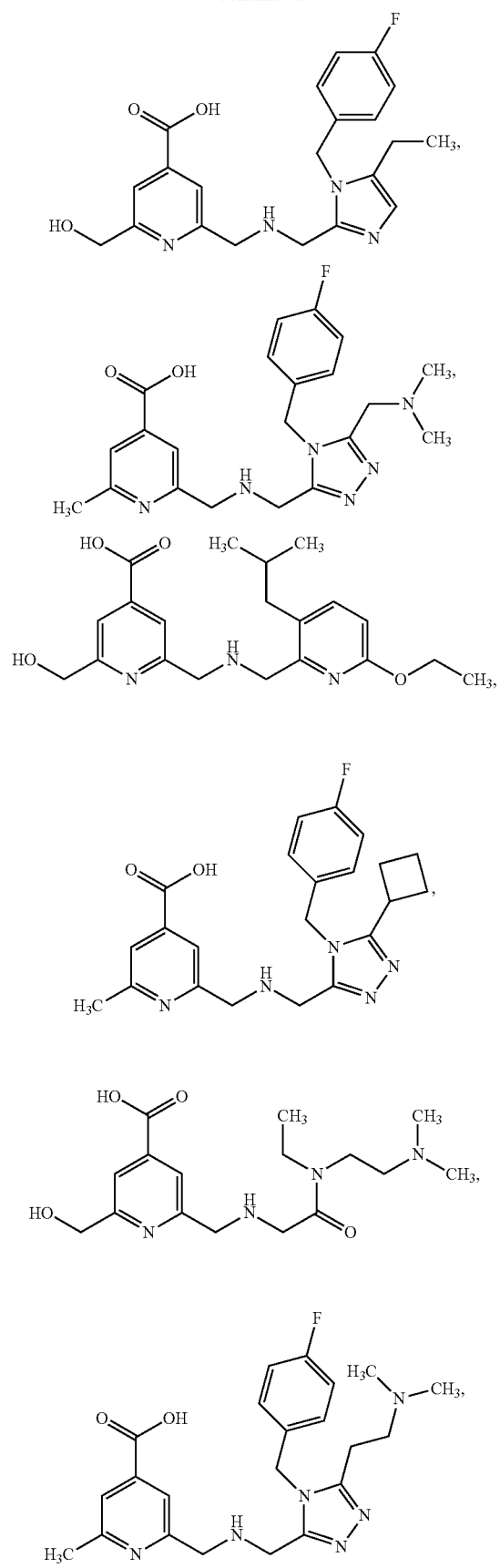
268
-continued
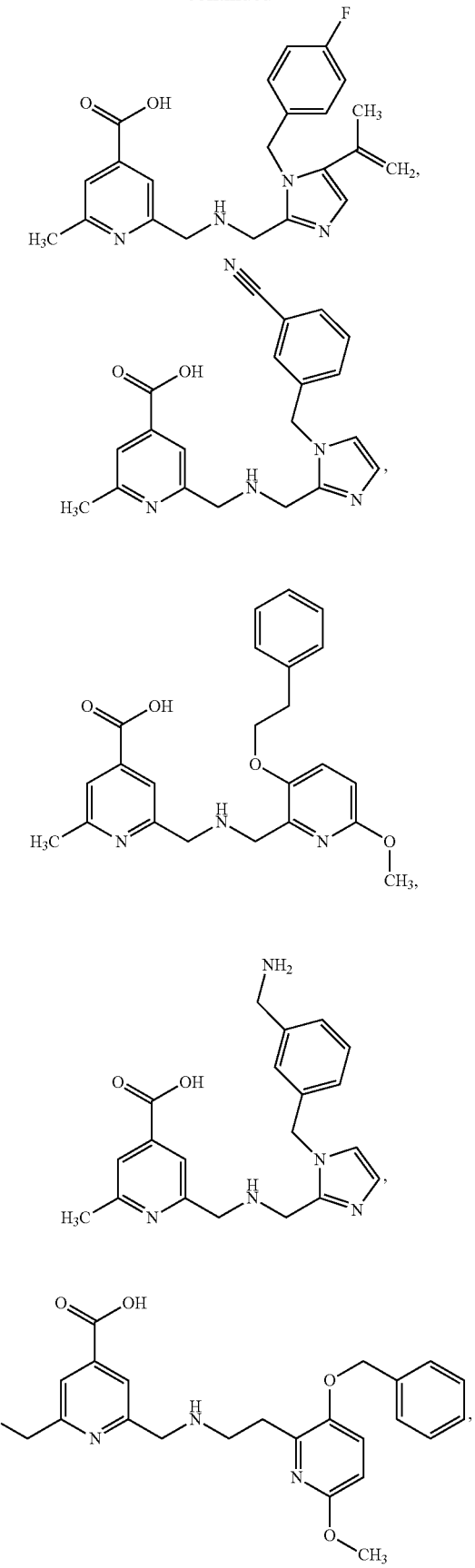

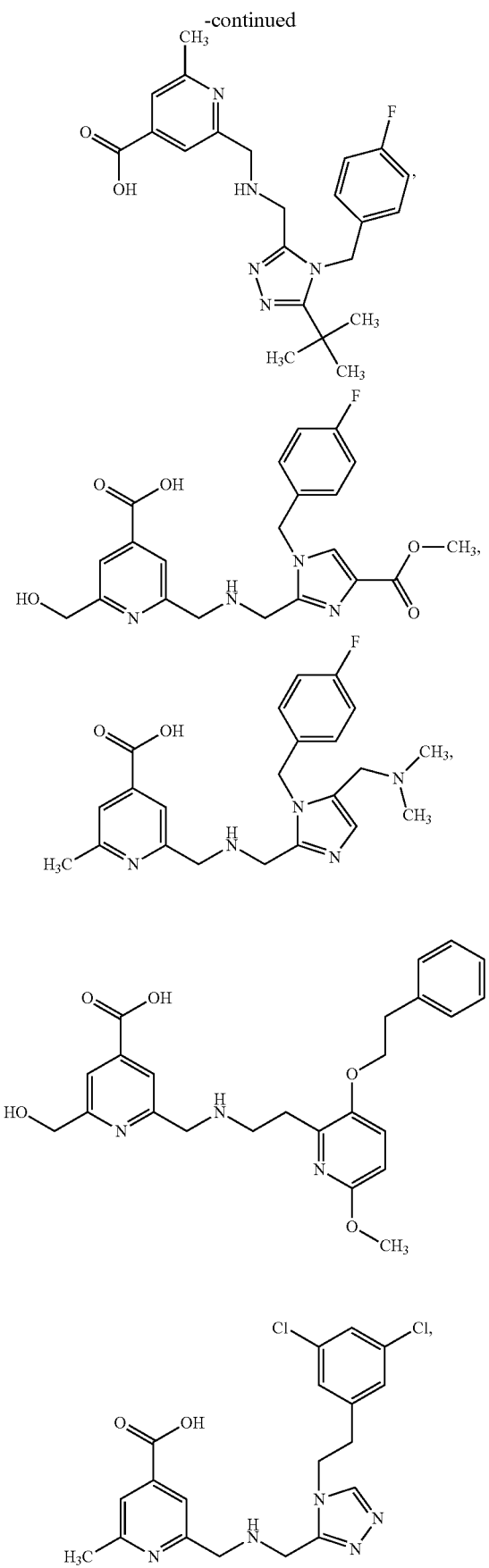
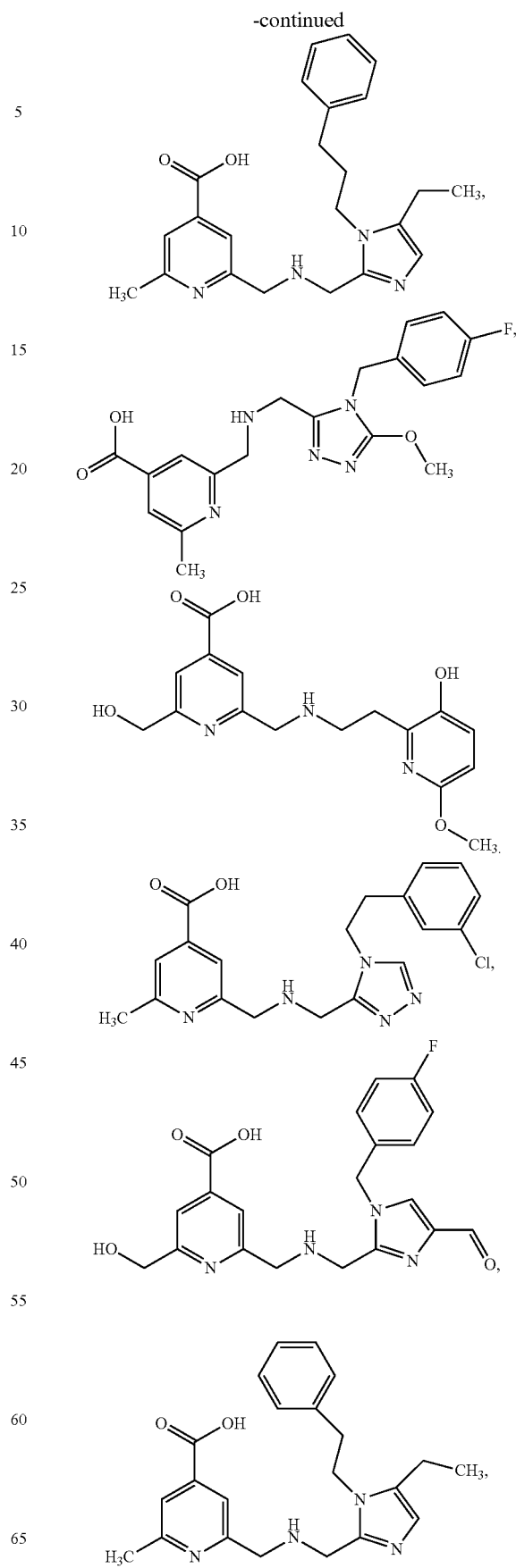

271
-continued
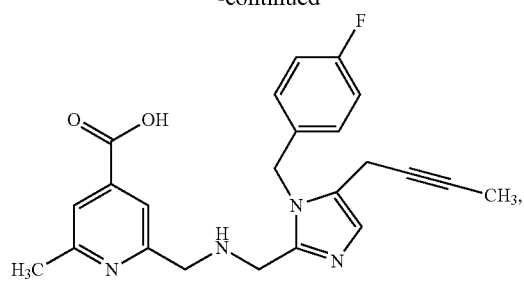
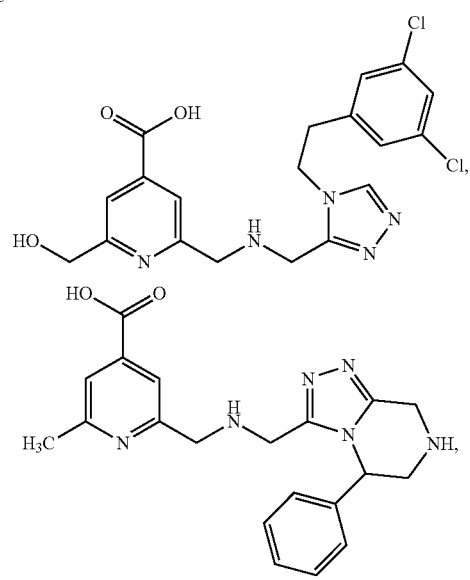
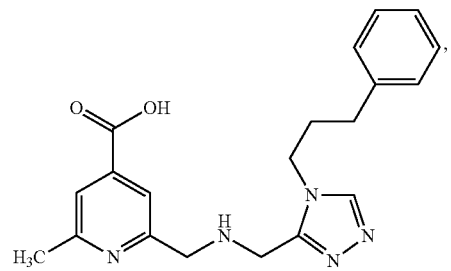
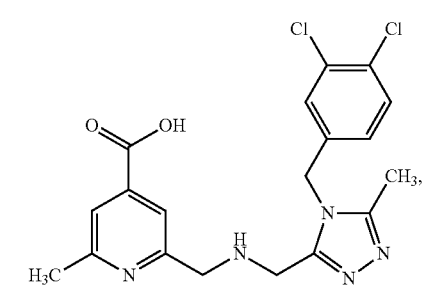
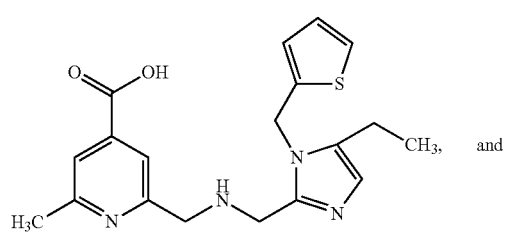
272
-continued
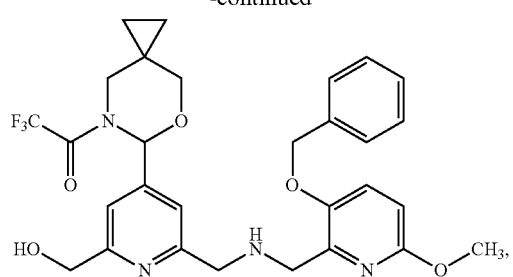
or a pharmaceutically acceptable salt or solvate thereof.
39. The compound of claim 1, selected from any one of the following:
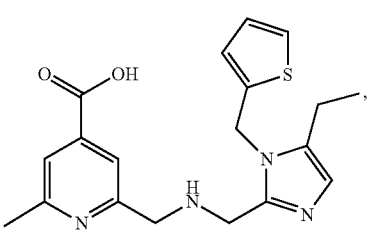
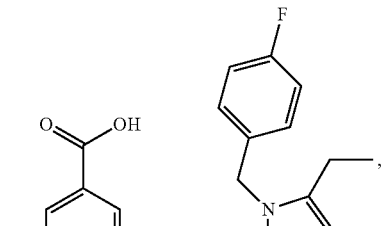
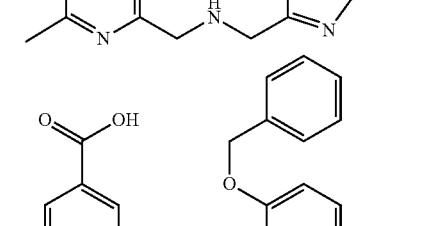
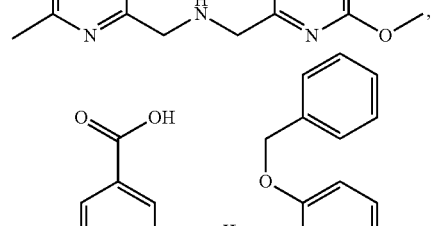
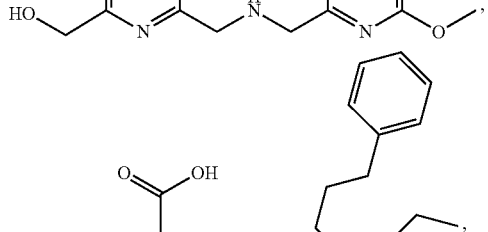
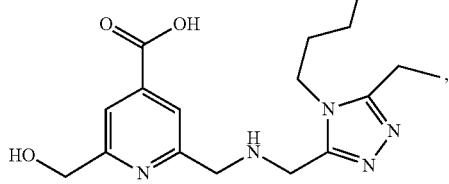

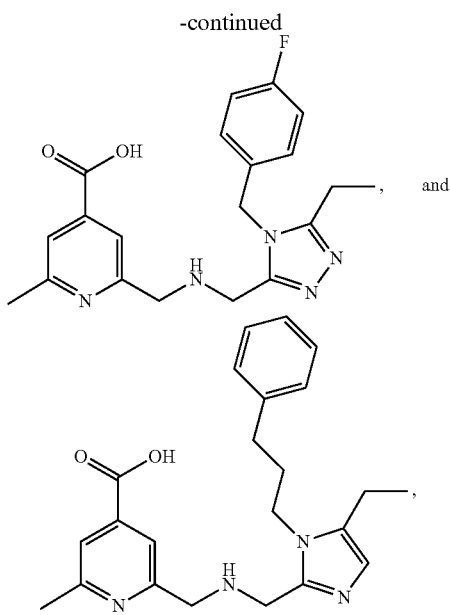

or a pharmaceutically acceptable salt or solvate thereof.

40. A pharmaceutical composition comprising at least one compound of claim 1, or a pharmaceutically acceptable salt or solvate thereof, and optionally one or more pharmaceutically acceptable excipients, diluents and/or carriers.

41. The pharmaceutical composition according to claim 40, which comprises one or more further active substances.

42. A method of reversing, alleviating, or inhibiting the process of a HDME-dependent disease in a subject in need thereof, wherein said method comprises administering to said subject a therapeutically effective amount of at least one compound according to claim 1, or a pharmaceutically acceptable salt or solvate thereof, to alleviate the symptoms of the HDME-dependent disease or to eliminate the HDME-dependent disease.

43. A method of inhibiting a HDME, comprising contacting a cell with a compound of claim 1 in an amount effective to produce a concentration sufficient to inhibit the demethylation of a histone in a cell.

44. The method of claim 43, wherein the HDME is a member of the KDM7 family, PHF8 family, KDM6 family, KDM5 family, KDM4 family, or KDM2 family.

45. The method of claim 43, wherein the HDME is KDM4C, KDM2B, PHF8, KDM6A, or KDM5B.

46. A pharmaceutical composition comprising at least one compound of claim 24, or a pharmaceutically acceptable salt or solvate thereof, and optionally one or more pharmaceutically acceptable excipients, diluents and/or carriers.

47. A method of reversing, alleviating, or inhibiting the process of a HDME-dependent disease in a subject in need thereof, wherein said method comprises administering to said subject a therapeutically effective amount of at least one compound according to claim 24, or a pharmaceutically acceptable salt or solvate thereof, to alleviate the symptoms of the HDME-dependent disease or to eliminate the HDME-dependent disease.

* * * * *

SEQUENCE LISTING

```
<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: biotinylated peptide
<220> FEATURE:
<221> NAME/KEY: MOD_RES
<222> LOCATION: (9)..(9)
<223> OTHER INFORMATION: dimethylated

<400> SEQUENCE: 1

Ala Arg Thr Lys Gln Thr Ala Arg Lys Ser Thr Gly Gly Lys Ala Pro
1               5                   10                  15

Arg Lys Gln

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: biotinylated peptide
<220> FEATURE:
<221> NAME/KEY: MOD_RES
<222> LOCATION: (9)..(9)
<223> OTHER INFORMATION: trimethylated

<400> SEQUENCE: 2

Ala Arg Thr Lys Gln Thr Ala Arg Lys Ser Thr Gly Gly Lys Ala Pro
```

```
1               5                   10                  15

Arg Lys Gln

<210> SEQ ID NO 3
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Biotinylated Peptide
<220> FEATURE:
<221> NAME/KEY: MOD_RES
<222> LOCATION: (4)..(4)
<223> OTHER INFORMATION: trimethylated

<400> SEQUENCE: 3

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Biotinylated Peptide
<220> FEATURE:
<221> NAME/KEY: MOD_RES
<222> LOCATION: (7)..(7)
<223> OTHER INFORMATION: trimethylated

<400> SEQUENCE: 4

Ala Thr Lys Ala Ala Arg Lys Ser Ala Pro Ala Thr Gly Gly Val Lys
1               5                   10                  15

Lys Pro His Arg Tyr
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Biotinylated Peptide
<220> FEATURE:
<221> NAME/KEY: MOD_RES
<222> LOCATION: (11)..(11)
<223> OTHER INFORMATION: dimethylated

<400> SEQUENCE: 5

Arg Lys Ala Ala Pro Ala Thr Gly Gly Val Lys Lys Pro His Arg Tyr
1               5                   10                  15

Arg Pro Gly Thr Val Lys
            20
```